United States Patent
Nistala et al.

(10) Patent No.: US 12,083,141 B2
(45) Date of Patent: Sep. 10, 2024

(54) TREATMENT OF HYPERGLYCEMIA WITH SOLUTE CARRIER FAMILY 39 MEMBER 5 (SLC39A5) INHIBITORS

(71) Applicant: Regeneron Pharmaceuticals, Inc., Tarrytown, NY (US)

(72) Inventors: Harikiran Nistala, Tarrytown, NY (US); Cristopher Van Hout, Tarrytown, NY (US); Lyndon Mitnaul, Tarrytown, NY (US); Anthony Marcketta, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 604 days.

(21) Appl. No.: 16/816,515

(22) Filed: Mar. 12, 2020

(65) Prior Publication Data

US 2020/0297751 A1    Sep. 24, 2020

Related U.S. Application Data

(60) Provisional application No. 62/976,716, filed on Feb. 14, 2020, provisional application No. 62/818,811, filed on Mar. 15, 2019.

(51) Int. Cl.
| | | |
|---|---|---|
| *A61K 31/7105* | (2006.01) | |
| *A61K 33/30* | (2006.01) | |
| *C07K 14/435* | (2006.01) | |
| *C12Q 1/6876* | (2018.01) | |
| *C12Q 1/6897* | (2018.01) | |
| *G01N 33/66* | (2006.01) | |
| *G01N 33/68* | (2006.01) | |
| *G01N 33/74* | (2006.01) | |

(52) U.S. Cl.
CPC .......... *A61K 31/7105* (2013.01); *A61K 33/30* (2013.01); *C07K 14/435* (2013.01); *C12Q 1/6876* (2013.01); *C12Q 1/6897* (2013.01); *G01N 33/66* (2013.01); *G01N 33/6803* (2013.01); *G01N 33/74* (2013.01); *C12Q 2600/156* (2013.01); *G01N 2333/62* (2013.01); *G01N 2400/00* (2013.01)

(58) Field of Classification Search
None
See application file for complete search history.

(56) References Cited

U.S. PATENT DOCUMENTS 6,307,080 B1   10/2001 Pischel et al.

FOREIGN PATENT DOCUMENTS

EP        1256342        11/2002

OTHER PUBLICATIONS

Wang et al., The Mammalian Zip5 Protein Is a Zinc Transporter That Localizes to the Basolateral Surface of Polarized Cell. The Journal of Biological Chemistry (2004), 279(49): 51433-51441 (Year: 2004).*
Wang et al., The zinc transporter Slc39a5 controls glucose sensing and insulin secretion in pancreatic β-cells via Sirt1- and Pgc-1α-mediated regulation of Glut2. Protein Cell (2019), 10(6):436-449 (Year: 2018).*
Li et al., Knockdown of Zinc Transporter ZIP5 by RNA Interference Inhibits Esophageal Cancer Growth In Vivo. Oncology Research (2016), 24:205-214 (Year: 2016).*
Geiser et al., The Zinc Transporter Zip5 (Slc39a5) Regulates Intestinal Zinc Excretion and Protects the Pancreas against Zinc Toxicity. PLOS One (2013), 8(11) e82149: 1-11 (Year: 2013).*
Jin et al., Knockdown of zinc transporter ZIP5 (SLC39A5) expression significantly inhibits human esophageal cancer progression. Oncology Reports (2015), 34: 1431-1439 (Year: 2015).*
Chiarelli and Di Marzio, Peroxisome proliferator-activated receptor-γ agonists and diabetes: Current evidence and future perspectives. Vascular Health and Risk Management (2008), 4(2): 297-304 (Year: 2008).*
Abcam, Anti-ZIP-5 antibody (ab105194), https://www.abcam.com/zip-5-antibody-ab105194.html [retrieved Oct. 17, 2022] (Year: 2022).*
*Homo sapiens* solute carrier family 39 member 5 (SLC39A5), RefSeqGene on chromosome 12, NCBI Reference Sequence: NG_034265.1 https://www.ncbi.nlm.nih.gov/nuccore/688955998?sat=47&satkey=615175 [retrieved Oct. 17, 2022] (Year: 2017).*
Wu et al., Mimicking Strategy for Protein-Protein Interaction Inhibitor Discovery by Virtual Screening. Molecules (2019), 24: 4428, 1-14 (Year: 2019).*
Lv et al., METTL9 regulates N1-histidine methylation of zinc transporters to promote tumor growth. https://www.biorxiv.org/content/10.1101/2021.04.20.440582v1.full.pdf, available Apr. 23, 2021 (Year: 2021).*
Houseknecht et al., Peroxisome proliferator-activated receptor gamma (PPAR-gamma) and its ligands: A review. Domestic Animal Endocrinology (2002), 2(1): 1-23 (Year: 2002).*
Zhang et al., Quantity of glucose transporter and appetite-associated factor mRNA in various tissues after insulin injection in chickens selected for low or high body weight. Physiol Genomics (2013), 45: 1084-1094 (Year: 2013).*
Polakof et al., Glucose metabolism in fish: a review. J Comp Physiol B (2012). 182:1015-1045 (Year: 2012).*
Roussel et al., LowWater Intake and Risk for New-Onset Hyperglycemia. Diabetes Care (2011), 34: 2551-2554 (Year: 2011).*
Nelson and Cox, Lehninger Principles of Biochemistry, 4th Edition (2004), WH Freeman, Chapters 15 and 23 (Year: 2004).*

(Continued)

*Primary Examiner* — Celine X Qian
*Assistant Examiner* — Catherine Konopka
(74) *Attorney, Agent, or Firm* — Armstrong Teasdale LLP

(57) ABSTRACT

The present disclosure provides methods of treating subjects having increased serum glucose level and/or hyperglycemia, methods of identifying subjects having an increased risk of developing increased serum glucose level and/or hyperglycemia, and methods of detecting human Solute Carrier Family 39 Member 5 variant nucleic acid molecules and variant polypeptides.

12 Claims, 115 Drawing Sheets
(113 of 115 Drawing Sheet(s) Filed in Color)
Specification includes a Sequence Listing.

(56) References Cited

OTHER PUBLICATIONS

Linda Rath, What Are Insulin Dosages for Type 2 Diabetes, WebMD (2020), https://web.archive.org/web/20201020065045/https://www.webmd.com/diabetes/diabetes-insulin-dosages [retrieved Oct. 4, 2023] (Year: 2020).*

Jain et al., Drugs and hyperglycemia: A practical guide. Maturitas (2017), 104: 80-83, Section 2.8 (Year: 2017).*

Metformin (Oral Route), https://www.mayoclinic.org/drugs-supplements/metformin-oral-route/proper-use/drg-20067074, [retrieved Feb. 1, 2024] (Year: 2024).*

Lixisenatide (Subcutaneous Route), https://www.mayoclinic.org/drugs-supplements/lixisenatide-subcutaneous-route/proper-use/drg-20312437, [retrieved Feb. 1, 2024] (Year: 2024).*

Hage et al., Thyroid Disorders and DiabetesMellitus. Journal of Thyroid Research (2011), 43963, 1-7 (Year: 2011).*

Levothyroxine, National Health Service, https://www.nhs.uk/medicines/levothyroxine, [retrieved Feb. 5, 2024] (Year: 2024).*

Woodruff et al., The Zinc Transporter SLC39A7 (ZIP7) Is Essential for Regulation of Cytosolic Zinc Levels. Molecular Pharmacology (2018), 94: 1092-1100 (Year: 2018).*

Lamoia et al., Cellular and Molecular Mechanisms of Metformin Action. Endocrine Reviews (2021), 41(a): 77-96 (Year: 2021).*

Davis and Sandoval, Glucagon-like Peptide-1: Actions and Influence on Pancreatic Hormone Function. Compr Physiol (2020), 19(2): 577-595 (Year: 2020).*

GLP-1 Agonists, https://my.clevelandclinic.org/health/treatments/13901-glp-1-agonists, [retrieved Feb. 6, 2024] (Year: 2024).*

Yoshikawa et al., Alpha-glucosidase inhibitory effect of antidiabetic metal ions and their complexes. Biochimie (2009), 91: 1339-1341 (Year: 2009).*

Maria Alemany, Estrogens and the regulation of glucose metabolism. World Journal of Diabetes (2021), 12: 1622-1654 (Year: 2021).*

Leif Groop, Sulfonylureas in NIDDM. Diabetes Care (1992), 15:737-754 (Year: 1992).*

Adulcikas et al., "Targeting the Zinc Transporter ZIP7 in the Treatment of Insulin Resistance and Type 2 Diabetes", Nutrients, 2019, 11(408), pp. 1-15.

Capdor et al., "Zinc and glycemic control: A meta-analysis of randomised placebo controlled supplementation trials in humans", Journal of Trace Elements in Medicine and Biology, 2013, 27, pp. 137-142.

Guo et al., "SLC39A5 mutations interfering with the BMP/TGF-[beta] pathway in non-syndromic high myopia", Journal of Medical Genetics, 2014, 51(8), pp. 518-525.

Li et al., "Knockdown of Zinc Transporter ZIP5 by RNA Interference Inhibits Esophageal Cancer Growth In Vivo", Oncology Research, 2016, 24(3), pp. 205-214.

Weaver et al., "Regulation of zinc-responsive Slc39a5 (Zip5) translation is mediated by conserved elements in the 3'-untranslated region", Biometals, 2011, 25(2), pp. 319-335.

International Search Report and Written Opinion mailed Sep. 15, 2020 for International Patent Application No. PCT/US2020/022251.

Jiang et al., "Dectection of Mutations in LRPAP1, CTSH, LEPREL1, ZNF644, SLC39A5, and SCO2 in 298 Families With Early-Onset High Myopia by Exome Sequencing", Investigative Ophthalmology & Visual Science, 2015, 56(1), pp. 339-345.

Anonymous, "SLC39A5 solute carrier family 39 metal ion transporter, member 5—KOMP Knockout Mouse Project", 2015, http://web.archive.org/web/20150913094434/https://www.komp.org/geneinfo.php?geneid=79393.

Anonymous, "KOMP Allele Types", 2017, http:/web.archive.org/web/20170725082255/https://www.komp.org/alleles.php.

Geiser et al., "The Zinc Transporter Zip5 (Slc39a5) Regulates Intestinal Zinc Excretion and Protects the Pancreas against Zinc Toxicity", Plos ONE, 2013, 8(11), e82149.

Taylor et al., "Zinc, the Pancreas, and Diabetes: Insights from Rodent Studies and Future Directions", Biometals, 2005, 18(4), pp. 305-312.

Wang et al., "The zinc transporter Slc39a5 controls glucose sensing and insulin secretion in pancreatic [beta]-cells via Sirt1- and Pgc-1 [alpha]-mediated regulation of Glut2", Protein and Cell, 2018, 10(6), pp. 436-449.

International Search Report and Written Opinion mailed May 20, 2020 for International Patent Application No. PCT/US2020/022281.

Maxfield et al., "Zinc Deficiency", StatPearls, Treasure Island (FL): StatPearls Publishing, 2023, pp. 1-11.

Karaki et al., "Antisense Oligonucleotides, A Novel Developing Targeting Therapy", Antisense Therapy, 2019, pp. 1-19.

Harborth et al., "Identification of essential genes in cultured mammalian cells using small interfering RNAs", J Cell Sci, 2001, 114(24), pp. 4557-4565.

Holen et al., "Positional effects of short interfering RNAs targeting the human coagulation trigger Tissue Factor", Nucleic Acids Research, 2002, 30(8), pp. 1757-1766.

Reynolds et al., "Rational siRNA design for RNA Interference", Nature Biotechnology, 2004, 22, pp. 326-330.

Ozcan et al., "Preclinical and clinical development of siRNA-based therapeutics", Advanced Drug Discovery Reviews, 2015, 87, pp. 108-119.

* cited by examiner

Normal chow; Zinc 87ppm; oGTT (20wk) after 16hr fast – 2mg/g body weight; *p<0.05, **p<0.01; Error bars: SEM Normal chow; Zinc 87ppm; oGTT (20wk) after 16hr fast – 2mg/g body weight; *p<0.05, **p<0.01; Error bars: SEM Normal chow; Zinc 87ppm; oGTT (20wk) after 16hr fast – 2mg/g body weight; *p<0.05, **p<0.01; Error bars: SEM Normal chow; Zinc 87ppm; oGTT (20wk) after 16hr fast – 2mg/g body weight; *p<0.05, **p<0.01; Error bars: SEM Normal chow; Zinc 87ppm; oGTT (20wk) after 16hr fast – 2mg/g body weight; *p<0.05, **p<0.01; Error bars: SEM Normal chow; Zinc 87ppm; oGTT (20wk) after 16hr fast – 2mg/g body weight; *p<0.05, **p<0.01; Error bars: SEM High fat high fructose (HFFD) or Normal Chow (NC) for 18weeks; Zinc 34ppm; oGTT after 16hr fast, 2mg/g body weight; *p<0.05, **p<0.01

High fat high fructose (HFFD) or Normal Chow (NC) for 18weeks; Zinc 34ppm; oGTT after 16hr fast, 2mg/g body weight; *p<0.05, **p<0.01

Oral glucose tolerance test

High fat high fructose (HFFD) or Normal Chow (NC) for 18weeks; Zinc 34ppm; oGTT after 16hr fast, 2mg/g body weight; *p<0.05, **p<0.01

High fat high fructose (HFFD) or Normal Chow (NC) for 18weeks; Zinc 34ppm; oGTT after 16hr fast, 2mg/g body weight; *p<0.05, **p<0.01

Liver histology – 29 weeks; NAFLD Composite Score: Macrovesicular Steatosis, Microvesicular Steatosis, Hepatocellular Hypertrophy, Inflammation, Fibrosis; *p<0.05, **p<0.01; Error bars: SEM Liver histology – 29 weeks; NAFLD Composite Score: Macrovesicular Steatosis, Microvesicular Steatosis, Hepatocellular Hypertrophy, Inflammation, Fibrosis; *p<0.05, **p<0.01; Error bars: SEM Liver histology – 29 weeks; NAFLD Composite Score: Macrovesicular Steatosis, Microvesicular Steatosis, Hepatocellular Hypertrophy, Inflammation, Fibrosis; *p<0.05, **p<0.01; Error bars: SEM Hepatic ion quantification and Taqman analysis – 29 weeks; *p<0.05, **p<0.01; Error bars: SEM Hepatic ion quantification and Taqman analysis – 29 weeks; *p<0.05, **p<0.01;
Error bars: SEM Hepatic ion quantification and Taqman analysis – 29 weeks; *p<0.05, **p<0.01; Error bars: SEM Hepatic ion quantification and Taqman analysis – 29 weeks; *p<0.05, **p<0.01; Error bars: SEM Hepatic ion quantification and Taqman analysis – 29 weeks; *p<0.05, **p<0.01; Error bars: SEM Hepatic ion quantification and Taqman analysis – 29 weeks; *p<0.05, **p<0.01; Error bars: SEM Hepatic ion quantification and Taqman analysis – 29 weeks; *p<0.05, **p<0.01;
Error bars: SEM Hepatic ion quantification and Taqman analysis – 29 weeks; $*p<0.05$, $**p<0.01$; Error bars: SEM Hepatic ion quantification and Taqman analysis – 29 weeks; *p<0.05, **p<0.01; Error bars: SEM Hepatic ion quantification and Taqman analysis – 29 weeks; *p<0.05, **p<0.01; Error bars: SEM Liver lysates - 29 weeks; *p<0.05, **p<0.01; Error bars: SEM Liver lysates - 29 weeks; *p<0.05, **p<0.01; Error bars: SEM Liver lysates - 29 weeks; *p<0.05, **p<0.01; Error bars: SEM Liver lysates - 29 weeks; *p<0.05, p<0.01; Error bars: SEM Normal Chow (Zinc 87ppm); Fasting blood glucose: 32weeks (Fed) and 34weeks (16hr/Fast)**; *p<0.05, p<0.01; Error bars: SEM Normal Chow (Zinc 87ppm); Fasting blood glucose: 32weeks (Fed) and 34weeks (16hr/Fast)**;
*p<0.05, p<0.01; Error bars: SEM Normal Chow (Zinc 87ppm); Fasting blood glucose: 32weeks (Fed) and 34weeks (16hr/Fast)**; *p<0.05, p<0.01; Error bars: SEM Normal Chow (Zinc 87ppm); Fasting blood glucose: 32weeks (Fed) and 34weeks (16hr/Fast)**; *p<0.05, p<0.01; Error bars: SEM Normal Chow (Zinc 87ppm); Fasting blood glucose: 32weeks (Fed) and 34weeks (16hr/Fast)**; *p<0.05, p<0.01; Error bars: SEM Normal Chow (Zinc 87ppm); Fasting blood glucose: 32weeks (Fed) and 34weeks (16hr/Fast)**; *p<0.05, **p<0.01; Error bars: SEM Normal chow; Zinc 87ppm; oGTT (20wk) after 16hr fast – 2mg/g body weight;
*$p<0.05$, **$p<0.01$; Error bars: SEM Normal chow; Zinc 87ppm; oGTT (20wk) after 16hr fast – 2mg/g body weight; *p<0.05, **p<0.01; Error bars: SEM Hepatic ion quantification and Taqman analysis - 29 weeks; *p<0.05, **p<0.01; Error bars: SEM Hepatic ion quantification and Taqman analysis - 29 weeks; *p<0.05, **p<0.01; Error bars: SEM Hepatic ion quantification and Taqman analysis - 29 weeks; *p<0.05, **p<0.01; Error bars: SEM Hepatic ion quantification and Taqman analysis - 29 weeks; *$p<0.05$, **$p<0.01$; Error bars: SEM Hepatic ion quantification and Taqman analysis - 29 weeks; *p<0.05, **p<0.01; Error bars: SEM Hepatic ion quantification and Taqman analysis - 29 weeks; *p<0.05, **p<0.01; Error bars: SEM Liver lysates - 29 weeks; *p<0.05, **p<0.01; Error bars: SEM Liver lysates - 29 weeks; *p<0.05, **p<0.01; Error bars: SEM Liver lysates - 29 weeks; *p<0.05, **p<0.01; Error bars: SEM Liver lysates - 29 weeks; *p<0.05, **p<0.01; Error bars: SEM

US 12,083,141 B2

TREATMENT OF HYPERGLYCEMIA WITH SOLUTE CARRIER FAMILY 39 MEMBER 5 (SLC39A5) INHIBITORS

REFERENCE TO SEQUENCE LISTING

This application includes a Sequence Listing submitted electronically as a text file named 18923802301SEQ, created on Mar. 12, 2020, with a size of 136 kilobytes. The Sequence Listing is incorporated herein by reference.

FIELD

The present disclosure relates generally to the treatment of subjects having hyperglycemia with Solute Carrier Family 39 Member 5 (SLC39A5) inhibitors, methods of identifying subjects having an increased risk of developing hyperglycemia, and methods of detecting SLC39A5 variant nucleic acid molecules and variant polypeptides.

BACKGROUND

SLC39A5 belongs to the ZIP (Zrt and Irt-like proteins) superfamily of metal ion transporters. In mice, 14 members of this family have been identified, and almost all of these genes are conserved in humans. ZIP proteins have 8 predicted transmembrane domains (SLC39A5 has 6 transmembrane domains), containing an intracellular loop between transmembrane domains 3 and 4 and an extracellular amino terminus that is histidine-rich and may play a role in metal transport. This zinc transporter localizes to the baso-lateral cell membrane and is expressed in the small intestine, pancreas, kidney and the liver with similar expression pattern in mouse. SLC39A5 is abundant specifically in intestinal enterocytes, pancreatic acinar cells, and embryonic visceral endoderm cells. SLC39A5 regulation also appears to be unique in that this protein is internalized and degraded coordinately in each of these cell-types during periods of dietary zinc deficiency. Translation of the SLC39A5 mRNA is stalled during zinc deficiency in a mechanism which involves a conserved 3'-untranslated region that is predicted to form a stable stem-loop structure and to interact with specific microRNAs. SLC39A4 and SLC39A5 are co-expressed in several tissues with antagonistic functions in maintaining zinc homeostasis. SLC39A4 is thought to facilitate absorption of dietary zinc, whereas SLC39A5 may function in the removal of zinc from the body. Previous studies revealed a role for enterocyte SLC39A5 in zinc excretion, and a role for pancreatic acinar cell SLC39A5 in protection against zinc toxicity.

SUMMARY

The present disclosure also provides methods of treating a subject having decreased serum zinc level, the methods comprising administering a Solute Carrier Family 39 Member 5 (SLC39A5) inhibitor to the subject.

The present disclosure also provides methods of treating a subject having increased serum glucose level, the methods comprising administering an SLC39A5 inhibitor to the subject.

The present disclosure also provides methods of treating a subject having hyperglycemia, the methods comprising administering an SLC39A5 inhibitor to the subject.

The present disclosure also provides methods of treating a subject with a therapeutic agent that treats or inhibits decreased serum zinc level, increased serum glucose level, and/or hyperglycemia wherein the subject is suffering from decreased serum zinc level, increased serum glucose level, and/or hyperglycemia, the methods comprising the steps of: determining whether the subject has an SLC39A5 predicted loss-of-function variant nucleic acid molecule encoding a human SLC39A5 polypeptide by: obtaining or having obtained a biological sample from the subject; and performing or having performed a genotyping assay on the biological sample to determine if the subject has a genotype comprising the SLC39A5 predicted loss-of-function variant nucleic acid molecule; and when the subject is SLC39A5 reference, then administering or continuing to administer to the subject the therapeutic agent that treats or inhibits decreased serum zinc level, increased serum glucose level, and/or hyperglycemia in a standard dosage amount, and administering to the subject an SLC39A5 inhibitor; and when the subject is heterozygous for an SLC39A5 predicted loss-of-function variant, then administering or continuing to administer to the subject the therapeutic agent that treats or inhibits decreased serum zinc level, increased serum glucose level, and/or hyperglycemia in an amount that is the same as or lower than a standard dosage amount, and administering to the subject an SLC39A5 inhibitor; wherein the presence of a genotype having the SLC39A5 predicted loss-of-function variant nucleic acid molecule encoding the human SLC39A5 polypeptide indicates the subject has a reduced risk of developing decreased serum zinc level, increased serum glucose level, and/or hyperglycemia.

The present disclosure also provides methods of identifying a human subject having an increased risk for developing decreased serum zinc level, increased serum glucose level, and/or hyperglycemia, wherein the methods comprise: determining or having determined the presence or absence of an SLC39A5 predicted loss-of-function variant nucleic acid molecule encoding a human SLC39A5 polypeptide in a biological sample obtained from the subject; wherein: when the human subject is SLC39A5 reference, then the human subject has an increased risk for developing decreased serum zinc level, increased serum glucose level, and/or hyperglycemia; and when the human subject is heterozygous for an SLC39A5 predicted loss-of-function variant or homozygous for an SLC39A5 predicted loss-of-function variant, then the human subject has a decreased risk for developing decreased serum zinc level, increased serum glucose level, and/or hyperglycemia.

The present disclosure also provides methods of detecting a human SLC39A5 variant nucleic acid molecule in a human subject comprising assaying a sample obtained from the human subject to determine whether a nucleic acid molecule in the sample comprises a nucleotide sequence comprising: i) a cytosine at a position corresponding to position 5,604 according to SEQ ID NO:4, or the complement thereof; ii) a cytosine at a position corresponding to position 1,141 according to SEQ ID NO:11, or the complement thereof; iii) a cytosine at a position corresponding to position 1,141 according to SEQ ID NO:18, or the complement thereof; iv) a cytosine at a position corresponding to position 6,899 according to SEQ ID NO:6, or the complement thereof; v) a cytosine at a position corresponding to position 1,468 according to SEQ ID NO:13, or the complement thereof; vi) a cytosine at a position corresponding to position 1,468 according to SEQ ID NO:20, or the complement thereof; vii) an adenine or guanine at a position corresponding to position 1,353 according to SEQ ID NO:2 or SEQ ID NO:3, or the complement thereof; viii) an adenine or guanine at a position corresponding to position 371 according to SEQ ID NO:9 or SEQ ID NO:10, or the complement thereof; ix) an adenine or guanine at a position corresponding to position 371 according to SEQ ID NO:16 or SEQ ID NO:17, or the complement thereof; x) a thymine at a position corresponding to position 6,352 according to SEQ ID NO:5, or the complement thereof; xi) a uracil at a position corresponding to position 1,194 according to SEQ ID NO:12, or the complement thereof; xii) a thymine at a position corresponding to position 1,194 according to SEQ ID NO:19, or the complement thereof; xiii) a thymine at a position corresponding to position 5,624 according to SEQ ID NO:7, or the complement thereof; xiv) a uracil at a position corresponding to position 1,161 according to SEQ ID NO:14, or the complement thereof; or xv) a thymine at a position corresponding to position 1,161 according to SEQ ID NO:21, or the complement thereof.

The present disclosure also provides methods of detecting the presence of a human SLC39A5 variant polypeptide, comprising performing an assay on a sample obtained from a human subject to determine whether an SLC39A5 protein in the sample: i) comprises a threonine at a position corresponding to position 304 according to SEQ ID NO:24; ii) comprises a alanine at a position corresponding to position 413 according to SEQ ID NO:26; iii) is an SLC39A5 truncated variant polypeptide having an amino acid sequence consisting of SEQ ID NO:23; iv) is an SLC39A5 truncated variant polypeptide having an amino acid sequence consisting of SEQ ID NO:25; or v) is an SLC39A5 truncated variant polypeptide having an amino acid sequence consisting of SEQ ID NO:27.

The present disclosure also provides therapeutic agents that treat or inhibit decreased serum zinc level, increased serum glucose level, and/or hyperglycemia for use in the treatment of decreased serum zinc level, increased serum glucose level, and/or hyperglycemia in a human subject having: i) a genomic nucleic acid molecule having a nucleotide sequence encoding a human SLC39A5 polypeptide, wherein the nucleotide sequence comprises: a cytosine at a position corresponding to position 5,604 according to SEQ ID NO:4, or the complement thereof; a cytosine at a position corresponding to position 6,899 according to SEQ ID NO:6, or the complement thereof; an adenine or guanine at a position corresponding to position 1,353 according to SEQ ID NO:2 or SEQ ID NO:3, or the complement thereof; a thymine at a position corresponding to position 6,352 according to SEQ ID NO:5, or the complement thereof; or a thymine at a position corresponding to position 5,624 according to SEQ ID NO:7, or the complement thereof; ii) an mRNA molecule having a nucleotide sequence encoding a human SLC39A5 polypeptide, wherein the nucleotide sequence comprises: a cytosine at a position corresponding to position 1,141 according to SEQ ID NO:11, or the complement thereof; a cytosine at a position corresponding to position 1,468 according to SEQ ID NO:13, or the complement thereof; an adenine or guanine at a position corresponding to position 371 according to SEQ ID NO:9 or SEQ ID NO:10, or the complement thereof; a uracil at a position corresponding to position 1,194 according to SEQ ID NO:12, or the complement thereof; or a uracil at a position corresponding to position 1,161 according to SEQ ID NO:14, or the complement thereof; or iii) a cDNA molecule having a nucleotide sequence encoding a human SLC39A5 polypeptide, wherein the nucleotide sequence comprises: a cytosine at a position corresponding to position 1,141 according to SEQ ID NO:18, or the complement thereof; a cytosine at a position corresponding to position 1,468 according to SEQ ID NO:20, or the complement thereof; an adenine or guanine at a position corresponding to position 371 according to SEQ ID NO:16 or SEQ ID NO:17, or the complement thereof; a thymine at a position corresponding to position 1,194 according to SEQ ID NO:19, or the complement thereof; or a thymine at a position corresponding to position 1,161 according to SEQ ID NO:21, or the complement thereof.

The present disclosure also provides SLC39A5 inhibitors for use in the treatment of decreased serum zinc level, increased serum glucose level, and/or hyperglycemia in a human subject having: i) a genomic nucleic acid molecule having a nucleotide sequence encoding a human SLC39A5 polypeptide, wherein the nucleotide sequence comprises: a cytosine at a position corresponding to position 5,604 according to SEQ ID NO:4, or the complement thereof; a cytosine at a position corresponding to position 6,899 according to SEQ ID NO:6, or the complement thereof; an adenine or guanine at a position corresponding to position 1,353 according to SEQ ID NO:2 or SEQ ID NO:3, or the complement thereof; a thymine at a position corresponding to position 6,352 according to SEQ ID NO:5, or the complement thereof; or a thymine at a position corresponding to position 5,624 according to SEQ ID NO:7, or the complement thereof; ii) an mRNA molecule having a nucleotide sequence encoding a human SLC39A5 polypeptide, wherein the nucleotide sequence comprises: a cytosine at a position corresponding to position 1,141 according to SEQ ID NO:11, or the complement thereof; a cytosine at a position corresponding to position 1,468 according to SEQ ID NO:13, or the complement thereof; an adenine or guanine at a position corresponding to position 371 according to SEQ ID NO:9 or SEQ ID NO:10, or the complement thereof; a uracil at a position corresponding to position 1,194 according to SEQ ID NO:12, or the complement thereof; or a uracil at a position corresponding to position 1,161 according to SEQ ID NO:14, or the complement thereof; or iii) a cDNA molecule having a nucleotide sequence encoding a human SLC39A5 polypeptide, wherein the nucleotide sequence comprises: a cytosine at a position corresponding to position 1,141 according to SEQ ID NO:18, or the complement thereof; a cytosine at a position corresponding to position 1,468 according to SEQ ID NO:20, or the complement thereof; an adenine or guanine at a position corresponding to position 371 according to SEQ ID NO:16 or SEQ ID NO:17, or the complement thereof; a thymine at a position corresponding to position 1,194 according to SEQ ID NO:19, or the complement thereof; or a thymine at a position corresponding to position 1,161 according to SEQ ID NO:21, or the complement thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying figures, which are incorporated in and constitute a part of this specification, illustrate several aspects and together with the description serve to explain the principles of the present disclosure.

FIG. 24: male mice).

FIG. 31B, male). Loss of function of Slc39a5 results in increased hepatic zinc levels in leptin receptor deficient mice (both sexes) with concomitant activation of hepatic AMPK signaling. Hepatic triglyceride levels are reduced with an increase in hepatic beta-hydroxybutyrate levels suggesting increased β-oxidation. Moreover, loss of Slc39a5 results in a downregulation of Fasn indicative of reduced de novo lipogenesis.

DESCRIPTION

Figure 1A:
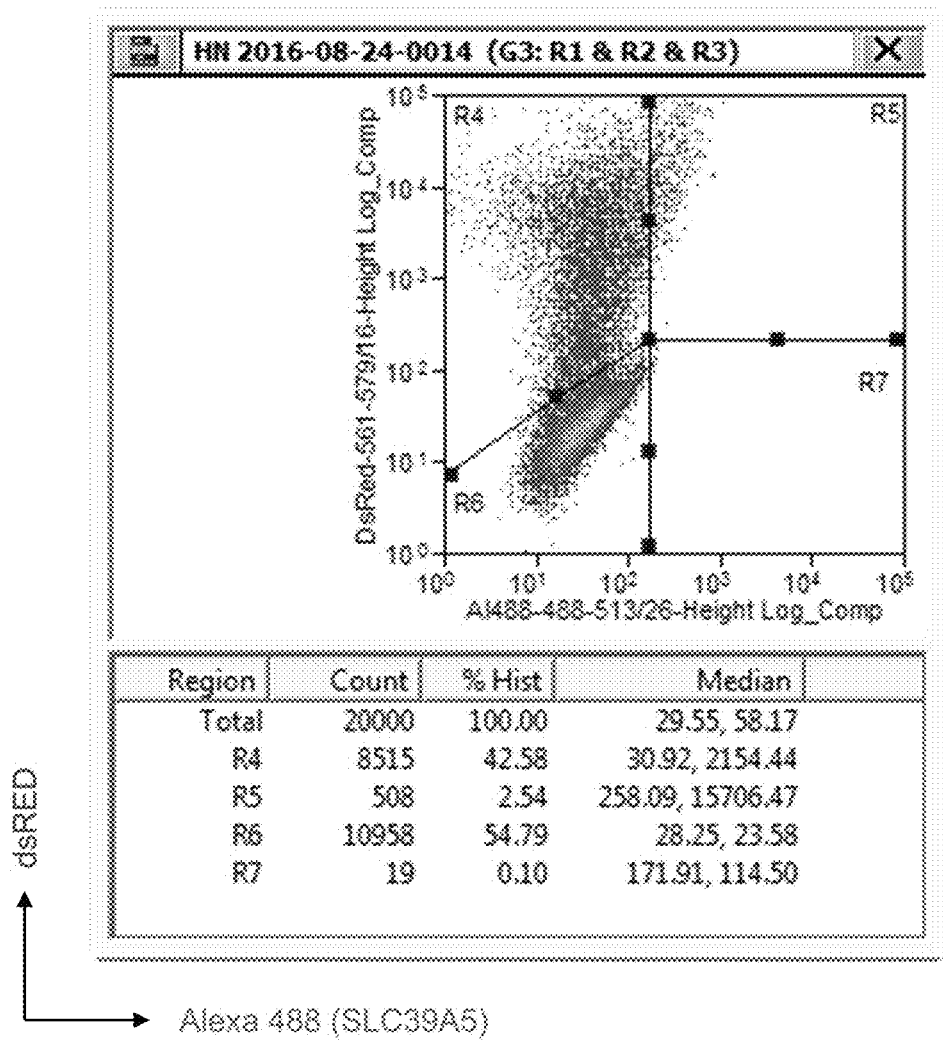
FIG. 1A shows SLC39A5 mutant expression in dsRED reporter system.
Figure 1A:
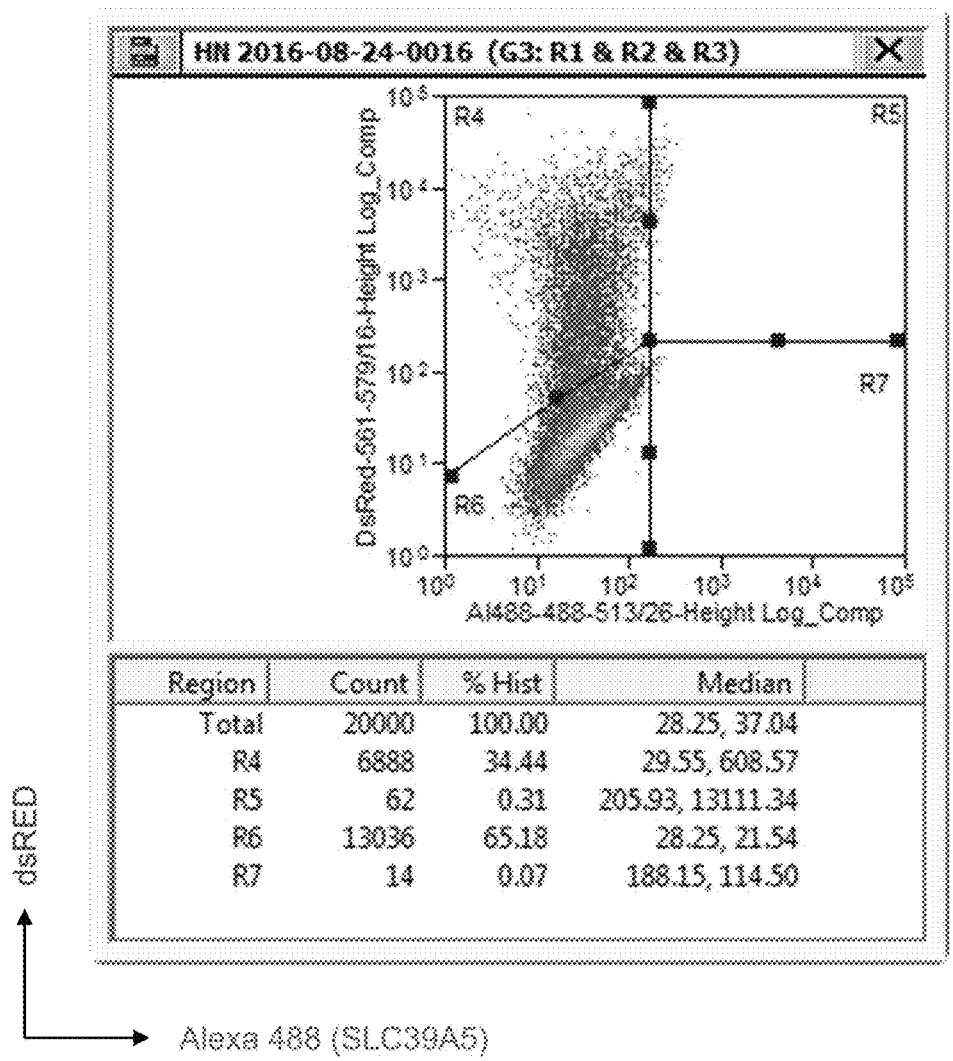
Figure 1A:
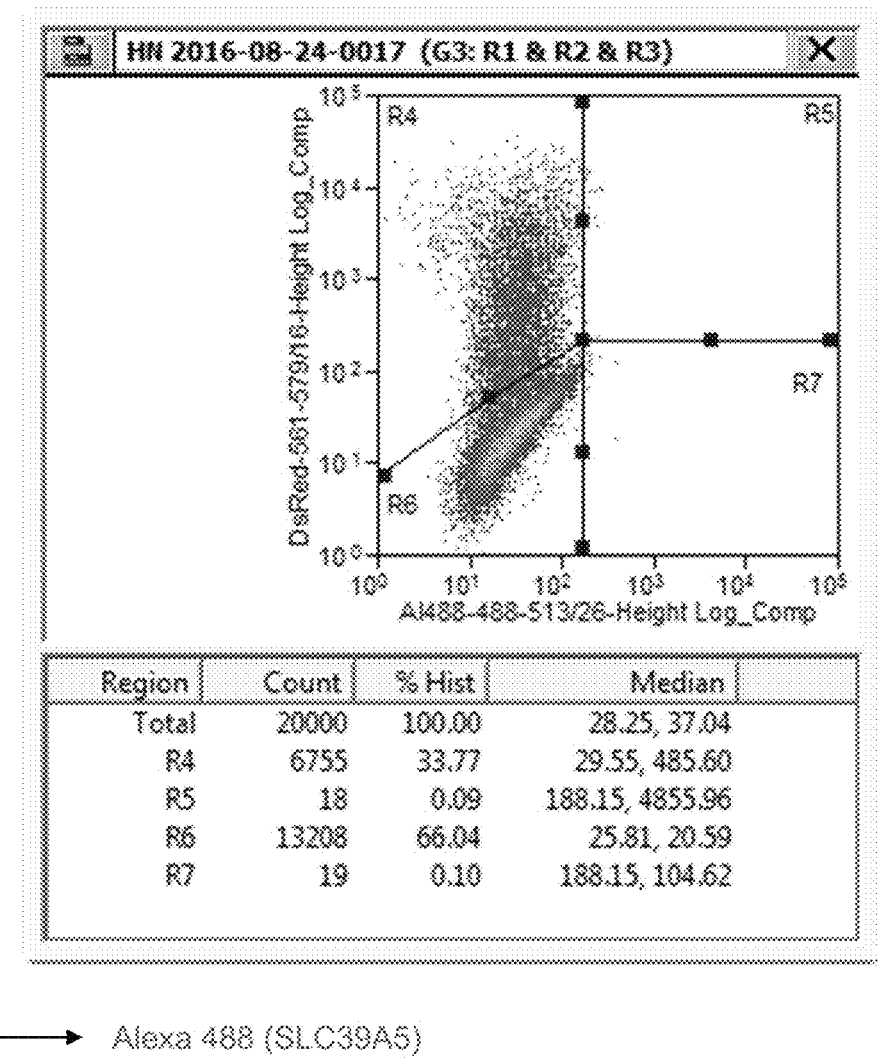
Figure 1A:
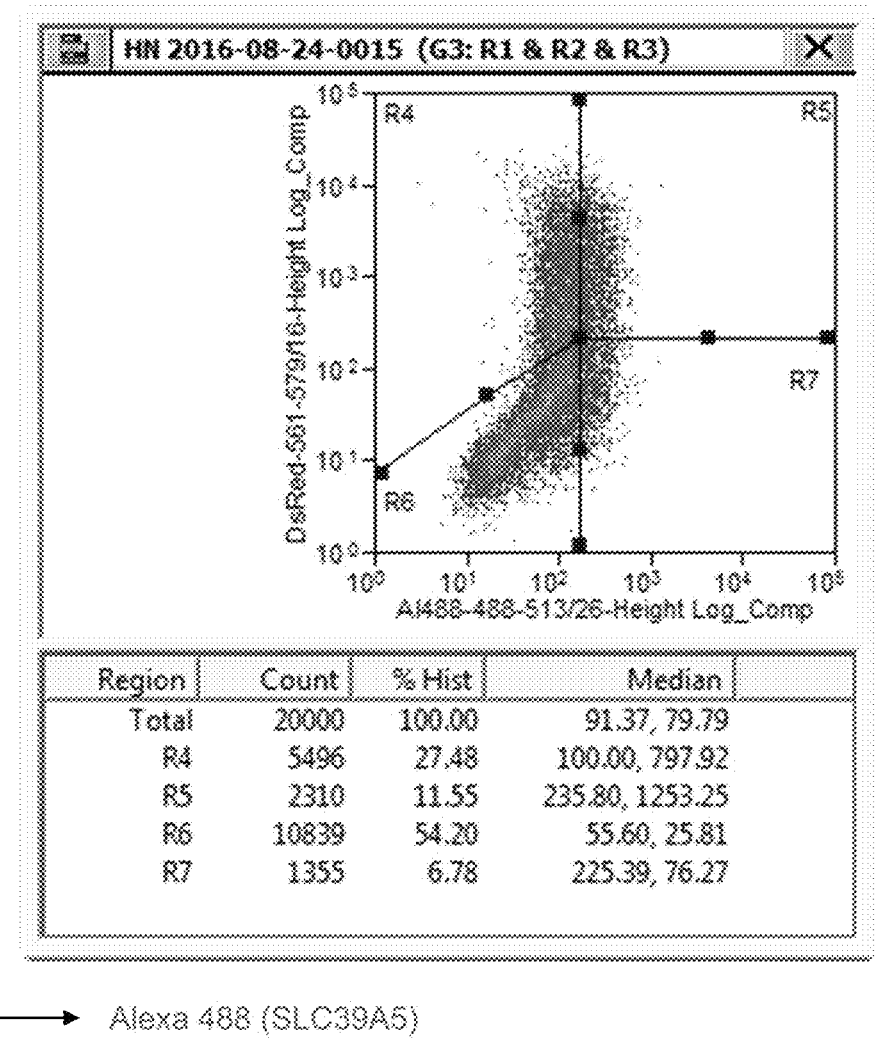

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human.

As used herein, a "nucleic acid," a "nucleic acid molecule," a "nucleic acid sequence," a "polynucleotide," or an "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "comprising" may be replaced with "consisting" or "consisting essentially of" in particular embodiments as desired.

A rare variant in the SLC39A5 gene associated with increased serum zinc levels and a decreased risk of developing increased serum glucose level and/or hyperglycemia, and improved liver function in human subjects has been identified in accordance with the present disclosure. For example, a genetic alteration that changes the thymine nucleotide of position 5,604 in the human SLC39A5 reference (see, SEQ ID NO:1) to cytosine, or the guanine nucleotide of position 6,899 in the human SLC39A5 reference (see, SEQ ID NO:1) to cytosine, or the cytosine nucleotide of position 1,353 in the human SLC39A5 reference (see, SEQ ID NO:1) to adenine or guanine, or the cytosine nucleotide of position 6,352 in the human SLC39A5 reference (see, SEQ ID NO:1) to thymine, or the cytosine nucleotide of position 5,624 in the human SLC39A5 reference (see, SEQ ID NO:1) to thymine, has been observed to indicate that the human having such an alteration may have increased serum zinc levels and a decreased risk of developing increased serum glucose level and/or hyperglycemia. It is believed that no variants of the SLC39A5 gene or protein have any known association with increased serum zinc levels and a decreased risk of developing increased serum glucose level and/or hyperglycemia. Altogether, the genetic analyses described herein surprisingly indicate that the SLC39A5 gene and, in particular, a variant in the SLC39A5 gene, associates with increased serum zinc levels and a decreased risk of developing increased serum glucose level and/or hyperglycemia. Therefore, human subjects that are SLC39A5 reference that have an increased risk of developing increased serum glucose level and/or hyperglycemia, may be treated such that the increased serum glucose level and/or hyperglycemia is prevented, the symptoms thereof are reduced, and/or development of symptoms is repressed. Accordingly, the present disclosure provides methods of leveraging the identification of such variants in subjects to identify or stratify risk in such subjects of developing increased serum glucose level and/or hyperglycemia, or to diagnose subjects as having an increased risk of developing increased serum glucose level and/or hyperglycemia, such that subjects at risk or subjects with active disease may be treated accordingly. Additionally, the present disclosure provides isolated SLC39A5 variant genomic nucleic acid molecules, variant mRNA molecules, and variant cDNA molecules. Accordingly, provided herein are SLC39A5 loss-of-function variant nucleic acid molecules discovered to be associated with increased serum zinc levels and a decreased risk of developing increased serum glucose level and/or hyperglycemia.

For purposes of the present disclosure, any particular human can be categorized as having one of three SLC39A5 genotypes: i) SLC39A5 reference; ii) heterozygous for an SLC39A5 predicted loss-of-function variant; or iii) homozygous for an SLC39A5 predicted loss-of-function variant. A human is SLC39A5 reference when the human does not have a copy of an SLC39A5 predicted loss-of-function variant nucleic acid molecule. A human is heterozygous for an SLC39A5 predicted loss-of-function variant when the human has a single copy of an SLC39A5 predicted loss-of-function variant nucleic acid molecule. An SLC39A5 predicted loss-of-function variant nucleic acid molecule is any SLC39A5 nucleic acid molecule (such as, a genomic nucleic acid molecule, an mRNA molecule, or a cDNA molecule) encoding an SLC39A5 polypeptide having a partial loss-of-function, a complete loss-of-function, a predicted partial loss-of-function, or a predicted complete loss-of-function. A human who has an SLC39A5 polypeptide having a partial loss-of-function (or predicted partial loss-of-function) is hypomorphic for SLC39A5. The SLC39A5 predicted loss-of-function variant nucleic acid molecule can be any nucleic acid molecule encoding SLC39A5 M304T, G413A, Y47Stop, R322Stop, or R311Stop. The SLC39A5 M304T and G413A are predicted partial loss-of-function variant nucleic acid molecules. In some embodiments, the SLC39A5 predicted loss-of-function variant nucleic acid molecule encodes SLC39A5 Y47Stop, R322Stop, or R311Stop. A human is homozygous for an SLC39A5 predicted loss-of-function variant when the human has two copies of any of the SLC39A5 predicted loss-of-function variant nucleic acid molecules.

For human subjects that are genotyped or determined to be SLC39A5 reference, such human subjects have an increased risk of developing increased serum glucose level and/or hyperglycemia. For human subjects that are genotyped or determined to be either SLC39A5 reference or heterozygous for an SLC39A5 predicted loss-of-function variant, such human subjects can be treated with an SLC39A5 inhibitor. In some embodiments, such human subjects can be treated with zinc. In some embodiments, such human subjects can be treated with a therapeutic agent that treats or inhibits increased serum glucose level and/or hyperglycemia. In some embodiments, the human subject is a female. In some embodiments, the human subject is a male.

The present disclosure provides methods of treating a subject having decreased serum zinc level, the methods comprising administering an SLC39A5 inhibitor to the subject.

The present disclosure provides methods of treating a subject having increased serum glucose level, the methods comprising administering an SLC39A5 inhibitor to the subject.

The present disclosure provides methods of treating a subject having hyperglycemia, the methods comprising administering an SLC39A5 inhibitor to the subject.

In some embodiments, the SLC39A5 inhibitor comprises an antibody, or an antigen-binding fragment thereof. In some embodiments, the antibody specifically binds to a protein comprising SEQ ID NO:22, or a fragment thereof. In some embodiments, the antibody specifically binds to a protein comprising SEQ ID NO:23, SEQ ID NO:25, or SEQ ID NO:27, or a fragment thereof. In some embodiments, the antibody specifically binds to a peptide comprising the amino acid sequence GPSGWGDQEESKAPDLHG (SEQ ID NO:67). In some embodiments, the antibody comprises a heavy chain comprising the amino acid sequence according to SEQ ID NO:58. In some embodiments, the heavy chain is encoded by a polynucleotide comprising the nucleotide sequence according to SEQ ID NO:57. In some embodiments, the antibody comprises a light chain comprising the amino acid sequence according to SEQ ID NO:60. In some embodiments, the light chain is encoded by a polynucleotide comprising the nucleotide sequence according to SEQ ID NO:59. In some embodiments, the antibody comprises a heavy chain comprising the amino acid sequence according to SEQ ID NO:58, and a light chain comprising the amino acid sequence according to SEQ ID NO:60. In some embodiments, the heavy chain of the antibody comprises one or more complementarity-determining regions (CDRs) selected from: FSLTGYAVN (SEQ ID NO:61), WLGVIWGDGRTDY (SEQ ID NO:62), and ARFGNSY-ALDY (SEQ ID NO:63). In some embodiments, the light chain of the antibody comprises one or more CDRs selected from: QSLLNSRTRKNYLA (SEQ ID NO:64), LLIY-WASTRES (SEQ ID NO:65), and KQSYNLH (SEQ ID NO:66). In some embodiments, the antibody fragment may comprise a single chain (scFv), diabodies, Fv, and (Fab % triabodies, Fc, Fab, CDR1, CDR2, CDR3, combinations of CDR's, variable regions, tetrabodies, bifunctional hybrid antibodies, framework regions, constant regions, and the like.

In some embodiments, the SLC39A5 inhibitor comprises an antisense molecule. Examples of antisense molecules include, but are not limited to, antisense nucleic acid molecules, small interfering RNAs (siRNAs), and short hairpin RNAs (shRNAs). Such antisense molecules can be designed to target any region of an SLC39A5 mRNA. In some embodiments, the antisense RNA, siRNA, or shRNA hybridizes to a sequence within an SLC39A5 genomic nucleic acid molecule or mRNA molecule and decreases expression of the SLC39A5 polypeptide in a cell in the subject. In some embodiments, the SLC39A5 inhibitor comprises an antisense RNA that hybridizes to an SLC39A5 genomic nucleic acid molecule or mRNA molecule and decreases expression of the SLC39A5 polypeptide in a cell in the subject. In some embodiments, the SLC39A5 inhibitor comprises an siRNA that hybridizes to an SLC39A5 genomic nucleic acid molecule or mRNA molecule and decreases expression of the SLC39A5 polypeptide in a cell in the subject. In some embodiments, the SLC39A5 inhibitor comprises an shRNA that hybridizes to an SLC39A5 genomic nucleic acid molecule or mRNA molecule and decreases expression of the SLC39A5 polypeptide in a cell in the subject.

In some embodiments, the SLC39A5 inhibitor comprises a nuclease agent that induces one or more nicks or double-strand breaks at a recognition sequence(s) or a DNA-binding protein that binds to a recognition sequence within an SLC39A5 genomic nucleic acid molecule. The recognition sequence can be located within a coding region of the SLC39A5 gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of the SLC39A5 gene. For example, the recognition sequence can be located from about 10, 20, 30, 40, 50, 100, 200, 300, 400, 500, or 1,000 nucleotides of the start codon. As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/ CRISPR-associated (Cas) systems. The length of the recognition sequence can vary, and includes, for example, recognition sequences that are about 30-36 bp for a zinc finger protein or ZFN pair (i.e., about 15-18 bp for each ZFN), about 36 bp for a TALE protein or TALEN, and about 20 bp for a CRISPR/Cas guide RNA.

In some embodiments, CRISPR/Cas systems can be used to modify an SLC39A5 genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of SLC39A5 nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in an SLC39A5 genomic nucleic acid molecule or it can be a nickase that creates a single-strand break in an SLC39A5 genomic nucleic acid molecule. Additional examples of Cas proteins include, but are not limited to, Cas1, Cas1B, Cast, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (Cas6), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of SLC39A5 genomic nucleic acid molecules can be generated by contacting a cell with a Cas protein and one or more gRNAs that hybridize to one or more gRNA recognition sequences within a target genomic locus in the SLC39A5 genomic nucleic acid molecule. For example, a gRNA recognition sequence can be located within a region of SEQ ID NO:1. The gRNA recognition sequence can also include or be proximate to a position corresponding to position i) 5,604, ii) 6,899, iii) 1,353, iv) 6,352, or v) 5,624 according to SEQ ID NO:1. For example, the gRNA recognition sequence can be located from about 1000, 500, 400, 300, 200, 100, 50, 45, 40, 35, 30, 25, 20, 15, 10, or 5 nucleotides of a position corresponding to position i) 5,604, ii) 6,899, iii) 1,353, iv) 6,352, or v) 5,624 according to SEQ ID NO:1. The gRNA recognition sequence can include or be proximate to the start codon of an SLC39A5 genomic nucleic acid molecule or the stop codon of an SLC39A5 genomic nucleic acid molecule. For example, the gRNA recognition sequence can be located from about 10, 20, 30, 40, 50, 100, 200, 300, 400, 500, or 1,000 nucleotides of the start codon or the stop codon.

The gRNA recognition sequences within a target genomic locus in an SLC39A5 genomic nucleic acid molecule are located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where "N" is any nucleobase followed by two guanine ("G") nucleobases. gRNAs can transport Cas9 to anywhere in the genome for gene editing, but no editing can occur at any site other than one at which Cas9 recognizes PAM. In addition, 5'-NGA-3' can be a highly efficient non-canonical PAM for human cells. Generally, the PAM is about 2-6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10, about 2 to about 5 base pairs, or three base pairs upstream or downstream of the PAM sequence. In some embodiments (such as when Cas9 from *S. pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within an SLC39A5 genomic nucleic acid molecule. An exemplary gRNA is a gRNA effective to direct a Cas enzyme to bind to or cleave an SLC39A5 genomic nucleic acid molecule, wherein the gRNA comprises a DNA-targeting segment that hybridizes to a gRNA recognition sequence within the SLC39A5 genomic nucleic acid molecule that includes or is proximate to a position corresponding to position i) 5,604, ii) 6,899, iii) 1,353, iv) 6,352, or v) 5,624 according to SEQ ID NO:1. For example, a gRNA can be selected such that it hybridizes to a gRNA recognition sequence that is located from about 5, 10, 15, 20, 25, 30, 35, 40, 45, 50, 100, 200, 300, 400, 500, or 1,000 nucleotides of a position corresponding to position i) 5,604, ii) 6,899, iii) 1,353, iv) 6,352, or v) 5,624 according to SEQ ID NO:1. Other exemplary gRNAs comprise a DNA-targeting segment that hybridizes to a gRNA recognition sequence within an SLC39A5 genomic nucleic acid molecule that includes or is proximate to the start codon or the stop codon. For example, a gRNA can be selected such that it hybridizes to a gRNA recognition sequence that is located from about 5, 10, 15, 20, 25, 30, 35, 40, 45, 50, 100, 200, 300, 400, 500, or 1,000 nucleotides of the start codon or located from about 5, 10, 15, 20, 25, 30, 35, 40, 45, 50, 100, 200, 300, 400, 500, or 1,000 nucleotides of the start codon or stop codon. The design and synthesis of gRNAs are described in, for example, Mali et al., Science, 2013, 339, 823-826; Jinek et al., Science, 2012, 337, 816-821; Hwang et al., Nat. Biotechnol., 2013, 31, 227-229; Jiang et al., Nat. Biotechnol., 2013, 31, 233-239; and Cong et al., Science, 2013, 339, 819-823. Suitable gRNAs can comprise from about 17 to about 23 nucleotides, from about 18 to about 22 nucleotides, or from about 19 to about 21 nucleotides. In some embodiments, the gRNAs can comprise 20 nucleotides.

Examples of suitable gRNA recognition sequences located within the human SLC39A5 reference gene are set forth in Table 1 as SEQ ID NOS:28-56.

TABLE 1

Guide RNA Recognition Sequences Near SLC39A5 Variation

| Strand | Guide RNA Recognition Sequence | SEQ ID NO: |
|---|---|---|
| + | CGCAACTTGGATCCGGAGAATGG | 28 |
| + | GAATCTCGAAACACGCAACTTGG | 29 |
| + | CGAAACACGCAACTTGGATCCGG | 30 |
| + | TGGATCCGGAGAATGGCAGTGGG | 31 |
| + | AGGCAGCTCCAGGTGACTAGAGG | 32 |
| + | GATGGCCCTTCAGCCCCTACAGG | 33 |
| − | AAATAGGAGGGCATCCCTCCTGG | 34 |
| + | TTGGATCCGGAGAATGGCAGTGG | 35 |
| − | GTCACCTGGAGCTGCCTGTAGGG | 36 |
| − | AATTTCTCCTCTAGTCACCTGG | 37 |
| − | TCACCTGGAGCTGCCTGTAGGGG | 38 |
| + | TCCTATTTCAGAGATGCTGCAGG | 39 |
| − | TGCAGCATCTCTGAAATAGGAGG | 40 |
| + | GTGTTCATCTTCCCAGCTTGTGG | 41 |
| − | TGAACACCTGGTTCCACCTCTGG | 42 |
| + | CATCTTCCCAGCTTGTGGCCTGG | 43 |
| − | TAGGAGGGCATCCCTCCTGGTGG | 44 |
| + | GATGCTGCAGGCGAAAATGAAGG | 45 |
| − | AAGCTGGGAAGATGAACACCTGG | 46 |
| − | GCAGCATCTCTGAAATAGGAGGG | 47 |
| − | CAGCAGAGCCAGGGACTAAGGGG | 48 |
| − | GCCTGCAGCATCTCTGAAATAGG | 49 |
| − | GCCATCCCACTGCCATTCTCCGG | 50 |
| − | GGGAAGCCAGGCCACAAGCTGGG | 51 |
| − | AGCTGCCTGTAGGGGCTGAAGGG | 52 |

TABLE 1-continued

Guide RNA Recognition Sequences Near SLC39A5 Variation

| Strand | Guide RNA Recognition Sequence | SEQ ID NO: |
|---|---|---|
| − | GGGGAAGCCAGGCCACAAGCTGG | 53 |
| − | AGTCACCTGGAGCTGCCTGTAGG | 54 |
| − | GCAGCAGAGCCAGGGACTAAGGG | 55 |
| + | CCTGGCTTTCCCTTAGTCCCTGG | 56 |

The Cas protein and the gRNA form a complex, and the Cas protein cleaves the target SLC39A5 genomic nucleic acid molecule. The Cas protein can cleave the nucleic acid molecule at a site within or outside of the nucleic acid sequence present in the target SLC39A5 genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the SLC39A5 genomic nucleic acid molecule to which a DNA-targeting segment of a gRNA will bind.

Such methods can result, for example, in an SLC39A5 genomic nucleic acid molecule in which a region of SEQ ID NO:1 is disrupted, the start codon is disrupted, the stop codon is disrupted, or the coding sequence is disrupted or deleted. Optionally, the cell can be further contacted with one or more additional gRNAs that hybridize to additional gRNA recognition sequences within the target genomic locus in the SLC39A5 genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, the treatment methods further comprise detecting the presence or absence of an SLC39A5 predicted loss-of-function variant nucleic acid molecule encoding a human SLC39A5 polypeptide in a biological sample from the subject. As used throughout the present disclosure a "SLC39A5 predicted loss-of-function variant nucleic acid molecule" is any SLC39A5 nucleic acid molecule (such as, for example, genomic nucleic acid molecule, mRNA molecule, or cDNA molecule) encoding an SLC39A5 polypeptide having a partial loss-of-function, a complete loss-of-function, a predicted partial loss-of-function, or a predicted complete loss-of-function.

The present disclosure also provides methods of treating a subject with a therapeutic agent that treats or inhibits increased serum glucose level and/or hyperglycemia, wherein the subject is suffering from increased serum glucose level and/or hyperglycemia, the method comprising the steps of: determining whether the subject has an SLC39A5 predicted loss-of-function variant nucleic acid molecule encoding a human SLC39A5 polypeptide by: obtaining or having obtained a biological sample from the subject; and performing or having performed a genotyping assay on the biological sample to determine if the subject has a genotype comprising the SLC39A5 predicted loss-of-function variant nucleic acid molecule; and when the subject is SLC39A5 reference, then administering or continuing to administer to the subject the therapeutic agent that treats or inhibits increased serum glucose level and/or hyperglycemia in a standard dosage amount, and administering to the subject an SLC39A5 inhibitor; and when the subject is heterozygous for an SLC39A5 predicted loss-of-function variant, then administering or continuing to administer to the subject the therapeutic agent that treats or inhibits increased serum glucose level and/or hyperglycemia in an amount that is the same as or lower than a standard dosage amount, and administering to the subject an SLC39A5 inhibitor; wherein the presence of a genotype having the SLC39A5 predicted loss-of-function variant nucleic acid molecule encoding the human SLC39A5 polypeptide indicates the subject has a reduced risk of developing increased serum glucose level and/or hyperglycemia. In some embodiments, the subject is SLC39A5 reference. In some embodiments, the subject is heterozygous for an SLC39A5 predicted loss-of-function variant.

For human subjects that are genotyped or determined to be either SLC39A5 reference or heterozygous for an SLC39A5 predicted loss-of-function variant, such human subjects can be treated with an SLC39A5 inhibitor, as described herein.

In any of the embodiments described herein, the SLC39A5 predicted loss-of-function variant nucleic acid molecule can be any SLC39A5 nucleic acid molecule (such as, for example, genomic nucleic acid molecule, mRNA molecule, or cDNA molecule) encoding an SLC39A5 polypeptide having a partial loss-of-function, a complete loss-of-function, a predicted partial loss-of-function, or a predicted complete loss-of-function. For example, the SLC39A5 predicted loss-of-function variant nucleic acid molecule can be any nucleic acid molecule encoding any of the SLC39A5 polypeptides described herein including, for example, SLC39A5 M304T, G413A, Y47Stop, R322Stop, or R311Stop.

In any of the embodiments described herein, the SLC39A5 predicted loss-of-function variant nucleic acid molecule can also be any SLC39A5 nucleic acid molecule (such as, for example, genomic nucleic acid molecule, mRNA molecule, or cDNA molecule) that comprises: i) a point mutation in an exon of a reference SLC39A5 gene; ii) a deletion, in whole or in part, of the coding sequence of a reference SLC39A5 gene, such as, for example, a deletion that comprises exon 1, in whole or in part, and/or exon 2, in whole or in part. In some embodiments, the deletion comprises a coding portion of exon 1 and a portion of exon 2 of a reference SLC39A5 gene. In some embodiments, the deletion comprises a nucleic acid sequence from the nucleotide after the ATG start codon in exon 1 through the fifth nucleotide before the 3' end of exon 2 of a reference SLC39A5 gene.

Detecting the presence or absence of an SLC39A5 predicted loss-of-function variant nucleic acid molecule in a biological sample from a subject and/or determining whether a subject has an SLC39A5 predicted loss-of-function variant nucleic acid molecule can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the human subject.

In some embodiments, when the subject is SLC39A5 reference, the subject is also administered a therapeutic agent that treats or inhibits increased serum glucose level and/or hyperglycemia in a standard dosage amount. In some embodiments, when the subject is heterozygous for an SLC39A5 predicted loss-of-function variant, the subject is also administered a therapeutic agent that treats or inhibits increased serum glucose level and/or hyperglycemia in a dosage amount that is the same as or lower than the standard dosage amount.

In some embodiments, the treatment methods further comprise detecting the presence or absence of an SLC39A5 predicted loss-of-function polypeptide in a biological sample from the subject. In some embodiments, when the subject does not have an SLC39A5 predicted loss-of-function polypeptide, the subject is also administered a therapeutic agent that treats or inhibits increased serum glucose level and/or hyperglycemia in a standard dosage amount. In some embodiments, when the subject has an SLC39A5 predicted loss-of-function polypeptide, the subject is also administered a therapeutic agent that treats or inhibits increased serum glucose level and/or hyperglycemia in a dosage amount that is the same as or lower than the standard dosage amount.

The present disclosure also provides methods of treating a subject with a therapeutic agent that treats or inhibits increased serum glucose level and/or hyperglycemia, wherein the subject is suffering from increased serum glucose level and/or hyperglycemia, the method comprising the steps of: determining whether the subject has an SLC39A5 predicted loss-of-function polypeptide by: obtaining or having obtained a biological sample from the subject; and performing or having performed an assay on the biological sample to determine if the subject has an SLC39A5 predicted loss-of-function polypeptide; and when the subject does not have an SLC39A5 predicted loss-of-function polypeptide, then administering or continuing to administer to the subject the therapeutic agent that treats or inhibits increased serum glucose level and/or hyperglycemia in a standard dosage amount, and administering to the subject an SLC39A5 inhibitor; and when the subject has an SLC39A5 predicted loss-of-function polypeptide, then administering or continuing to administer to the subject the therapeutic agent that treats or inhibits increased serum glucose level and/or hyperglycemia in an amount that is the same as or lower than a standard dosage amount, and administering to the subject an SLC39A5 inhibitor; wherein the presence of an SLC39A5 predicted loss-of-function polypeptide indicates the subject has a reduced risk of developing increased serum glucose level and/or hyperglycemia. In some embodiments, the subject has an SLC39A5 predicted loss-of-function polypeptide. In some embodiments, the subject does not have an SLC39A5 predicted loss-of-function polypeptide.

In any of the embodiments described herein, the SLC39A5 predicted loss-of-function polypeptide can be any SLC39A5 polypeptide having a partial loss-of-function, a complete loss-of-function, a predicted partial loss-of-function, or a predicted complete loss-of-function. In any of the embodiments described herein, the SLC39A5 predicted loss-of-function polypeptide can be any of the SLC39A5 polypeptides described herein including, for example, SLC39A5 M304T, G413A, Y47Stop, R322Stop, or R311Stop. In some embodiments, the SLC39A5 polypeptide is SLC39A5 Y47Stop, R322Stop, or R311Stop.

Detecting the presence or absence of an SLC39A5 predicted loss-of-function polypeptide in a biological sample from a subject and/or determining whether a subject has an SLC39A5 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell obtained from the human subject.

In any of the embodiments described herein, the subject may have decreased serum zinc level or decreased bone zinc level, or both. In any of the embodiments described herein, the subject may have any one or more of the following: increased serum glucose level, hyperglycemia, Type 2 diabetes, steroid-induced diabetes, increased low density lipoprotein (LDL), and decreased high density lipoprotein (HDL). In any of the embodiments described herein, the subject may have increased serum glucose level and may be treated by the methods described herein. In any of the embodiments described herein, the subject may have hyperglycemia and may be treated by the methods described herein. In any of the embodiments described herein, the subject may have steroid-induced diabetes and may be treated by the methods described herein. In any of the embodiments described herein, the subject may have increased LDL and may be treated by the methods described herein. In any of the embodiments described herein, the subject may have decreased HDL and may be treated by the methods described herein. In any of the embodiments described herein, the subject may have Type 2 diabetes and may be treated by the methods described herein. In any of the embodiments described herein, the subject may have any one or more of increased serum glucose level, hyperglycemia, Type 2 diabetes, steroid-induced diabetes, increased LDL, and decreased HDL, with or without concomitant liver dysfunction. Liver dysfunction includes any one or more of the following: fatty liver disease (including alcoholic fatty liver disease (AFLD) and non-alcoholic fatty liver disease (NAFLD)), steatohepatitis, hepatic encephalopathy, liver fibrosis, increased liver enzymes (including alanine transaminase (ALT) and aspartate transaminase (AST)), and iron overload diseases such as hemochromatosis. In any of the embodiments described herein, the subject may have any one or more of increased serum glucose level, hyperglycemia, Type 2 diabetes, steroid-induced diabetes, increased LDL, and decreased HDL, with or without decreased serum zinc level or decreased bone zinc level, or both.

Examples of therapeutic agents that treat or inhibit increased serum glucose level and/or hyperglycemia include, but are not limited to: a statin, a PPAR agonist, a hormone, a sulfonylurea-based agent, a biguanide, an α-glucosidase inhibitor, and a GLP-1 agonist.

Statins include, but are not limited to: atorvastatin, pravastatin, fluvastatin, lovastatin, simvastatin, and cerivastatin.

PPAR agonists include thiazolidinediones and fibrates. Thiazolidinediones include, but are not limited to: 5-((4-(2-(methyl-2-pyridinylamino)ethoxy)phenyl)methyl)-2,4-thiazolidinedione, troglitazone, pioglitazone, ciglitazone, WAY-120,744, englitazone, AD 5075, darglitazone, and rosiglitazone. Fibrates include, but are not limited to: gemfibrozil, fenofibrate, clofibrate, or ciprofibrate.

Hormones include, but are not limited to: thyroid hormone, estrogen, and insulin. Suitable insulins include, but are not limited to: injectable insulin, transdermal insulin, inhaled insulin, or any combination thereof. As an alternative to insulin, an insulin derivative, secretagogue, sensitizer or mimetic may be used. Insulin secretagogues include, but are not limited to: forskolin, dibutryl cAMP or isobutylmethylxanthine (IBMX).

Sulfonylurea-based agents include, but are not limited to: glisoxepid, glyburide, acetohexamide, chlorpropamide, glibornuride, tolbutamide, tolazamide, glipizide, gliclazide, gliquidone, glyhexamide, phenbutamide, and tolcyclamide.

Biguanides include, but are not limited to: metformin, phenformin, and buformin.

α-glucosidase inhibitors include, but are not limited to: acarbose and miglitol.

GLP-1 agonists include, but are not limited to: VICTOZA® or SAXENDA® (liraglutide), BYETTA® or BYDUREON® (exenatide), LYXUMIA® (lixisenatide), TANZEUM® (albiglutide), TRULICITY® (dulaglutide), and OZEMPIC® (semaglutide).

In some embodiments, the dose of the therapeutic agents that treat or inhibit increased serum glucose level and/or hyperglycemia can be reduced by about 10%, by about 20%, by about 30%, by about 40%, by about 50%, by about 60%, by about 70%, by about 80%, or by about 90% for subjects that are heterozygous for an SLC39A5 predicted loss-of-function variant (i.e., a lower than the standard dosage amount) compared to subjects that are SLC39A5 reference (who may receive a standard dosage amount). In some embodiments, the dose of the therapeutic agents that treat or inhibit increased serum glucose level and/or hyperglycemia can be reduced by about 10%, by about 20%, by about 30%, by about 40%, or by about 50%. In addition, the dose of therapeutic agents that treat or inhibit increased serum glucose level and/or hyperglycemia in subjects that are heterozygous for an SLC39A5 predicted loss-of-function variant can be administered less frequently compared to subjects that are SLC39A5 reference.

Administration of the therapeutic agents that treat or inhibit increased serum glucose level and/or hyperglycemia and/or SLC39A5 inhibitors can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the therapeutic agents that treat or inhibit increased serum glucose level and/or hyperglycemia and/or SLC39A5 inhibitors can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

In any of the embodiments described herein, the human subject can be administered zinc. Zinc can be administered orally as a zinc salt such as, for example, zinc sulfate or zinc gluconate. Zinc can be administered in an amount from about 5 to about 100 mg/day, from about 5 to about 80 mg/day, from about 5 to about 60 mg/day, from about 5 to about 50 mg/day, from about 5 to about 40 mg/day, from about 5 to about 25 mg/day, from about 5 to about 15 mg/day, from about 10 to about 100 mg/day, from about 15 to about 100 mg/day, from about 20 to about 100 mg/day, from about 25 to about 100 mg/day, from about 10 to about 50 mg/day, from about 15 to about 40 mg/day, or from about 20 to about 30 mg/day.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in increased serum glucose level and/or hyperglycemia, a decrease/reduction in the severity of increased serum glucose level and/or hyperglycemia (such as, for example, a reduction or inhibition of development of increased serum glucose level and/or hyperglycemia), a decrease/reduction in symptoms and increased serum glucose level- and/or hyperglycemia-related effects, delaying the onset of symptoms and increased serum glucose level- and/or hyperglycemia-related effects, reducing the severity of symptoms of increased serum glucose level- and/or hyperglycemia-related effects, reducing the severity of an acute episode, reducing the number of symptoms and increased serum glucose level- and/or hyperglycemia-related effects, reducing the latency of symptoms and increased serum glucose level- and/or hyperglycemia-related effects, an amelioration of symptoms and increased serum glucose level- and/or hyperglycemia-related effects, reducing secondary symptoms, reducing secondary infections, preventing relapse to increased serum glucose level and/or hyperglycemia, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of increased serum glucose level and/or hyperglycemia development/progression (such as, for example, a complete or partial avoidance/inhibition or a delay), and an increased survival time of the affected host animal, following administration of a therapeutic protocol. Treatment of increased serum glucose level and/or hyperglycemia encompasses the treatment of subjects already diagnosed as having any form of increased serum glucose level and/or hyperglycemia at any clinical stage or manifestation, the delay of the onset or evolution or aggravation or deterioration of the symptoms or signs of increased serum glucose level and/or hyperglycemia, and/or preventing and/or reducing the severity of increased serum glucose level and/or hyperglycemia.

The present disclosure also provides methods of identifying a human subject having an increased risk for developing increased serum glucose level and/or hyperglycemia, wherein the method comprises: determining or having determined in a biological sample obtained from the subject the presence or absence of an SLC39A5 predicted loss-of-function variant nucleic acid molecule (such as a genomic nucleic acid molecule, mRNA molecule, and/or cDNA molecule) encoding a human SLC39A5 polypeptide; wherein: i) when the human subject lacks an SLC39A5 predicted loss-of-function variant nucleic acid molecule (i.e., the human subject is genotypically categorized as an SLC39A5 reference), then the human subject has an increased risk for developing increased serum glucose level and/or hyperglycemia; and ii) when the human subject has an SLC39A5 predicted loss-of-function variant nucleic acid molecule (i.e., the human subject is categorized as heterozygous for an SLC39A5 predicted loss-of-function variant or homozygous for an SLC39A5 predicted loss-of-function variant), then the human subject has a decreased risk for developing increased serum glucose level and/or hyperglycemia. Having a single copy of an SLC39A5 predicted loss-of-function variant nucleic acid molecule may be more protective of a human subject from developing increased serum glucose level and/or hyperglycemia than having no copies of an SLC39A5 predicted loss-of-function variant nucleic acid molecule.

Without intending to be limited to any particular theory or mechanism of action, it is believed that a single copy of an SLC39A5 predicted loss-of-function variant nucleic acid molecule (i.e., heterozygous for an SLC39A5 predicted loss-of-function variant) is protective of a human subject from developing increased serum glucose level and/or hyperglycemia, and it is also believed that having two copies of an SLC39A5 predicted loss-of-function variant nucleic acid molecule (i.e., homozygous for an SLC39A5 predicted loss-of-function variant) may be more protective of a human subject from developing increased serum glucose level and/or hyperglycemia iency, relative to a human subject with a single copy. Thus, in some embodiments, a single copy of an SLC39A5 predicted loss-of-function variant nucleic acid molecule may not be completely protective, but instead, may be partially or incompletely protective of a human subject from developing increased serum glucose level and/or hyperglycemia. While not desiring to be bound by any particular theory, there may be additional factors or molecules involved in the development of increased serum glucose level and/or hyperglycemia that are still present in a human subject having a single copy of an SLC39A5 predicted loss-of-function variant nucleic acid molecule, thus resulting in less than complete protection from the development of increased serum glucose level and/or hyperglycemia.

In any of the embodiments described herein, the SLC39A5 predicted loss-of-function variant nucleic acid molecule can be any SLC39A5 nucleic acid molecule (such as, for example, genomic nucleic acid molecule, mRNA molecule, or cDNA molecule) encoding an SLC39A5 polypeptide having a partial loss-of-function, a complete loss-of-function, a predicted partial loss-of-function, or a predicted complete loss-of-function. For example, the SLC39A5 predicted loss-of-function variant nucleic acid molecule can be any nucleic acid molecule encoding SLC39A5 M304T, G413A, Y47Stop, R322Stop, or R311Stop. In some embodiments, the SLC39A5 predicted loss-of-function variant nucleic acid molecule encodes SLC39A5 Y47Stop, R322Stop, or R311Stop.

Determining whether a human subject has an SLC39A5 predicted loss-of-function variant nucleic acid molecule in a biological sample can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the human subject.

In any of the embodiments described herein, the subject may have decreased serum zinc level or decreased bone zinc level, or both. In any of the embodiments described herein, the subject may have any one or more of the following: increased serum glucose level, hyperglycemia, Type 2 diabetes, steroid-induced diabetes, increased low density lipoprotein (LDL), and decreased high density lipoprotein (HDL). In any of the embodiments described herein, the subject may have increased serum glucose level and may be treated by the methods described herein. In any of the embodiments described herein, the subject may have hyperglycemia and may be treated by the methods described herein. In any of the embodiments described herein, the subject may have steroid-induced diabetes and may be treated by the methods described herein. In any of the embodiments described herein, the subject may have increased LDL and may be treated by the methods described herein. In any of the embodiments described herein, the subject may have decreased HDL and may be treated by the methods described herein. In any of the embodiments described herein, the subject may have Type 2 diabetes and may be treated by the methods described herein. In any of the embodiments described herein, the subject may have any one or more of increased serum glucose level, hyperglycemia, Type 2 diabetes, steroid-induced diabetes, increased LDL, and decreased HDL, with or without concomitant liver dysfunction. Liver dysfunction includes any one or more of the following: fatty liver disease (including alcoholic fatty liver disease (AFLD) and non-alcoholic fatty liver disease (NAFLD)), steatohepatitis, hepatic encephalopathy, liver fibrosis, increased liver enzymes (including alanine transaminase (ALT) and aspartate transaminase (AST)), and iron overload diseases such as hemochromatosis. In any of the embodiments described herein, the subject may have any one or more of increased serum glucose level, hyperglycemia, Type 2 diabetes, steroid-induced diabetes, increased LDL, and decreased HDL, with or without decreased serum zinc level or decreased bone zinc level, or both.

In some embodiments, when a human subject is identified as having an increased risk of developing increased serum glucose level and/or hyperglycemia, the human subject is further treated with a therapeutic agent that treats or inhibits increased serum glucose level and/or hyperglycemia and/or an SLC39A5 inhibitor, as described herein. For example, when the human subject is SLC39A5 reference, and therefore has an increased risk for developing increased serum glucose level and/or hyperglycemia, the human subject is administered an SLC39A5 inhibitor. In some embodiments, such a subject is also administered a therapeutic agent that treats or inhibits increased serum glucose level and/or hyperglycemia. In some embodiments, when the subject is heterozygous for an SLC39A5 predicted loss-of-function variant, the subject is administered the therapeutic agent that treats or inhibits increased serum glucose level and/or hyperglycemia in a dosage amount that is the same as or lower than the standard dosage amount, and is also administered an SLC39A5 inhibitor. In some embodiments, the subject is SLC39A5 reference. In some embodiments, the subject is heterozygous for an SLC39A5 predicted loss-of-function variant.

The present disclosure also provides methods of detecting the presence of an SLC39A5 predicted loss-of-function variant genomic nucleic acid molecule, an SLC39A5 predicted loss-of-function variant mRNA molecule, and/or an SLC39A5 predicted loss-of-function variant cDNA molecule in a biological sample from a subject human. It is understood that gene sequences within a population and mRNA molecules encoded by such genes can vary due to polymorphisms such as single-nucleotide polymorphisms. The sequences provided herein for the SLC39A5 variant genomic nucleic acid molecule, SLC39A5 variant mRNA molecule, and SLC39A5 variant cDNA molecule are only exemplary sequences. Other sequences for the SLC39A5 variant genomic nucleic acid molecule, variant mRNA molecule, and variant cDNA molecule are also possible.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting any SLC39A5 variant nucleic acid molecule, preliminary processing designed to isolate or enrich the sample for the genomic DNA can be employed. A variety of known techniques may be used for this purpose. When detecting the level of any SLC39A5 variant mRNA, different techniques can be used enrich the biological sample with mRNA. Various methods to detect the presence or level of a mRNA or the presence of a particular variant genomic DNA locus can be used.

In some embodiments, detecting a human SLC39A5 predicted loss-of-function variant nucleic acid molecule in a human subject comprises assaying or genotyping a biological sample obtained from the human subject to determine whether an SLC39A5 genomic nucleic acid molecule, an SLC39A5 mRNA molecule, or an SLC39A5 cDNA molecule in the biological sample comprises one or more variations that cause a loss-of-function (partial or complete) or are predicted to cause a loss-of-function (partial or complete).

In some embodiments, the methods of detecting the presence or absence of an SLC39A5 predicted loss-of-function variant nucleic acid molecule (such as, for example, a genomic nucleic acid molecule, an mRNA molecule, and/or a cDNA molecule) in a human subject, comprise: performing an assay on a biological sample obtained from the human subject, which assay determines whether a nucleic acid molecule in the biological sample comprises a particular nucleotide sequence. In some embodiments, the nucleotide sequence comprises: i) a cytosine at a position corresponding to position 5,604 according to SEQ ID NO:4 (for genomic nucleic acid molecules); ii) a cytosine at a position corresponding to position 1,141 according to SEQ ID NO:11 (for mRNA molecules); or iii) a cytosine at a position corresponding to position 1,141 according to SEQ ID NO:18 (for cDNA molecules obtained from mRNA molecules).

In some embodiments, the nucleotide sequence comprises: i) a cytosine at a position corresponding to position 6,899 according to SEQ ID NO:6 (for genomic nucleic acid molecules); ii) a cytosine at a position corresponding to position 1,468 according to SEQ ID NO:13 (for mRNA molecules); or iii) a cytosine at a position corresponding to position 1,468 according to SEQ ID NO:20 (for cDNA molecules obtained from mRNA molecules).

In some embodiments, the nucleotide sequence comprises: i) an adenine or guanine at a position corresponding to position 1,353 according to SEQ ID NO:2 or SEQ ID NO:3 (for genomic nucleic acid molecules); ii) an adenine or guanine at a position corresponding to position 371 according to SEQ ID NO:9 or SEQ ID NO:10 (for mRNA molecules); or iii) an adenine or guanine at a position corresponding to position 371 according to SEQ ID NO:16 or SEQ ID NO:17 (for cDNA molecules produced from mRNA molecules).

In some embodiments, the nucleotide sequence comprises: i) a thymine at a position corresponding to position 6,352 according to SEQ ID NO:5 (for genomic nucleic acid molecules); ii) a uracil at a position corresponding to position 1,194 according to SEQ ID NO:12 (for mRNA molecules); or iii) a thymine at a position corresponding to position 1,194 according to SEQ ID NO:19 (for cDNA molecules produced from mRNA molecules).

In some embodiments, the nucleotide sequence comprises: i) a thymine at a position corresponding to position 5,624 according to SEQ ID NO:7 (for genomic nucleic acid molecules); ii) a uracil at a position corresponding to position 1,161 according to SEQ ID NO:14 (for mRNA molecules); or iii) a thymine at a position corresponding to position 1,161 according to SEQ ID NO:21 (for cDNA molecules produced from mRNA molecules).

In some embodiments, the biological sample comprises a cell or cell lysate. Such methods can further comprise, for example, obtaining a biological sample from the subject comprising an SLC39A5 genomic nucleic acid molecule or mRNA molecule, and if mRNA, optionally reverse transcribing the mRNA into cDNA. Such assays can comprise, for example determining the identity of these positions of the particular SLC39A5 nucleic acid molecule.

In some embodiments, the method is an in vitro method.

In some embodiments, the determining step, detecting step, or genotyping assay comprises sequencing at least a portion of the nucleotide sequence of the SLC39A5 genomic nucleic acid molecule, the SLC39A5 mRNA molecule, or the SLC39A5 cDNA molecule in the biological sample, wherein the sequenced portion comprises one or more variations that cause a loss-of-function (partial or complete) or are predicted to cause a loss-of-function (partial or complete).

In some embodiments, the determining step, detecting step, or genotyping assay comprises sequencing at least a portion of: i) the nucleotide sequence of the SLC39A5 genomic nucleic acid molecule in the biological sample, wherein the sequenced portion comprises a position corresponding to position 5,604 according to SEQ ID NO:4, or the complement thereof; ii) the nucleotide sequence of the SLC39A5 mRNA molecule in the biological sample, wherein the sequenced portion comprises a position corresponding to position 1,141 according to SEQ ID NO:11, or the complement thereof; and/or iii) the nucleotide sequence of the SLC39A5 cDNA molecule produced from the mRNA in the biological sample, wherein the sequenced portion comprises a position corresponding to position 1,141 according to SEQ ID NO:18, or the complement thereof. When the sequenced portion of the SLC39A5 nucleic acid molecule in the biological sample comprises: a cytosine at a position corresponding to position 5,604 according to SEQ ID NO:4, a cytosine at a position corresponding to position 1,141 according to SEQ ID NO:11, or a cytosine at a position corresponding to position 1,141 according to SEQ ID NO:18, then the SLC39A5 nucleic acid molecule in the biological sample is an SLC39A5 predicted loss-of-function variant nucleic acid molecule.

In some embodiments, the determining step, detecting step, or genotyping assay comprises sequencing at least a portion of: i) the nucleotide sequence of the SLC39A5 genomic nucleic acid molecule in the biological sample, wherein the sequenced portion comprises a position corresponding to position 6,899 according to SEQ ID NO:6, or the complement thereof; ii) the nucleotide sequence of the SLC39A5 mRNA molecule in the biological sample, wherein the sequenced portion comprises a position corresponding to position 1,468 according to SEQ ID NO:13, or the complement thereof; and/or iii) the nucleotide sequence of the SLC39A5 cDNA molecule produced from the mRNA in the biological sample, wherein the sequenced portion comprises a position corresponding to position 1,468 according to SEQ ID NO:20, or the complement thereof. When the sequenced portion of the SLC39A5 nucleic acid molecule in the biological sample comprises: a cytosine at a position corresponding to position 6,899 according to SEQ ID NO:6, a cytosine at a position corresponding to position 1,468 according to SEQ ID NO:13, or a cytosine at a position corresponding to position 1,468 according to SEQ ID NO:20, then the SLC39A5 nucleic acid molecule in the biological sample is an SLC39A5 predicted loss-of-function variant nucleic acid molecule.

In some embodiments, the determining step, detecting step, or genotyping assay comprises sequencing at least a portion of: i) the nucleotide sequence of the SLC39A5 genomic nucleic acid molecule in the biological sample, wherein the sequenced portion comprises a position corresponding to position 1,353 according to SEQ ID NO:2 or SEQ ID NO:3, or the complement thereof; ii) the nucleotide sequence of the SLC39A5 mRNA molecule in the biological sample, wherein the sequenced portion comprises a position corresponding to position 371 according to SEQ ID NO:9 or SEQ ID NO:10, or the complement thereof; and/or iii) the nucleotide sequence of the SLC39A5 cDNA molecule produced from the mRNA in the biological sample, wherein the sequenced portion comprises a position corresponding to position 371 according to SEQ ID NO:16 or SEQ ID NO:17, or the complement thereof. When the sequenced portion of the SLC39A5 nucleic acid molecule in the biological sample comprises: an adenine or guanine at a position corresponding to position 1,353 according to SEQ ID NO:2 or SEQ ID NO:3, an adenine or guanine at a position corresponding to position 371 according to SEQ ID NO:9 or SEQ ID NO:10, or an adenine or guanine at a position corresponding to position 371 according to SEQ ID NO:16 or SEQ ID NO:17, then the SLC39A5 nucleic acid molecule in the biological sample is an SLC39A5 predicted loss-of-function variant nucleic acid molecule.

In some embodiments, the determining step, detecting step, or genotyping assay comprises sequencing at least a portion of: i) the nucleotide sequence of the SLC39A5 genomic nucleic acid molecule in the biological sample, wherein the sequenced portion comprises a position corresponding to position 6,352 according to SEQ ID NO:5, or the complement thereof; ii) the nucleotide sequence of the SLC39A5 mRNA molecule in the biological sample, wherein the sequenced portion comprises a position corresponding to position 1,194 according to SEQ ID NO:12, or the complement thereof; and/or iii) the nucleotide sequence of the SLC39A5 cDNA molecule produced from the mRNA in the biological sample, wherein the sequenced portion comprises a position corresponding to position 1,194 according to SEQ ID NO:19, or the complement thereof. When the sequenced portion of the SLC39A5 nucleic acid molecule in the biological sample comprises: a thymine at a position corresponding to position 6,352 according to SEQ ID NO:5, a uracil at a position corresponding to position 1,194 according to SEQ ID NO:12, or a thymine at a position corresponding to position 1,194 according to SEQ ID NO:19, then the SLC39A5 nucleic acid molecule in the biological sample is an SLC39A5 predicted loss-of-function variant nucleic acid molecule.

In some embodiments, the determining step, detecting step, or genotyping assay comprises sequencing at least a portion of: i) the nucleotide sequence of the SLC39A5 genomic nucleic acid molecule in the biological sample, wherein the sequenced portion comprises a position corresponding to position 5,624 according to SEQ ID NO:7, or the complement thereof; ii) the nucleotide sequence of the SLC39A5 mRNA molecule in the biological sample, wherein the sequenced portion comprises a position corresponding to position 1,161 according to SEQ ID NO:14, or the complement thereof; and/or iii) the nucleotide sequence of the SLC39A5 cDNA molecule produced from the mRNA in the biological sample, wherein the sequenced portion comprises a position corresponding to position 1,161 according to SEQ ID NO:21, or the complement thereof. When the sequenced portion of the SLC39A5 nucleic acid molecule in the biological sample comprises: a thymine at a position corresponding to position 5,624 according to SEQ ID NO:7, a uracil at a position corresponding to position 1,161 according to SEQ ID NO:14, or a thymine at a position corresponding to position 1,161 according to SEQ ID NO:21, then the SLC39A5 nucleic acid molecule in the biological sample is an SLC39A5 predicted loss-of-function variant nucleic acid molecule.

In some embodiments, the determining step, detecting step, or genotyping assay comprises: a) contacting the biological sample with a primer hybridizing to a portion of the nucleotide sequence of the SLC39A5: i) genomic nucleic acid molecule that is proximate to a position corresponding to position 5,604 according to SEQ ID NO:4; ii) mRNA molecule that is proximate to a position corresponding to position 1,141 according to SEQ ID NO:11; and/or iii) cDNA molecule that is proximate to a position corresponding to position 1,141 according to SEQ ID NO:18; b) extending the primer at least through the position of the nucleotide sequence of the SLC39A5: i) genomic nucleic acid molecule corresponding to position 5,604 according to SEQ ID NO:4; ii) mRNA molecule corresponding to position 1,141 according to SEQ ID NO:11; and/or iii) cDNA molecule corresponding to position 1,141 according to SEQ ID NO:18; and c) determining whether the extension product of the primer comprises: i) a cytosine at a position corresponding to position 5,604 according to SEQ ID NO:4; ii) a cytosine at a position corresponding to position 1,141 according to SEQ ID NO:11; and/or iii) a cytosine at a position corresponding to position 1,141 according to SEQ ID NO:18.

In some embodiments, the determining step, detecting step, or genotyping assay comprises: a) contacting the biological sample with a primer hybridizing to a portion of the nucleotide sequence of the SLC39A5: i) genomic nucleic acid molecule that is proximate to a position corresponding to position 5,604 according to SEQ ID NO:6; ii) mRNA molecule that is proximate to a position corresponding to position 1,468 according to SEQ ID NO:13; and/or iii) cDNA molecule that is proximate to a position corresponding to position 1,468 according to SEQ ID NO:20; b) extending the primer at least through the position of the nucleotide sequence of the SLC39A5: i) genomic nucleic acid molecule corresponding to position 6,899 according to SEQ ID NO:6; ii) mRNA molecule corresponding to position 1,468 according to SEQ ID NO:13; and/or iii) cDNA molecule corresponding to position 1,468 according to SEQ ID NO:20; and c) determining whether the extension product of the primer comprises: i) a cytosine at a position corresponding to position 6,899 according to SEQ ID NO:6; ii) a cytosine at a position corresponding to position 1,468 according to SEQ ID NO:13; and/or iii) a cytosine at a position corresponding to position 1,468 according to SEQ ID NO:20.

In some embodiments, the determining step, detecting step, or genotyping assay comprises: a) contacting the biological sample with a primer hybridizing to a portion of the nucleotide sequence of the SLC39A5: i) genomic nucleic acid molecule that is proximate to a position corresponding to position 1,353 according to SEQ ID NO:2 or SEQ ID NO:3; ii) mRNA molecule that is proximate to a position corresponding to position 371 according to SEQ ID NO:9 or SEQ ID NO:10; and/or iii) cDNA molecule that is proximate to a position corresponding to position 371 according to SEQ ID NO:16 or SEQ ID NO:17; b) extending the primer at least through the position of the nucleotide sequence of the SLC39A5: i) genomic nucleic acid molecule corresponding to position 1,353 according to SEQ ID NO:2 or SEQ ID NO:3; ii) mRNA molecule corresponding to position 371 according to SEQ ID NO:9 or SEQ ID NO:10; and/or iii) cDNA molecule corresponding to position 371 according to SEQ ID NO:16 or SEQ ID NO:17; and c) determining whether the extension product of the primer comprises: i) an adenine or guanine at a position corresponding to position 1,353 according to SEQ ID NO:2 or SEQ ID NO:3; ii) an adenine or guanine at a position corresponding to position 371 according to SEQ ID NO:9 or SEQ ID NO:10; and/or iii) an adenine or guanine at a position corresponding to position 371 according to SEQ ID NO:16 or SEQ ID NO:17.

In some embodiments, the determining step, detecting step, or genotyping assay comprises: a) contacting the biological sample with a primer hybridizing to a portion of the nucleotide sequence of the SLC39A5: i) genomic nucleic acid molecule that is proximate to a position corresponding to position 6,352 according to SEQ ID NO:5; ii) mRNA molecule that is proximate to a position corresponding to position 1,194 according to SEQ ID NO:12; and/or iii) cDNA molecule that is proximate to a position corresponding to position 1,194 according to SEQ ID NO:19; b) extending the primer at least through the position of the nucleotide sequence of the SLC39A5: i) genomic nucleic acid molecule corresponding to position 6,352 according to SEQ ID NO:5; ii) mRNA molecule corresponding to position 1,194 according to SEQ ID NO:12; and/or iii) cDNA molecule corresponding to position 1,194 according to SEQ ID NO:19; and c) determining whether the extension product of the primer comprises: i) a thymine at a position corresponding to position 6,352 according to SEQ ID NO:5; ii) a uracil at a position corresponding to position 1,194 according to SEQ ID NO:12; and/or iii) a thymine at a position corresponding to position 1,194 according to SEQ ID NO:19.

In some embodiments, the determining step, detecting step, or genotyping assay comprises: a) contacting the biological sample with a primer hybridizing to a portion of the nucleotide sequence of the SLC39A5: i) genomic nucleic acid molecule that is proximate to a position corresponding to position 5,624 according to SEQ ID NO:7; ii) mRNA molecule that is proximate to a position corresponding to position 1,161 according to SEQ ID NO:14; and/or iii) cDNA molecule that is proximate to a position corresponding to position 1,161 according to SEQ ID NO:21; b) extending the primer at least through the position of the nucleotide sequence of the SLC39A5: i) genomic nucleic acid molecule corresponding to position 5,624 according to SEQ ID NO:7; ii) mRNA molecule corresponding to position 1,161 according to SEQ ID NO:14; and/or iii) cDNA molecule corresponding to position 1,161 according to SEQ ID NO:21; and c) determining whether the extension product of the primer comprises: i) a thymine at a position corresponding to position 5,624 according to SEQ ID NO:7; ii) a uracil at a position corresponding to position 1,161 according to SEQ ID NO:14; and/or iii) a thymine at a position corresponding to position 1,161 according to SEQ ID NO:21.

In some embodiments, the assay comprises sequencing the entire nucleic acid molecule. In some embodiments, only an SLC39A5 genomic nucleic acid molecule is analyzed. In some embodiments, only an SLC39A5 mRNA is analyzed. In some embodiments, only an SLC39A5 cDNA obtained from SLC39A5 mRNA is analyzed.

In some embodiments, the determining step, detecting step, or genotyping assay comprises: a) amplifying at least a portion of the nucleic acid molecule that encodes the human SLC39A5 polypeptide, wherein the amplified portion comprises: i) a cytosine at a position corresponding to position 5,604 according to SEQ ID NO:4, or the complement thereof; ii) a cytosine at a position corresponding to position 1,141 according to SEQ ID NO:11, or the complement thereof; and/or iii) a cytosine at a position corresponding to position 1,141 according to SEQ ID NO:18, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) a cytosine at a position corresponding to position 5,604 according to SEQ ID NO:4, or the complement thereof; ii) a cytosine at a position corresponding to position 1,141 according to SEQ ID NO:11, or the complement thereof; and/or iii) a cytosine at a position corresponding to position 1,141 according to SEQ ID NO:18, or the complement thereof; and d) detecting the detectable label.

In some embodiments, the determining step, detecting step, or genotyping assay comprises: a) amplifying at least a portion of the nucleic acid molecule that encodes the human SLC39A5 polypeptide, wherein the amplified portion comprises: i) a cytosine at a position corresponding to position 6,899 according to SEQ ID NO:6, or the complement thereof; ii) a cytosine at a position corresponding to position 1,468 according to SEQ ID NO:13, or the complement thereof; and/or iii) a cytosine at a position corresponding to position 1,468 according to SEQ ID NO:20, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) a cytosine at a position corresponding to position 6,899 according to SEQ ID NO:6, or the complement thereof; ii) a cytosine at a position corresponding to position 1,468 according to SEQ ID NO:13, or the complement thereof; and/or iii) a cytosine at a position corresponding to position 1,468 according to SEQ ID NO:20, or the complement thereof; and d) detecting the detectable label.

In some embodiments, the determining step, detecting step, or genotyping assay comprises: a) amplifying at least a portion of the nucleic acid molecule that encodes the human SLC39A5 polypeptide, wherein the amplified portion comprises: i) an adenine or guanine at a position corresponding to position 1,353 according to SEQ ID NO:2 or SEQ ID NO:3, or the complement thereof; ii) an adenine or guanine at a position corresponding to position 371 according to SEQ ID NO:9 or SEQ ID NO:10, or the complement thereof; and/or iii) an adenine or guanine at a position corresponding to position 371 according to SEQ ID NO:16 or SEQ ID NO:17, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) an adenine or guanine at a position corresponding to position 1,353 according to SEQ ID NO:2 or SEQ ID NO:3, or the complement thereof; ii) an adenine or guanine at a position corresponding to position 371 according to SEQ ID NO:9 or SEQ ID NO:10, or the complement thereof; and/or iii) an adenine or guanine at a position corresponding to position 371 according to SEQ ID NO:16 or SEQ ID NO:17, or the complement thereof; and d) detecting the detectable label.

In some embodiments, the determining step, detecting step, or genotyping assay comprises: a) amplifying at least a portion of the nucleic acid molecule that encodes the human SLC39A5 polypeptide, wherein the amplified portion comprises: i) a thymine at a position corresponding to position 6,352 according to SEQ ID NO:5, or the complement thereof; ii) a uracil at a position corresponding to position 1,194 according to SEQ ID NO:12, or the complement thereof; and/or iii) a thymine at a position corresponding to position 1,194 according to SEQ ID NO:19, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) a thymine at a position corresponding to position 6,352 according to SEQ ID NO:5, or the complement thereof; ii) a uracil at a position corresponding to position 1,194 according to SEQ ID NO:12, or the complement thereof; and/or iii) a thymine at a position corresponding to position 1,194 according to SEQ ID NO:19, or the complement thereof; and d) detecting the detectable label.

In some embodiments, the determining step, detecting step, or genotyping assay comprises: a) amplifying at least a portion of the nucleic acid molecule that encodes the human SLC39A5 polypeptide, wherein the amplified portion comprises: i) a thymine at a position corresponding to position 5,624 according to SEQ ID NO:7, or the complement thereof; ii) a uracil at a position corresponding to position 1,161 according to SEQ ID NO:14, or the complement thereof; and/or iii) a thymine at a position corresponding to position 1,161 according to SEQ ID NO:21, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: i) a thymine at a position corresponding to position 5,624 according to SEQ ID NO:7, or the complement thereof; ii) a uracil at a position corresponding to position 1,161 according to SEQ ID NO:14, or the complement thereof; and/or iii) a thymine at a position corresponding to position 1,161 according to SEQ ID NO:21, or the complement thereof; and d) detecting the detectable label.

In some embodiments, the nucleic acid molecule is mRNA and the determining step further comprises reverse-transcribing the mRNA into a cDNA prior to the amplifying step.

In some embodiments, the determining step, detecting step, or genotyping assay comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: i) a cytosine at a position corresponding to position 5,604 according to SEQ ID NO:4, or the complement thereof; ii) a cytosine at a position corresponding to position 1,141 according to SEQ ID NO:11, or the complement thereof; and/or a cytosine at a position corresponding to position 1,141 according to SEQ ID NO:18, or the complement thereof; and detecting the detectable label.

In some embodiments, the determining step, detecting step, or genotyping assay comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: i) a cytosine at a position corresponding to position 6,899 according to SEQ ID NO:6, or the complement thereof; ii) a cytosine at a position corresponding to position 1,468 according to SEQ ID NO:13, or the complement thereof; and/or a cytosine at a position corresponding to position 1,468 according to SEQ ID NO:20, or the complement thereof; and detecting the detectable label.

In some embodiments, the determining step, detecting step, or genotyping assay comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: i) an adenine or guanine at a position corresponding to position 1,353 according to SEQ ID NO:2 or SEQ ID NO:3, or the complement thereof; ii) an adenine or guanine at a position corresponding to position 371 according to SEQ ID NO:9 or SEQ ID NO:10, or the complement thereof; and/or an adenine or guanine at a position corresponding to position 371 according to SEQ ID NO:16 or SEQ ID NO:17, or the complement thereof; and detecting the detectable label.

In some embodiments, the determining step, detecting step, or genotyping assay comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: i) a thymine at a position corresponding to position 6,352 according to SEQ ID NO:5, or the complement thereof; ii) a uracil at a position corresponding to position 1,194 according to SEQ ID NO:12, or the complement thereof; and/or a thymine at a position corresponding to position 1,194 according to SEQ ID NO:19, or the complement thereof; and detecting the detectable label.

In some embodiments, the determining step, detecting step, or genotyping assay comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: i) a thymine at a position corresponding to position 5,624 according to SEQ ID NO:7, or the complement thereof; ii) a uracil at a position corresponding to position 1,161 according to SEQ ID NO:14, or the complement thereof; and/or a thymine at a position corresponding to position 1,161 according to SEQ ID NO:21, or the complement thereof; and detecting the detectable label.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the human subject.

The SLC39A5 predicted loss-of-function variant nucleic acid molecule can be any SLC39A5 nucleic acid molecule (such as, for example, genomic nucleic acid molecule, mRNA molecule, or cDNA molecule) encoding an SLC39A5 polypeptide having a partial loss-of-function, a complete loss-of-function, a predicted partial loss-of-function, or a predicted complete loss-of-function. For example, the SLC39A5 predicted loss-of-function variant nucleic acid molecule can be any nucleic acid molecule encoding SLC39A5 M304T, G413A, Y47Stop, R322Stop, or R311Stop. In some embodiments, the SLC39A5 predicted loss-of-function variant nucleic acid molecule encodes SLC39A5 Y47Stop, R322Stop, or R311Stop.

In some embodiments, the assay comprises contacting the biological sample with a primer or probe, such as an alteration-specific primer or alteration-specific probe, that specifically hybridizes to an SLC39A5 variant genomic sequence, variant mRNA sequence, or variant cDNA sequence and not the corresponding SLC39A5 reference sequence under stringent conditions, and determining whether hybridization has occurred.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising an SLC39A5 variant genomic nucleic acid molecule, variant mRNA molecule, or variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

In some embodiments, to determine whether an SLC39A5 nucleic acid molecule (genomic nucleic acid molecule, mRNA molecule, or cDNA molecule), or complement thereof, within a biological sample comprises a nucleotide sequence comprising a cytosine at a position corresponding to position 5,604 according to SEQ ID NO:4 (genomic nucleic acid molecule), or a cytosine at a position corresponding to position 1,141 according to SEQ ID NO:11 (mRNA molecule), or a cytosine at a position corresponding to position 1,141 according to SEQ ID NO:18 (cDNA molecule), the biological sample can be subjected to an amplification method using a primer pair that includes a first primer derived from the 5' flanking sequence adjacent to a cytosine at a position corresponding to position 5,604 according to SEQ ID NO:4, or a cytosine at a position corresponding to position 1,141 according to SEQ ID NO:11, or a cytosine at a position corresponding to position 1,141 according to SEQ ID NO:18, and a second primer derived from the 3' flanking sequence adjacent to a cytosine at a position corresponding to position 5,604 according to SEQ ID NO:4, or a cytosine at a position corresponding to position 1,141 according to SEQ ID NO:11, or a cytosine at a position corresponding to position 1,141 according to SEQ ID NO:18 to produce an amplicon that is indicative of the presence of the SNP at positions encoding a cytosine at a position corresponding to position 5,604 according to SEQ ID NO:4, or a cytosine at a position corresponding to position 1,141 according to SEQ ID NO:11, or a cytosine at a position corresponding to position 1,141 according to SEQ ID NO:18. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a cytosine at a position corresponding to position 5,604 according to SEQ ID NO:4, or a cytosine at a position corresponding to position 1,141 according to SEQ ID NO:11, or a cytosine at a position corresponding to position 1,141 according to SEQ ID NO:18, and at least 1, 2, 3, 4, 5, 6, 7, 8, 9, 10, or more nucleotides on each side of positions comprising a cytosine at a position corresponding to position 5,604 according to SEQ ID NO:4, or a cytosine at a position corresponding to position 1,141 according to SEQ ID NO:11, or a cytosine at a position corresponding to position 1,141 according to SEQ ID NO:18.

In some embodiments, to determine whether an SLC39A5 nucleic acid molecule (genomic nucleic acid molecule, mRNA molecule, or cDNA molecule), or complement thereof, within a biological sample comprises a nucleotide sequence comprising a cytosine at a position corresponding to position 6,899 according to SEQ ID NO:6 (genomic nucleic acid molecule), or a cytosine at a position corresponding to position 1,468 according to SEQ ID NO:13 (mRNA molecule), or a cytosine at a position corresponding to position 1,468 according to SEQ ID NO:20 (cDNA molecule), the biological sample can be subjected to an amplification method using a primer pair that includes a first primer derived from the 5' flanking sequence adjacent to a cytosine at a position corresponding to position 6,899 according to SEQ ID NO:6, or a cytosine at a position corresponding to position 1,468 according to SEQ ID NO:13, or a cytosine at a position corresponding to position 1,468 according to SEQ ID NO:20, and a second primer derived from the 3' flanking sequence adjacent to a cytosine at a position corresponding to position 6,899 according to SEQ ID NO:6, or a cytosine at a position corresponding to position 1,468 according to SEQ ID NO:13, or a cytosine at a position corresponding to position 1,468 according to SEQ ID NO:20 to produce an amplicon that is indicative of the presence of the SNP at positions encoding a cytosine at a position corresponding to position 6,899 according to SEQ ID NO:6, or a cytosine at a position corresponding to position 1,468 according to SEQ ID NO:13, or a cytosine at a position corresponding to position 1,468 according to SEQ ID NO:20. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a cytosine at a position corresponding to position 6,899 according to SEQ ID NO:6, or a cytosine at a position corresponding to position 1,468 according to SEQ ID NO:13, or a cytosine at a position corresponding to position 1,468 according to SEQ ID NO:20, and at least 1, 2, 3, 4, 5, 6, 7, 8, 9, 10, or more nucleotides on each side of positions comprising a cytosine at a position corresponding to position 6,899 according to SEQ ID NO:6, or a cytosine at a position corresponding to position 1,468 according to SEQ ID NO:13, or a cytosine at a position corresponding to position 1,468 according to SEQ ID NO:20.

In some embodiments, to determine whether an SLC39A5 nucleic acid molecule (genomic nucleic acid molecule, mRNA molecule, or cDNA molecule produced from an mRNA molecule), or complement thereof, within a biological sample comprises a nucleotide sequence comprising an adenine or guanine at a position corresponding to position 1,353 according to SEQ ID NO:2 or SEQ ID NO:3 (genomic nucleic acid molecule), or an adenine or guanine at a position corresponding to position 371 according to SEQ ID NO:9 or SEQ ID NO:10 (mRNA molecule), or an adenine or guanine at a position corresponding to position 371 according to SEQ ID NO:16 or SEQ ID NO:17 (cDNA molecule), the biological sample can be subjected to an amplification method using a primer pair that includes a first primer derived from the 5' flanking sequence adjacent to an adenine or guanine at a position corresponding to position 1,353 according to SEQ ID NO:2 or SEQ ID NO:3, or an adenine or guanine at a position corresponding to position 371 according to SEQ ID NO:9 or SEQ ID NO:10, or an adenine or guanine at a position corresponding to position 371 according to SEQ ID NO:16 or SEQ ID NO:17, and a second primer derived from the 3' flanking sequence adjacent to an adenine or guanine at a position corresponding to position 1,353 according to SEQ ID NO:2 or SEQ ID NO:3, or an adenine or guanine at a position corresponding to position 371 according to SEQ ID NO:9 or SEQ ID NO:10, or an adenine or guanine at a position corresponding to position 371 according to SEQ ID NO:16 or SEQ ID NO:17 to produce an amplicon that is indicative of the presence of the SNP at positions encoding an adenine or guanine at a position corresponding to position 1,353 according to SEQ ID NO:2 or SEQ ID NO:3, or an adenine or guanine at a position corresponding to position 371 according to SEQ ID NO:9 or SEQ ID NO:10, or an adenine or guanine at a position corresponding to position 371 according to SEQ ID NO:16 or SEQ ID NO:17. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an adenine or guanine at a position corresponding to position 1,353 according to SEQ ID NO:2 or SEQ ID NO:3, or an adenine or guanine at a position corresponding to position 371 according to SEQ ID NO:9 or SEQ ID NO:10, or an adenine or guanine at a position corresponding to position 371 according to SEQ ID NO:16 or SEQ ID NO:17, and at least 1, 2, 3, 4, 5, 6, 7, 8, 9, 10, or more nucleotides on each side of positions comprising an adenine or guanine at a position corresponding to position 1,353 according to SEQ ID NO:2 or SEQ ID NO:3, or an adenine or guanine at a position corresponding to position 371 according to SEQ ID NO:9 or SEQ ID NO:10, or an adenine or guanine at a position corresponding to position 371 according to SEQ ID NO:16 or SEQ ID NO:17.

In some embodiments, to determine whether an SLC39A5 nucleic acid molecule (genomic nucleic acid molecule, mRNA molecule, or cDNA molecule), or complement thereof, within a biological sample comprises a nucleotide sequence comprising a thymine at a position corresponding to position 6,352 according to SEQ ID NO:5 (genomic nucleic acid molecule), or a uracil at a position corresponding to position 1,194 according to SEQ ID NO:12 (mRNA molecule), or a thymine at a position corresponding to position 1,194 according to SEQ ID NO:19 (cDNA molecule), the biological sample can be subjected to an amplification method using a primer pair that includes a first primer derived from the 5' flanking sequence adjacent to a thymine at a position corresponding to position 6,352 according to SEQ ID NO:5, or a uracil at a position corresponding to position 1,194 according to SEQ ID NO:12, or a thymine at a position corresponding to position 1,194 according to SEQ ID NO:19, and a second primer derived from the 3' flanking sequence adjacent to a thymine at a position corresponding to position 6,352 according to SEQ ID NO:5, or a uracil at a position corresponding to position 1,194 according to SEQ ID NO:12, or a thymine at a position corresponding to position 1,194 according to SEQ ID NO:19 to produce an amplicon that is indicative of the presence of the SNP at positions encoding a thymine at a position corresponding to position 6,352 according to SEQ ID NO:5, or a uracil at a position corresponding to position 1,194 according to SEQ ID NO:12, or a thymine at a position corresponding to position 1,194 according to SEQ ID NO:19. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a thymine at a position corresponding to position 6,352 according to SEQ ID NO:5, or a uracil at a position corresponding to position 1,194 according to SEQ ID NO:12, or a thymine at a position corresponding to position 1,194 according to SEQ ID NO:19, and at least 1, 2, 3, 4, 5, 6, 7, 8, 9, 10, or more nucleotides on each side of positions comprising a thymine at a position corresponding to position 6,352 according to SEQ ID NO:5, or a uracil at a position corresponding to position 1,194 according to SEQ ID NO:12, or a thymine at a position corresponding to position 1,194 according to SEQ ID NO:19.

In some embodiments, to determine whether an SLC39A5 nucleic acid molecule (genomic nucleic acid molecule, mRNA molecule, or cDNA molecule), or complement thereof, within a biological sample comprises a nucleotide sequence comprising a thymine at a position corresponding to position 5,624 according to SEQ ID NO:7 (genomic nucleic acid molecule), or a uracil at a position corresponding to position 1,161 according to SEQ ID NO:14 (mRNA molecule), or a thymine at a position corresponding to position 1,161 according to SEQ ID NO:21 (cDNA molecule), the biological sample can be subjected to an amplification method using a primer pair that includes a first primer derived from the 5' flanking sequence adjacent to a thymine at a position corresponding to position 5,624 according to SEQ ID NO:7, or a uracil at a position corresponding to position 1,161 according to SEQ ID NO:14, or a thymine at a position corresponding to position 1,161 according to SEQ ID NO:21, and a second primer derived from the 3' flanking sequence adjacent to a thymine at a position corresponding to position 5,624 according to SEQ ID NO:7, or a uracil at a position corresponding to position 1,161 according to SEQ ID NO:14, or a thymine at a position corresponding to position 1,161 according to SEQ ID NO:21 to produce an amplicon that is indicative of the presence of the SNP at positions encoding a thymine at a position corresponding to position 5,624 according to SEQ ID NO:7, or a uracil at a position corresponding to position 1,161 according to SEQ ID NO:14, or a thymine at a position corresponding to position 1,161 according to SEQ ID NO:21. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a thymine at a position corresponding to position 5,624 according to SEQ ID NO:7, or a uracil at a position corresponding to position 1,161 according to SEQ ID NO:14, or a thymine at a position corresponding to position 1,161 according to SEQ ID NO:21, and at least 1, 2, 3, 4, 5, 6, 7, 8, 9, 10, or more nucleotides on each side of positions comprising a thymine at a position corresponding to position 5,624 according to SEQ ID NO:7, or a uracil at a position corresponding to position 1,161 according to SEQ ID NO:14, or a thymine at a position corresponding to position 1,161 according to SEQ ID NO:21.

Similar amplicons can be generated from the mRNA and/or cDNA sequences. PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using known guidelines.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in Current Protocols in Molecular Biology, John Wiley & Sons, N.Y. (1989), 6.3.1-6.3.6. Typically, stringent conditions for hybridization and detection will be those in which the salt concentration is less than about 1.5 M $Na^+$ ion, typically about 0.01 to 1.0 M $Na^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure also provides molecular complexes comprising any of the SLC39A5 nucleic acid molecules (genomic nucleic acid molecules, mRNA molecules, or cDNA molecules), or complement thereof, described herein and any of the allele-specific primers or allele-specific probes described herein. In some embodiments, the SLC39A5 nucleic acid molecules (genomic nucleic acid molecules, mRNA molecules, or cDNA molecules), or complement thereof, in the molecular complexes are single-stranded. In some embodiments, the SLC39A5 nucleic acid molecule is any of the genomic nucleic acid molecules described herein. In some embodiments, the SLC39A5 nucleic acid molecule is any of the mRNA molecules described herein. In some embodiments, the SLC39A5 nucleic acid molecule is any of the cDNA molecules described herein. In some embodiments, the molecular complex comprises any of the SLC39A5 nucleic acid molecules (genomic nucleic acid molecules, mRNA molecules, or cDNA molecules), or complement thereof, described herein and any of the allele-specific primers described herein. In some embodiments, the molecular complex comprises any of the SLC39A5 nucleic acid molecules (genomic nucleic acid molecules, mRNA molecules, or cDNA molecules), or complement thereof, described herein and any of the allele-specific probes described herein. In some embodiments, the complexes further comprise a non-human polymerase.

In some embodiments, the molecular complex comprises an SLC39A5 variant genomic nucleic acid molecule comprising a nucleotide sequence according to SEQ ID NO:4, and the allele-specific primer or allele-specific probe that hybridizes to the cytosine at position 5,604 thereof. In some embodiments, the molecular complex comprises an SLC39A5 variant mRNA molecule comprising a nucleotide sequence according to SEQ ID NO:11, and the allele-specific primer or allele-specific probe that hybridizes to the cytosine at position 1,141 thereof. In some embodiments, the molecular complex comprises an SLC39A5 variant cDNA molecule comprising a nucleotide sequence according to SEQ ID NO:18, and the allele-specific primer or allele-specific probe that hybridizes to the cytosine at position 1,141 thereof.

In some embodiments, the molecular complex comprises an SLC39A5 variant genomic nucleic acid molecule comprising a nucleotide sequence according to SEQ ID NO:6, and the allele-specific primer or allele-specific probe that hybridizes to the cytosine at position 6,899 thereof. In some embodiments, the molecular complex comprises an SLC39A5 variant mRNA molecule comprising a nucleotide sequence according to SEQ ID NO:13, and the allele-specific primer or allele-specific probe that hybridizes to the cytosine at position 1,468 thereof. In some embodiments, the molecular complex comprises an SLC39A5 variant cDNA molecule comprising a nucleotide sequence according to SEQ ID NO:20, and the allele-specific primer or allele-specific probe that hybridizes to the cytosine at position 1,468 thereof.

In some embodiments, the molecular complex comprises an SLC39A5 variant genomic nucleic acid molecule comprising a nucleotide sequence according to SEQ ID NO:2 or SEQ ID NO:3, and the allele-specific primer or allele-specific probe that hybridizes to the adenine or guanine at position 1,353 thereof, respectively. In some embodiments, the molecular complex comprises an SLC39A5 variant mRNA molecule comprising a nucleotide sequence according to SEQ ID NO:9 or SEQ ID NO:10, and the allele-specific primer or allele-specific probe that hybridizes to the adenine or guanine at position 371 thereof, respectively. In some embodiments, the molecular complex comprises an SLC39A5 variant cDNA molecule comprising a nucleotide sequence according to SEQ ID NO:16 or SEQ ID NO:17, and the allele-specific primer or allele-specific probe that hybridizes to the adenine or guanine at position 371 thereof, respectively.

In some embodiments, the molecular complex comprises an SLC39A5 variant genomic nucleic acid molecule comprising a nucleotide sequence according to SEQ ID NO:5, and the allele-specific primer or allele-specific probe that hybridizes to the thymine at position 6,352 thereof. In some embodiments, the molecular complex comprises an SLC39A5 variant mRNA molecule comprising a nucleotide sequence according to SEQ ID NO:12, and the allele-specific primer or allele-specific probe that hybridizes to the uracil at position 1,194 thereof. In some embodiments, the molecular complex comprises an SLC39A5 variant cDNA molecule comprising a nucleotide sequence according to SEQ ID NO:19, and the allele-specific primer or allele-specific probe that hybridizes to the thymine at position 1,194 thereof.

In some embodiments, the molecular complex comprises an SLC39A5 variant genomic nucleic acid molecule comprising a nucleotide sequence according to SEQ ID NO:7, and the allele-specific primer or allele-specific probe that hybridizes to the thymine at position 5,624 thereof. In some embodiments, the molecular complex comprises an SLC39A5 variant mRNA molecule comprising a nucleotide sequence according to SEQ ID NO:14, and the allele-specific primer or allele-specific probe that hybridizes to the uracil at position 1,161 thereof. In some embodiments, the molecular complex comprises an SLC39A5 variant cDNA molecule comprising a nucleotide sequence according to SEQ ID NO:21, and the allele-specific primer or allele-specific probe that hybridizes to the thymine at position 1,161 thereof.

The present disclosure also provides methods of detecting the presence of a human SLC39A5 predicted loss-of-function polypeptide comprising performing an assay on a sample obtained from a human subject to determine whether an SLC39A5 polypeptide in the subject contains one or more variations that causes the polypeptide to have a loss-of-function (partial or complete) or predicted loss-of-function (partial or complete). In some embodiments, the methods detect the presence of SLC39A5 M304T, G413A, Y47Stop, R322Stop, or R311Stop. In some embodiments, the methods detect the presence of SLC39A5 Y47Stop, R322Stop, or R311Stop.

In some embodiments, the methods comprise performing an assay on a sample obtained from a human subject to determine whether an SLC39A5 polypeptide in the sample comprises a threonine at a position corresponding to position 304 according to SEQ ID NO:24. In some embodiments, the methods comprise performing an assay on a sample obtained from a human subject to determine whether an SLC39A5 polypeptide in the sample comprises a alanine at a position corresponding to position 413 according to SEQ ID NO:26.

In some embodiments, the methods comprise performing an assay on a sample obtained from a human subject to determine whether the sample contains an SLC39A5 truncated variant polypeptide terminating at a position corresponding to position 46 according to SEQ ID NO:23. In some embodiments, the SLC39A5 truncated variant polypeptide lacks amino acids at positions corresponding to positions 47 to 540 according to SEQ ID NO:22. In some embodiments, the SLC39A5 truncated variant polypeptide comprises or consists of SEQ ID NO:23.

In some embodiments, the methods comprise performing an assay on a sample obtained from a human subject to determine whether the sample contains an SLC39A5 truncated variant polypeptide terminating at a position corresponding to position 321 according to SEQ ID NO:25. In some embodiments, the SLC39A5 truncated variant polypeptide lacks amino acids at positions corresponding to positions 322 to 540 according to SEQ ID NO:22. In some embodiments, the SLC39A5 truncated variant polypeptide comprises or consists of SEQ ID NO:25.

In some embodiments, the methods comprise performing an assay on a sample obtained from a human subject to determine whether the sample contains an SLC39A5 truncated variant polypeptide terminating at a position corresponding to position 310 according to SEQ ID NO:27. In some embodiments, the SLC39A5 truncated variant polypeptide lacks amino acids at positions corresponding to positions 311 to 540 according to SEQ ID NO:22. In some embodiments, the SLC39A5 truncated variant polypeptide comprises or consists of SEQ ID NO:27.

In some embodiments, the detecting step comprises sequencing at least a portion of the polypeptide that comprises a position corresponding to position 304 according to SEQ ID NO:22 or SEQ ID NO:24. In some embodiments, the detecting step comprises sequencing at least a portion of the polypeptide that comprises a position corresponding to position 413 according to SEQ ID NO:22 or SEQ ID NO:26. In some embodiments, the detecting step comprises sequencing the entire polypeptide.

In some embodiments, the sequenced SLC39A5 polypeptide comprises or consists of SEQ ID NO:23. In some embodiments, the sequenced SLC39A5 polypeptide consists of SEQ ID NO:23. In some embodiments, the detecting step comprises sequencing at least a portion of an SLC39A5 polypeptide that may comprise positions corresponding to any positions that are C-terminal to 46 according to SEQ ID NO:23. If amino acids are detected in the SLC39A5 polypeptide at positions corresponding to positions 47 to 540 according to SEQ ID NO:22, then such SLC39A5 polypeptide is an SLC39A5 reference polypeptide. An absence of positions 47 to 540 according to SEQ ID NO:22 in the SLC39A5 polypeptide indicates that the SLC39A5 polypeptide terminates at position 46 according to SEQ ID NO:23 and is an SLC39A5 predicted loss-of-function polypeptide. In some embodiments, the detecting step comprises sequencing the entire polypeptide.

In some embodiments, the sequenced SLC39A5 polypeptide comprises or consists of SEQ ID NO:25. In some embodiments, the sequenced SLC39A5 polypeptide consists of SEQ ID NO:25. In some embodiments, the detecting step comprises sequencing at least a portion of an SLC39A5 polypeptide that may comprise positions corresponding to any positions that are C-terminal to 321 according to SEQ ID NO:25. If amino acids are detected in the SLC39A5 polypeptide at positions corresponding to positions 322 to 540 according to SEQ ID NO:22, then such SLC39A5 polypeptide is an SLC39A5 reference polypeptide. An absence of positions 322 to 540 according to SEQ ID NO:22 in the SLC39A5 polypeptide indicates that the SLC39A5 polypeptide terminates at position 321 according to SEQ ID NO:25 and is an SLC39A5 predicted loss-of-function polypeptide. In some embodiments, the detecting step comprises sequencing the entire polypeptide.

In some embodiments, the sequenced SLC39A5 polypeptide comprises or consists of SEQ ID NO:27. In some embodiments, the sequenced SLC39A5 polypeptide consists of SEQ ID NO:27. In some embodiments, the detecting step comprises sequencing at least a portion of an SLC39A5 polypeptide that may comprise positions corresponding to any positions that are C-terminal to 310 according to SEQ ID NO:27. If amino acids are detected in the SLC39A5 polypeptide at positions corresponding to positions 311 to 540 according to SEQ ID NO:22, then such SLC39A5 polypeptide is an SLC39A5 reference polypeptide. An absence of positions 311 to 540 according to SEQ ID NO:22 in the SLC39A5 polypeptide indicates that the SLC39A5 polypeptide terminates at position 310 according to SEQ ID NO:27 and is an SLC39A5 predicted loss-of-function polypeptide. In some embodiments, the detecting step comprises sequencing the entire polypeptide.

In some embodiments, the detecting step comprises an immunoassay for detecting the presence of a polypeptide that comprises a position corresponding to position 304 according to SEQ ID NO:22 or SEQ ID NO:24. In some embodiments, the detecting step comprises an immunoassay for detecting the presence of a polypeptide that comprises a position corresponding to position 413 according to SEQ ID NO:22 or SEQ ID NO:26.

In some embodiments, the detecting step comprises an immunoassay for detecting the presence of an SLC39A5 polypeptide that comprises or consists of SEQ ID NO:23. In some embodiments, the SLC39A5 polypeptide consists of SEQ ID NO:23. In some embodiments, the detecting step comprises detecting at least a portion of an SLC39A5 polypeptide that may comprise positions corresponding to any positions that are C-terminal to 46 according to SEQ ID NO:23. If amino acids are detected in the SLC39A5 polypeptide at positions corresponding to positions 47 to 540 according to SEQ ID NO:22, then such SLC39A5 polypeptide is an SLC39A5 reference polypeptide. A lack of detection of positions 47 to 540 according to SEQ ID NO:22 in the SLC39A5 polypeptide indicates that the SLC39A5 polypeptide terminates at position 46 according to SEQ ID NO:23 and is an SLC39A5 predicted loss-of-function polypeptide.

In some embodiments, the detecting step comprises an immunoassay for detecting the presence of an SLC39A5 polypeptide that comprises or consists of SEQ ID NO:25. In some embodiments, the SLC39A5 polypeptide consists of SEQ ID NO:25. In some embodiments, the detecting step comprises detecting at least a portion of an SLC39A5 polypeptide that may comprise positions corresponding to any positions that are C-terminal to 321 according to SEQ ID NO:25. If amino acids are detected in the SLC39A5 polypeptide at positions corresponding to positions 322 to 540 according to SEQ ID NO:22, then such SLC39A5 polypeptide is an SLC39A5 reference polypeptide. A lack of detection of positions 322 to 540 according to SEQ ID NO:22 in the SLC39A5 polypeptide indicates that the SLC39A5 polypeptide terminates at position 321 according to SEQ ID NO:25 and is an SLC39A5 predicted loss-of-function polypeptide.

In some embodiments, the detecting step comprises an immunoassay for detecting the presence of an SLC39A5 polypeptide that comprises or consists of SEQ ID NO:27. In some embodiments, the SLC39A5 polypeptide consists of SEQ ID NO:27. In some embodiments, the detecting step comprises detecting at least a portion of an SLC39A5 polypeptide that may comprise positions corresponding to any positions that are C-terminal to 310 according to SEQ ID NO:27. If amino acids are detected in the SLC39A5 polypeptide at positions corresponding to positions 311 to 540 according to SEQ ID NO:22, then such SLC39A5 polypeptide is an SLC39A5 reference polypeptide. A lack of detection of positions 311 to 540 according to SEQ ID NO:22 in the SLC39A5 polypeptide indicates that the SLC39A5 polypeptide terminates at position 310 according to SEQ ID NO:27 and is an SLC39A5 predicted loss-of-function polypeptide.

In some embodiments, when the human subject does not have an SLC39A5 predicted loss-of-function polypeptide, then the human subject has an increased risk for developing increased serum glucose level and/or hyperglycemia; and when the human subject has an SLC39A5 predicted loss-of-function polypeptide, then the human subject has a decreased risk for developing increased serum glucose level and/or hyperglycemia.

The probes and/or primers (including alteration-specific probes and alteration-specific primers) described herein comprise or consist of from about 15 to about 100, from about 15 to about 35 nucleotides. In some embodiments, the alteration-specific probes and alteration-specific primers comprise DNA. In some embodiments, the alteration-specific probes and alteration-specific primers comprise RNA. In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers (including alteration-specific probes and alteration-specific primers) specifically hybridize to any of the nucleic acid molecules disclosed herein under stringent conditions. In the context of the disclosure "specifically hybridizes" means that the probe or primer (including alteration-specific probes and alteration-specific primers) does not hybridize to a nucleic acid sequence encoding an SLC39A5 reference genomic nucleic acid molecule, an SLC39A5 reference mRNA molecule, and/or an SLC39A5 reference cDNA molecule. In some embodiments, the probes (such as, for example, an alteration-specific probe) comprise a label. In some embodiments, the label is a fluorescent label, a radiolabel, or biotin.

The nucleotide sequence of an SLC39A5 reference genomic nucleic acid molecule is set forth in SEQ ID NO:1. Referring to SEQ ID NO:1, position 5,604 is a thymine. Referring to SEQ ID NO:1, position 6,899 is a guanine. Referring to SEQ ID NO:1, position 1,353 is a cytosine, and codon positions 1,351 to 1,353 is a TAC codon. Referring to SEQ ID NO:1, position 6,352 is a cytosine, and codon positions 6,352 to 6,354 is a CGA codon. Referring to SEQ ID NO:1, position 5,624 is a cytosine, and codon positions 5,624 to 5,626 is a CGA codon.

A variant genomic nucleic acid molecule of SLC39A5 exists, wherein the thymine at position 5,604 is replaced with cytosine. The nucleotide sequence of this SLC39A5 variant genomic nucleic acid molecule is set forth in SEQ ID NO:4. Another variant genomic nucleic acid molecule of SLC39A5 exists, wherein the guanine at position 6,899 is replaced with cytosine. The nucleotide sequence of this SLC39A5 variant genomic nucleic acid molecule is set forth in SEQ ID NO:6. Another variant genomic nucleic acid molecule of SLC39A5 exists, wherein the cytosine at position 1,353 according to SEQ ID NO:1 is replaced with adenine or guanine, and the TAC codon at positions 1,351 to 1,353 according to SEQ ID NO:1 is replaced with TAA or TAG. The nucleotide sequence of this SLC39A5 variant genomic nucleic acid molecule is set forth in SEQ ID NO:2 or SEQ ID NO:3. Another variant genomic nucleic acid molecule of SLC39A5 exists, wherein the cytosine at position 6,352 according to SEQ ID NO:1 is replaced with thymine, and the CGA codon at positions 6,352 to 6,354 according to SEQ ID NO:1 is replaced with TGA. The nucleotide sequence of this SLC39A5 variant genomic nucleic acid molecule is set forth in SEQ ID NO:5. Another variant genomic nucleic acid molecule of SLC39A5 exists, wherein the cytosine at position 5,624 according to SEQ ID NO:1 is replaced with thymine, and the CGA codon at positions 5,624 to 5,626 according to SEQ ID NO:1 is replaced with TGA. The nucleotide sequence of this SLC39A5 variant genomic nucleic acid molecule is set forth in SEQ ID NO:7.

The nucleotide sequence of an SLC39A5 reference mRNA molecule is set forth in SEQ ID NO:8. Referring to SEQ ID NO:8, position 1,141 is a uracil. Referring to SEQ ID NO:8, position 1,468 is a guanine. Referring to SEQ ID NO:8, position 371 is a cytosine, and codon positions 369 to 371 is a UAC codon. Referring to SEQ ID NO:8, position 1,194 is a cytosine, and codon positions 1,194 to 1,196 is a CGA codon. Referring to SEQ ID NO:8, position 1,161 is a cytosine, and codon positions 1,161 to 1,163 is a CGA codon.

A variant mRNA molecule of SLC39A5 exists, wherein the uracil at position 1,141 is replaced with cytosine. The nucleotide sequence of this SLC39A5 variant mRNA molecule is set forth in SEQ ID NO:11. Another variant mRNA molecule of SLC39A5 exists, wherein the guanine at position 1,468 is replaced with cytosine. The nucleotide sequence of this SLC39A5 variant mRNA molecule is set forth in SEQ ID NO:13. Another variant mRNA molecule of SLC39A5 exists, wherein the cytosine at position 371 according to SEQ ID NO:8 is replaced with adenine or guanine, and the UAC codon at positions 369 to 371 according to SEQ ID NO:8 is replaced with UAA or UAG. The nucleotide sequence of this SLC39A5 variant mRNA molecule is set forth in SEQ ID NO:9 or SEQ ID NO:10. Another variant mRNA molecule of SLC39A5 exists, wherein the cytosine at position 1,194 according to SEQ ID NO:8 is replaced with uracil, and the CGA codon at positions 1,194 to 1,196 according to SEQ ID NO:8 is replaced with UGA. The nucleotide sequence of this SLC39A5 variant mRNA molecule is set forth in SEQ ID NO:12. Another variant mRNA molecule of SLC39A5 exists, wherein the cytosine at position 1,161 according to SEQ ID NO:8 is replaced with uracil, and the CGA codon at positions 1,161 to 1,163 according to SEQ ID NO:8 is replaced with UGA. The nucleotide sequence of this SLC39A5 variant mRNA molecule is set forth in SEQ ID NO:14.

The nucleotide sequence of an SLC39A5 reference cDNA molecule is set forth in SEQ ID NO:15. Referring to SEQ ID NO:15, position 1,141 is a thymine. Referring to SEQ ID NO:15, position 1,468 is a guanine. Referring to SEQ ID NO:15, position 371 is a cytosine, and codon positions 369 to 371 is a TAC codon. Referring to SEQ ID NO:15, position 1,194 is a cytosine, and codon positions 1,194 to 1,196 is a CGA codon. Referring to SEQ ID NO:15, position 1,161 is a cytosine, and codon positions 1,161 to 1,163 is a CGA codon.

A variant cDNA molecule of SLC39A5 exists, wherein the thymine at position 1,141 is replaced with cytosine. The nucleotide sequence of this SLC39A5 variant cDNA molecule is set forth in SEQ ID NO:18. Another variant cDNA molecule of SLC39A5 exists, wherein the guanine at position 1,468 is replaced with cytosine. The nucleotide sequence of this SLC39A5 variant cDNA molecule is set forth in SEQ ID NO:20. Another variant cDNA molecule of SLC39A5 exists, wherein the cytosine at position 371 according to SEQ ID NO:15 is replaced with adenine or guanine, and the TAC codon at positions 369 to 371 according to SEQ ID NO:15 is replaced with TAA or TAG. The nucleotide sequence of this SLC39A5 variant cDNA molecule is set forth in SEQ ID NO:16 or SEQ ID NO:17. Another variant cDNA molecule of SLC39A5 exists, wherein the cytosine at position 1,194 according to SEQ ID NO:15 is replaced with thymine, and the CGA codon at positions 1,194 to 1,196 according to SEQ ID NO:15 is replaced with TGA. The nucleotide sequence of this SLC39A5 variant cDNA molecule is set forth in SEQ ID NO:19. Another variant cDNA molecule of SLC39A5 exists, wherein the cytosine at position 1,161 according to SEQ ID NO:15 is replaced with thymine, and the CGA codon at positions 1,161 to 1,163 according to SEQ ID NO:15 is replaced with TGA. The nucleotide sequence of this SLC39A5 variant cDNA molecule is set forth in SEQ ID NO:21.

The amino acid sequence of an SLC39A5 reference polypeptide is set forth in SEQ ID NO:22. Referring to SEQ ID NO:22, the SLC39A5 reference polypeptide is 540 amino acids in length. Referring to SEQ ID NO:22, position 304 is methionine. Referring to SEQ ID NO:22, position 413 is glycine. Referring to SEQ ID NO:22, position 47 is tyrosine. Referring to SEQ ID NO:22, position 322 is an arginine. Referring to SEQ ID NO:22, position 311 is an arginine.

An SLC39A5 variant polypeptide exists (M304T or Met304Thr), the amino acid sequence of which is set forth in SEQ ID NO:24. Referring to SEQ ID NO:24, the SLC39A5 variant polypeptide is 540 amino acids in length. Referring to SEQ ID NO:24, position 304 is threonine. Another SLC39A5 variant polypeptide exists (G413A or Gly413Ala), the amino acid sequence of which is set forth in SEQ ID NO:26. Referring to SEQ ID NO:26, the SLC39A5 variant polypeptide is 540 amino acids in length. Referring to SEQ ID NO:26, position 413 is alanine. An SLC39A5 truncated variant polypeptide exists (Y47Stop or Tyr47Stop), the amino acid sequence of which is set forth in SEQ ID NO:23. Referring to SEQ ID NO:23, the SLC39A5 variant polypeptide is 46 amino acids in length. Referring to SEQ ID NO:23, the SLC39A5 variant polypeptide is truncated at position 46 and does not contain amino acids at positions corresponding to positions 47 to 540 according to SEQ ID NO:22. Another SLC39A5 truncated variant polypeptide exists (R322Stop or Arg322Stop), the amino acid sequence of which is set forth in SEQ ID NO:25. Referring to SEQ ID NO:25, the SLC39A5 variant polypeptide is 321 amino acids in length. Referring to SEQ ID NO:25, the SLC39A5 variant polypeptide is truncated at position 321 and does not contain amino acids at positions corresponding to positions 322 to 540 according to SEQ ID NO:22. Another SLC39A5 truncated variant polypeptide exists (R311Stop or Arg311Stop), the amino acid sequence of which is set forth in SEQ ID NO:27. Referring to SEQ ID NO:27, the SLC39A5 variant polypeptide is 310 amino acids in length. Referring to SEQ ID NO:27, the SLC39A5 variant polypeptide is truncated at position 310 and does not contain amino acids at positions corresponding to positions 311 to 540 according to SEQ ID NO:22.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence (such as, for example, SEQ ID NO:1, SEQ ID NO:8, or SEQ ID NO:15). In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

For example, a nucleic acid molecule comprising a nucleotide sequence encoding a human SLC39A5 polypeptide, wherein the nucleotide sequence comprises a cytosine at a position corresponding to position 5,604 according to SEQ ID NO:4 means that if the nucleotide sequence of the SLC39A5 genomic nucleic acid molecule is aligned to the sequence of SEQ ID NO:4, the SLC39A5 sequence has a cytosine residue at the position that corresponds to position 5,604 according to SEQ ID NO:4. The same applies for mRNA molecules comprising a nucleotide sequence encoding a human SLC39A5 polypeptide, wherein the nucleotide sequence comprises a cytosine at a position corresponding to position 1,141 according to SEQ ID NO:11, and cDNA molecules comprising a nucleotide sequence encoding a human SLC39A5 polypeptide, wherein the nucleotide sequence comprises a cytosine at a position corresponding to position 1,141 according to SEQ ID NO:18. In other words, these phrases refer to a nucleic acid molecule encoding an SLC39A5 polypeptide, wherein the genomic nucleic acid molecule has a nucleotide sequence that comprises a cytosine residue that is homologous to the cytosine residue at position 5,604 according to SEQ ID NO:4 (or wherein the mRNA molecule has a nucleotide sequence that comprises a cytosine residue that is homologous to the cytosine residue at position 1,141 according to SEQ ID NO:11, or wherein the cDNA molecule has a nucleotide sequence that comprises a cytosine residue that is homologous to the cytosine residue at position 1,141 according to SEQ ID NO:18). Herein, such a sequence is also referred to as "SLC39A5 sequence with the M304I alteration" or "SLC39A5 sequence with the M304I variation" referring to genomic nucleic acid molecules (or "SLC39A5 sequence with the U1,141C alteration" or "SLC39A5 sequence with the U1,141C variation" referring to mRNA molecules, and "SLC39A5 sequence with the T1,141C alteration" or "SLC39A5 sequence with the T1,141C variation" referring to cDNA molecules).

As described herein, a position within an SLC39A5 genomic nucleic acid molecule that corresponds to position 5,604 according to SEQ ID NO:4, for example, can be identified by performing a sequence alignment between the nucleotide sequence of a particular SLC39A5 nucleic acid molecule and the nucleotide sequence of SEQ ID NO:4. A variety of computational algorithms exist that can be used for performing a sequence alignment to identify a nucleotide position that corresponds to, for example, position 5,604 in SEQ ID NO:4. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence alignments may be performed. However, sequences can also be aligned manually.

The present disclosure also provides therapeutic agents that treat or inhibit increased serum glucose level and/or hyperglycemia for use in the treatment of increased serum glucose level and/or hyperglycemia (or for use in the preparation of a medicament for treating increased serum glucose level and/or hyperglycemia) in a human subject, wherein the human subject has: a genomic nucleic acid molecule having a nucleotide sequence encoding a human SLC39A5 polypeptide, wherein the nucleotide sequence comprises a cytosine at a position corresponding to position 5,604 according to SEQ ID NO:4, or the complement thereof; an mRNA molecule having a nucleotide sequence encoding a human SLC39A5 polypeptide, wherein the nucleotide sequence comprises a cytosine at a position corresponding to position 1,141 according to SEQ ID NO:11, or the complement thereof; a cDNA molecule having a nucleotide sequence encoding a human SLC39A5 polypeptide, wherein the nucleotide sequence comprises a cytosine at a position corresponding to position 1,141 according to SEQ ID NO:18, or the complement thereof; or an SLC39A5 polypeptide that comprises a threonine at a position corresponding to position 304 according to SEQ ID NO:24. The therapeutic agents that treat or inhibit increased serum glucose level and/or hyperglycemia can be any of the therapeutic agents that treat or inhibit increased serum glucose level and/or hyperglycemia described herein.

The present disclosure also provides SLC39A5 inhibitors for use in the treatment of increased serum glucose level and/or hyperglycemia (or for use in the preparation of a medicament for treating increased serum glucose level and/or hyperglycemia) in a human subject, wherein the human subject has: a genomic nucleic acid molecule having a nucleotide sequence encoding a human SLC39A5 polypeptide, wherein the nucleotide sequence comprises a cytosine at a position corresponding to position 5,604 according to SEQ ID NO:4, or the complement thereof; an mRNA molecule having a nucleotide sequence encoding a human SLC39A5 polypeptide, wherein the nucleotide sequence comprises a cytosine at a position corresponding to position 1,141 according to SEQ ID NO:11, or the complement thereof; a cDNA molecule having a nucleotide sequence encoding a human SLC39A5 polypeptide, wherein the nucleotide sequence comprises a cytosine at a position corresponding to position 1,141 according to SEQ ID NO:18, or the complement thereof; or an SLC39A5 polypeptide that comprises a threonine at a position corresponding to position 304 according to SEQ ID NO:24. The SLC39A5 inhibitors can be any of the SLC39A5 inhibitors described herein.

In some embodiments, the human subject has: a genomic nucleic acid molecule having a nucleotide sequence encoding a human SLC39A5 polypeptide, wherein the nucleotide sequence comprises a cytosine at a position corresponding to position 6,899 according to SEQ ID NO:6, or the complement thereof; an mRNA molecule having a nucleotide sequence encoding a human SLC39A5 polypeptide, wherein the nucleotide sequence comprises a cytosine at a position corresponding to position 1,468 according to SEQ ID NO:13, or the complement thereof; a cDNA molecule having a nucleotide sequence encoding a human SLC39A5 polypeptide, wherein the nucleotide sequence comprises a cytosine at a position corresponding to position 1,468 according to SEQ ID NO:20, or the complement thereof; or an SLC39A5 polypeptide that comprises a alanine at a position corresponding to position 413 according to SEQ ID NO:26.

In some embodiments, the human subject has: a genomic nucleic acid molecule having a nucleotide sequence encoding a human SLC39A5 polypeptide, wherein the nucleotide sequence comprises an adenine or guanine at a position corresponding to position 1,353 according to SEQ ID NO:2 or SEQ ID NO:3, or the complement thereof; an mRNA molecule having a nucleotide sequence encoding a human SLC39A5 polypeptide, wherein the nucleotide sequence comprises an adenine or guanine at a position corresponding to position 371 according to SEQ ID NO:9 or SEQ ID NO:10, or the complement thereof; a cDNA molecule having a nucleotide sequence encoding a human SLC39A5 polypeptide, wherein the nucleotide sequence comprises an adenine or guanine at a position corresponding to position 371 according to SEQ ID NO:16 or SEQ ID NO:17, or the complement thereof; or an SLC39A5 polypeptide that is truncated at position 46 according to SEQ ID NO:23 and does not contain amino acids at positions corresponding to positions 47 to 540 according to SEQ ID NO:22.

In some embodiments, the human subject has: a genomic nucleic acid molecule having a nucleotide sequence encoding a human SLC39A5 polypeptide, wherein the nucleotide sequence comprises a thymine at a position corresponding to position 6,352 according to SEQ ID NO:5, or the complement thereof; an mRNA molecule having a nucleotide sequence encoding a human SLC39A5 polypeptide, wherein the nucleotide sequence comprises a uracil at a position corresponding to position 1,194 according to SEQ ID NO:12, or the complement thereof; a cDNA molecule having a nucleotide sequence encoding a human SLC39A5 polypeptide, wherein the nucleotide sequence comprises a thymine at a position corresponding to position 1,194 according to SEQ ID NO:19, or the complement thereof; or an SLC39A5 polypeptide that is truncated at position 321 according to SEQ ID NO:25 and does not contain amino acids at positions corresponding to positions 322 to 540 according to SEQ ID NO:22.

In some embodiments, the human subject has: a genomic nucleic acid molecule having a nucleotide sequence encoding a human SLC39A5 polypeptide, wherein the nucleotide sequence comprises a thymine at a position corresponding to position 5,624 according to SEQ ID NO:7, or the complement thereof; an mRNA molecule having a nucleotide sequence encoding a human SLC39A5 polypeptide, wherein the nucleotide sequence comprises a uracil at a position corresponding to position 1,161 according to SEQ ID NO:14, or the complement thereof; a cDNA molecule having a nucleotide sequence encoding a human SLC39A5 polypeptide, wherein the nucleotide sequence comprises a thymine at a position corresponding to position 1,161 according to SEQ ID NO:21, or the complement thereof; or an SLC39A5 polypeptide that is truncated at position 310 according to SEQ ID NO:27 and does not contain amino acids at positions corresponding to positions 311 to 540 according to SEQ ID NO:22.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: SLC39A5 is Localized to the Cell-Surface and Mediates Zinc-Dependent Transcriptional Responses The SLC39A5 gene was expressed using the IRES-dsRED reporter system transfected into cells, and the expression was verified. One day after transfection, the cells were shifted to Zn-free media, and a day later were perfused with buffer containing (0-1 mM) free $Zn^{2+}$ with or without TREN/Zn-Pyr (a cell permeable, high-affinity heavy metal ($Zn^{2+}>Fe^{2+}>Mn^{2+}$) chelator that exhibits low affinity for $Mg^{2+}$ and $Ca^{2+}$). The zinc-dependent transcriptional responses were monitored through expression of luciferase reporter gene driven by a metal responsive element (MRE). The results showed that SLC35 is required for $Zn^{2+}$ mediated MRE activation.

Example 2: Truncating Variants in SLC39A5 Result in Loss-Of-Function

Figure 1B:
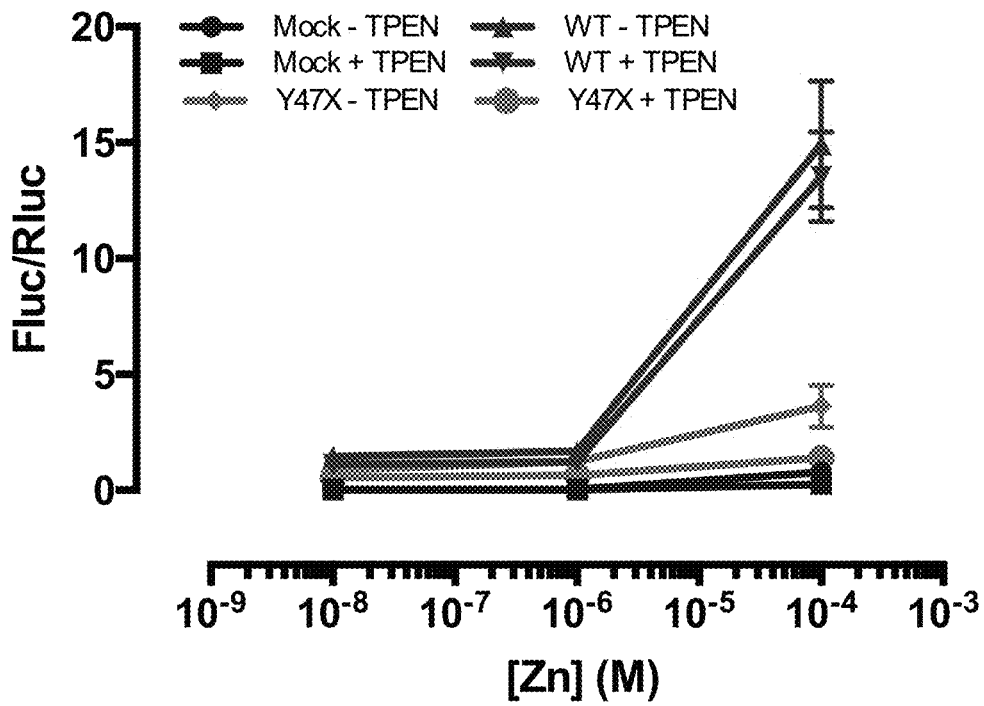
FIG. 1B shows that SLC39A5 mutations result in loss of function.
Figure 1B:
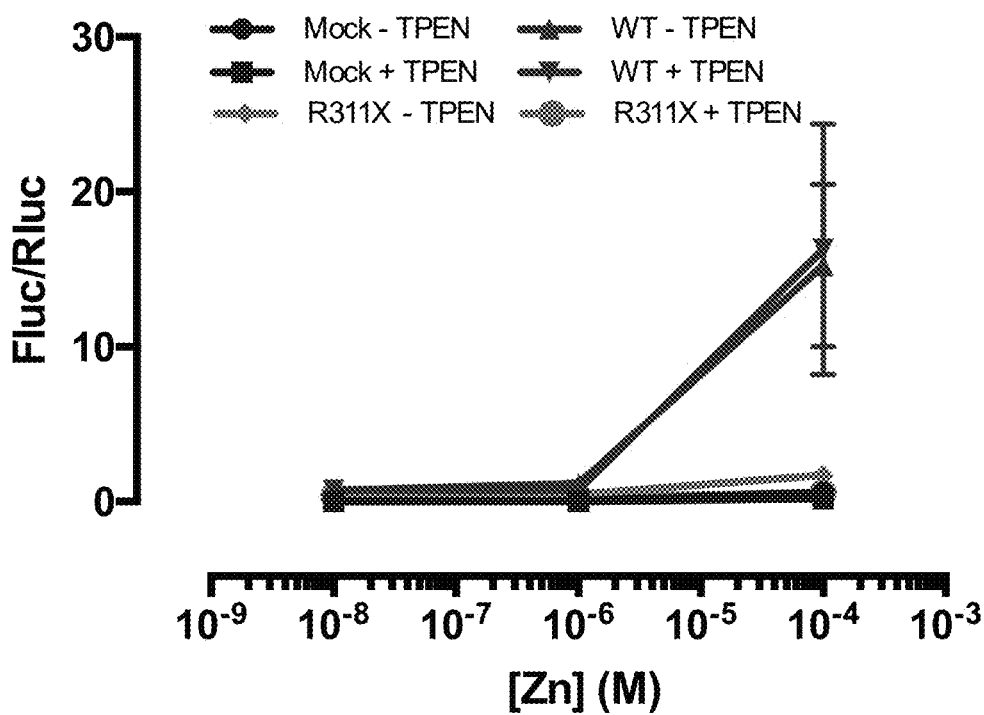
Figure 1B:
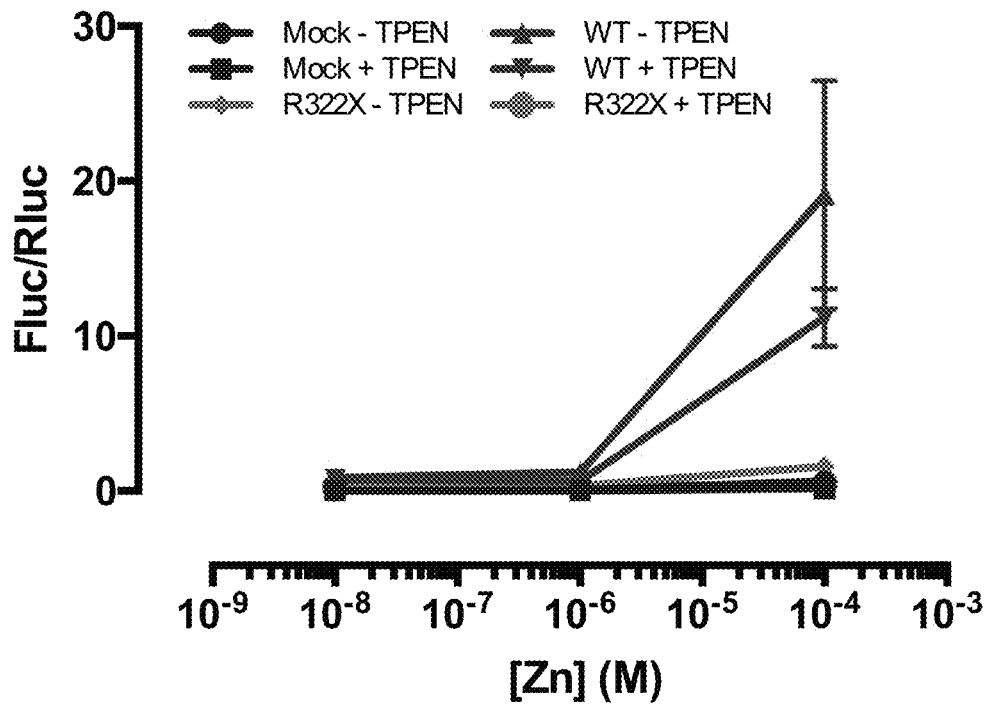
Figure 1B:
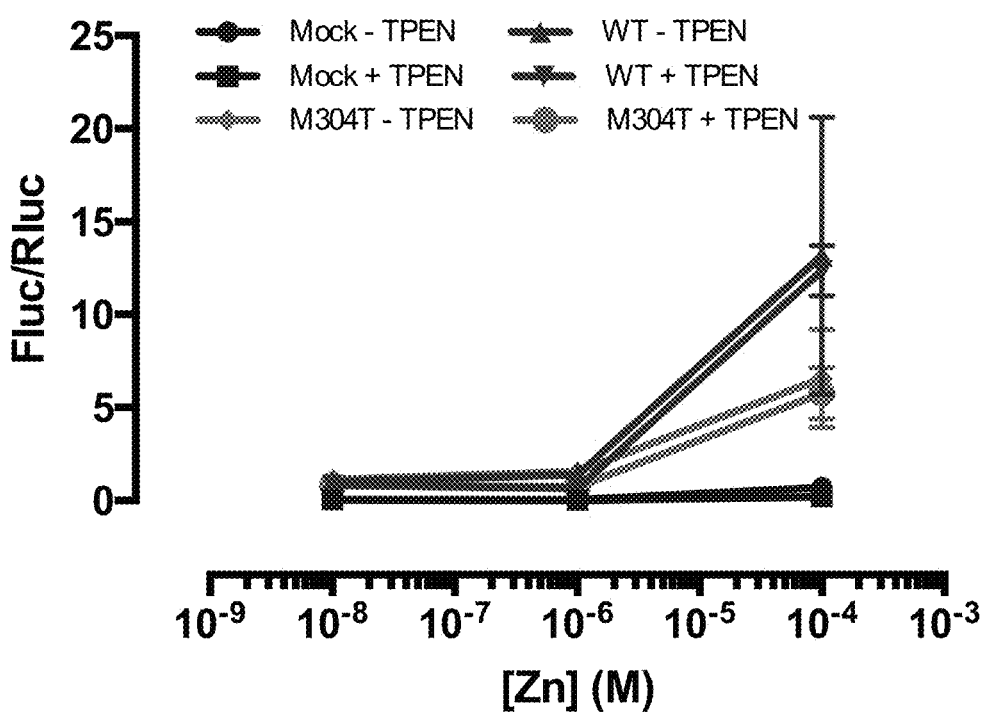

The functionality of several SLC39A5 variants (Y47× (Y47Stop), R311× (R311Stop), R322× (R322Stop), and M304T; Table 2) was examined using $Zn^{2+}$ mediated MRE activation. The results (FIGS. 1A and 1B) show that truncation variants display complete loss-of-function, while the substitution of methionine with threonine at position 304 of the SLC39A5 protein resulted in partial loss-of-function.

TABLE 2

| SLC39A5 Variants | | | |
|---|---|---|---|
| rsID | HGVS.c | HGVS.p | Protein Domain |
| rs148112570 | c.141C > A | p.Y47* | Ectodomain (21-212) |
| | c.141C > G | p.Y47* | Ectodomain (21-212) |
| | c.911T > C | p.M304T | TM3 (288-308) |
| | c.964C > T | p.R322* | Cytodomain (309-444) |
| | c.1238G > C | p.G413A | Cytodomain (309-444) |
| | c.932C > T | p.R311* | Cytodomain (309-444) |

Figure 2A:
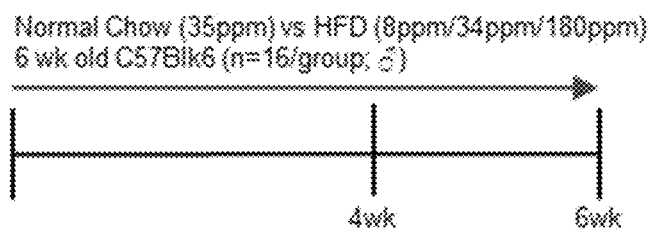
FIG. 2A shows a timeline of experiment testing zinc supplementation rescue of hepatic steatosis and glucose tolerance.
Figure 2B:
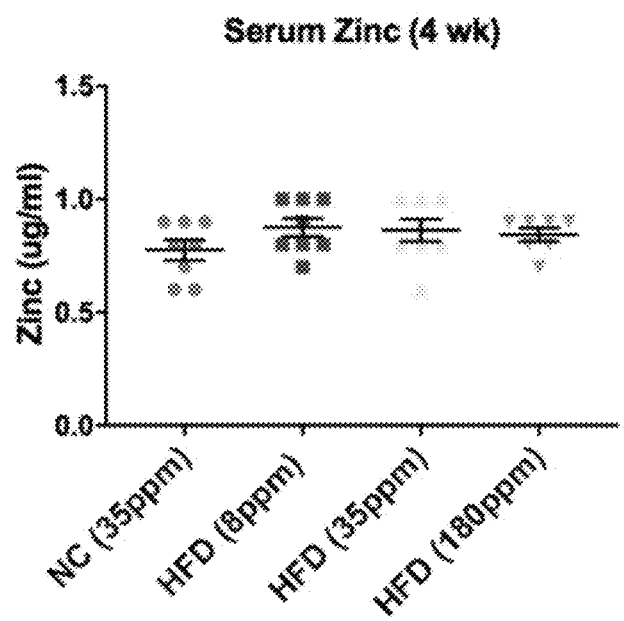
FIG. 2B shows serum zinc levels in mice following a 4-week high fat diet with or without zinc supplementation.
Figure 2C:
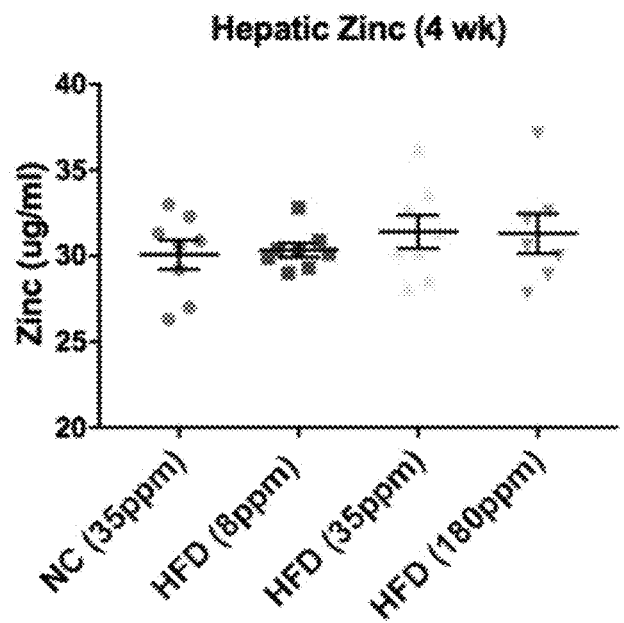
FIG. 2C shows hepatic zinc levels in mice following a 4-week high fat diet with or without zinc supplementation.
Figure 2D:
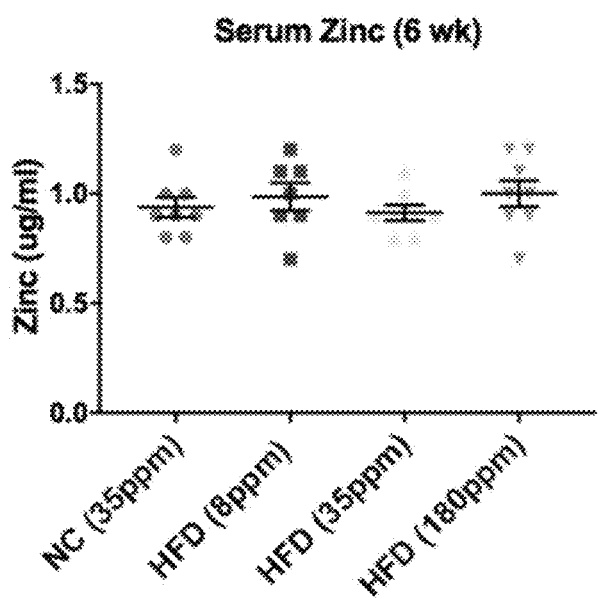
FIG. 2D shows serum zinc levels in mice following a 6-week high fat diet with or without zinc supplementation.
Figure 2E:
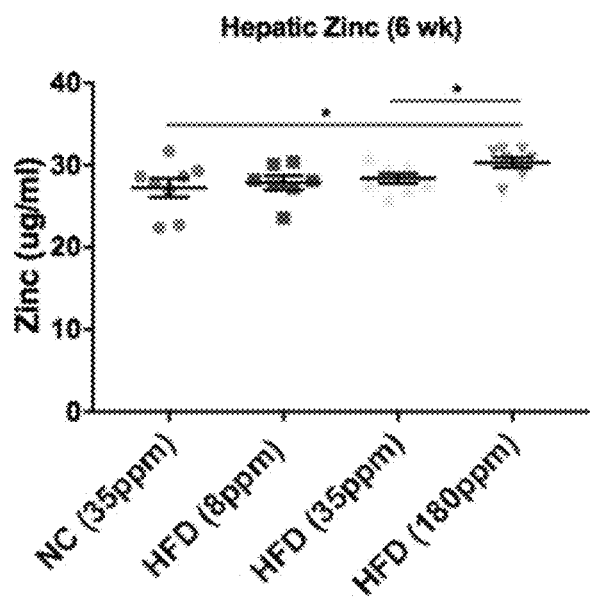
FIG. 2E shows hepatic zinc levels in mice following a 6-week high fat diet with or without zinc supplementation.

Example 3: Zinc Supplementation Rescues Hepatic Steatosis and Glucose Tolerance in DIO Four groups of 6-week old male mice (16 per group) were fed either normal chow or high fat diets supplemented with different zinc concentrations for either 4 or 6 weeks (FIG. 2A). The levels of zinc were analyzed after 4 weeks (FIGS. 2B and 2C) and after 6 weeks (FIGS. 2D and 2E). While there was no significant change in serum zinc levels (FIGS. 2B and 2D), or in hepatic zinc levels after 4 weeks (FIG. 2C), there was a statistically significant increase in hepatic zinc levels after 6 weeks (FIG. 2E) that correlated with the level of zinc in the diet.

Figure 3A:
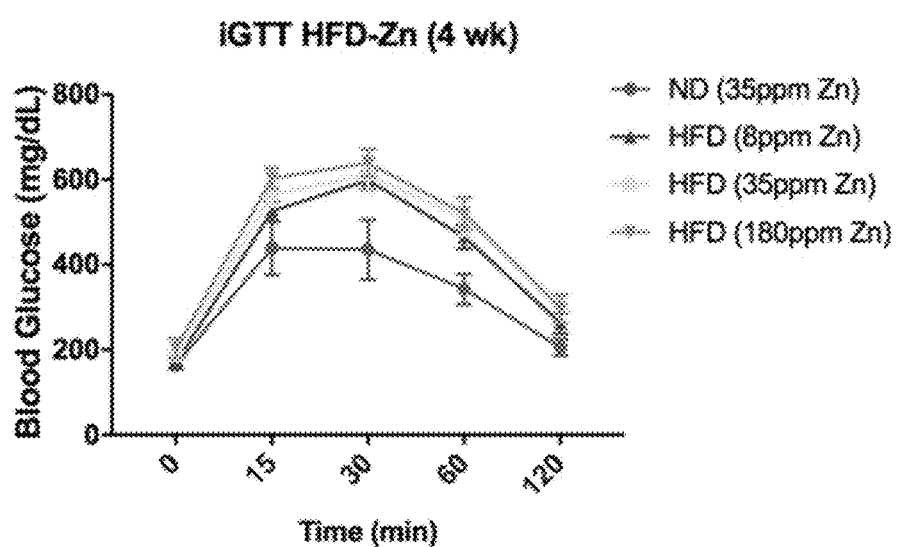
FIG. 3A shows intravenous glucose tolerance test results in mice following a 4-week high fat diet with or without zinc supplementation.
Figure 3B:
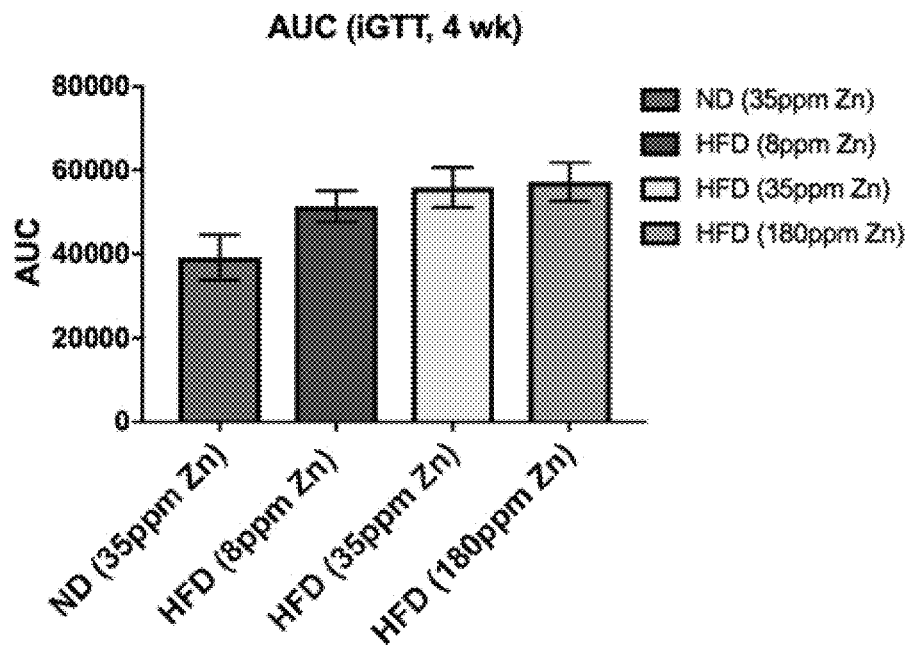
FIG. 3B shows area under the curve in mice following a 4-week high fat diet with or without zinc supplementation.
Figure 3C:
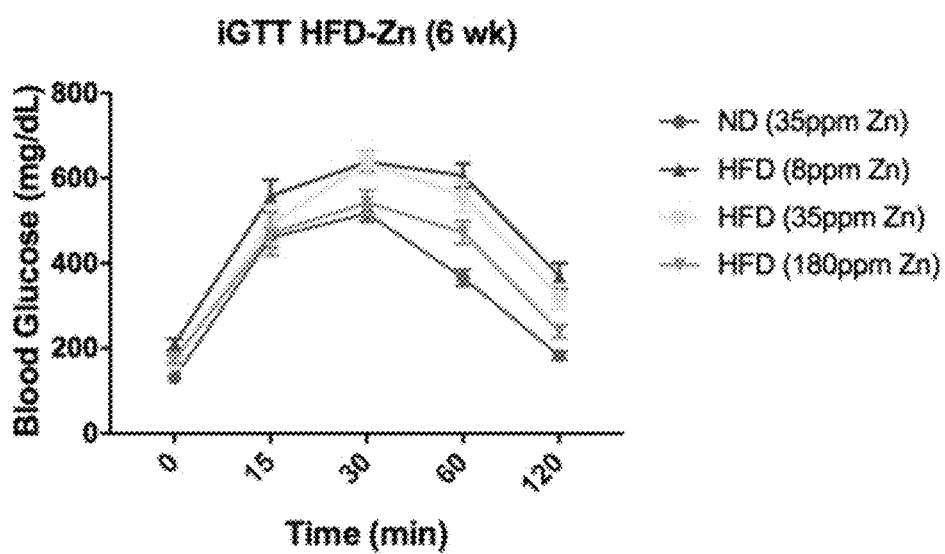
FIG. 3C shows intravenous glucose tolerance test results in mice following a 6-week high fat diet with or without zinc supplementation.
Figure 3D:
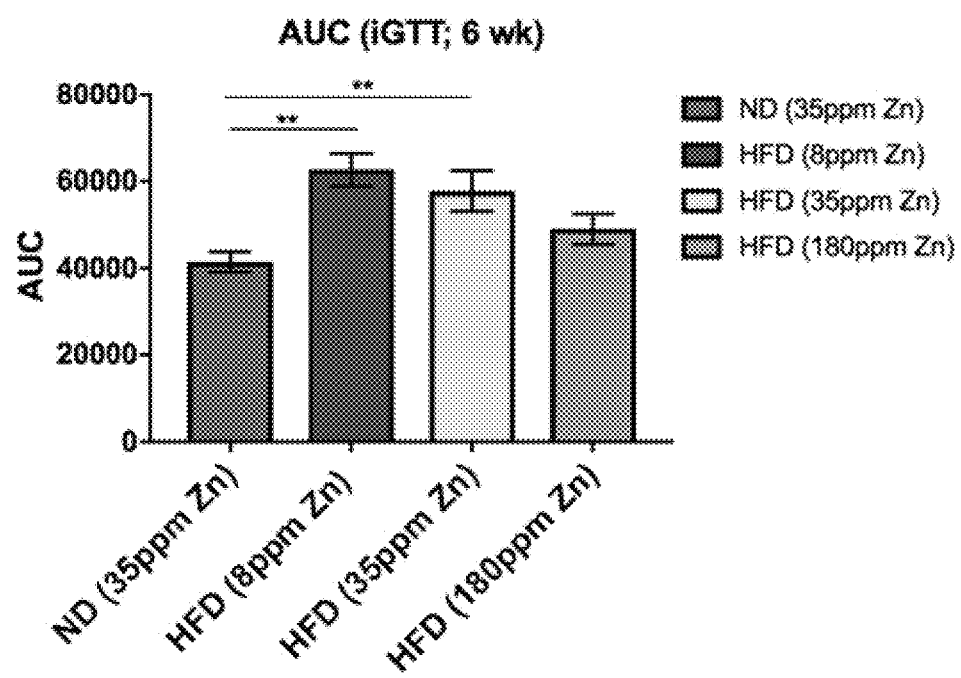
FIG. 3D shows area under the curve in mice following a 6-week high fat diet.
Figure 4:
FIG. 4 shows micrographs of mouse liver cross-sections following high fat diet with or without zinc supplementation.

The intravenous glucose tolerance tests (FIGS. 3A and 3C) showed that increasing diet zinc concentration mitigated blood glucose increase mediated by high fat diet, and reduced area under the curve (FIGS. 3B and 3D), although this effect was not statistically significant. The microscopic analysis of mouse liver showed that supplementing high fat diet with zinc reverses fat accumulation in liver (FIG. 4).

Figure 5A:
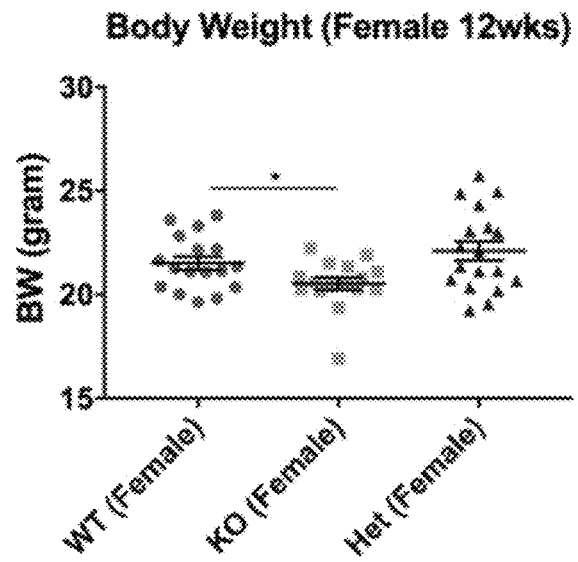
FIG. 5A shows body weights of 12-week old female mice having heterozygous or homozygous knockout of SLC39A5.
Figure 5B:
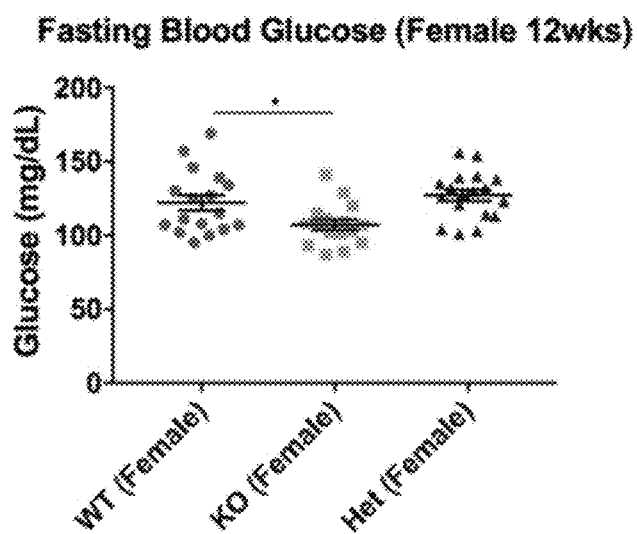
FIG. 5B shows fasting blood glucose levels in 12-week old female mice having heterozygous or homozygous knockout of SLC39A5.
Figure 5C:
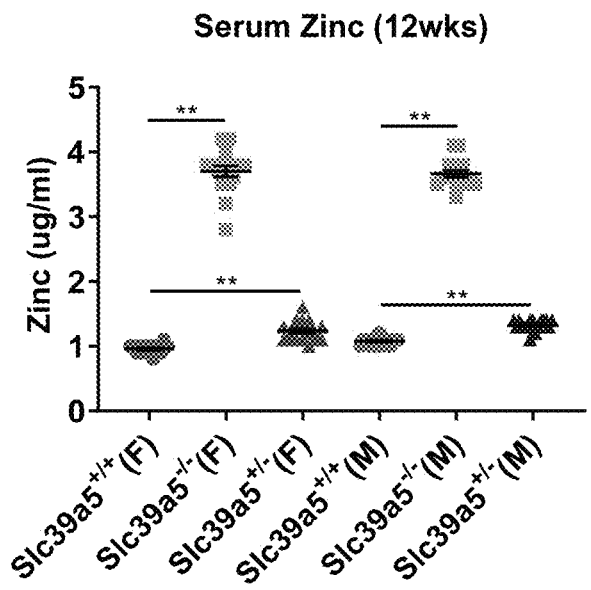
FIG. 5C shows serum zinc levels in 12-week old male and female mice having heterozygous or homozygous knockout of SLC39A5.
Figure 5D:
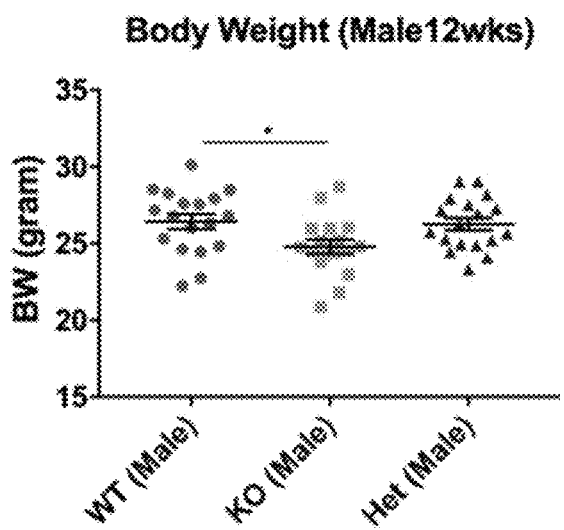
FIG. 5D shows body weights of 12-week old male mice having heterozygous or homozygous knockout of SLC39A5.
Figure 5E:
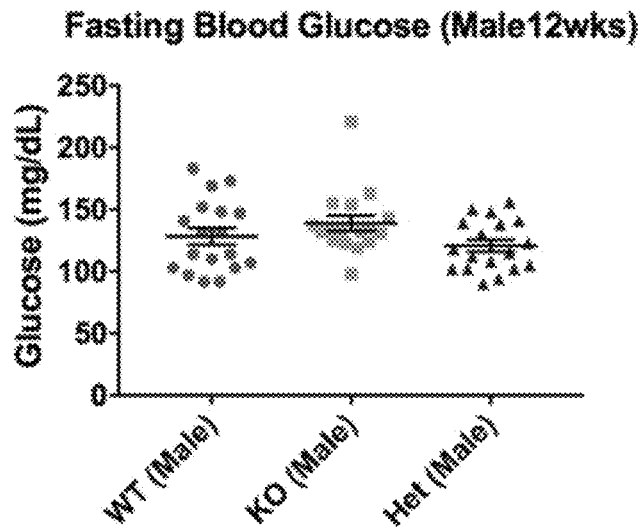
FIG. 5E shows fasting blood glucose levels in 12-week old male mice having heterozygous or homozygous knockout of SLC39A5.
Figure 5F:
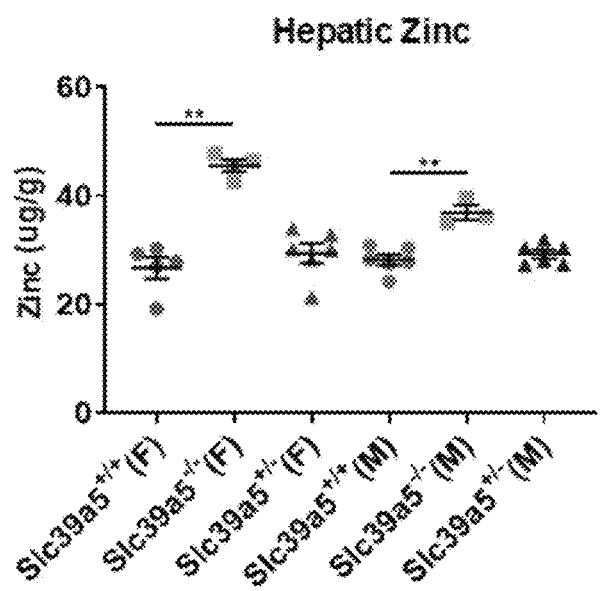
FIG. 5F shows hepatic zinc levels in 12-week old male and female mice having heterozygous or homozygous knockout of SLC39A5.
Figure 6A:
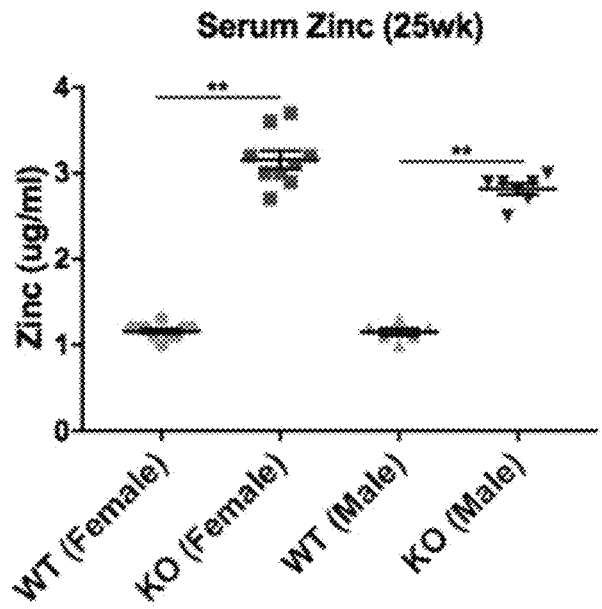
FIG. 6A shows serum zinc levels after 25 week of high fat diet in 31-week old mice having knockout of SLC39A5.
Figure 6B:
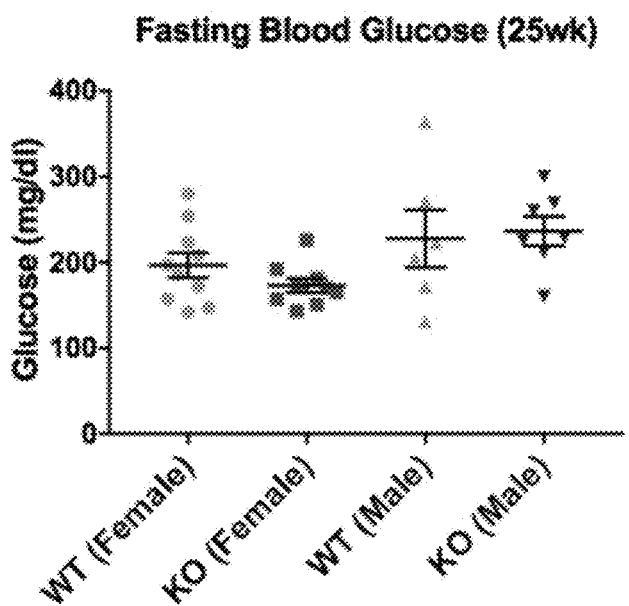
FIG. 6B shows fasting blood glucose levels after 25 weeks of high fat diet in 31-week old mice having knockout of SLC39A5.
Figure 6C:
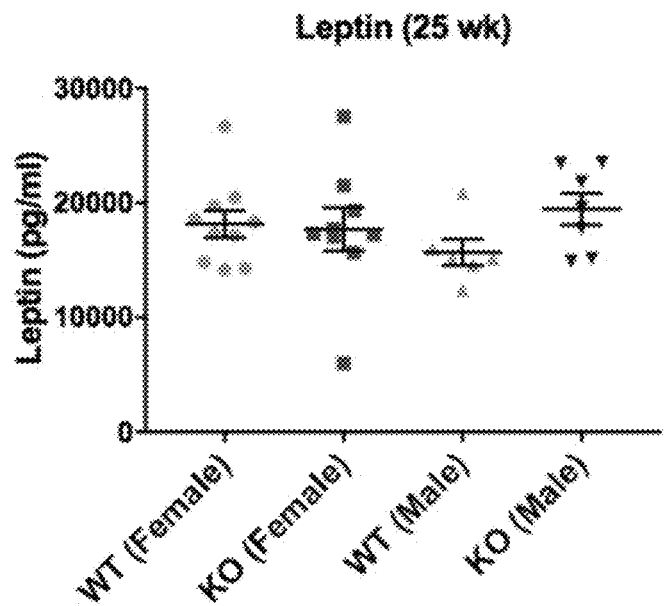
FIG. 6C shows leptin levels after 25 weeks of high fat diet in 31-week old mice having knockout of SLC39A5.
Figure 6D:
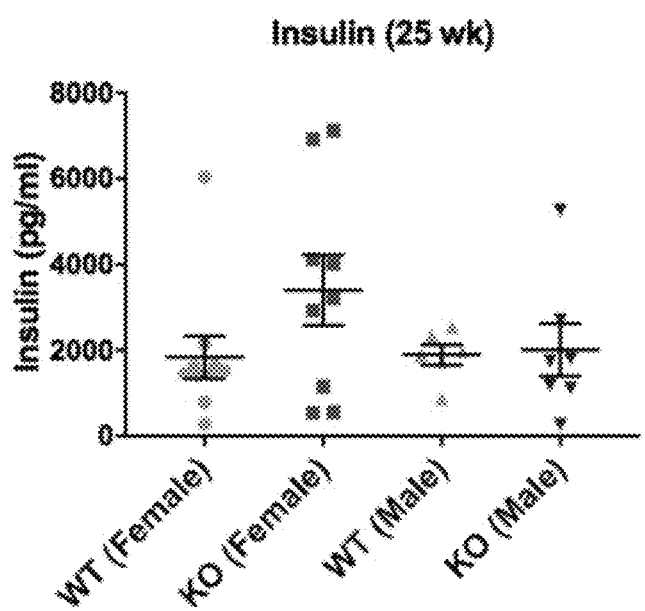
FIG. 6D shows insulin levels after 25 weeks of high fat diet in 31-week old mice having knockout of SLC39A5.
Figure 6E:
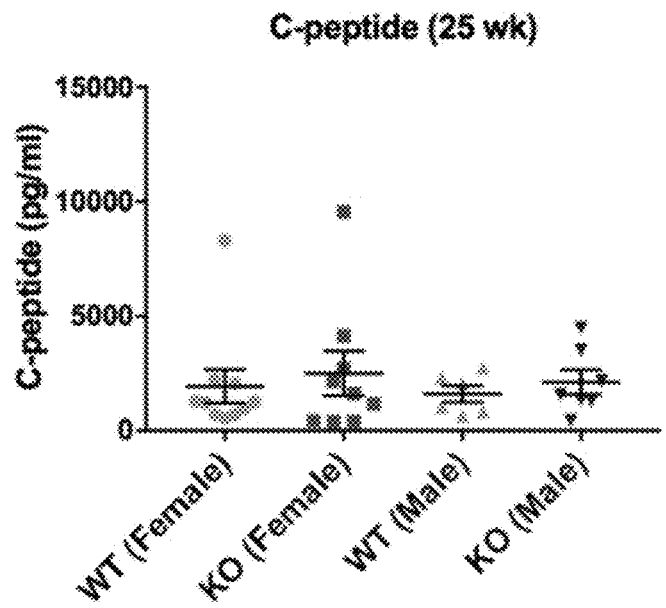
FIG. 6E shows c-peptide levels after 25 weeks of high fat diet in 31-week old mice having knockout of SLC39A5.
Figure 6F:
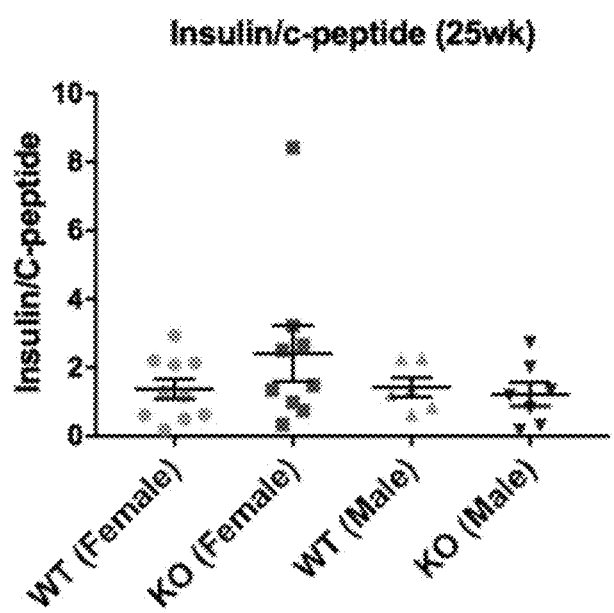
FIG. 6F shows insulin/c-peptide ratios after 25 weeks of high fat diet in 31-week old mice having knockout of SLC39A5.
Figure 9A:
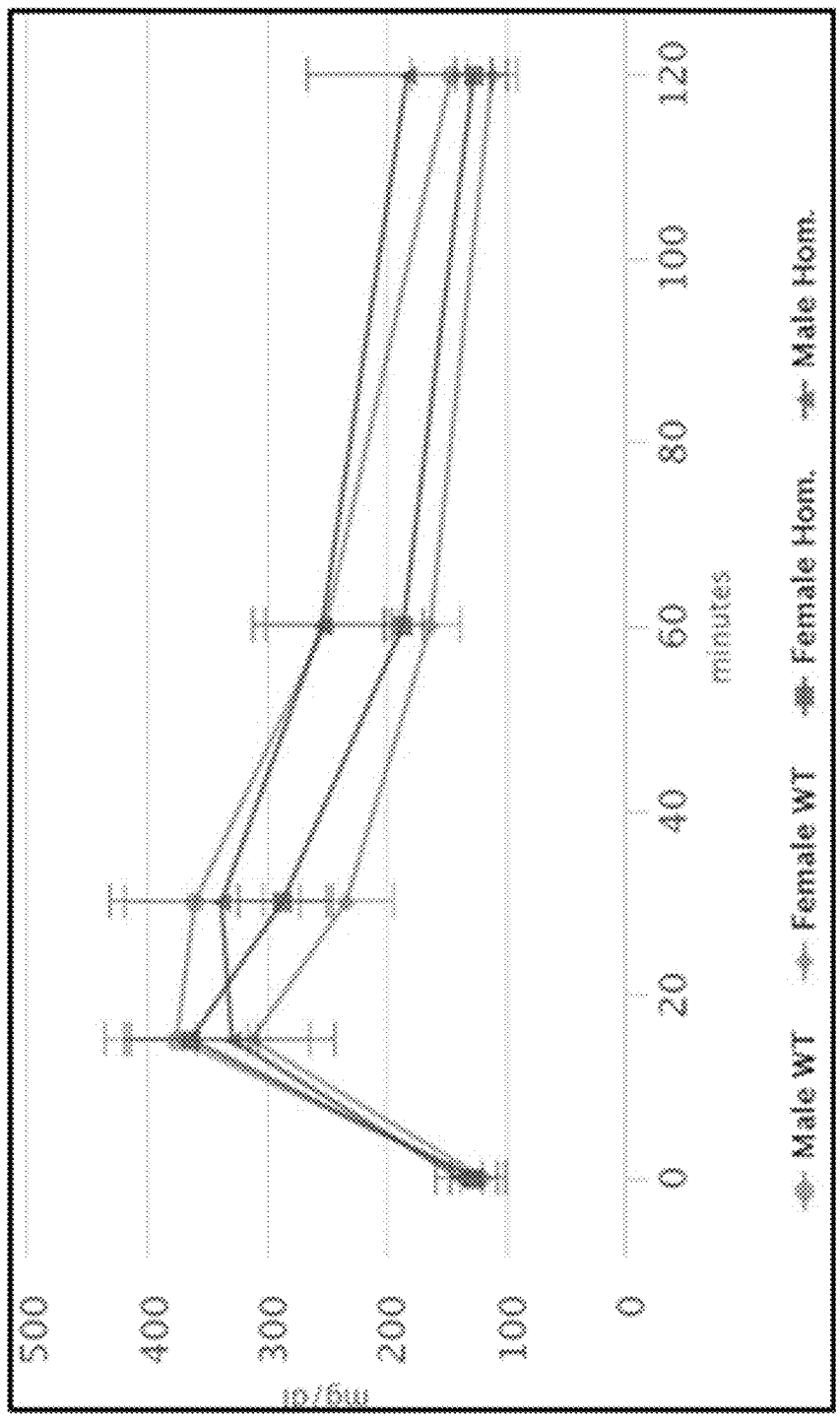
FIG. 9A shows intravenous glucose tolerance test results in SLC39A5 knockout mice following a 14-week high fat diet.
Figure 9B:
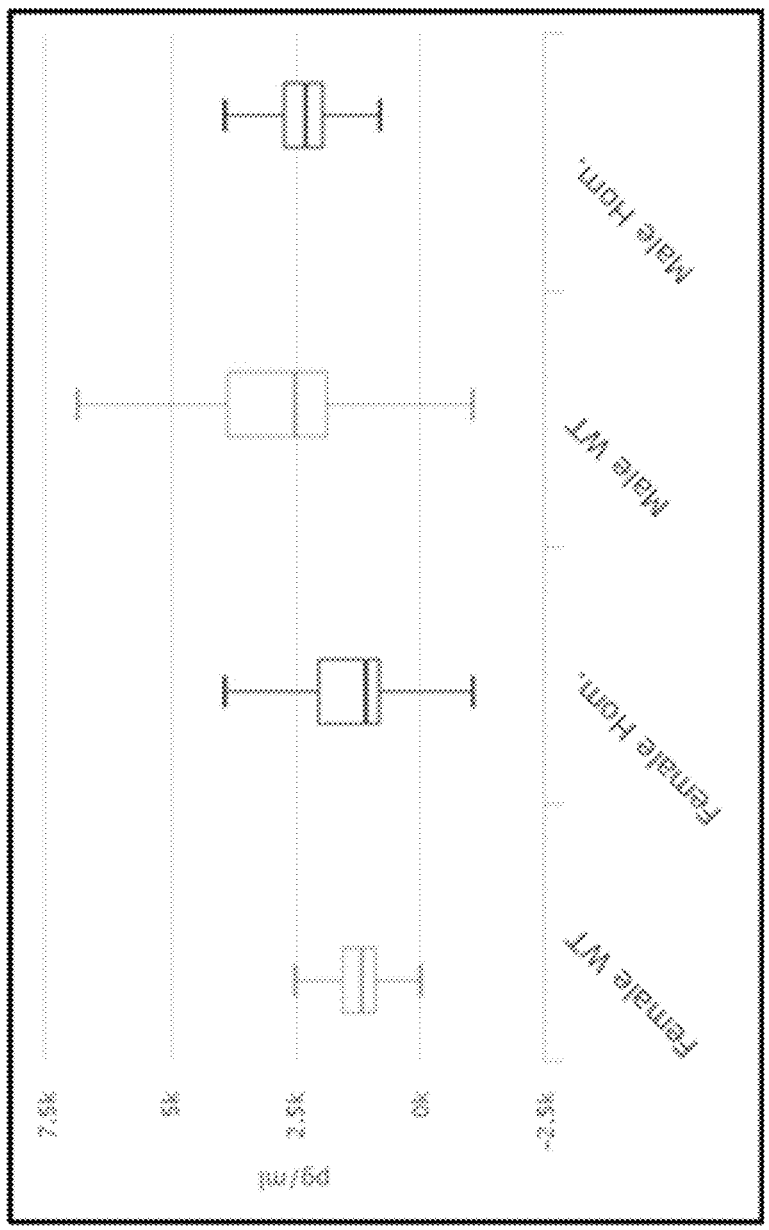
FIG. 9B shows insulin blood levels in SLC39A5 knockout mice following a 16-week high fat diet.

Example 4: Loss of Slc39a5 Results in Modest Reduction in Fasting Blood Glucose in Female Mice The effect of homologous and heterologous SLC39A knockout was examined in 12 week old male and female mice. The results show that statistically significant reduction in body weight for both male (FIG. 5D) and female (FIG. 5A) homologous SLC39A knockout mice. Homologous SLC39A knockout also resulted in statistically significant serum zinc (FIG. 5C) and hepatic zinc (FIG. 5F) increase in both male and female mice. However, only female homologous SLC39A knockout mice displayed statistically significant reduction in blood glucose (FIG. 5B). In contrast, no statistically significant changes of mean blood glycose levels were observed after 14 weeks of high fat diet (FIG. 9A), or in non-fasting/terminal insulin blood level after 146 weeks of high fat diet (FIG. 9B).

Example 5: Loss of Slc39a5 Results in Elevated Circulating Zinc Levels

Circulating zinc, glucose, leptin, insulin and C-peptide levels were examined in 31 week old male and female homologous SLC39A knockout mice following 25 weeks of high fat diet. No statistically significant changes were observed for any parameters except for serum zinc levels (FIGS. 6A-F).

Figure 7A:
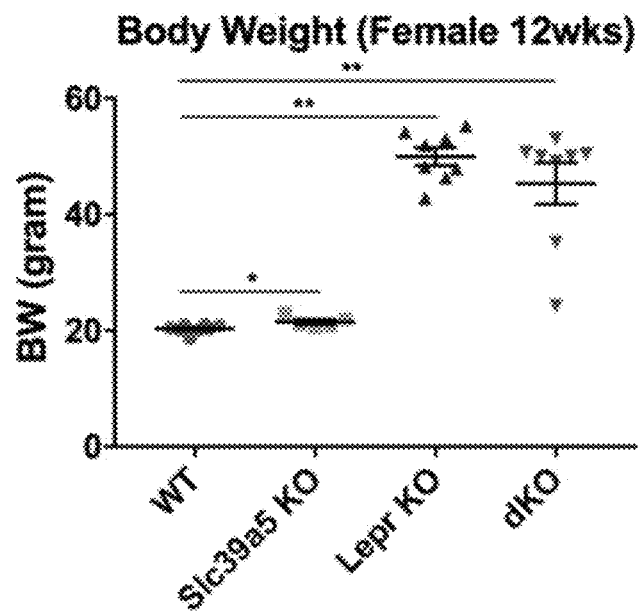
FIG. 7A shows body weights of 12-week old female mice having SLC39A5 knockout, leptin receptor (LEPR) knockout, or double SLC39A5/LEPR knockout.
Figure 7B:
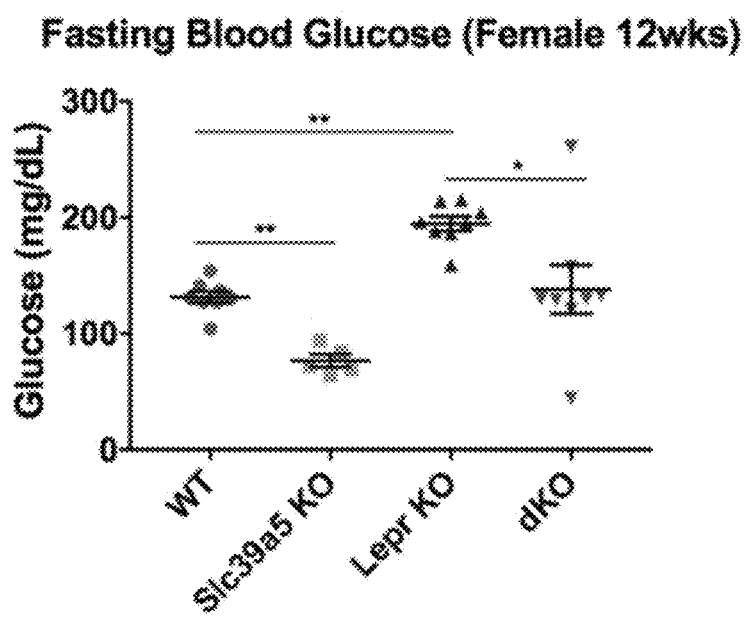
FIG. 7B shows fasting blood glucose levels in 12-week old female mice having SLC39A5 knockout, leptin receptor (LEPR) knockout, or double SLC39A5/LEPR knockout.
Figure 7C:
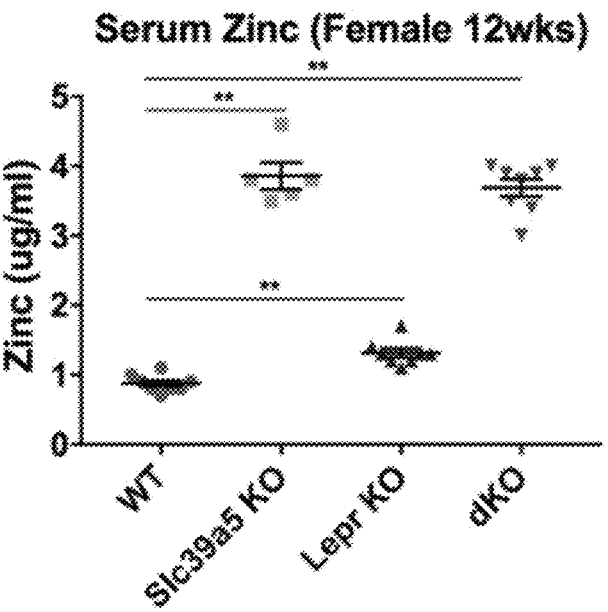
FIG. 7C shows serum zinc levels in 12-week old female mice having SLC39A5 knockout, leptin receptor (LEPR) knockout, or double SLC39A5/LEPR knockout.
Figure 7D:
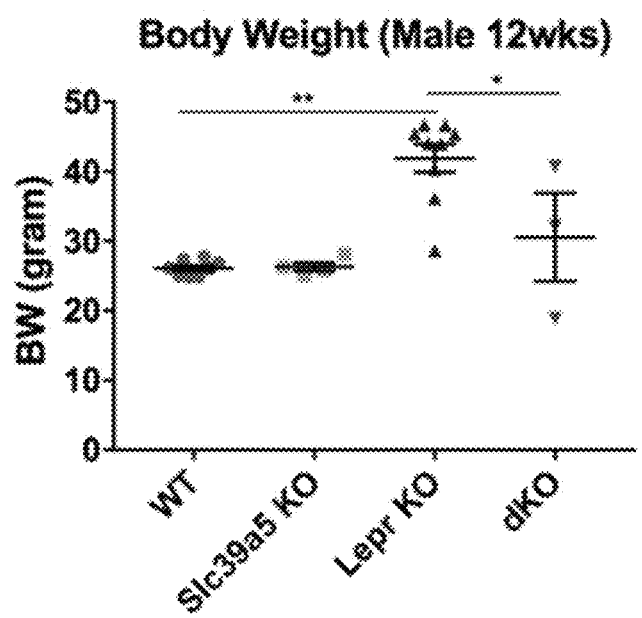
FIG. 7D shows body weights of 12-week old male mice having SLC39A5 knockout, leptin receptor (LEPR) knockout, or double SLC39A5/LEPR knockout.
Figure 7E:
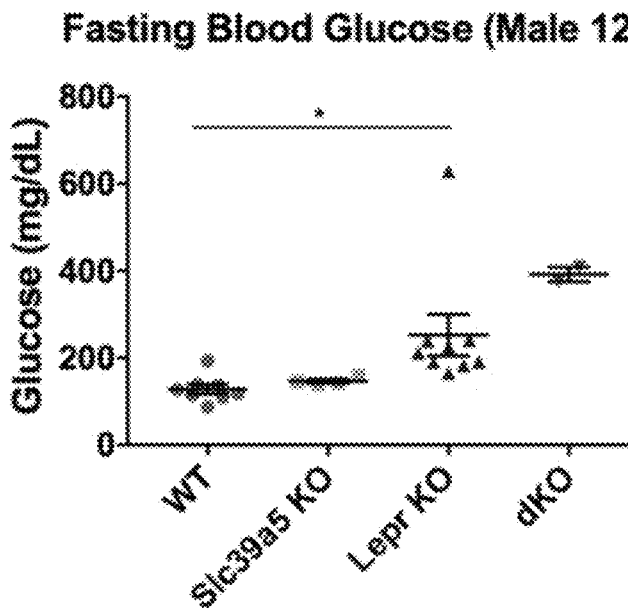
FIG. 7E shows fasting blood glucose levels in 12-week old male mice having SLC39A5 knockout, leptin receptor (LEPR) knockout, or double SLC39A5/LEPR knockout.
Figure 7F:
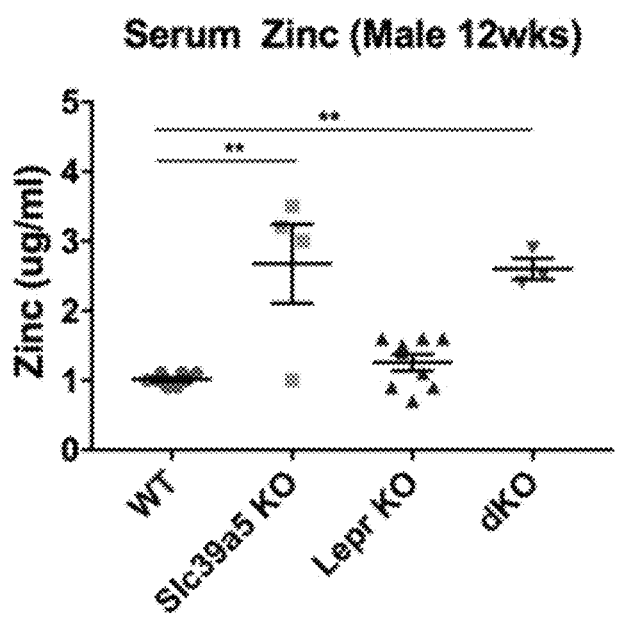
FIG. 7F shows serum zinc levels in 12-week old male mice having SLC39A5 knockout, leptin receptor (LEPR) knockout, or double SLC39A5/LEPR knockout.

Example 6: Slc39a5 LOF Rescues Hyperglycemia in Leptin Receptor Deficient (db/db, Female) Mice Body weight, fasting blood glucose, and serum zinc were examined in 31 week old male and female homologous SLC39A knockout, leptin receptor (Lepr) knockout, or double knockout mice fed normal diet. While all mice showed increase in body weight and fasting blood glucose, the concurrent knockout of SLC39A significantly reversed body weight in male but not female mice (FIGS. 7A and 7D). At the same time, concurrent knockout of SLC39A resulted in fasting blood glucose reduction in female but not male mice (FIGS. 7B and 7E). Lepr knockout had no effect on the increase of serum zinc resulting from SLC39A knockout (FIGS. 7C and 7F).

Figure 8A:
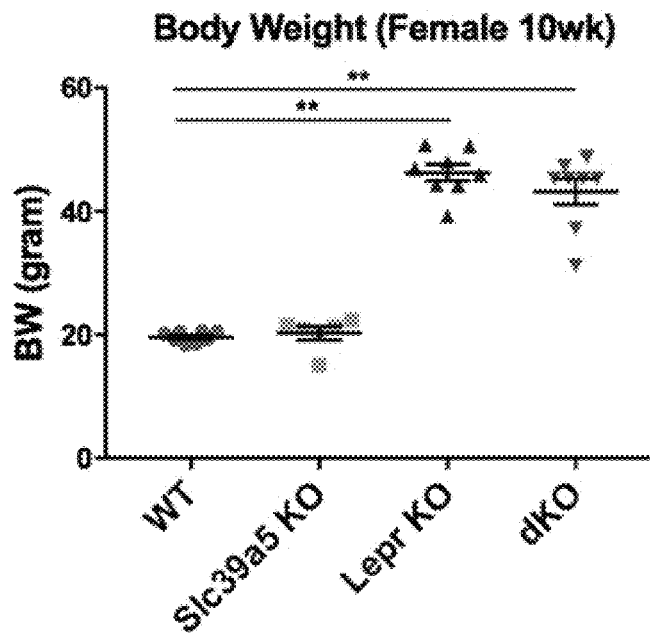
FIG. 8A shows body weights of 10-week old female mice having SLC39A5 knockout, leptin receptor (LEPR) knockout, or double SLC39A5/LEPR knockout.
Figure 8B:
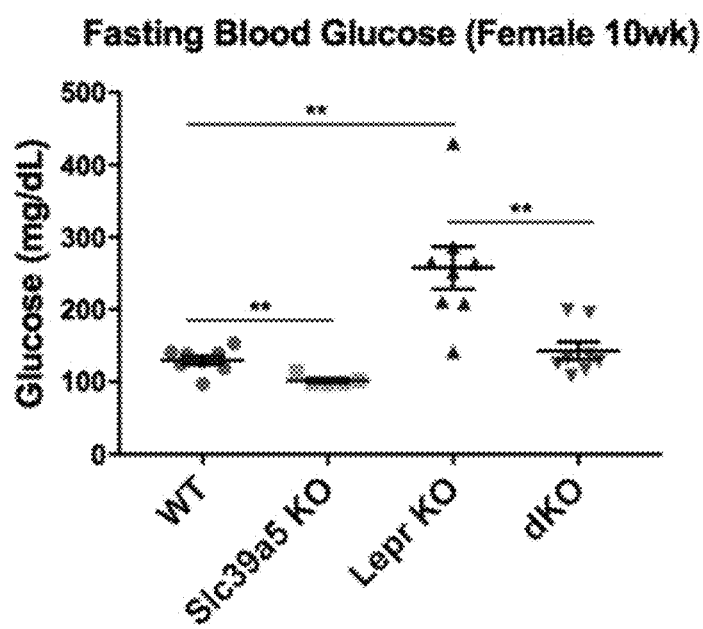
FIG. 8B shows fasting blood glucose levels in 10-week old female mice having SLC39A5 knockout, leptin receptor (LEPR) knockout, or double SLC39A5/LEPR knockout.
Figure 8C:
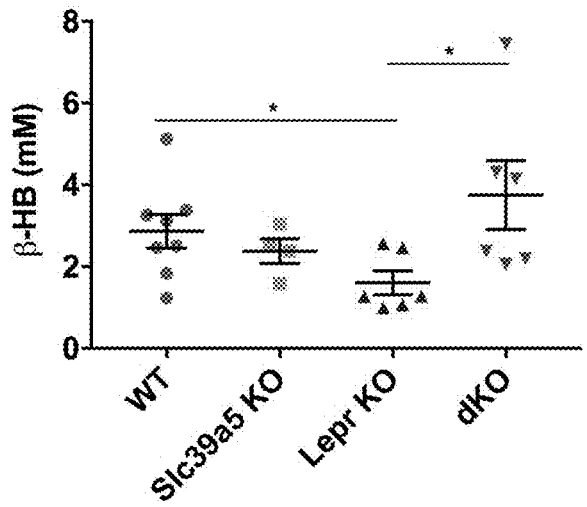
FIG. 8C shows β-hydroxybutyrate levels in 10-week old female mice having SLC39A5 knockout, leptin receptor (LEPR) knockout, or double SLC39A5/LEPR knockout.
Figure 8D:
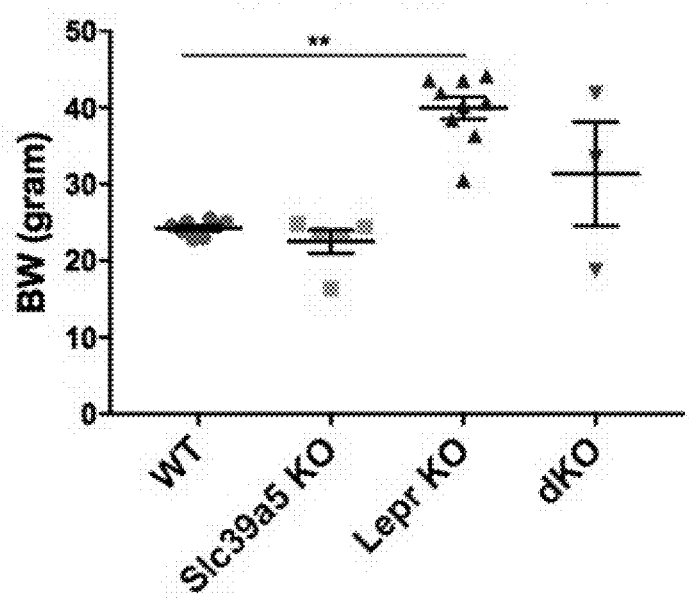
FIG. 8D shows body weights of 10-week old male mice having SLC39A5 knockout, leptin receptor (LEPR) knockout, or double SLC39A5/LEPR knockout.
Figure 8E:
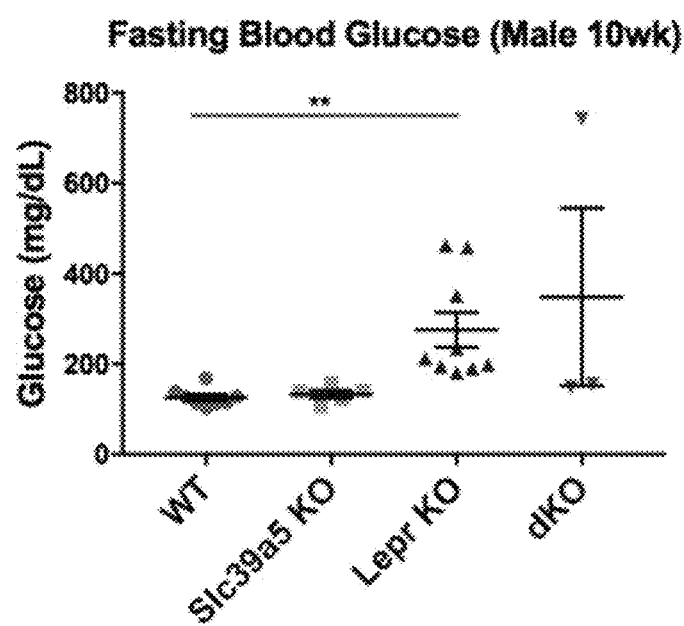
FIG. 8E shows fasting blood glucose levels in 10-week old male mice having SLC39A5 knockout, leptin receptor (LEPR) knockout, or double SLC39A5/LEPR knockout.

Example 7: Slc39a5 LOF Rescues Hyperglycemia in Leptin Receptor Deficient (db/db, Female) Mice with Concomitant Increase in Ketogenesis Body weight, fasting blood glucose, and β-hydroxybutyrate levels were examined in 10 week old male and female homologous SLC39A knockout, leptin receptor (Lepr) knockout, or double knockout mice fed normal diet. All mice showed increase in body weight and fasting blood glucose, and the concurrent knockout of SLC39A had no significant effect on body weight (FIGS. 8A and 8D). At the same time, knockout of SLC39A resulted in fasting blood glucose reduction in female but not male mice both in the presence and in the absence of Lepr knockout (FIGS. 8B and 8E). Both SLC39A knockout and Lepr knockout resulted in reduction of β-hydroxybutyrate levels in female mice, but, surprisingly, when both genes were knocked out this effect was reversed (FIG. 8C).

Example 8: SLC39A5 Heterozygous LOF have Elevated Serum Zinc

Figure 10:
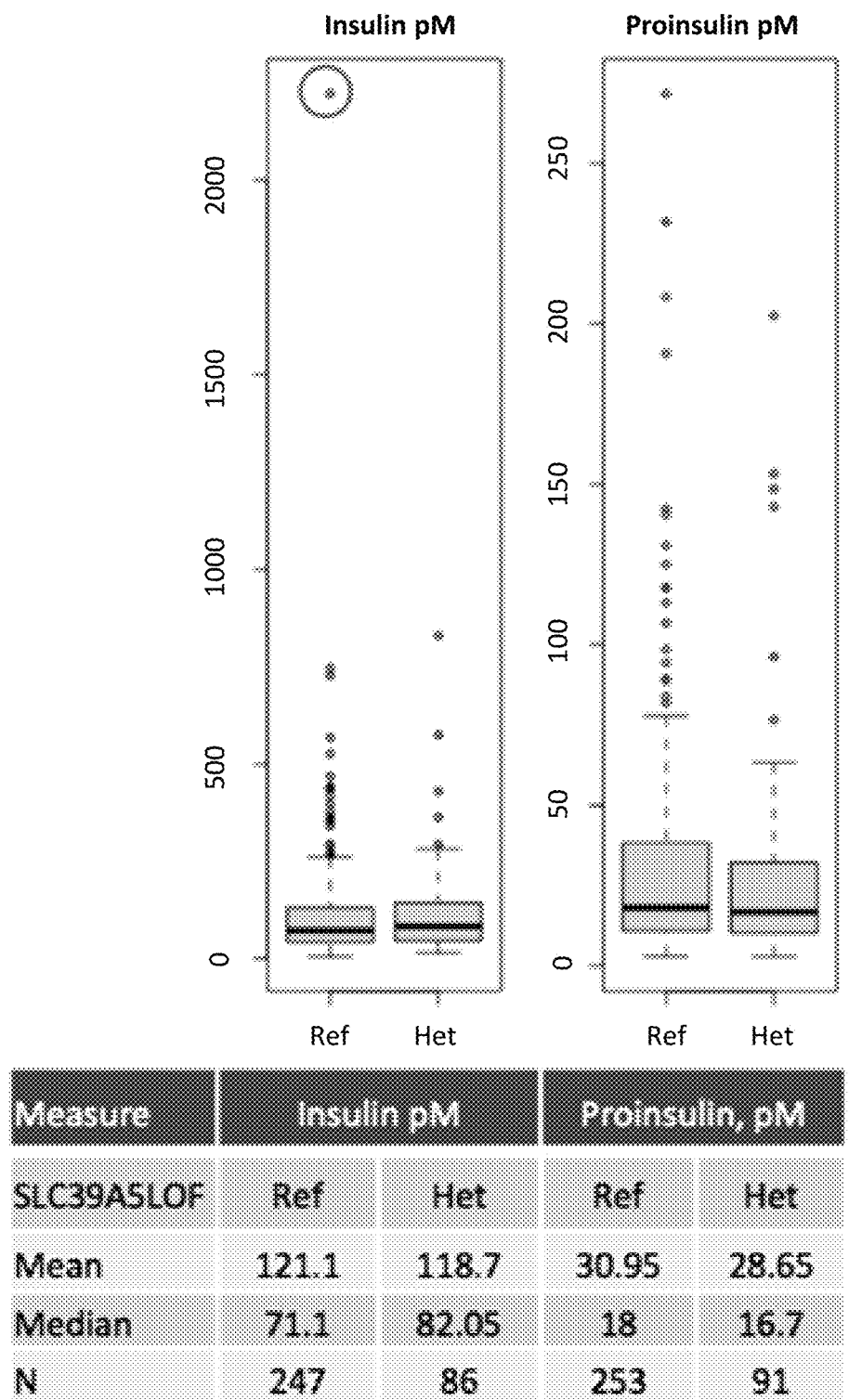
FIG. 10 shows comparative untransformed trait values for various traits in wild type and SLC39A5 knockout mice.
Figure 10:
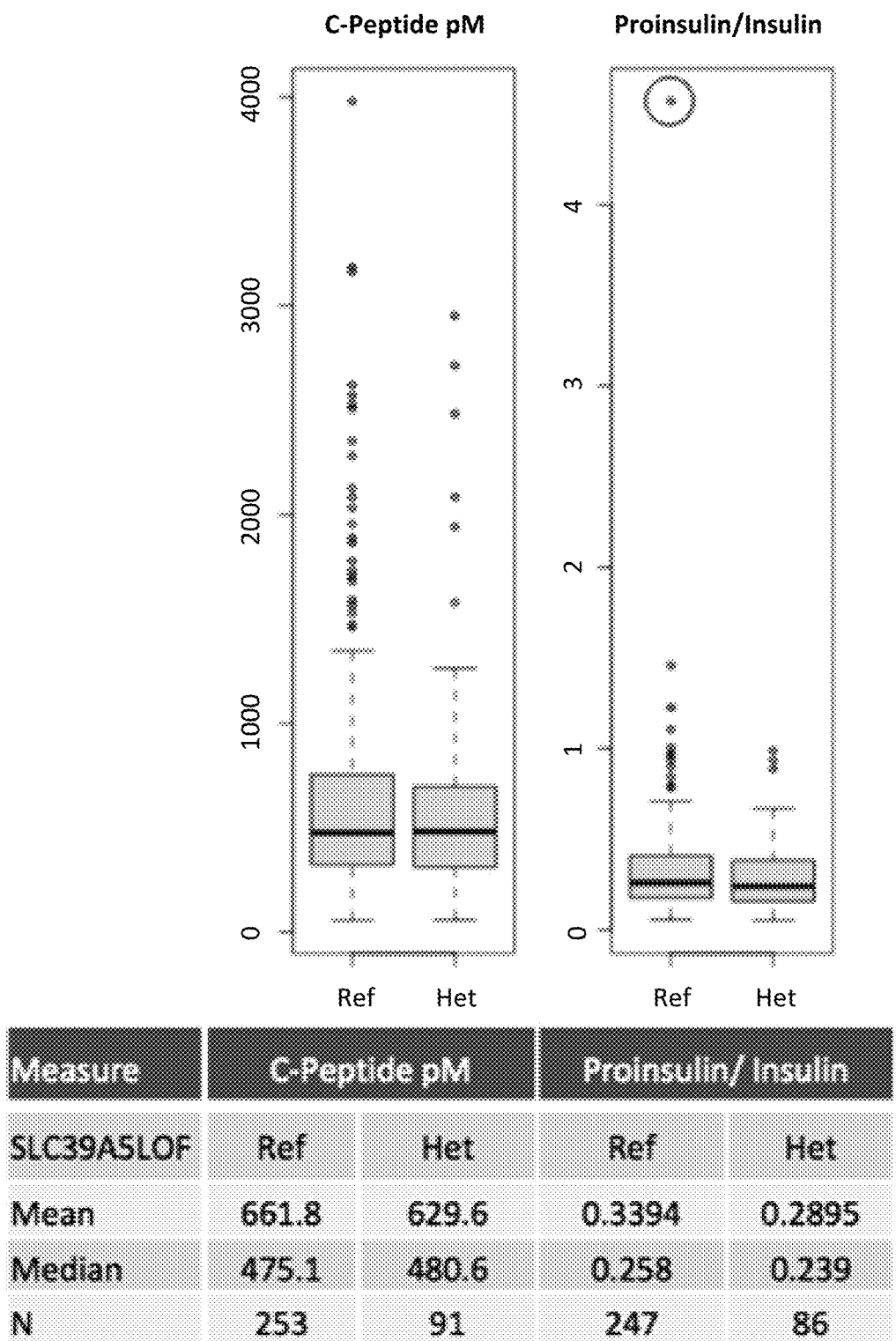
Figure 10:
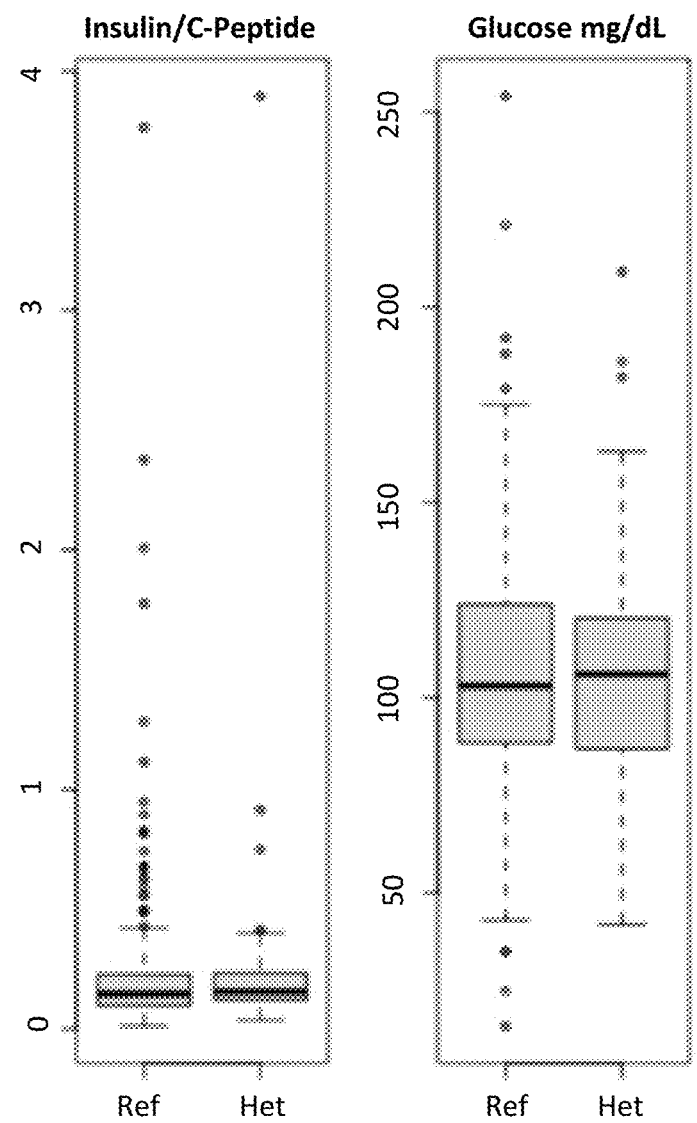
Figure 10:
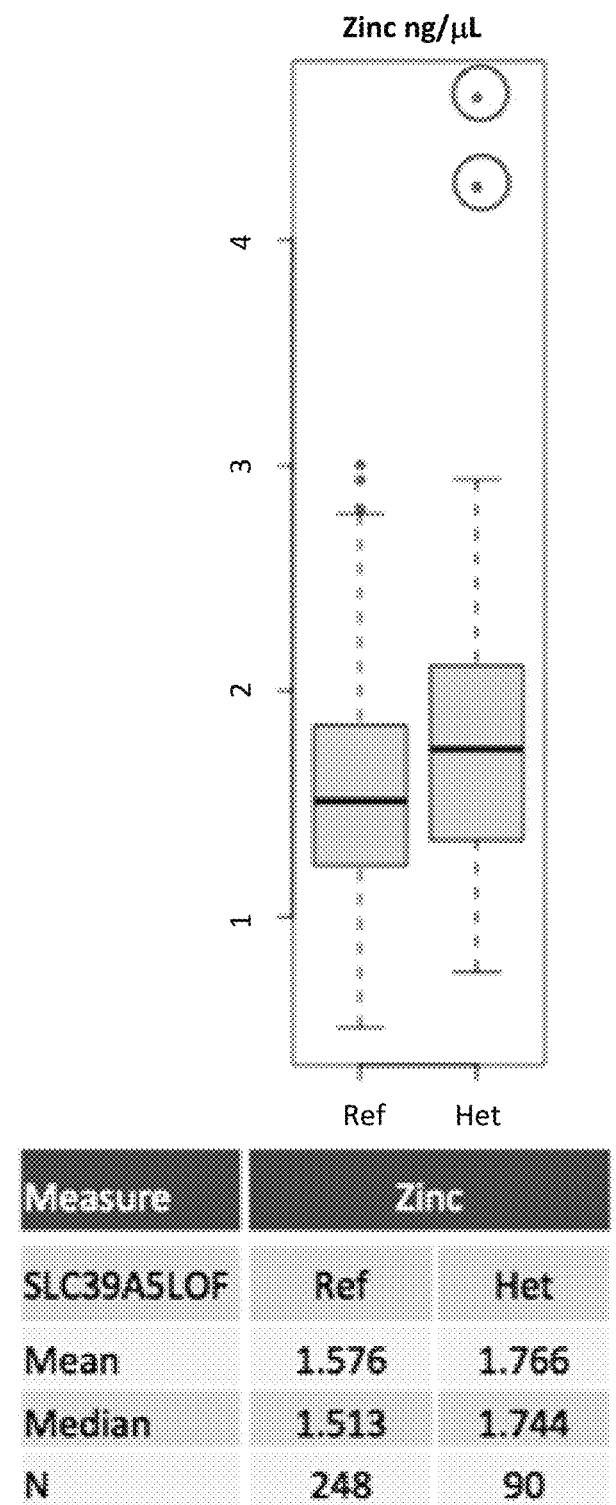

Comparative untransformed trait values for various traits in wild type and SLC39A5 knockout mice are shown in Table 3 and FIG. 10.

TABLE 3

| Trait | P | Beta (*log scale) | 95% CI (*log scale) | Covars |
|---|---|---|---|---|
| Insulin pM | 0.322 | 0.0458* | −0.0446, 0.136* | BMI |
| Proinsulin, pM | 0.669 | −0.0188* | −0.105, 0.0672* | BMI, Sex |
| C-Peptide pM | 0.947 | −0.00258* | −0.0789, 0.0737* | BMI |
| Proinsulin/Insulin | 0.12 | −0.0539* | −0.122, 0.0139* | BMI, Sex |
| Insulin/C-Peptide | 0.236 | 0.0501* | −0.0326, 0.133* | BMI, Age |
| Glucose | 0.991 | −0.0407 | −7.23, 7.15 | — |
| Zinc | 0.0024 | 0.1900 | 0.068, 0.311 | — |

Example 9: Loss of SLC39A5 Results in Increased Serum and Bone Zinc Levels

Generation of Slc39a5 Loss of Function Mice:

The genetically engineered Slc39a5$^{-/-}$ mouse strain was created using VelociGene® technology. Briefly, C57Bl/6NTac embryonic stem cells (ESC) were targeted for ablation of a portion of the Slc39a5 locus, beginning just after the start ATG and ending 5 base pairs before the 3' end of coding exon 2. This region contains the Slc39a5 signal peptide and much of the N-terminal extracellular domain. A lacZ reporter module was inserted in frame with the Slc39a5 start, followed by a fLoxed neomycin resistance cassette for selection in ESC. The resistance cassette was deleted prior to microinjection using self-deleting technology. The targeted cells were microinjected into 8-cell embryos from Charles River Laboratories Swiss Webster albino mice, yielding F0 VelociMice® that were 100% derived from the targeted cells. These mice were subsequently bred to homozygosity and maintained in an animal facility during the whole period. Slc39a5$^{-/+}$ heterozygous mice and C57Bl/6NTac wildtype littermates were used as controls.

Hepatic Function of Slc39a5 Loss of Function Mice on Long-Term High Fat Diet (HFD):

Mice homozygous for Slc39a5 loss of function and wild-type littermates were co-housed in a controlled environment (12 hour light/dark cycle, 22±1° C., 60-70% humidity) and fed ad-libitum with a high fat diet (Test Diet, Catalog #9GWP) containing 35 ppm zinc starting at 6 weeks of age. Both male and female mice were used in this study. Upon an overnight fast (lasting 16 hours), serum and hepatic zinc along ALT and AST were assessed at 40 weeks of high fat diet challenge. A separate cohort of age matched wild-type C57BLK/6 mice maintained on normal chow (Lab Diet, Catalog #5K52) containing 85 ppm zinc were obtained from Jackson Laboratories as controls. Serum and hepatic zinc analyses was conducted using flame atomic absorption spectroscopy as discussed below. Serum ALT and AST levels and other liver and lipid traits were measured using ADVIA Chemistry XPT System (Siemens Healthineers). For histology, explanted liver samples were fixed in 10% phosphate buffered formalin acetate at 4° C. overnight, thoroughly rinsed in phosphate-buffered saline and embedded in paraffin wax. Hematoxylin and eosin staining performed on 5 μm thick paraffin sections using standard histochemistry techniques. Sections were imaged using a 20× or 40× objective using the EVOS FL Auto microscope (Thermo Fisher Scientific).

Serum and Tissue Zinc Analyses:

All zinc measurements were performed using an Agilent Technologies 240 FS Atomic Absorption Spectrometer, in flame mode. Serum samples were quantitatively diluted in deionized water and subsequently analyzed. For the serum samples, a Seronorm Trace Elements Serum (L-2) was used as reference. Tissue, bone and other material were first digested in nitric acid. The samples were weighed and incubated overnight at 85° C. in nitric. The following day, the samples were cooled down to room temperature and quantitatively transferred to polystyrene tubes with deionized water. Subsequently, they were analyzed. For all tissue samples, a bovine liver standard reference material (SRM 1577c) from the National Institute of Standards and Technology was used as reference.

Liver and Lipid Traits:

Assays were performed on Siemens ADVIA Chemistry XPT. The liver and lipid profile contained the following reagents: Alanine Aminotransferase (ALT, Siemens REF 03036926), Aspartate Aminotransferase (AST, Siemens REF 07499718), Cholesterol (CHOL, Siemens REF 10376501), Direct HDL Cholesterol (DHDL, Siemens REF 07511947), LDL Cholesterol Direct (DLDL, Siemens REF 09793248), Non-Esterified Fatty Acids (NEFA, Wako 999-34691, 995-34791, 991-34891, 993-35191), Triglycerides (TRIG, Siemens REF 10335892). These reagents when mixed with sample will undergo redox reactions specific to the analyte of interest that bring about a color change proportional to the concentration of the analyte (colorimetric assay). Absorbance of light, in wavelength specific to the analyte, (from a Halogen light source) was measured and concentration determined. Each set of reagents was calibrated as recommended by the manufacturer and samples with known values (Multilevel Quality Controls) were measured daily. Parameters were never allowed to deviate from known means by more than one standard deviation. Samples were usually assayed undiluted, though they can be diluted up to 1.5× without affecting results. Samples were loaded into the analyzer in 0.6 ml microcentrifuge tubes and all reagent mixing, assay timing, absorbance and concentration calculation was performed by the analyzer.

Figure 11:
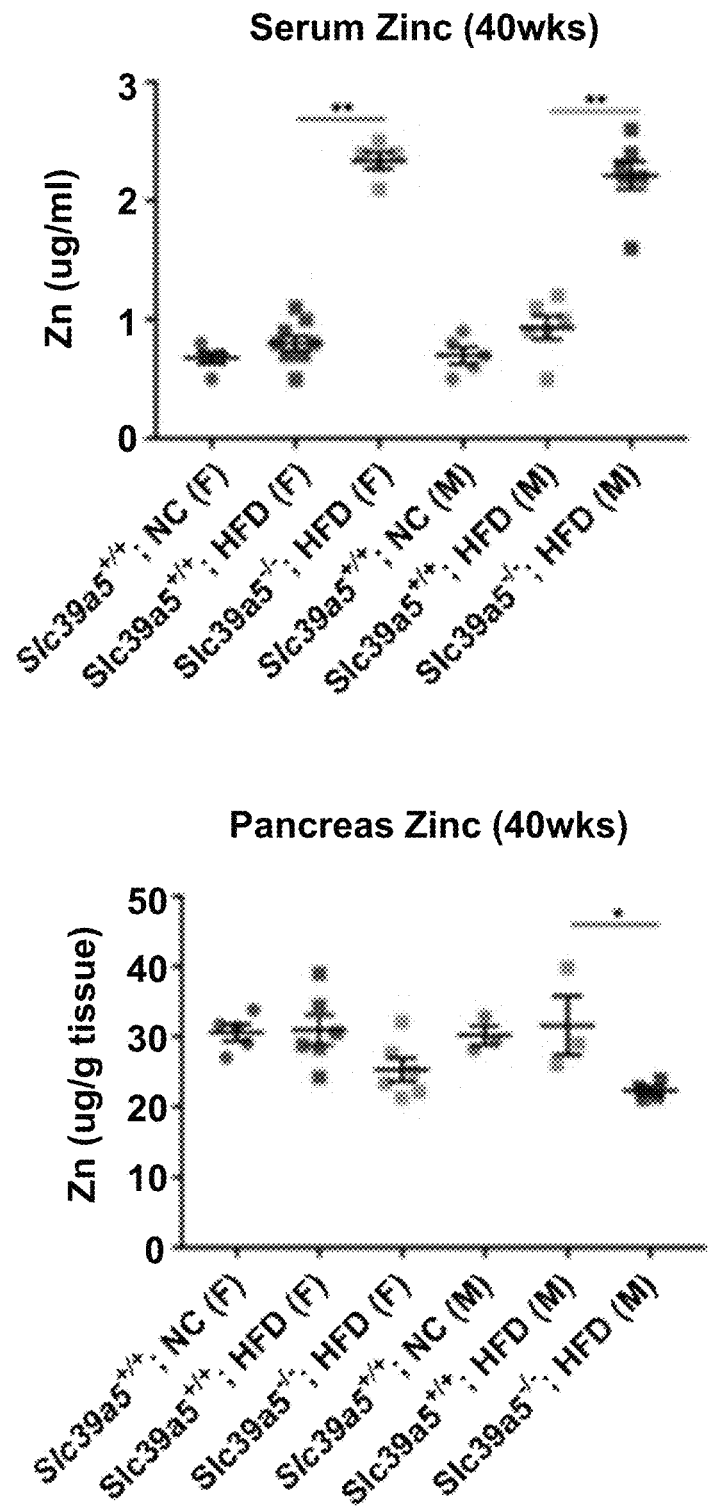
FIG. 11 shows loss of SLC39A5 results in an increase in serum and bone zinc levels in both sexes, whereas hepatic zinc is modestly elevated only in female mice.
Figure 11:
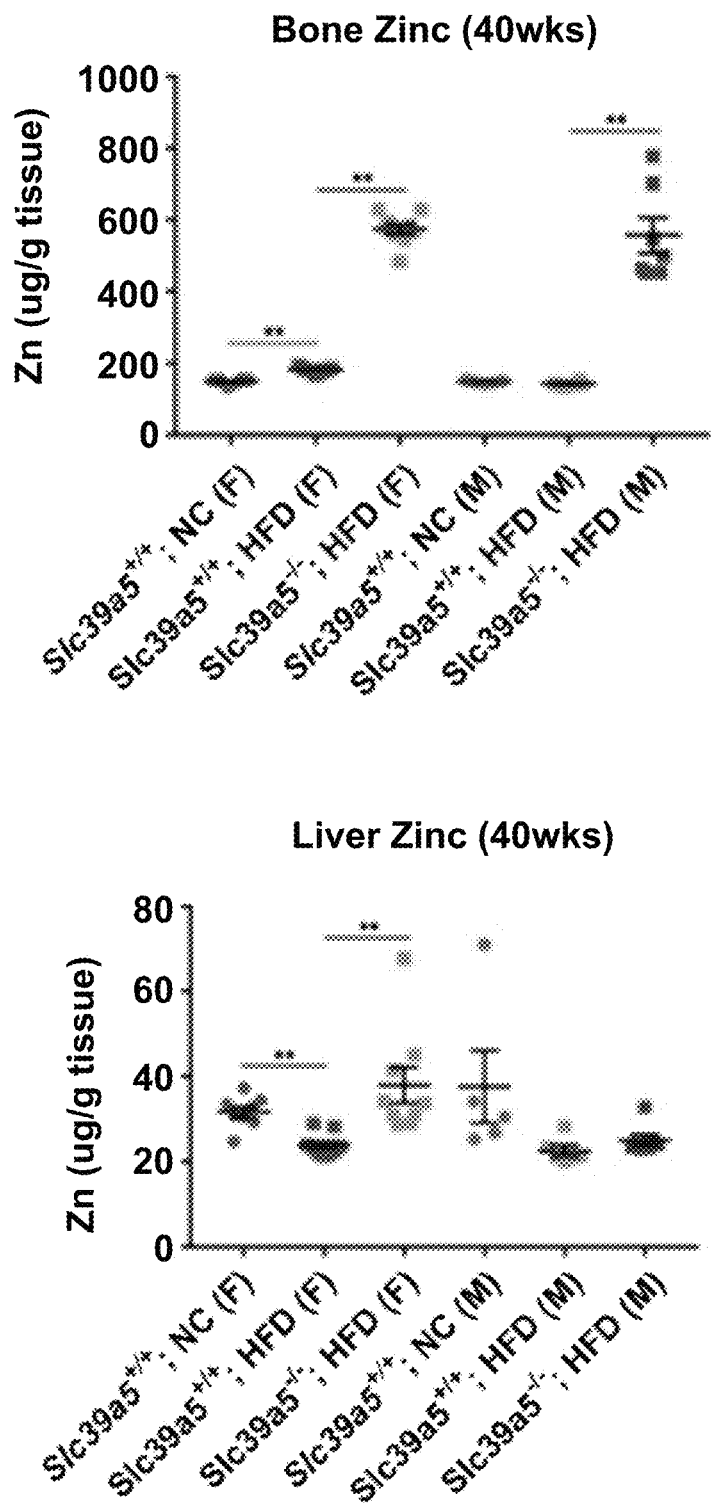
Figure 12:
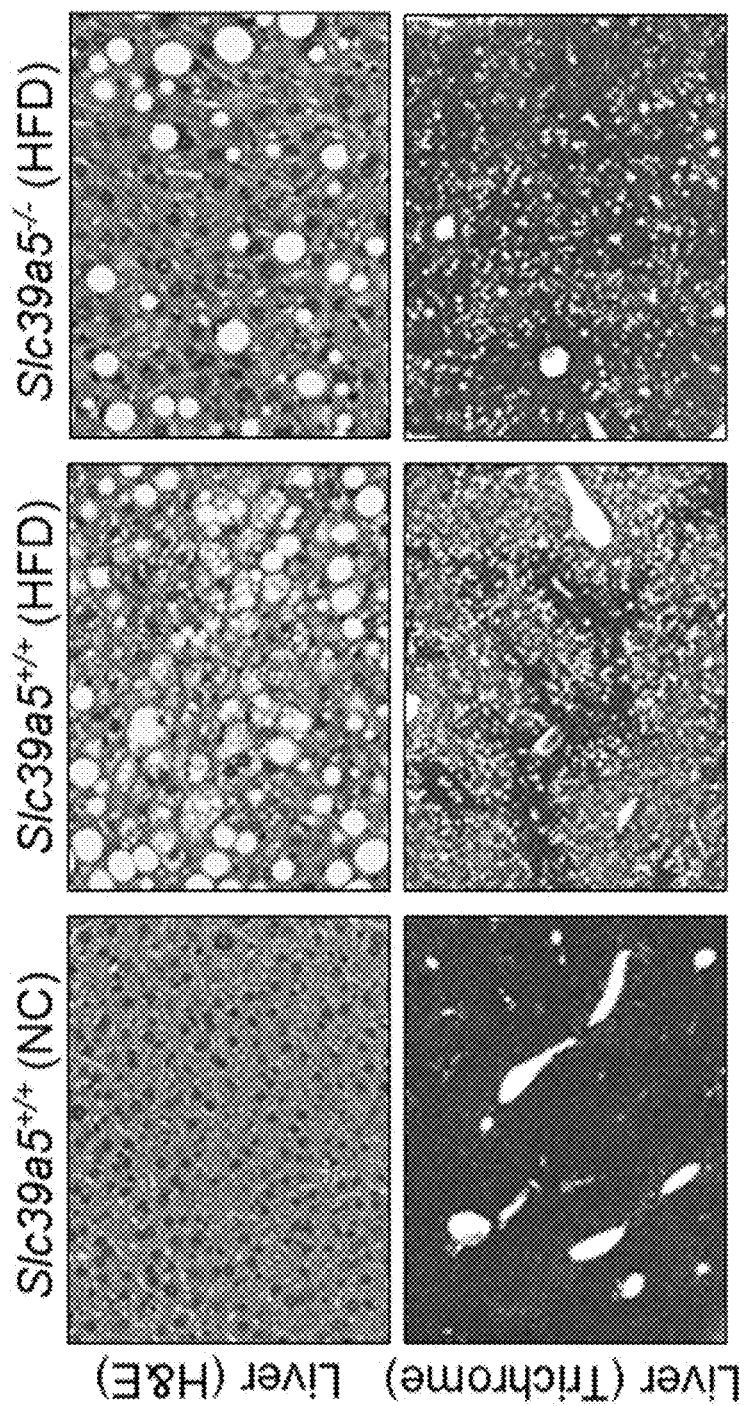
FIG. 12 shows loss of SLC39A5 improves hepatic steatosis in female mice resulting from diet-induced obesity.
Figure 12:
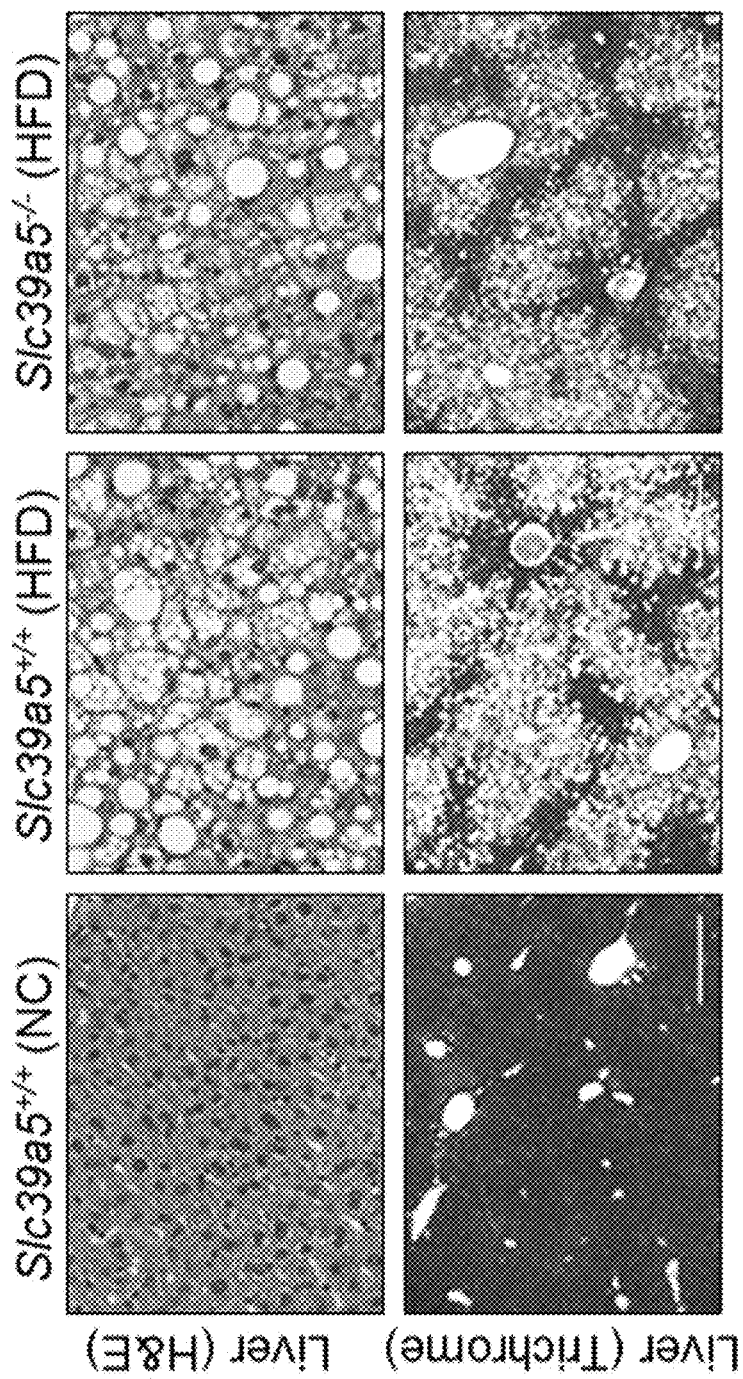
Figure 13:
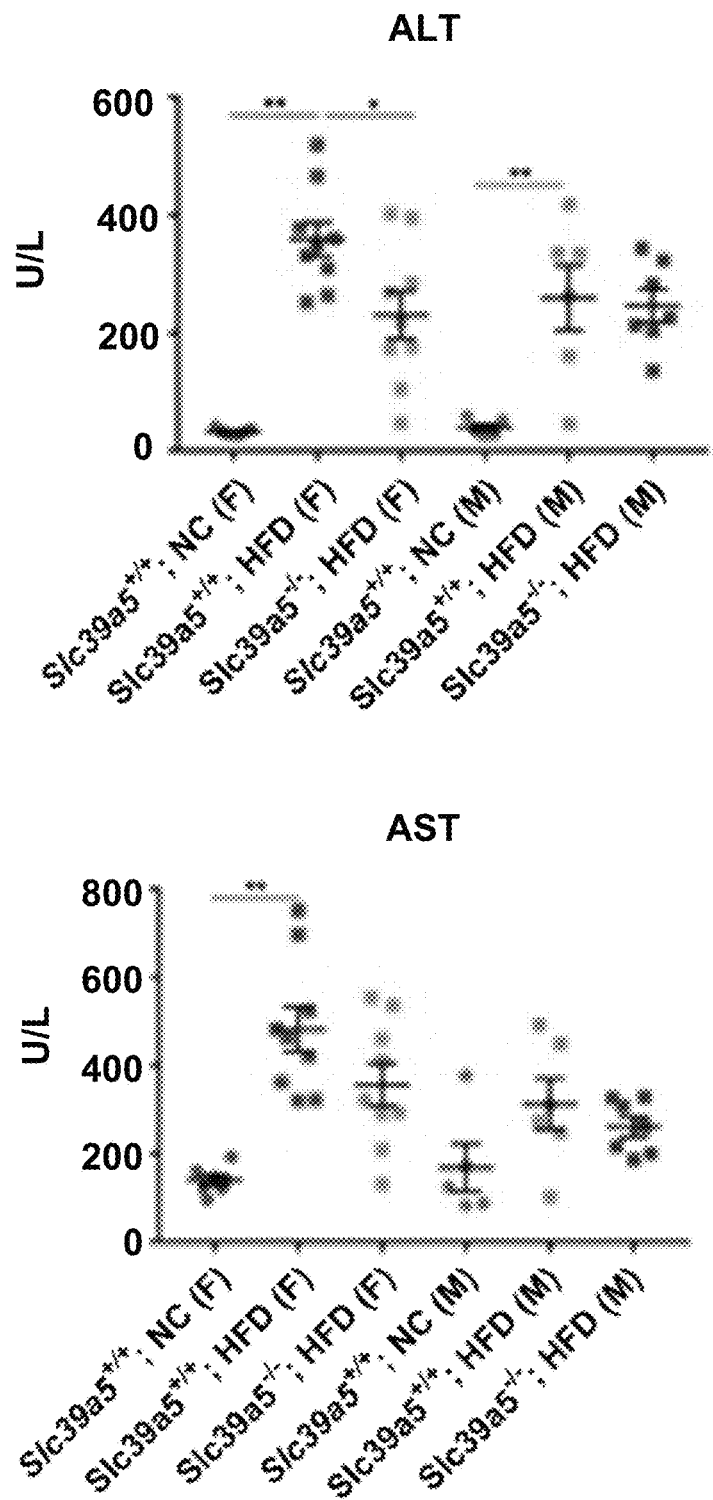
FIG. 13 shows loss of SLC39A5 improves liver function and certain lipid traits in female mice upon diet-induced obesity challenge.
Figure 13:
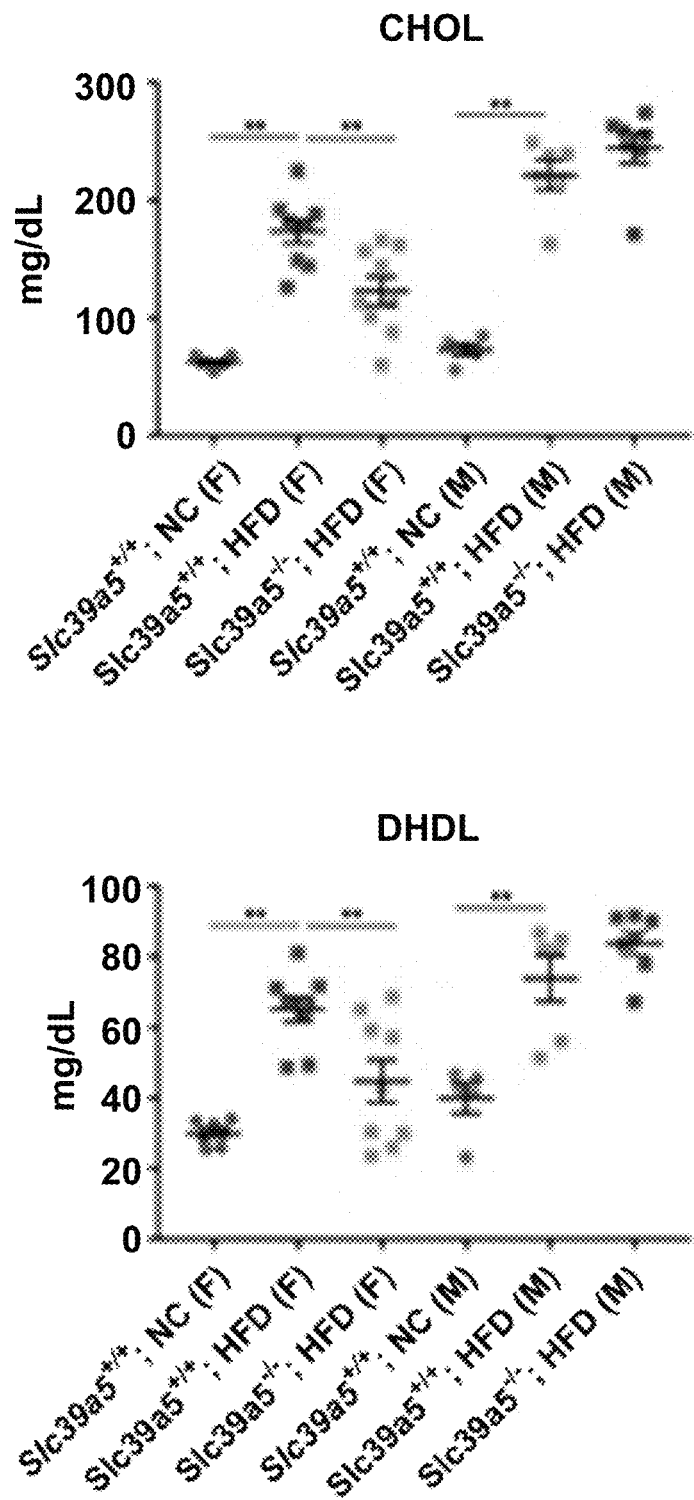
Figure 13:
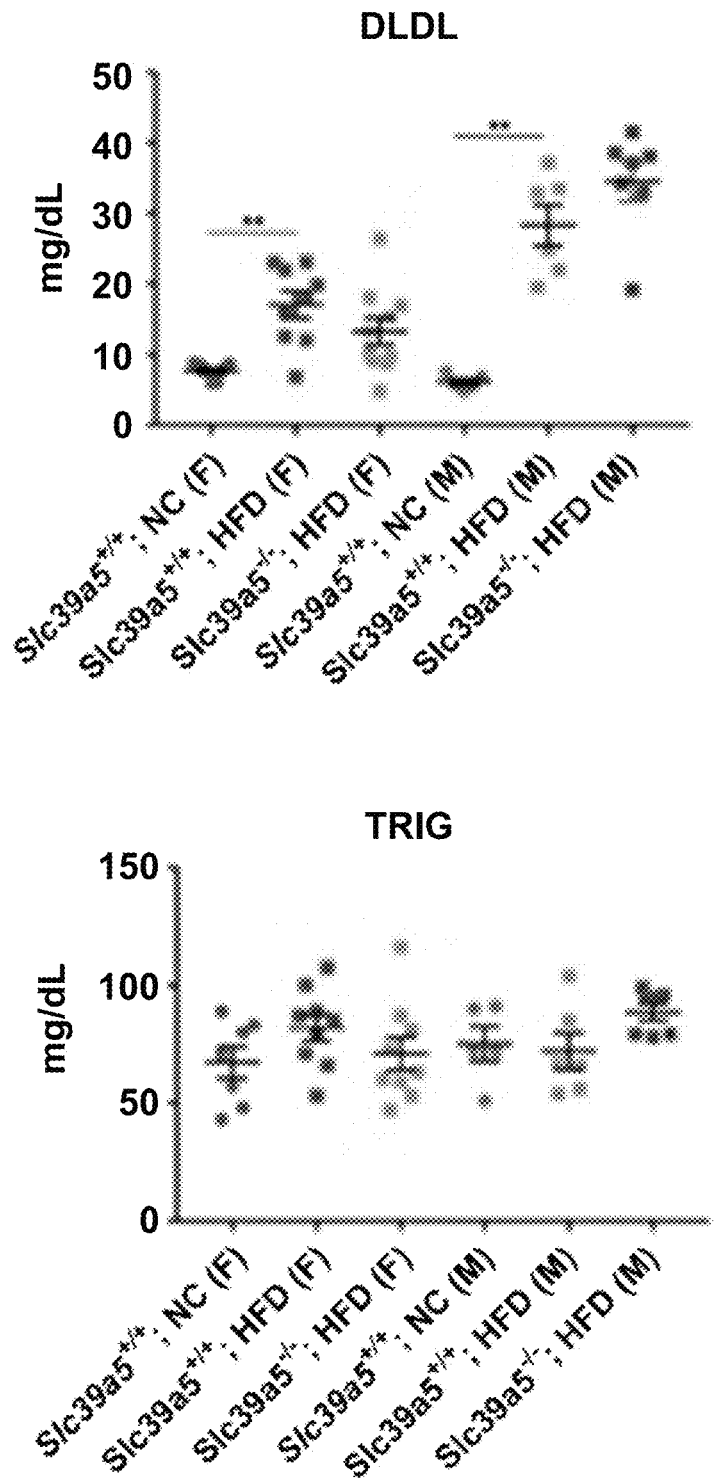
Figure 13:
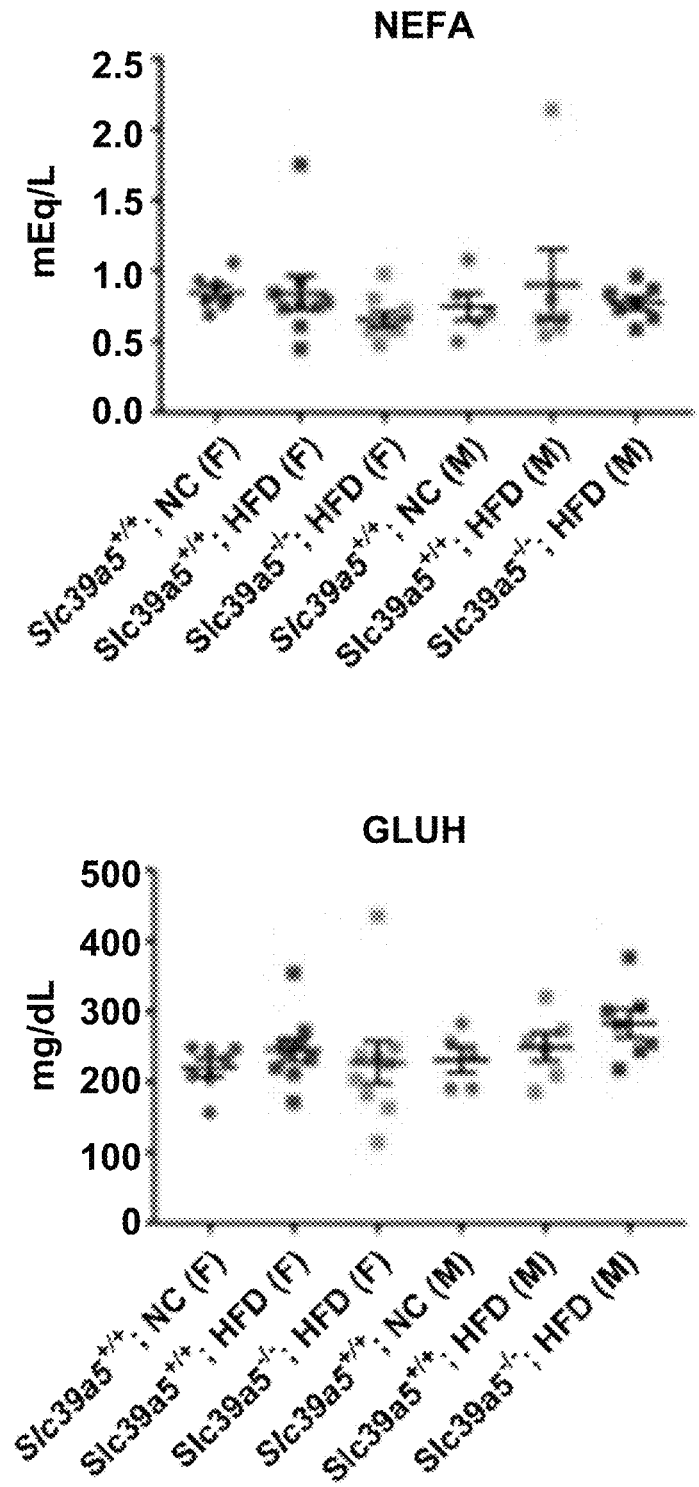

Liver Histology:

For hematoxylin and eosin staining, unstained slides were deparaffinized in xylene then hydrated through graded alcohols up to water. Sections were stained with Carazzi's hematoxylin, washed in tap water, and then put in 95% ethanol. From there, they were put in eosin-phloxine solution, then ran through graded alcohols to xylene. After xylene, the stained slides were cover-slipped and imaged. For Masson staining, the unstained slides were deparaffinized in xylene, hydrated through graded alcohols up to water, and then left in Bouin's solution overnight. They were then rinsed thoroughly and transferred to Weigert's hematoxylin. After hematoxylin, the slides were rinsed in water then placed in Biebrich scarlet-acid fuchsin solution. The slides were rinsed again in water, before transferring to phosphomolybidic-phosphotungstic acid solution. The slides were then rinsed in water and put in aniline blue, rinsed in water a final time, and then dehydrated through graded alcohols and placed in xylene. After xylene, the stained slides were cover-slipped imaged as described above.
Results:

FIGS. 11, 12, and 13 depict serum zinc, liver zinc, alanine aminotransferase, and aspartate aminotransferase levels of Slc39a5 loss-of-function mice at 40 weeks on a high-fat diet regimen. Female homozygous loss-of-function mice had elevated serum zinc and liver zinc levels as compared to wild-type mice on a normal chow (NC) or a high-fat diet (HFD). No differences were observed in male mice at this age. Furthermore, female homozygous loss-of-function mice had reduced alanine aminotransferase levels as compared to wild-type mice on a normal chow (NC) or a high-fat diet (HFD). No differences were observed in aspirate aminotransferase levels between the groups. Male homozygous loss-of-function mice had elevated serum zinc levels as compared to wild-type mice on a normal chow (NC) or a high-fat diet (HFD) at 40 weeks. No differences were observed in liver zinc, alanine aminotransferase and aspartate aminotransferase levels in male homozygous loss-of-function mice as compared to wild-type mice on a normal chow (NC) or a high-fat diet (HFD). In line with these observation, female homozygous loss-of-function mice had dramatic reduction in hepatic lipid accumulation as compared to wild-type mice on a normal chow (NC) or a high-fat diet (HFD) at 40 weeks based on hematoxylin and eosin staining and Masson's staining. Male homozygous loss-of-function mice also showed modest reduction in hepatic lipid accumulation as compared to male wild-type littermates on a normal chow (NC) or on a high-fat diet (HFD) at 40 weeks based on hematoxylin and eosin staining and Masson's staining.

Example 10: Loss of SLC39A5 Results in Reduced Hepatic Triglycerides

Hepatic β-Hydroxybutyrate Assay:

Assays were performed using β-hydroxybutyrate assay kit (SIGMA MAK041). Explanted liver samples (10 mg/sample) were homogenized in 4 volumes of cold β-hydroxybutyrate assay buffer as per the manufacturer's recommendations. Homogenized samples were centrifuged at 13000 g for 10 minutes at 4° C., and the resulting supernatant was used for downstream analyses. In this assay, β-hydroxybutyrate concentration was determined by a coupled enzyme reaction which results in a colorimetric (450 nm) product proportional to the β-hydroxybutyrate present.

Figure 14:
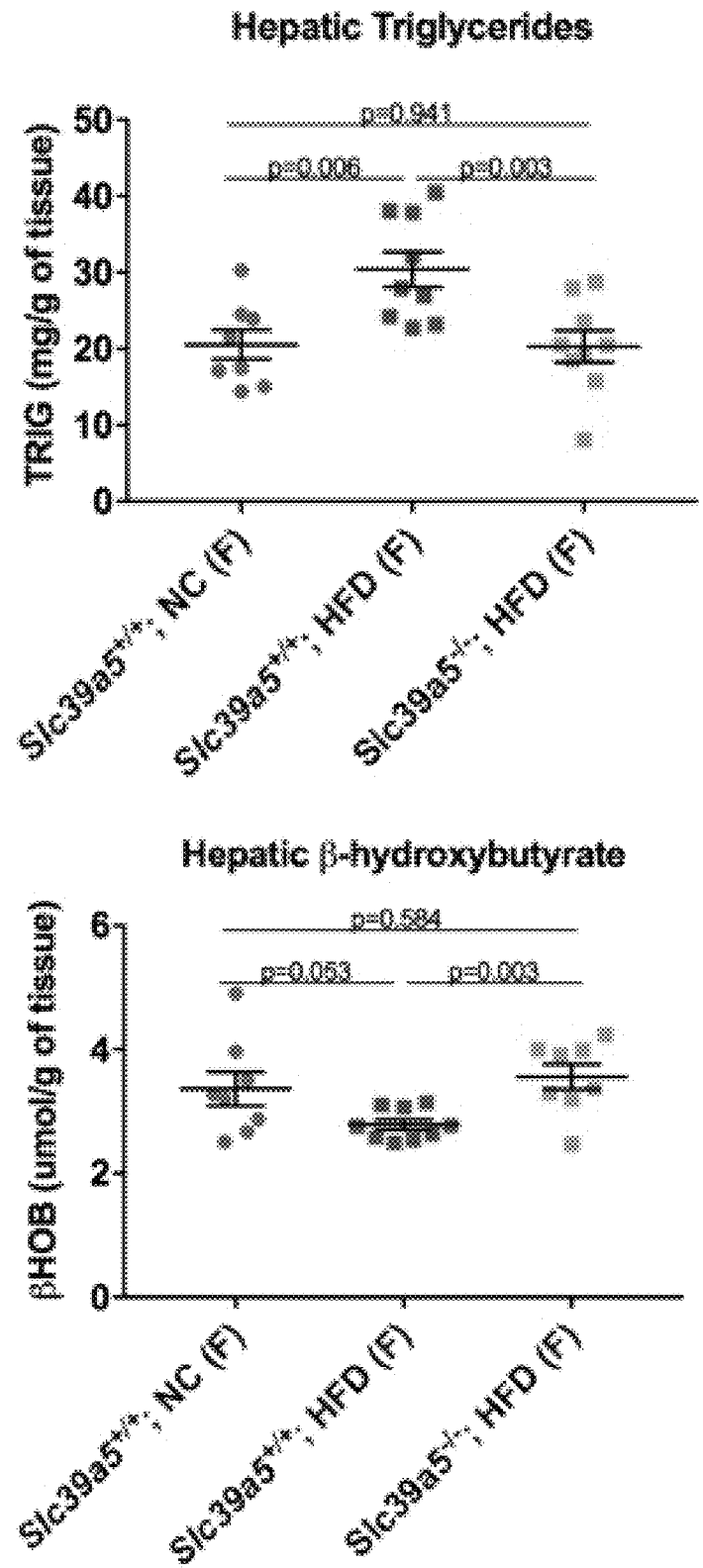
FIG. 14 shows loss of SLC39A5 results in reduced hepatic triglyceride content and increased ketogenesis in female mice on a high-fat challenge.

Hepatic Triglyceride Assay:

Assays were performed using Triglyceride Colorimetric Assay Kit (Cayman 10010303). Explanted liver samples (400 mg/sample) were homogenized in 2 ml of NP-40 Substitute Assay Reagent containing protease inhibitors. Homogenized samples were centrifuged at 10000 g for 10 minutes at 4° C., and the resulting supernatant was diluted at least 1:5 using NP-40 Substitute Assay Reagent for downstream analyses. This assay involves enzymatic hydrolysis of triglycerides by lipase to produce glycerol and free fatty acids. The glycerol released is subsequently measured by a coupled colorimetric enzymatic reaction. The absorbance was measured at 530-550 nm.
Results:

FIG. 14 depicts hepatic triglyceride and β-hydroxybutyrate levels of Slc39a5 loss-of-function female mice at 40 weeks on a high-fat diet regimen. Female homozygous loss-of-function mice had reduced hepatic triglyceride as compared to wild-type mice on a normal chow (NC) or a high-fat diet (HFD). Furthermore, female homozygous loss-of-function mice had elevated hepatic β-hydroxybutyrate levels as compared to wild-type mice on a normal chow (NC) or a high-fat diet (HFD).

Figure 15:
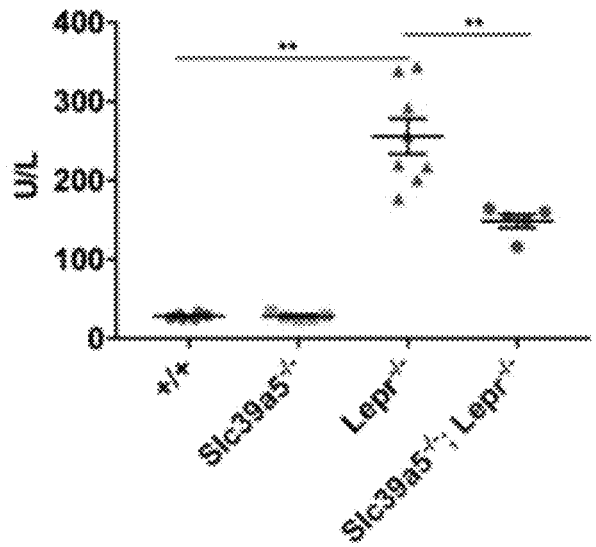
FIG. 15 shows SLC39A5 loss-of-function improves liver function in leptin receptor deficient mice.
Figure 15:
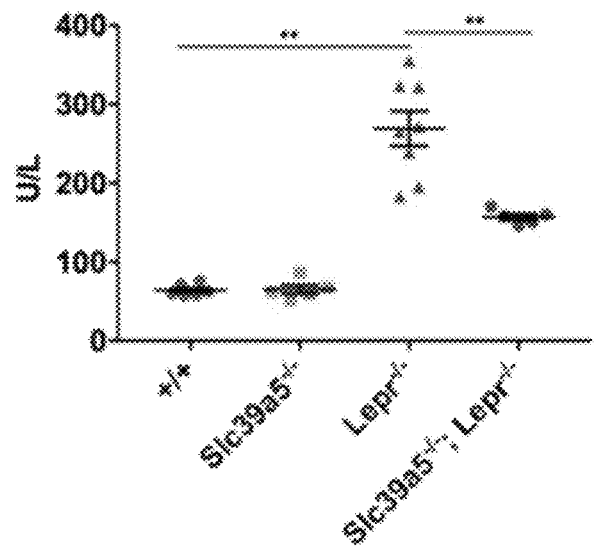
Figure 15:
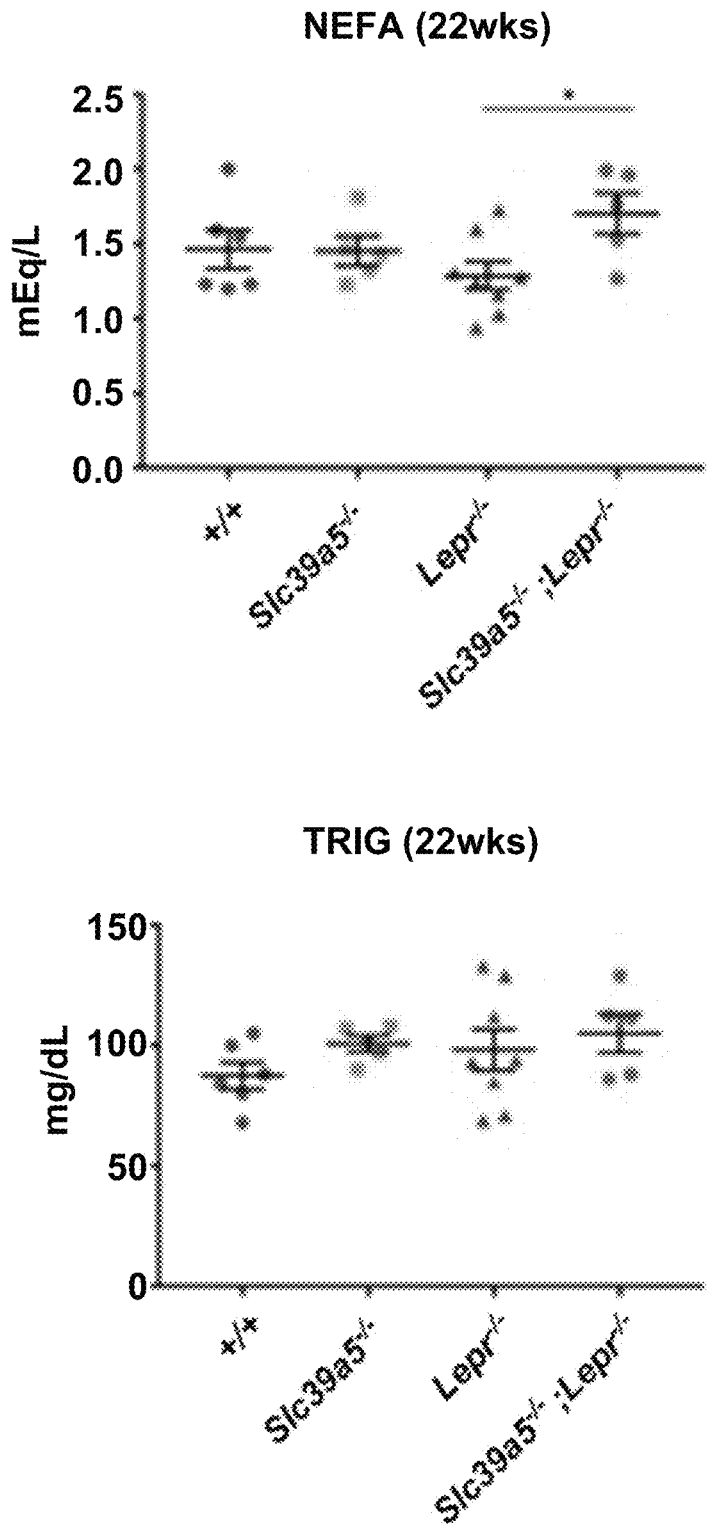
Figure 15:
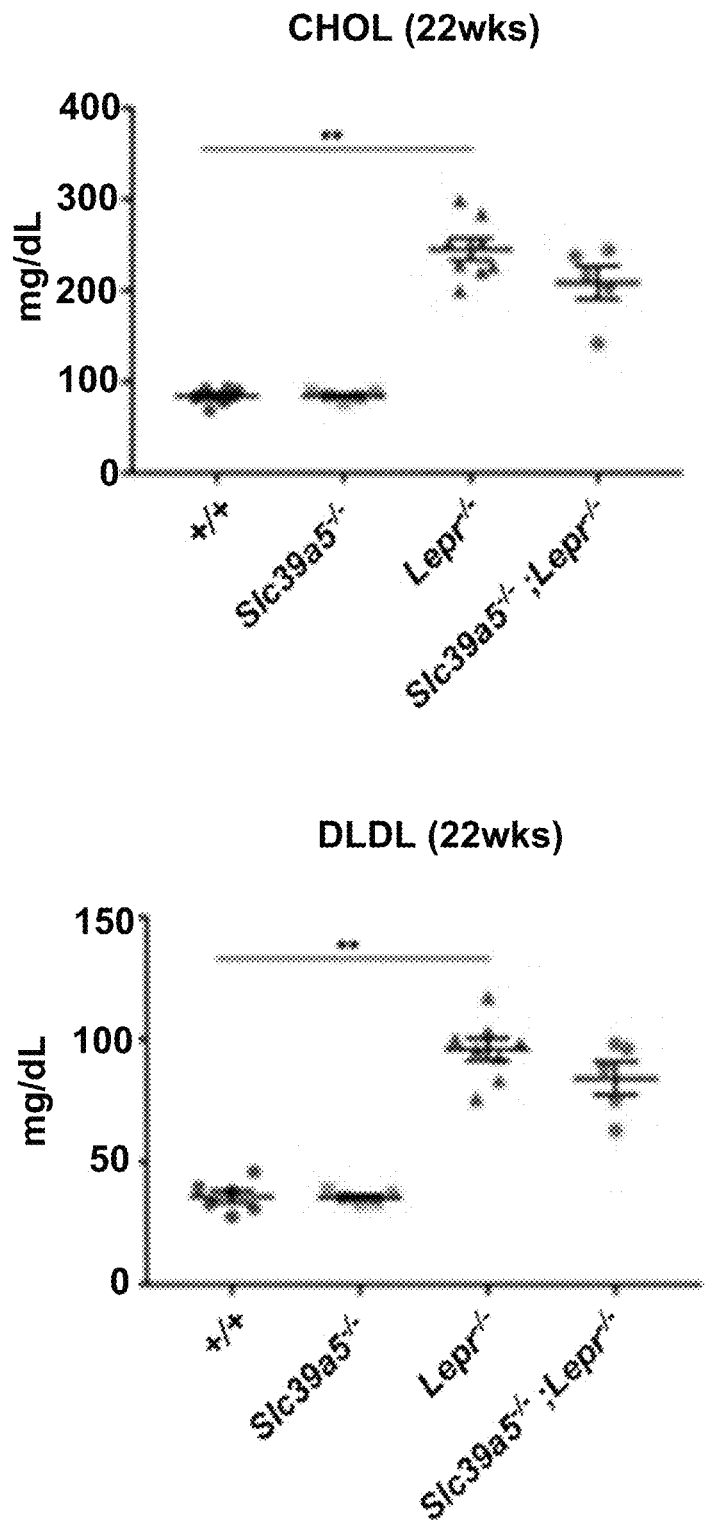
Figure 15:
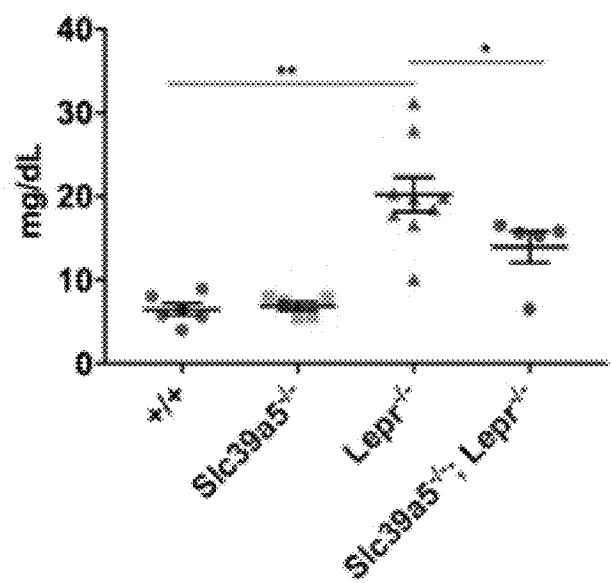
Figure 16:
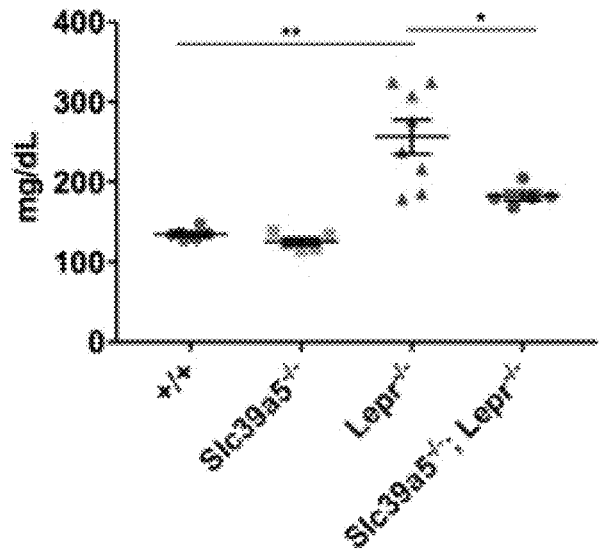
FIG. 16 shows SLC39A5 loss-of-function improves glycemic traits in leptin receptor deficient mice.
Figure 16:
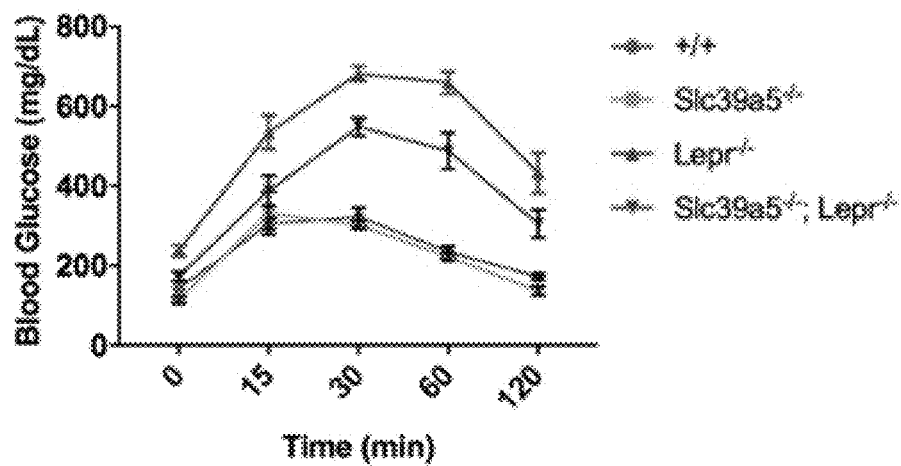
Figure 16:
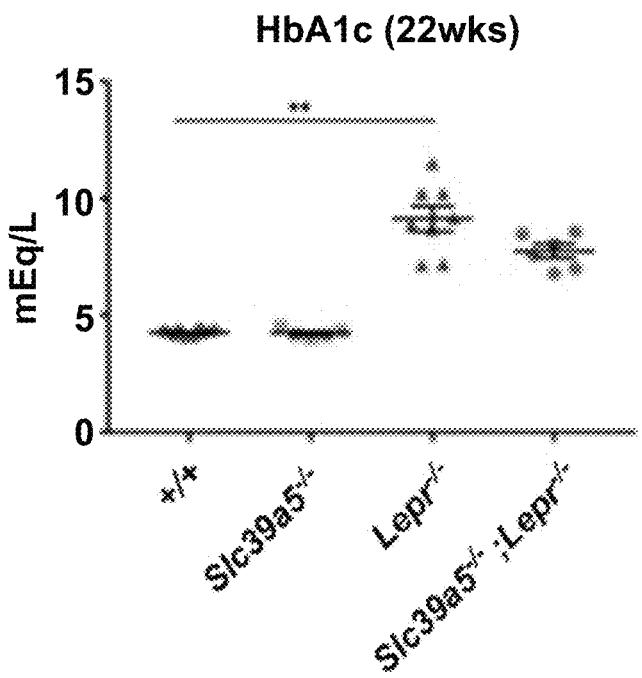
Figure 16:
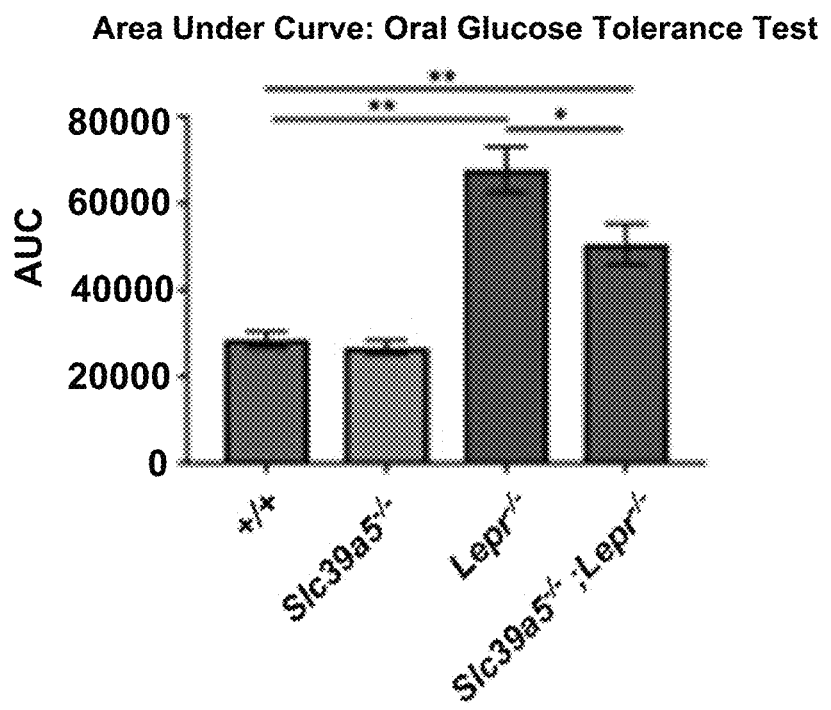

Example 11: Loss of SLC39A5 Results in Improved Liver Function and Glycemic Traits Liver, Lipid and Glycemic Traits of Mice Homozygous for Slc39a5 and Leptin-Receptor (Lepr) Loss-of-Function:

Female mice homozygous for Slc39a5 and Lepr loss of function and littermate controls (wild-type, Slc39a5$^{-/-}$, Lepr$^{-/-}$) were co-housed in a controlled environment (12 hour light/dark cycle, 22±1° C., 60-70% humidity) and fed ad-libitum with normal chow (PicoLab Rodent Diet 20, Catalog #5053) containing 87 ppm zinc. Mice were monitored for health and growth kinetics periodically. Upon an overnight fast (lasting 16 hours), serum ALT and AST along with DLDL and fasting blood glucose were measured when the mice were 22 weeks of age. Blood glucose was evaluated using AlphaTrak blood glucose monitoring system (Zoetis United States, Parsippany NJ) by sampling blood from the lateral tail vein. Liver and lipid traits were measured using a Siemens ADVIA Chemistry XPT as described previously. An oral glucose tolerance test was administered upon an overnight fast (lasting 16 hours) at 20 weeks of age by administering 2 g/kg of body weight of Dextrose (Hospira Inc, NDC 0409-4902-34) by oral gavage. Blood glucose was evaluated at defined time points (0, 15, 30, 60, and 120 minutes) using AlphaTrak blood glucose monitoring system (Zoetis United States, Parsippany NJ) by sampling blood from the lateral tail vein.
Results:

Female mice homozygous for Slc39a5 loss of function were bred in to a leptin-receptor deficient (Lepr$^{-/-}$) background (a commonly used rodent model of obesity induced hyperglycemia and type II diabetes). Leptin-receptor deficient mice were hyperglycemic and displayed elevated serum low-density lipoprotein levels. Furthermore, these mice had elevated serum ALT and AST levels suggesting impaired liver function at 22 weeks of age. Loss of Slc39a5 function in female Lepr receptor deficient mice significantly reduced fasting blood glucose, serum LDL-C, serum ALT and AST levels potentially ameliorating the obesity induced metabolic dysregulation in leptin-receptor deficient (see, FIGS. 15 and 16). In line with these observations, female mice homozygous for Slc39a5 and Lepr loss of function demonstrated improved glucose tolerance when challenged with an oral glucose load.

Example 12: Loss of SLC39A5 Results in Hepatic AMP-Activated Protein Kinase Activation Immunoblotting Analyses:

Liver protein was extracted using RIPA buffer (Cell signaling technology, Cat #9806) with Halt Protease & Phosphatase Inhibitor Cocktail (ThermoFisher Scientific, Cat #78440). Five microgram proteins of each sample were separated in NuPAGE 4-12% Bis-Tris protein gel (Invitrogen, Cat #WG1403BOX), and transferred to nitrocellulose membrane using Trans-Blot® Turbo™ Transfer System (BioRad). Blotting was performed using the following Cell Signaling Technology antibodies: Phospho-AMPKα (Thr172) (Cell signaling technology, Cat #2535), AMPKα (Cell signaling technology, Cat #5831), Phospho-AMPKP1 (Ser182) (Cell signaling technology, Cat #4186), SCD1 (Cell signaling technology, Cat #2794), Phospho-Acetyl CoA Carboxylase (Ser79) (Millipore Sigma, Cat #07-303), Acetyl CoA Carboxylase 1 (Millipore Sigma, Cat #MABS830), β-Actin (Sigma, Cat #5441), rabbit IgG conjugated to horseradish peroxidase (HRP) (Cell signaling technology, Cat #7074) and mouse IgG conjugated to HRP (Cell signaling technology, Cat #7076). Blots were developed using SuperSignal West Femto Substrate (ThermoFisher Scientific, Cat #34095). Signals were captured using ImageQuant LAS4000 (GE Healthcare).

Figure 17:
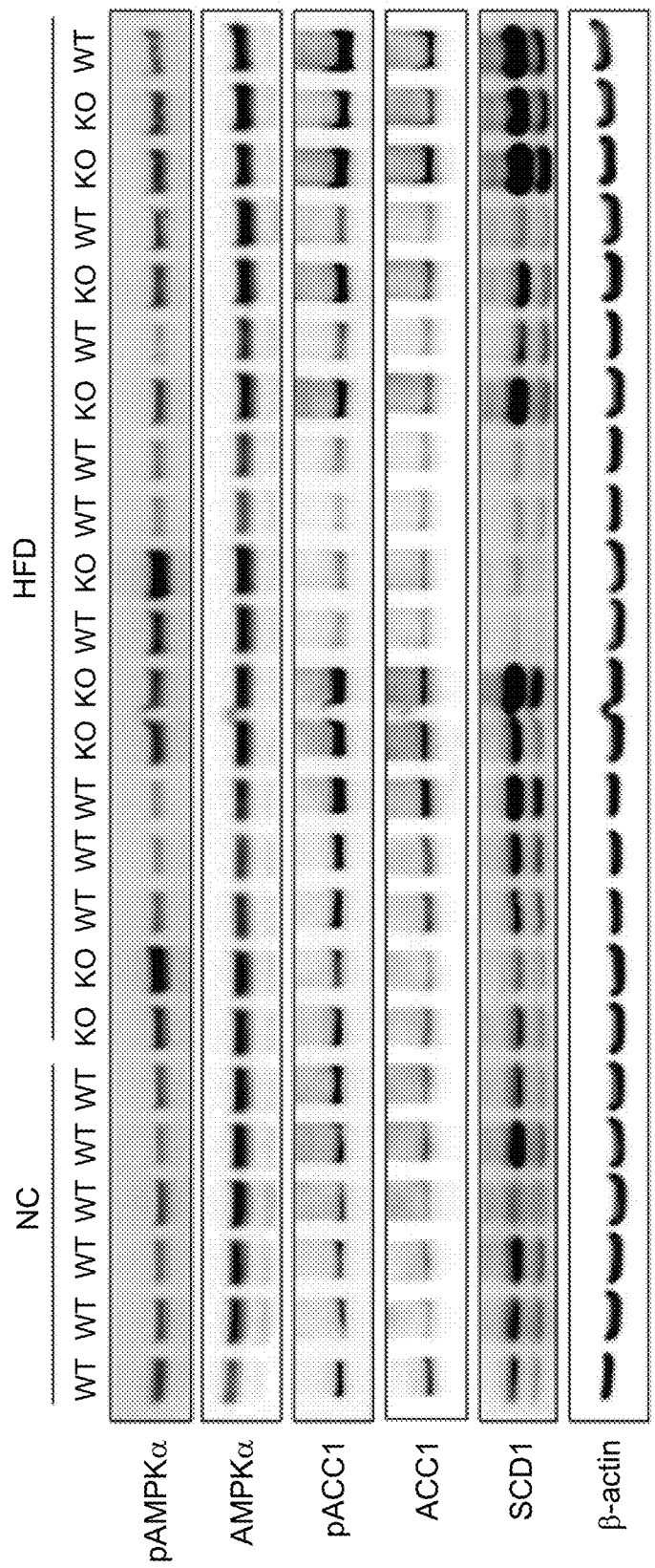
FIG. 17 shows loss of SLC39A5 results in hepatic AMP-activated protein kinase activation in female mice on HFD.
Figure 17:
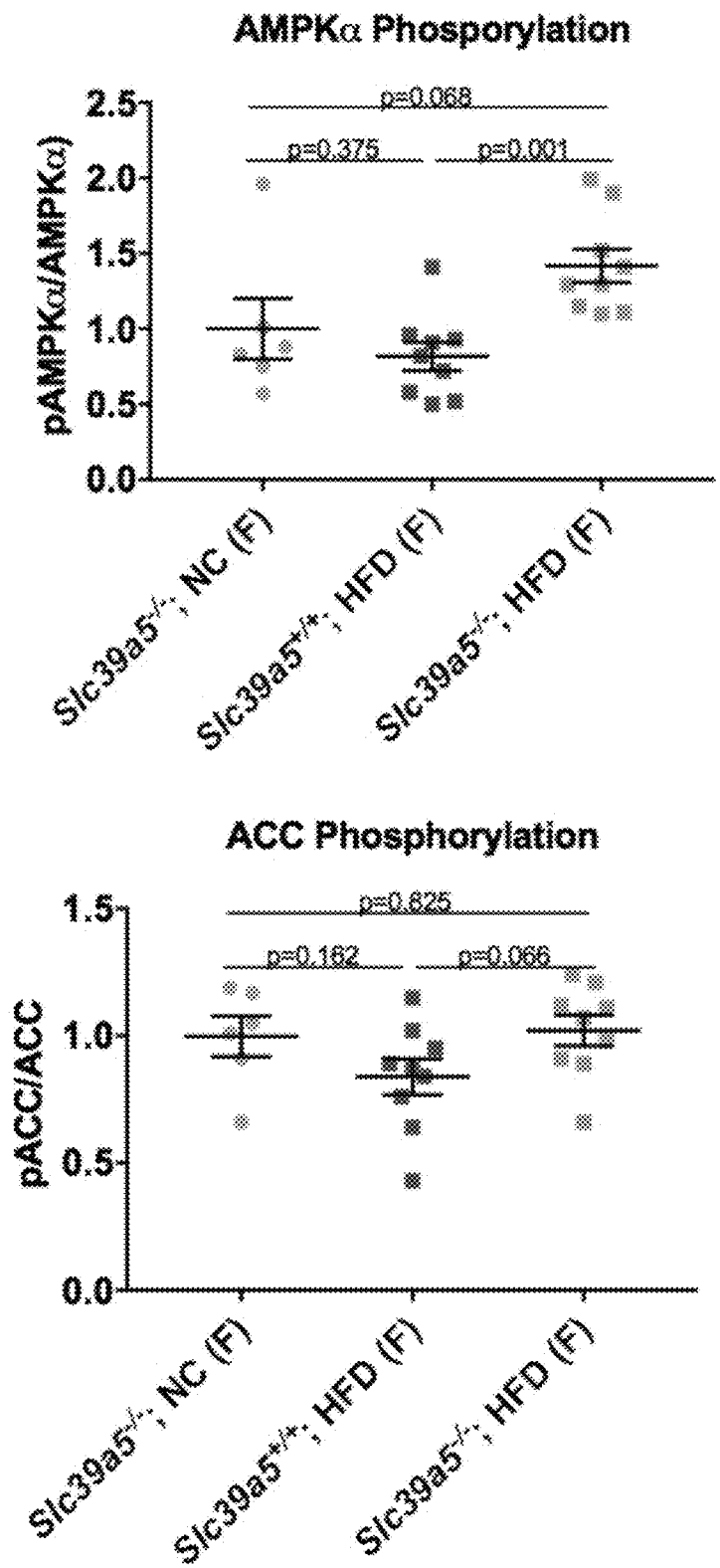
Figure 17:
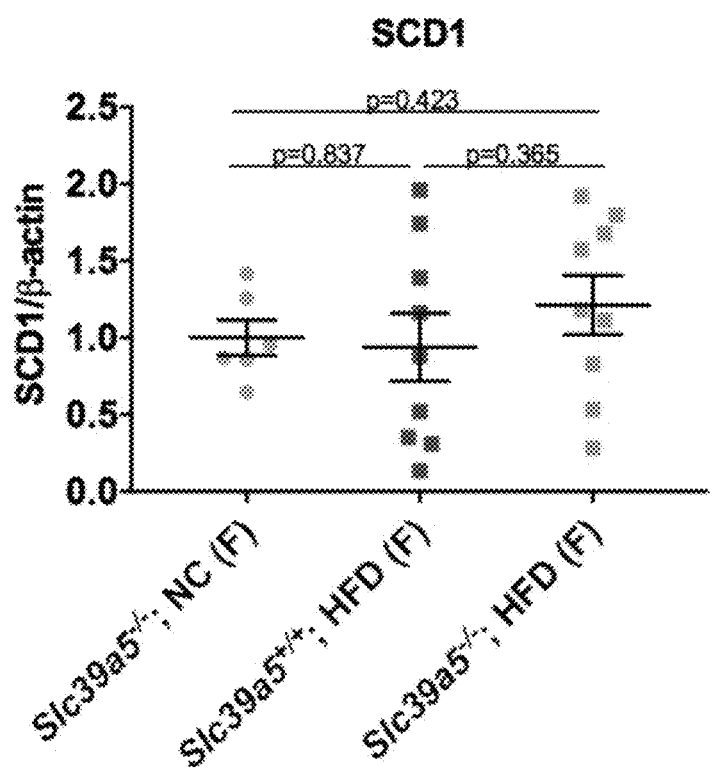

Results:

Referring to FIG. 17, female homozygous loss-of-function mice had elevated hepatic AMPK activation as observed by increased pAMPKα/AMPKα levels as compared to wild-type mice on a normal chow (NC) or on a high-fat diet (HFD). In addition, increased AMPK activation in these mice resulted in increased phosphorylation of acetyl-coA carboxylase (observed by increased pACC/ACC levels) as compared to wild-type mice on a normal chow (NC) or on a high-fat diet (HFD). No differences were observed the levels of stearoyl-CoA desaturase (SCD1) a key rate limiting enzyme in the formation of monounsaturated fatty acids including triglycerides.

Example 13: Preparation and Use of a Monoclonal Anti-SLC39A5 Antibody

Figure 18:
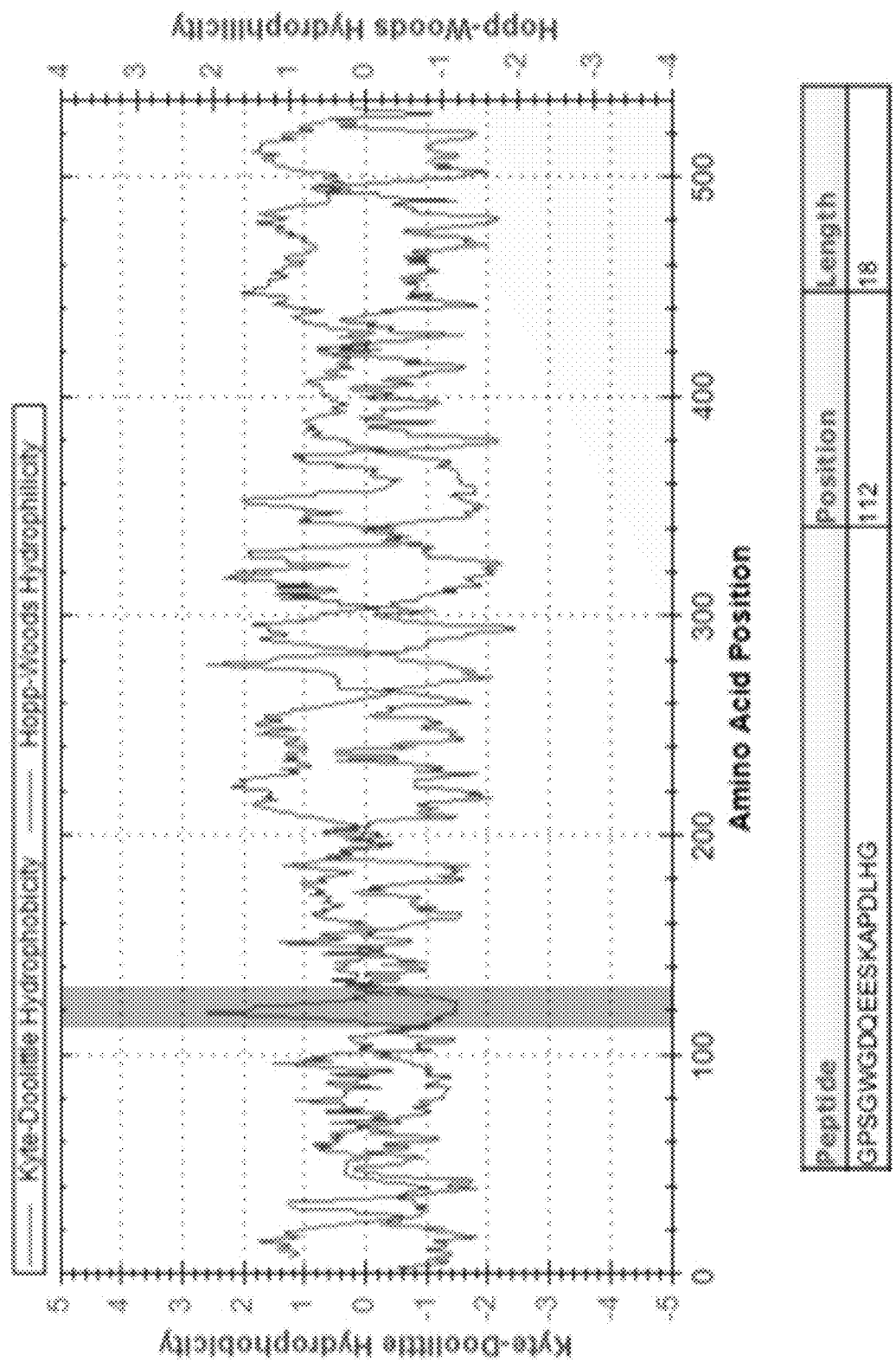
FIG. 18 shows the selection of an SLC39A5 target peptide for mouse immunization from the combined plots of Kyle-Doolitle hydrophobicity (green) and Hopp-Woods hydrophilicity (red) across the SLC39L5 sequence; the fragment selected for use as the immunization peptide (GPSGWGDQEESKAPDLHG; SEQ ID NO:67) is highlighted in purple.
Figure 19:
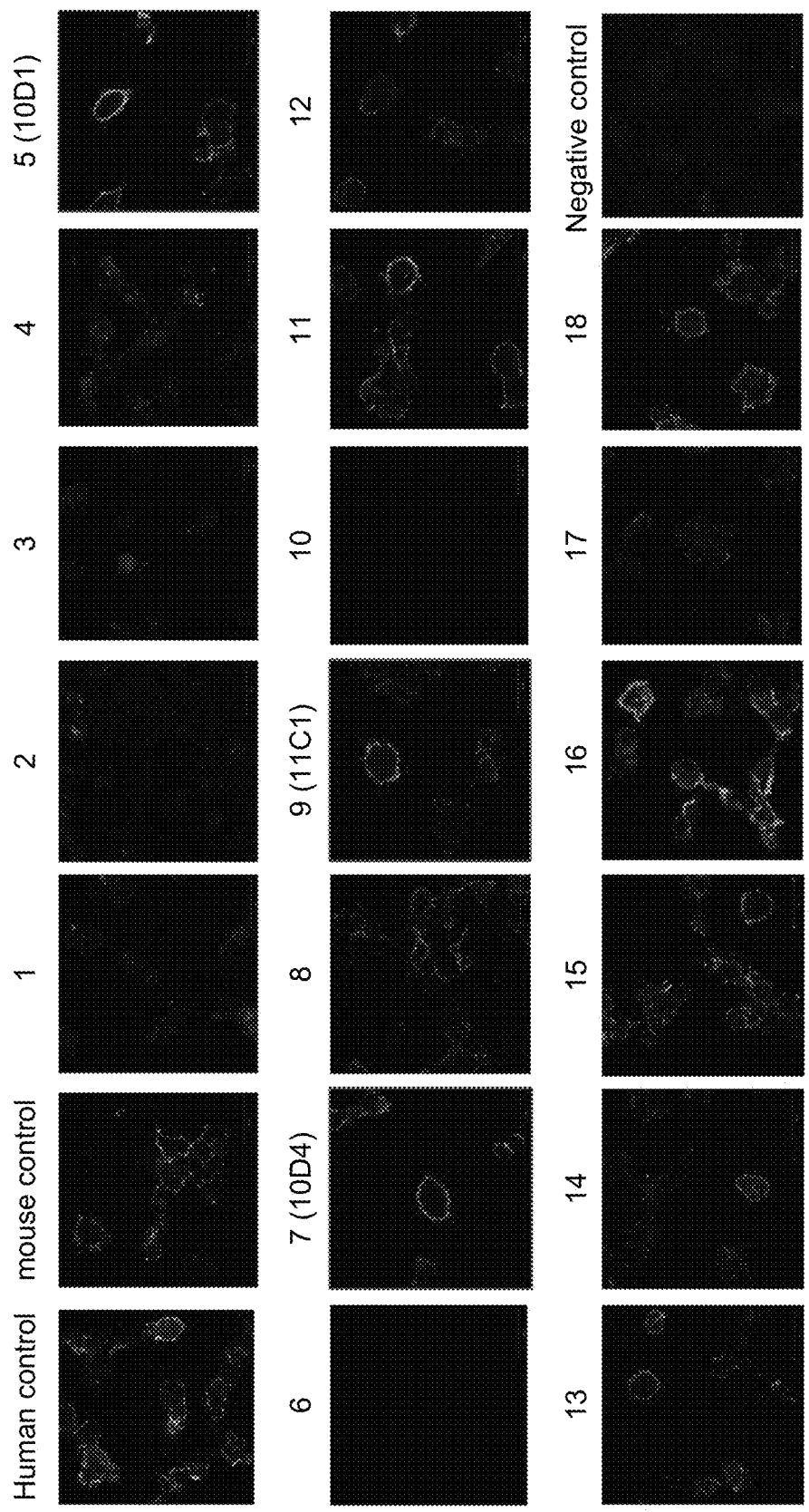
FIG. 19 shows Slc39a5 monoclonal antibody screening in HEK overexpressing murine Slc39a5.
Figure 20:
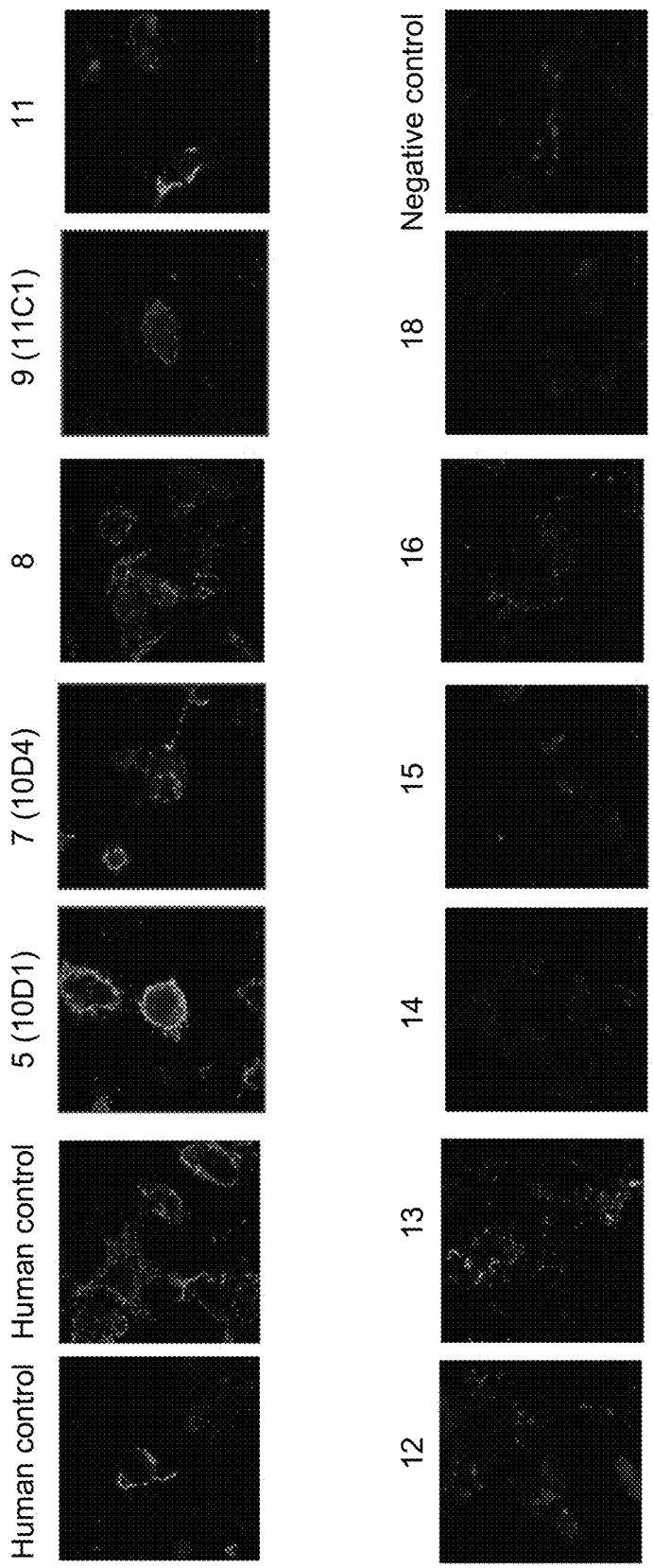
FIG. 20 shows Slc39a5 monoclonal antibody screening in HEK overexpressing human Slc39a5.
Figure 21:
FIG. 21 shows loss of function of Slc39a5 improves fasting blood glucose upon high fat high fructose dietary challenge. High fat high fructose dietary challenge results in significant increase in body weight across all genotypes in both sexes. Loss of function of Slc39a5 improves liver function as assessed by serum ALT and AST in both sexes at 16 weeks. Loss of function of Slc39a5 significantly improves hyperglycemia assessed by fasting blood glucose levels at endpoint (29 weeks). "NC": normal chow (NC); "HFFD": high fat high fructose diet.
Figure 21:
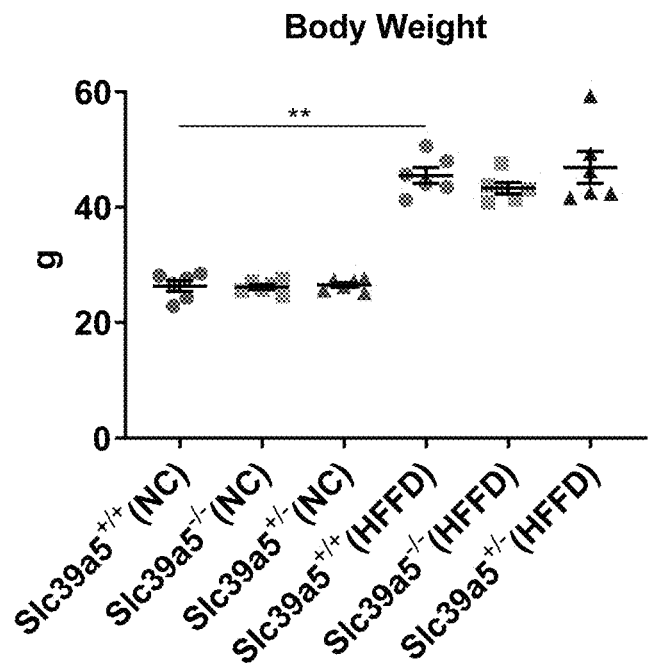
Figure 21:
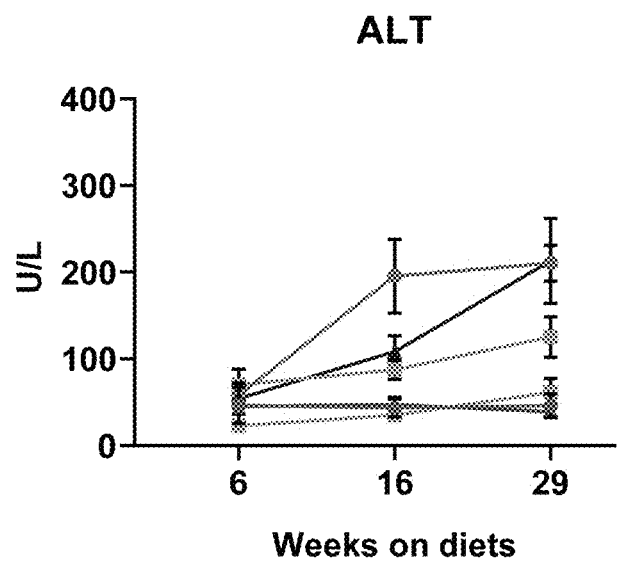
Figure 21:
Figure 21:
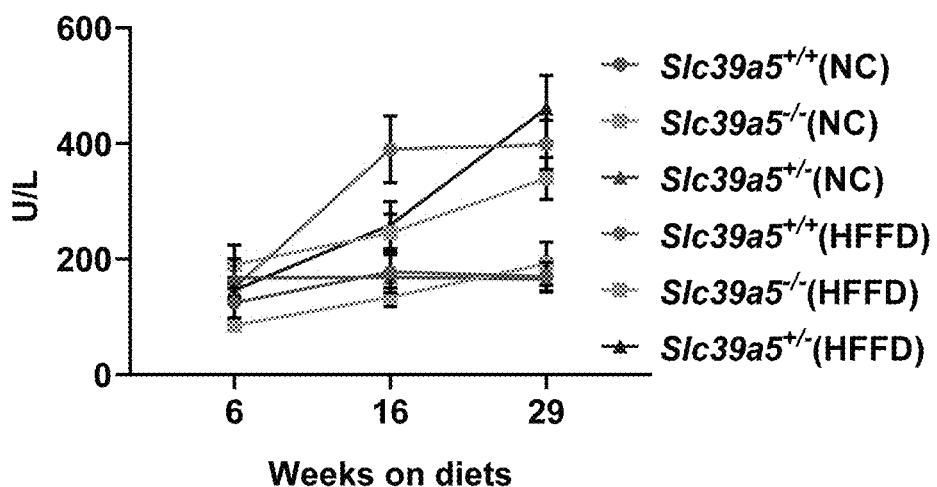
Figure 21:
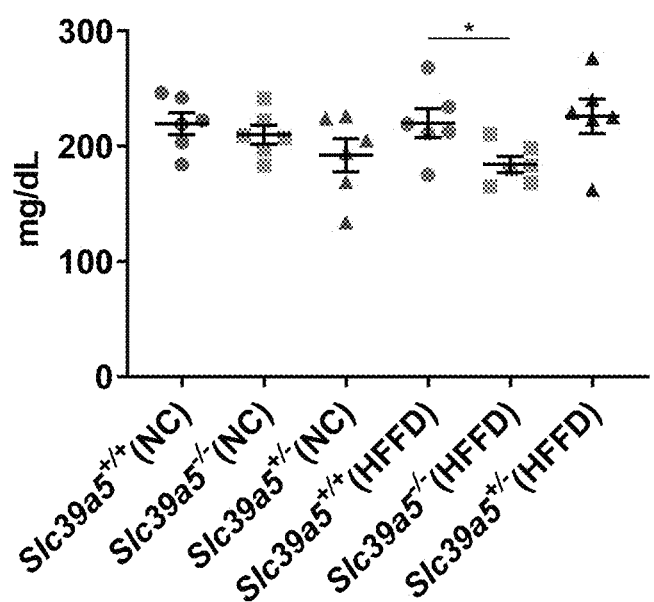
Figure 21:
Figure 21:
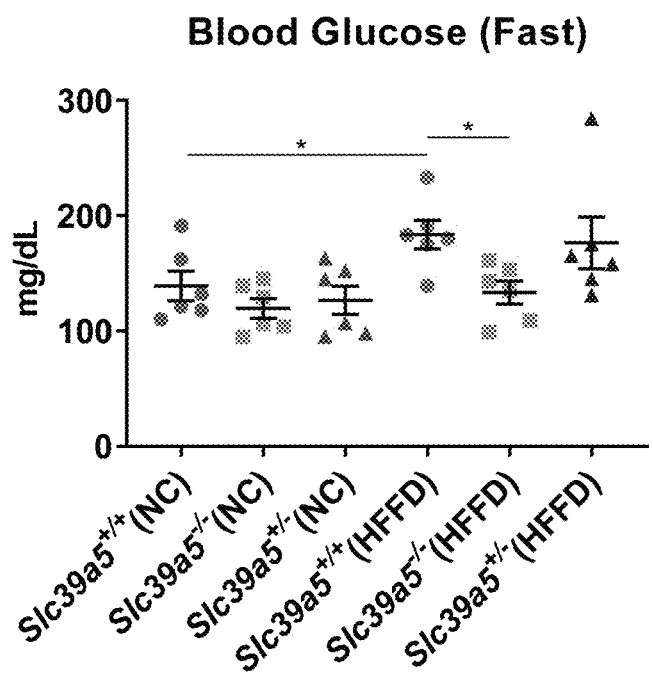
Figure 21:
Figure 21:
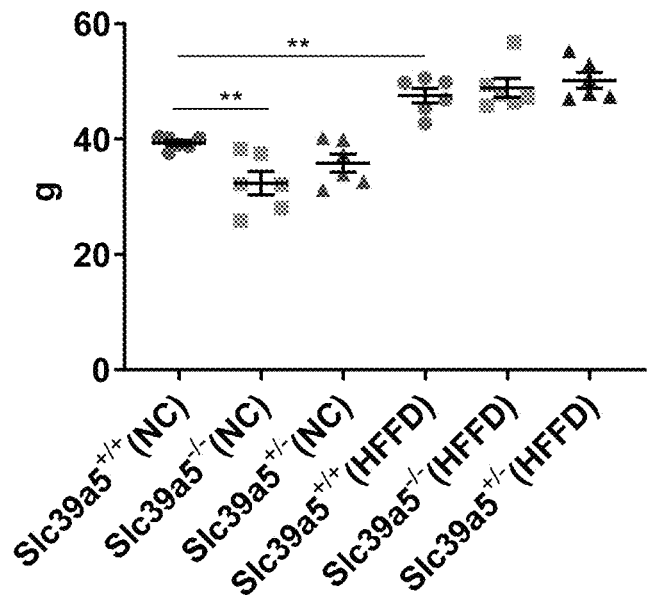
Figure 21:
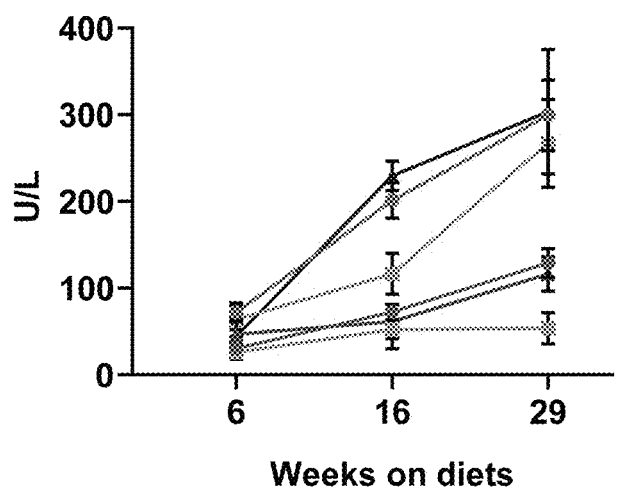
Figure 21:
Figure 21:
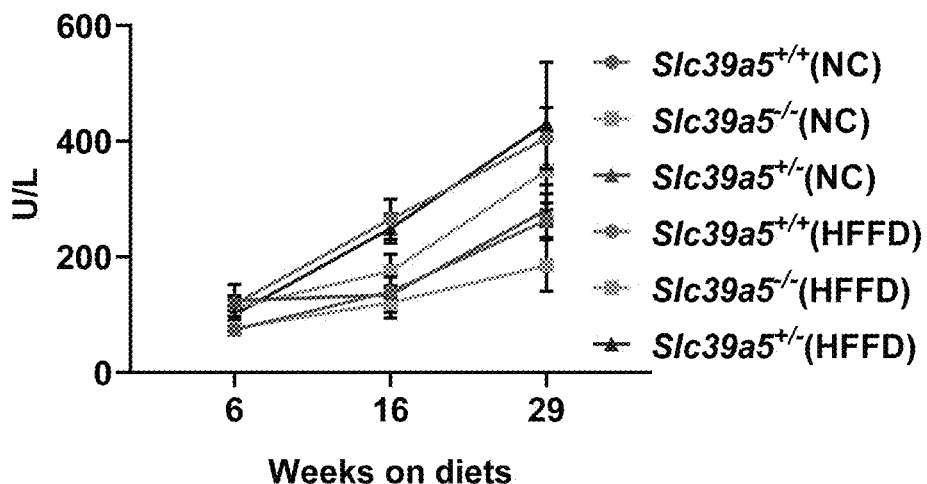
Figure 21:
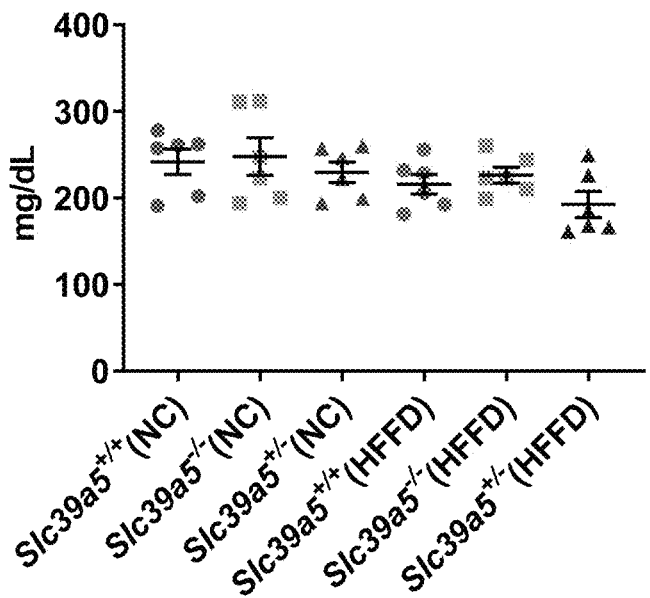
Figure 21:
Figure 21:
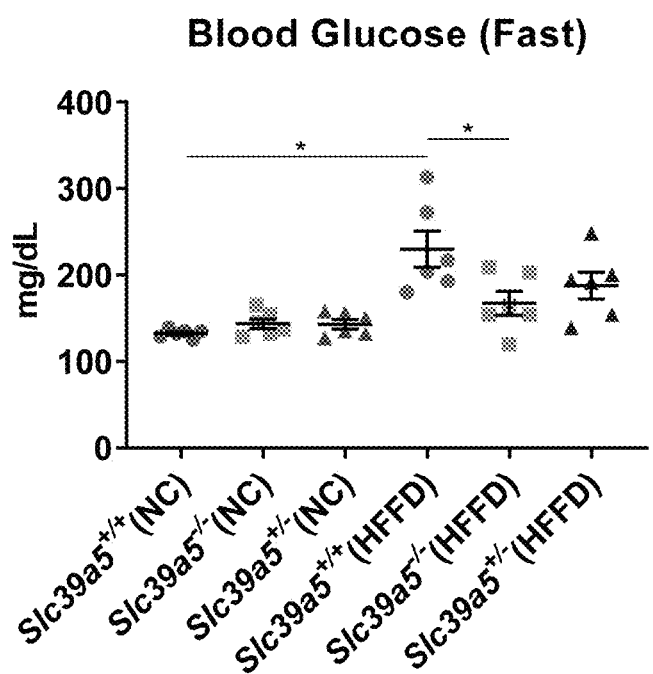
Figure 22:
FIG. 22 shows loss of function of Slc39a5 improves insulin sensitivity in mice challenged with high fat high fructose diet. Mice homozygous for Slc39a5 loss of function (regardless of sex) show marked improvement in insulin sensitivity compared to wild type counterparts assessed by oral glucose tolerance tests ("GTT").
Figure 22:
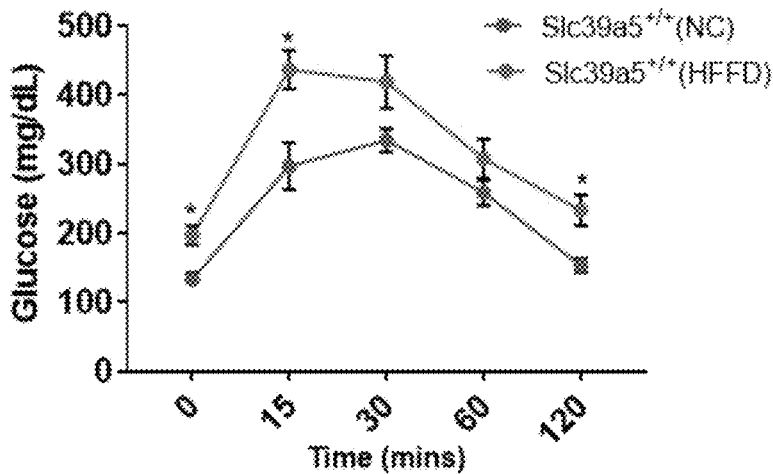
Figure 22:
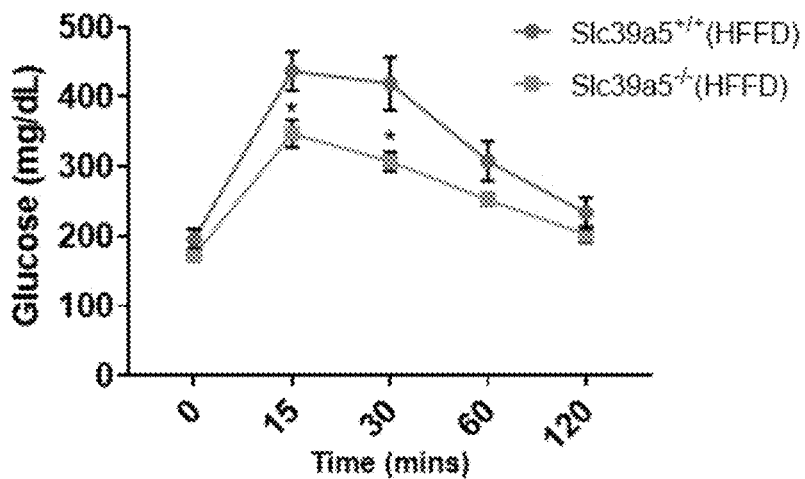
Figure 22:
Figure 22:
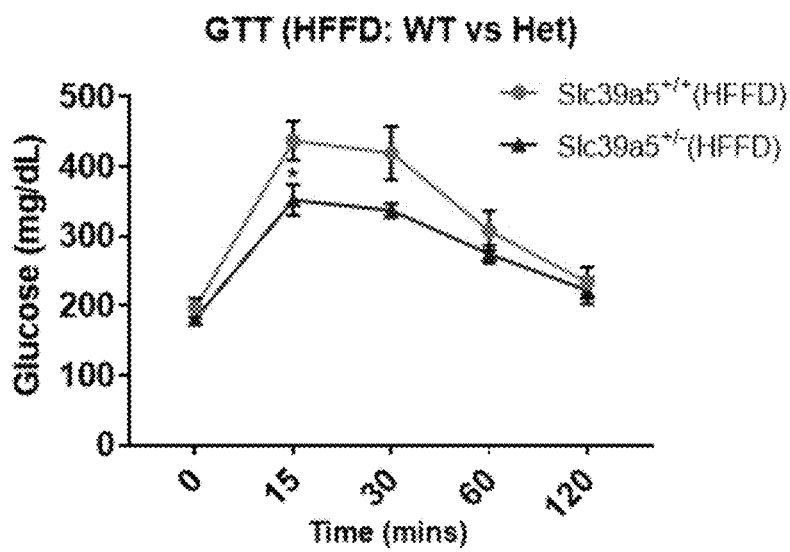
Figure 22:
Figure 22:
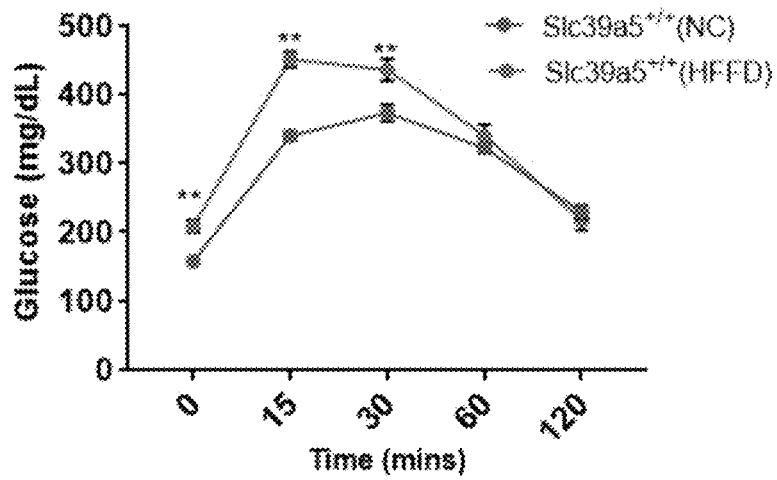
Figure 22:
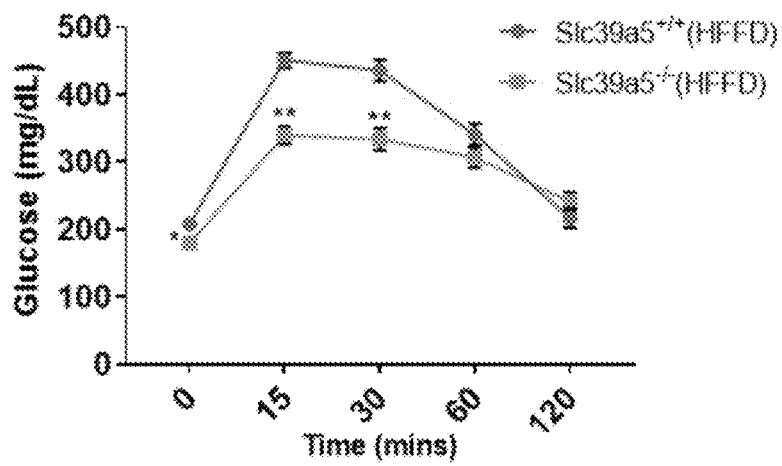
Figure 22:
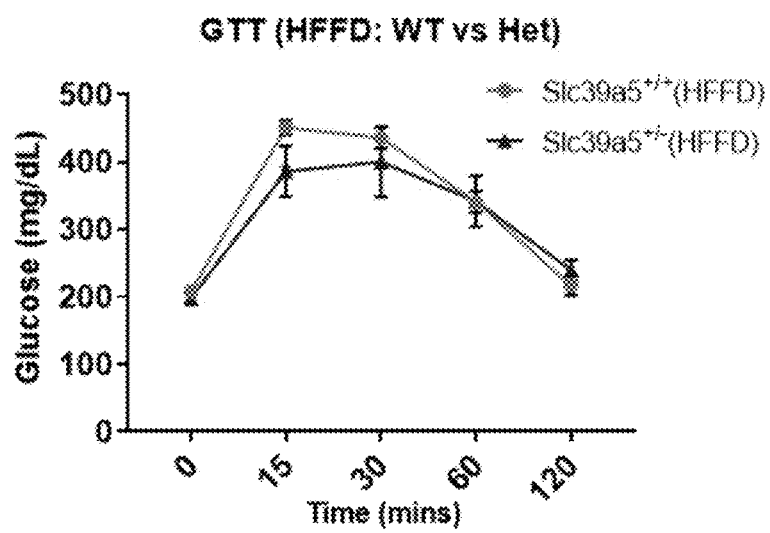
Figure 23:
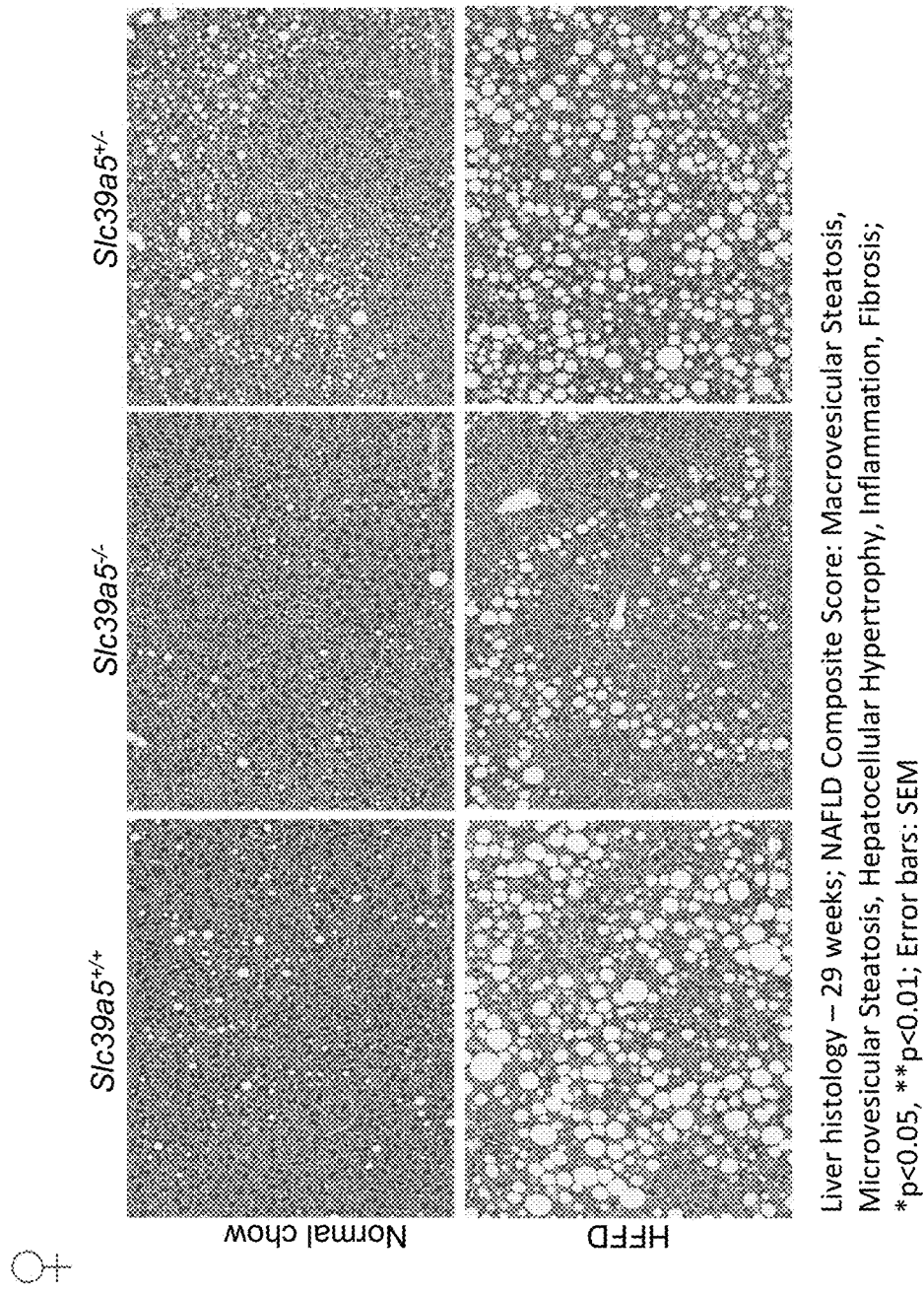
FIG. 23 shows loss of function of Slc39a5 improves hepatic steatosis upon HFFD challenge. Slc39a5 loss of function female mice are more protected than their male counterparts. NAFLD composite scores (assessed by two independent pathologists) representing an aggregate score of macrovesicular steatosis, microvesicular steatosis, hepatocellular hypertrophy, inflammation and fibrosis show a significant improvement in female Slc39a5 knockout mice as compared to wild type counterparts; whereas in male mice, loss of Slc39a5 improves hepatic steatosis on normal chow and accords no protection when challenged by high fat high fructose diet demonstrated by histopathology and NAFLD scores.
Figure 23:
Figure 23:
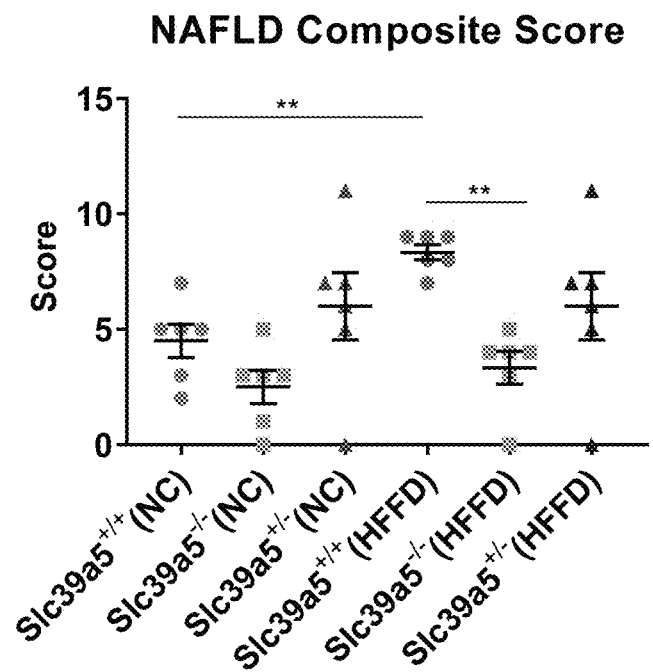
Figure 23:
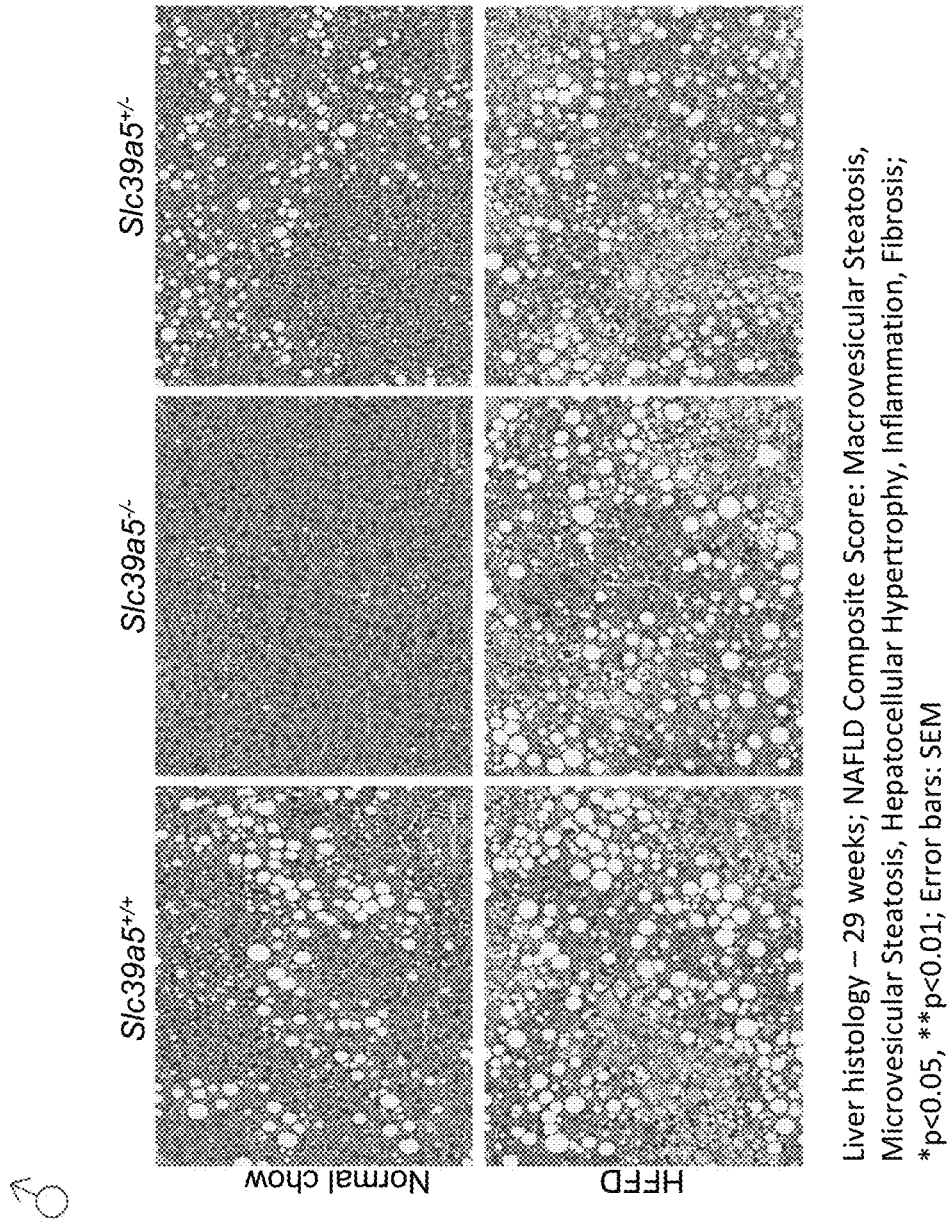
Figure 23:
Figure 23:
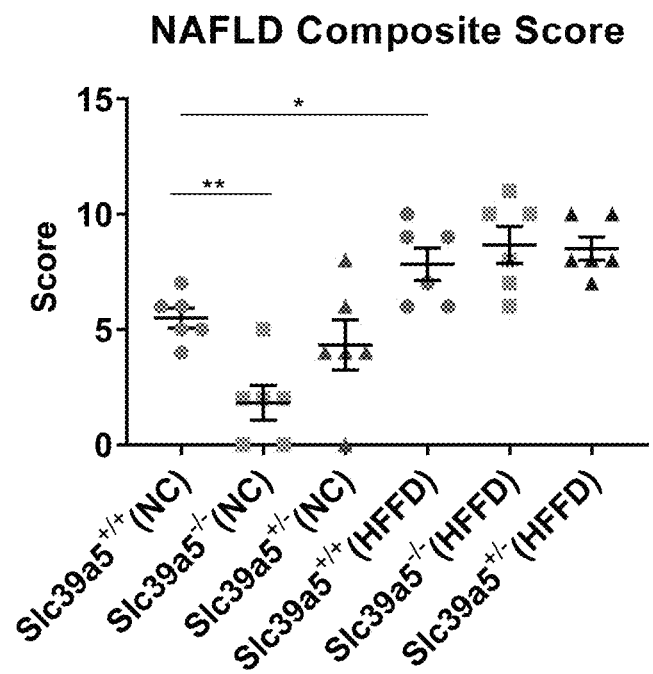
Figure 24A:
FIGS. 24A and 24B show loss of function of Slc39a5 results in increased hepatic zinc levels and a consequent elevation in hepatic metallothionein ("Mt1" and "Mt2") expression. Loss of function of Slc39a5 does not significantly influence hepatic iron, copper, cobalt, calcium and magnesium levels (FIG. 24A: female mice.
Figure 24A:
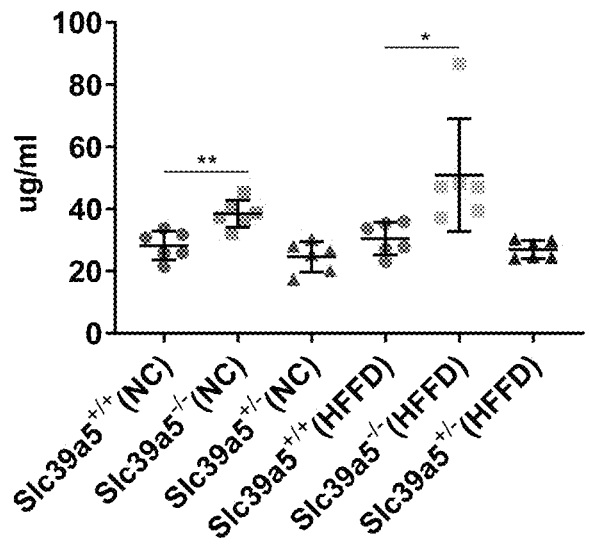
Figure 24A:
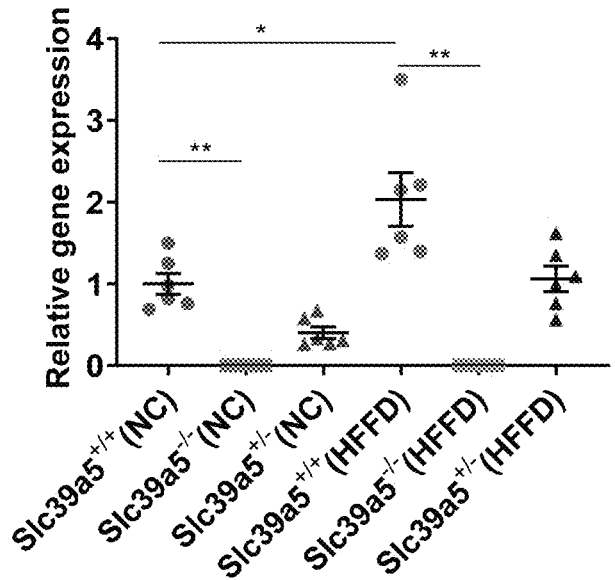
Figure 24A:
Figure 24A:
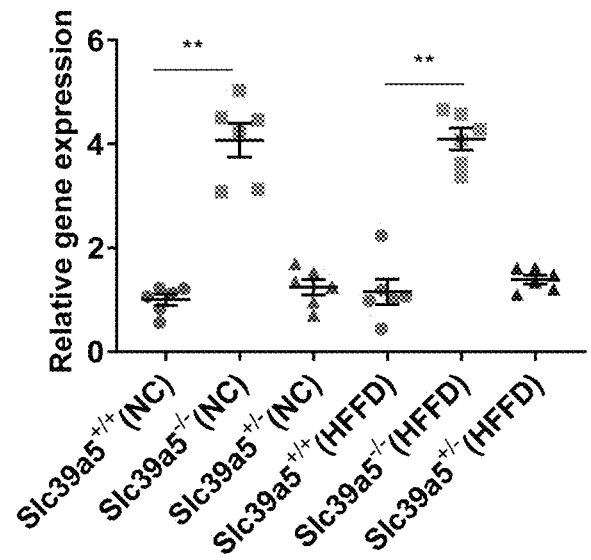
Figure 24A:
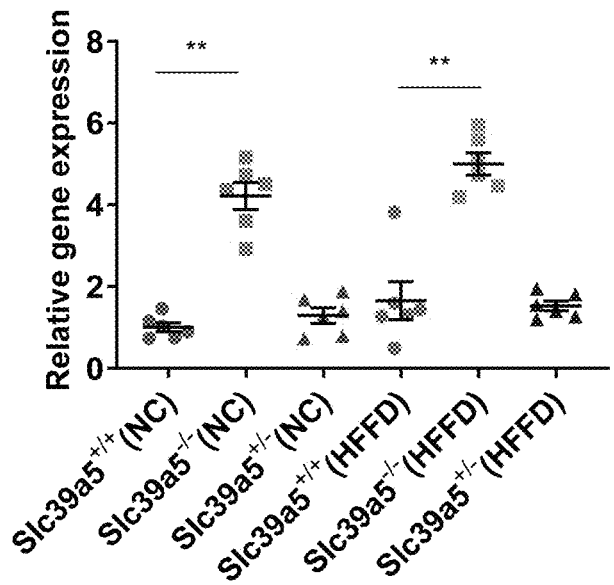
Figure 24A:
Figure 24A:
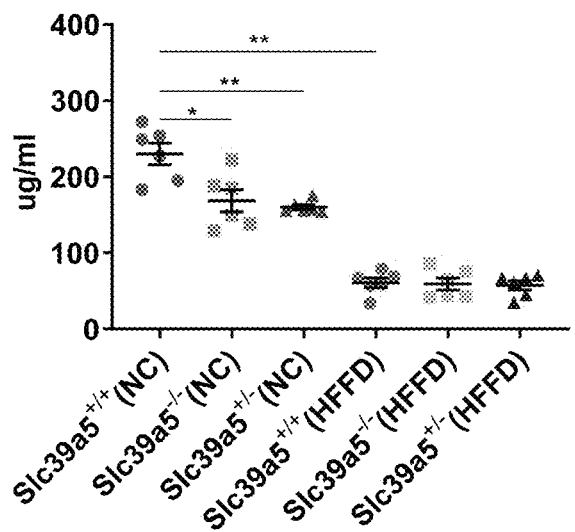
Figure 24A:
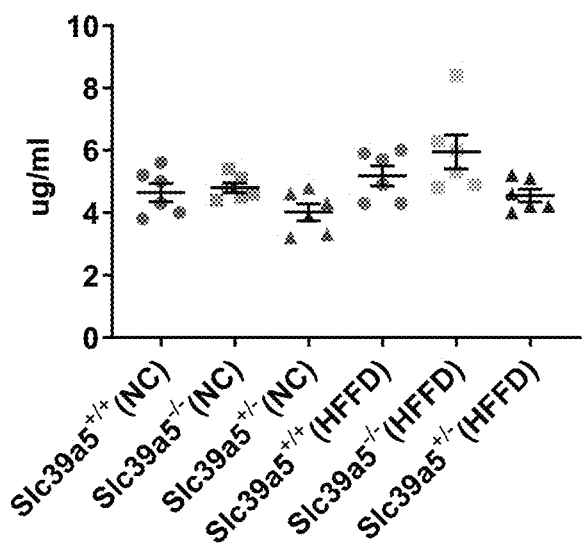
Figure 24A:
Figure 24A:
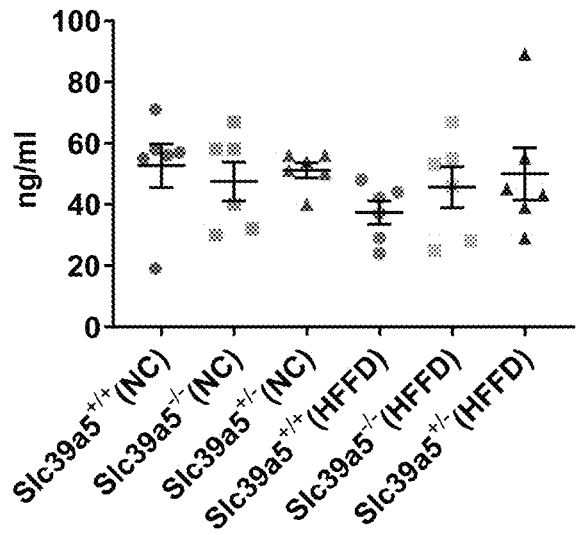
Figure 24A:
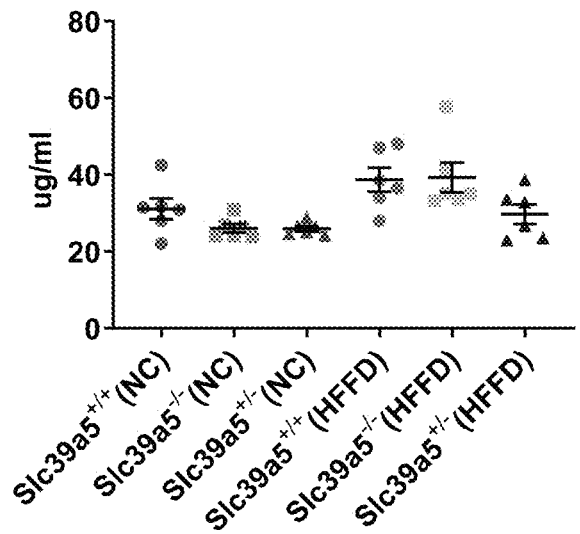
Figure 24A:
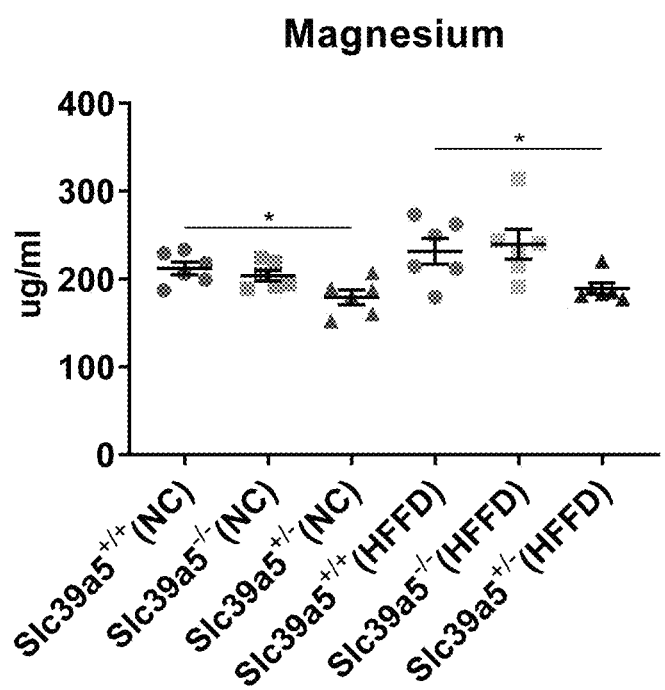
Figure 24B:
Figure 24B:
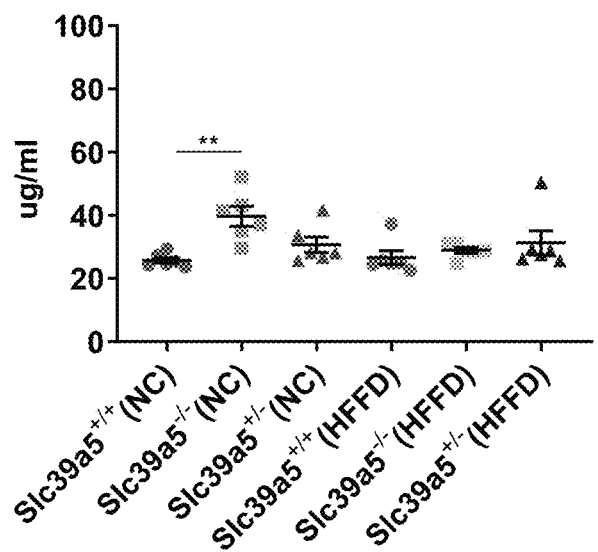
Figure 24B:
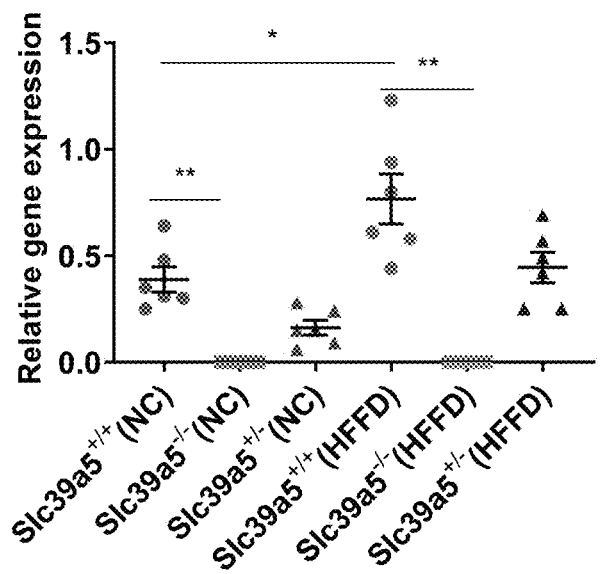
Figure 24B:
Figure 24B:
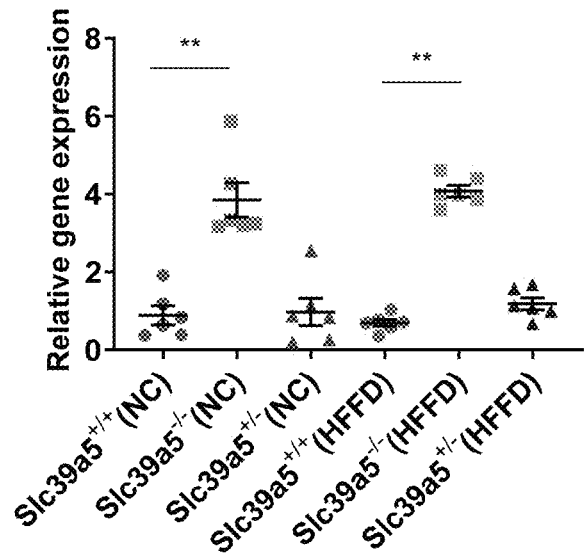
Figure 24B:
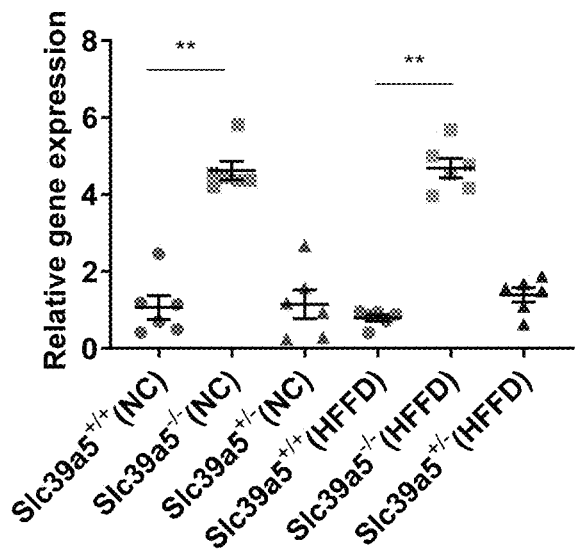
Figure 24B:
Figure 24B:
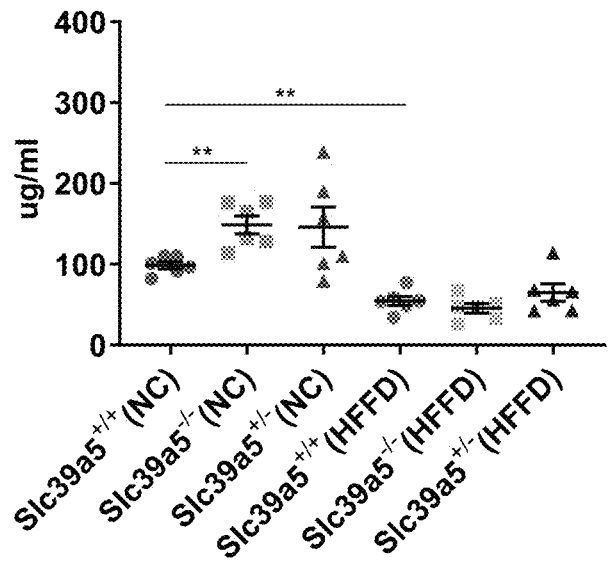
Figure 24B:
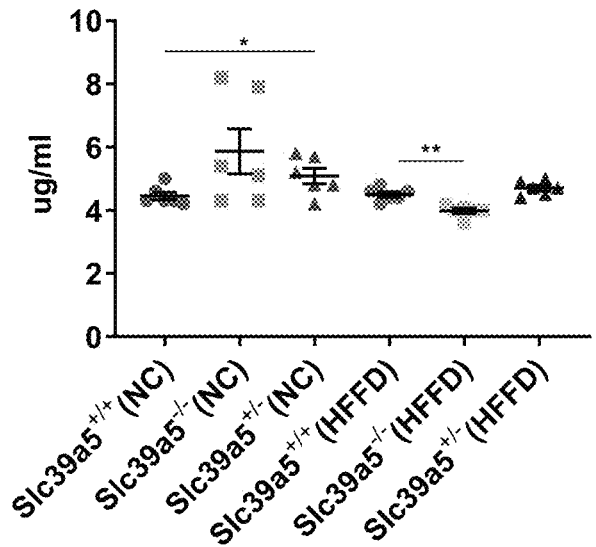
Figure 24B:
Figure 24B:
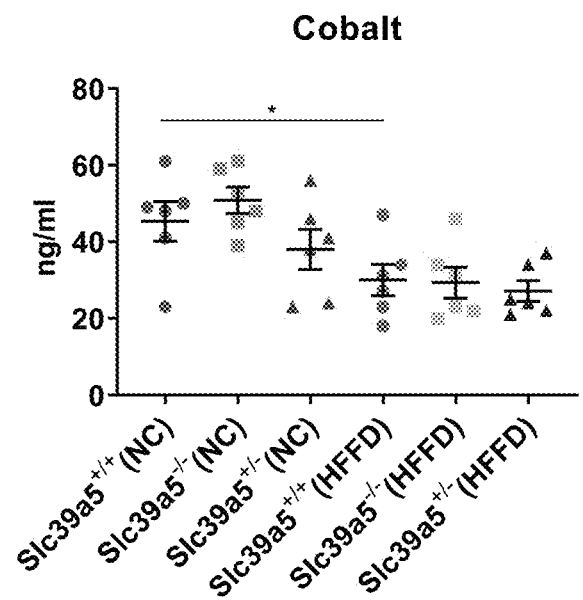
Figure 24B:
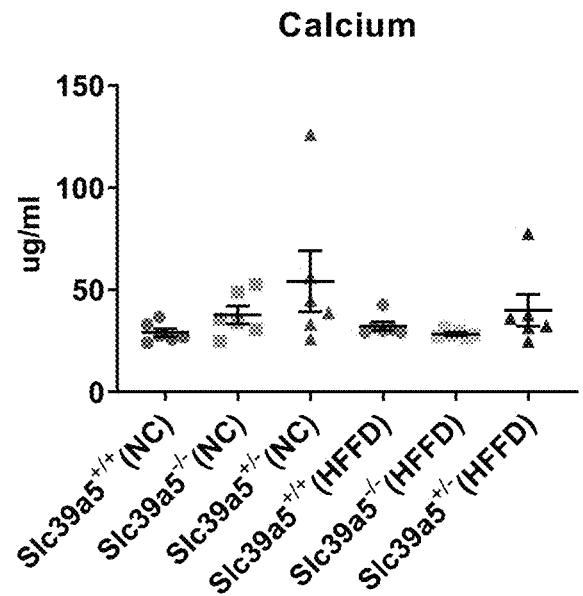
Figure 24B:
Figure 24B:
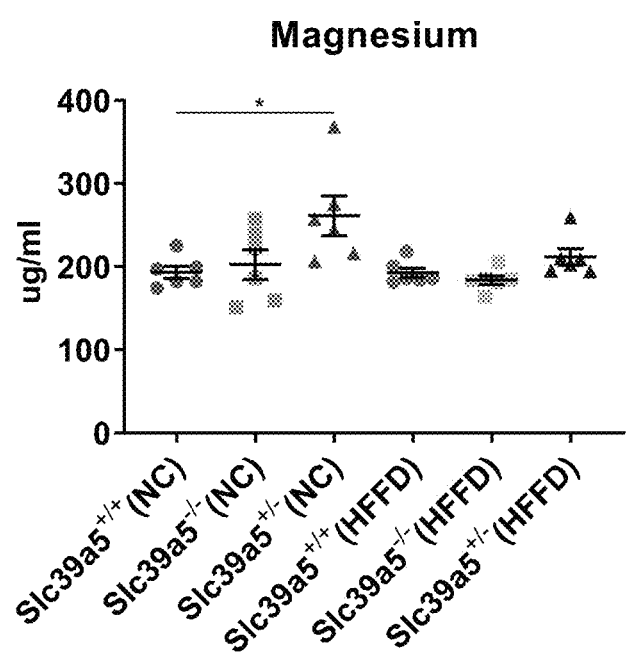
Figure 25A:
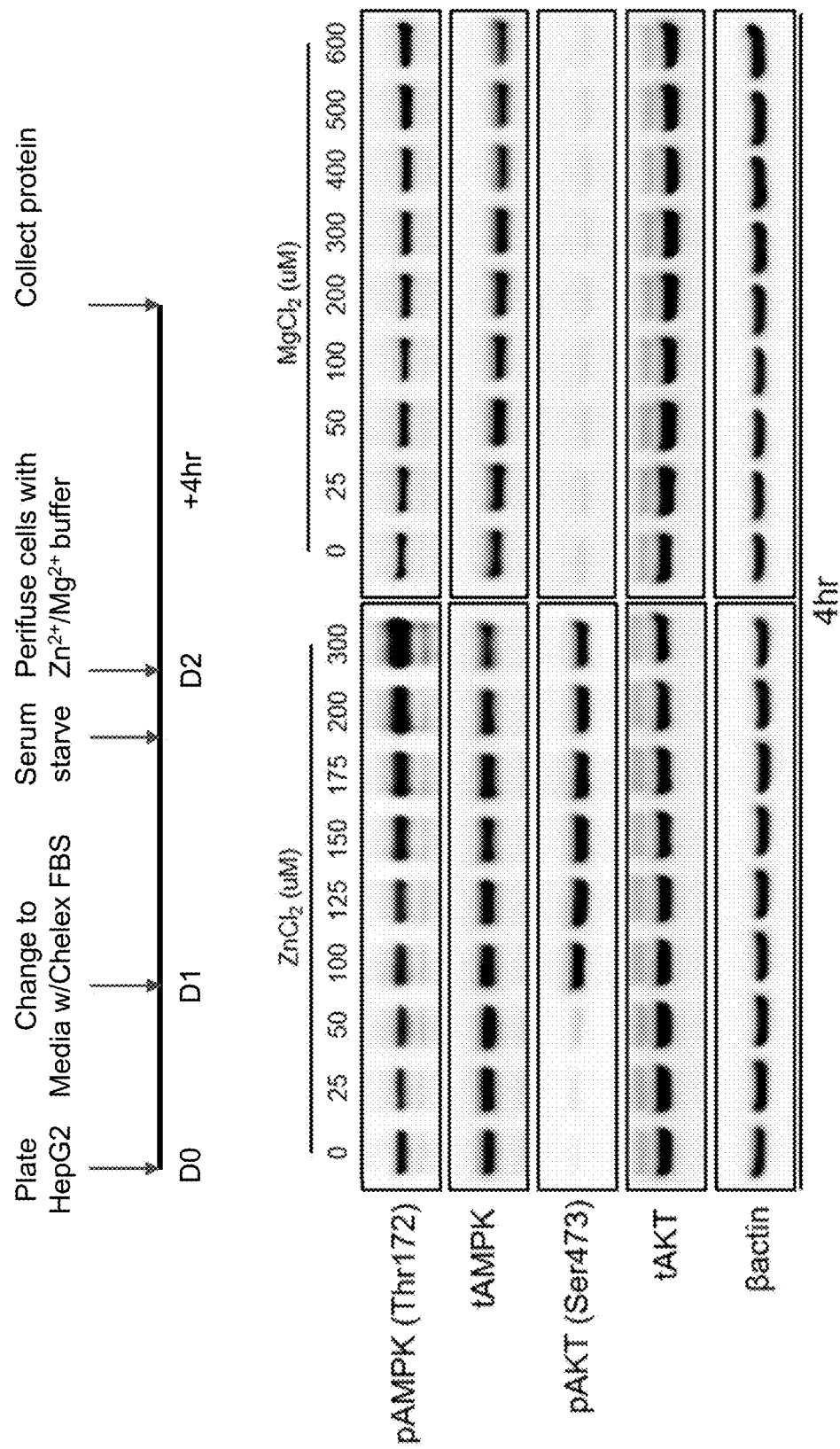
FIGS. 25A and 25B show zinc acutely activates LKB1/AMPK and AKT signaling pathways in dose dependent manner in human hepatoma HepG2 cells (FIG. 25A) and human primary hepatocytes (FIG. 25B).
Figure 25A:
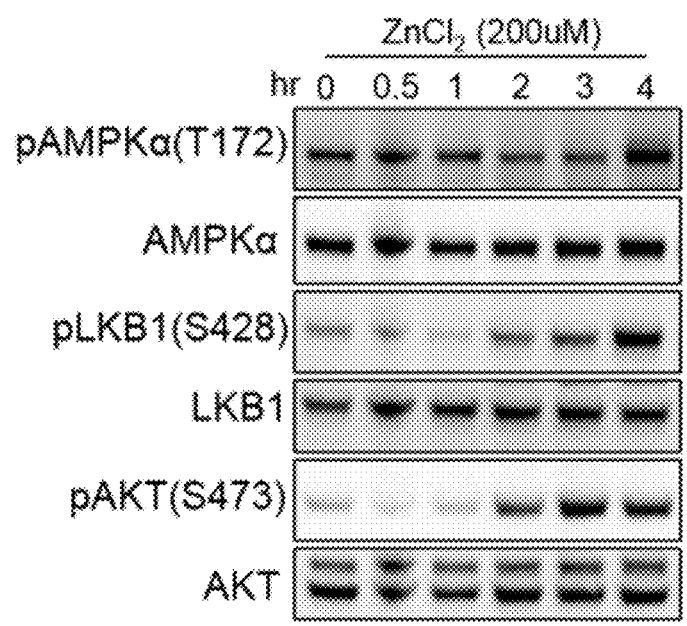
Figure 25B:
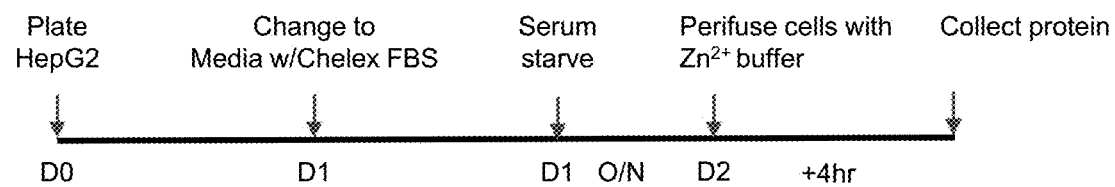
Figure 25B:
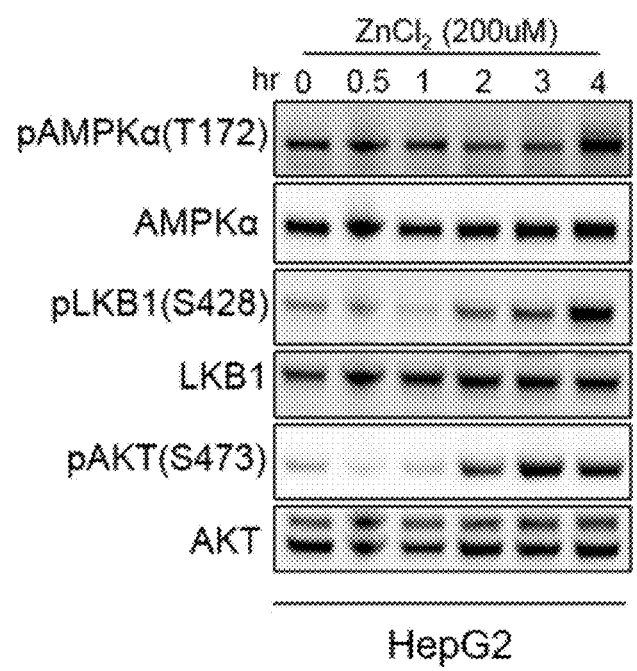
Figure 25B:
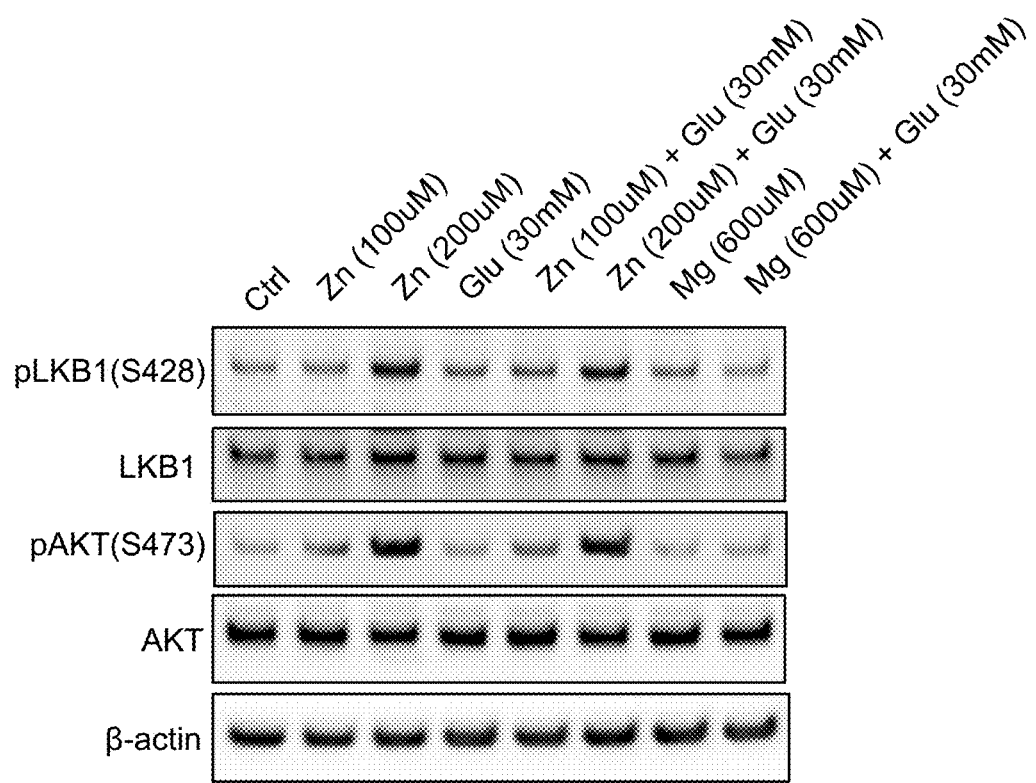
Figure 26A:
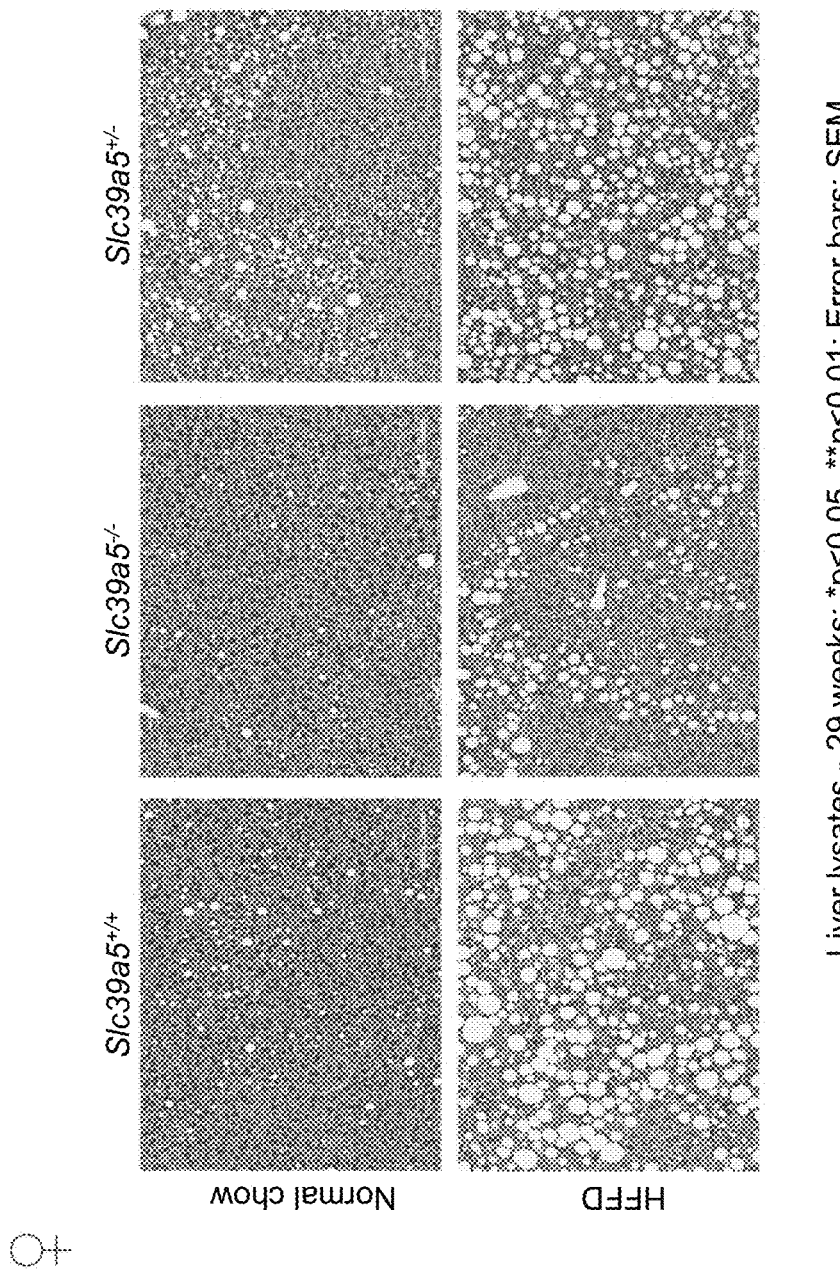
FIG. 26A shows loss of function of Slc39a5 improves hepatic steatosis in female mice challenged with high fat high fructose diet. Loss of function of Slc39a5 results in increased hepatic zinc levels with concomitant activation of hepatic AMPK and AKT signaling in female mice challenged with high fat high fructose diet. Hepatic triglyceride levels were reduced with an increase in hepatic beta-hydroxybutyrate levels, suggesting increased β-oxidation. Loss of function of Slc39a5 results in a downregulation of Fasn and G6pc genes involved in de novo lipogenesis and hepatic gluconeogenesis, respectively.
Figure 26A:
Figure 26A:
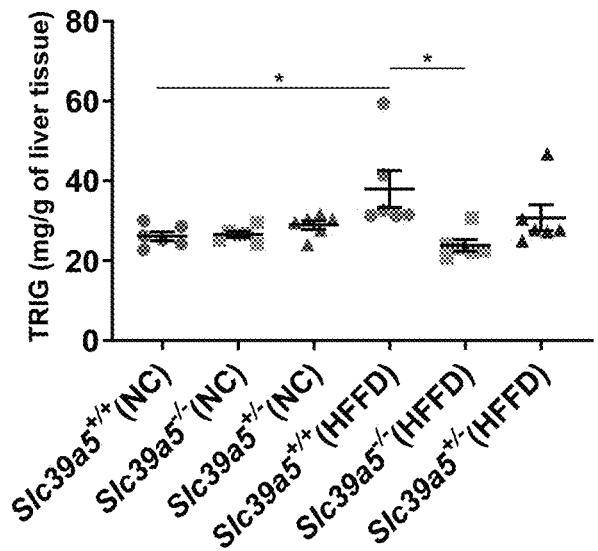
Figure 26A:
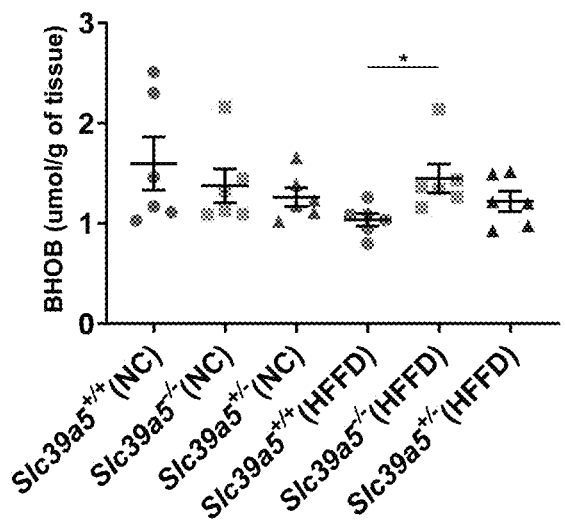
Figure 26A:
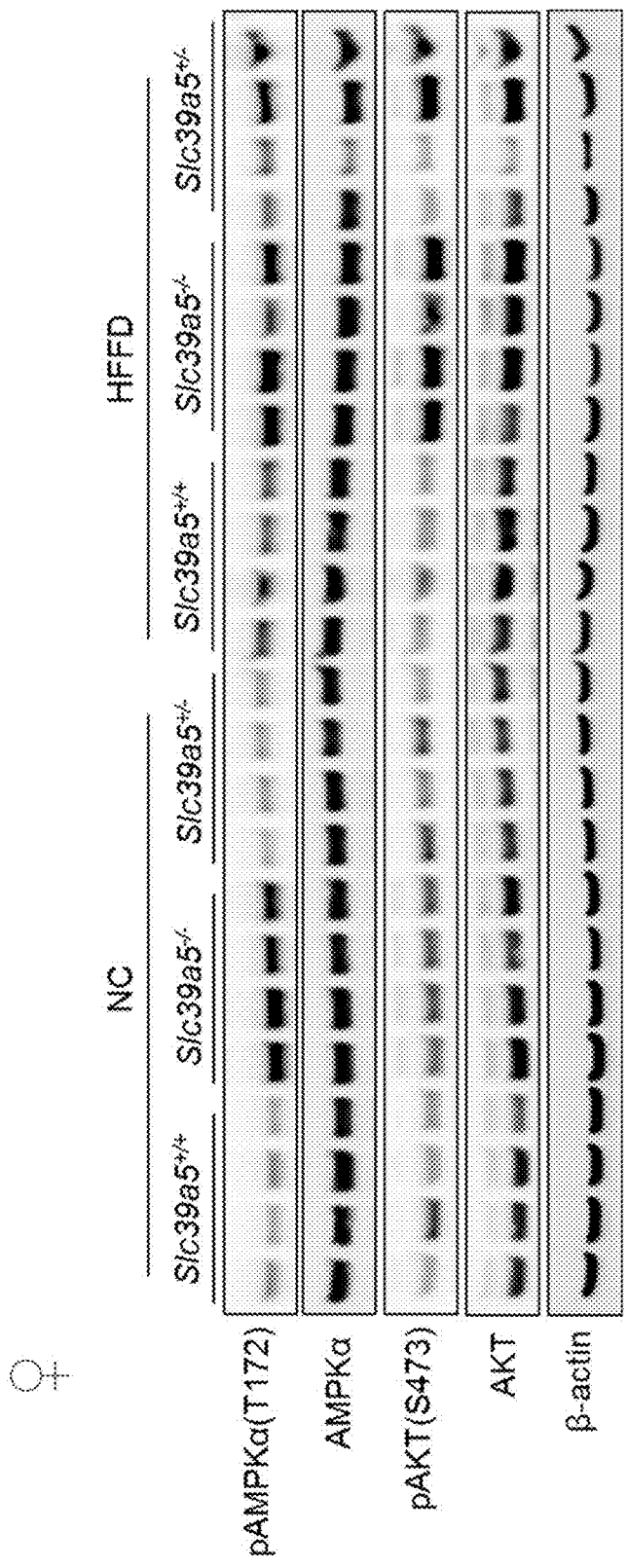
Figure 26A:
Figure 26A:
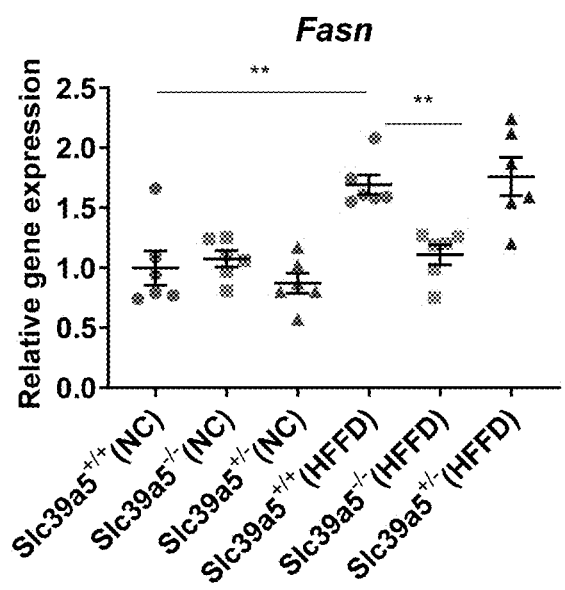
Figure 26A:
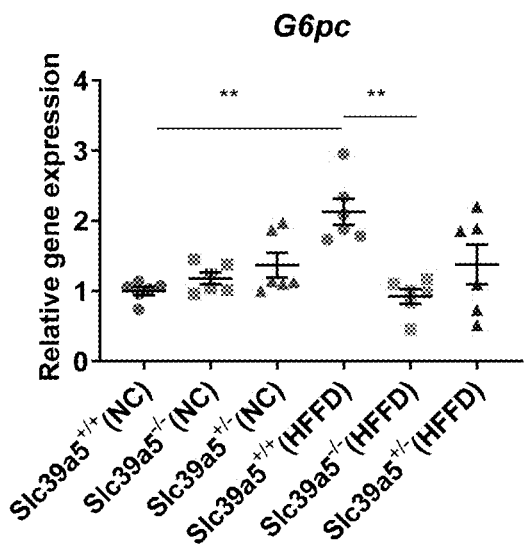
Figure 26B:
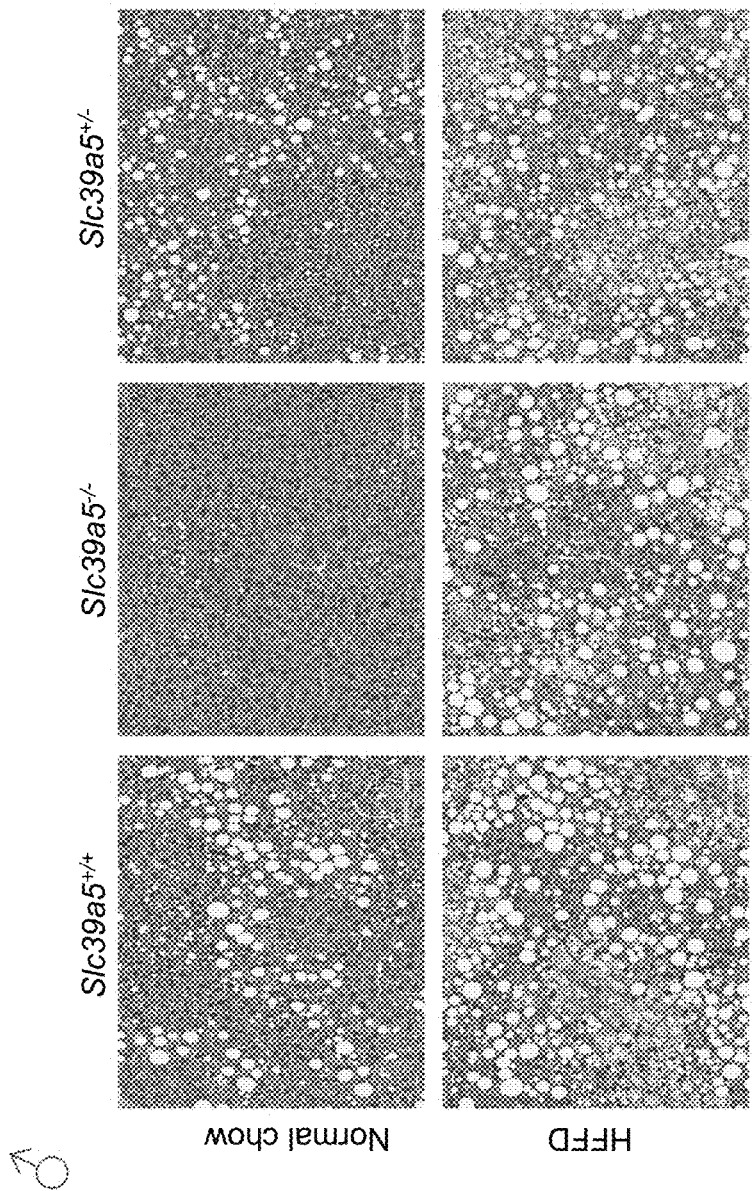
FIG. 26B shows loss of function of Slc39a5 improves hepatic steatosis in male mice fed with normal chow. Loss of Slc39a5 in male mice challenged with HFFD results in insignificant elevation in hepatic zinc levels with a modest activation of hepatic AMPK signaling. Hepatic triglyceride levels are slightly reduced with an increase in hepatic beta-hydroxybutyrate levels. Loss of function of Slc39a5 results in a modest repression of Fasn and significant downregulation of G6pc, genes involved in de novo lipogenesis and hepatic gluconeogenesis, respectively.
Figure 26B:
Figure 26B:
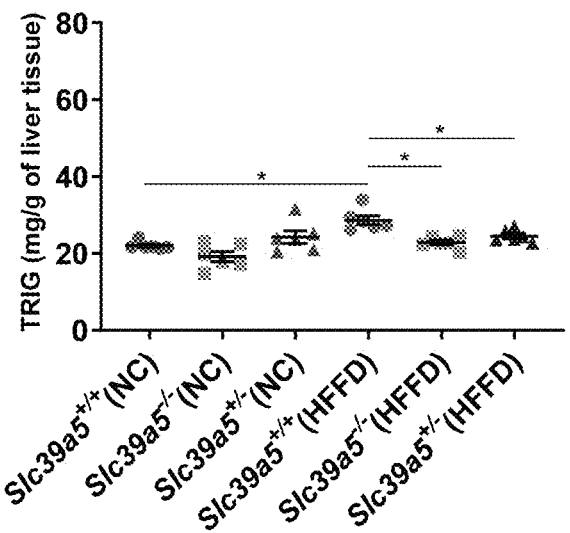
Figure 26B:
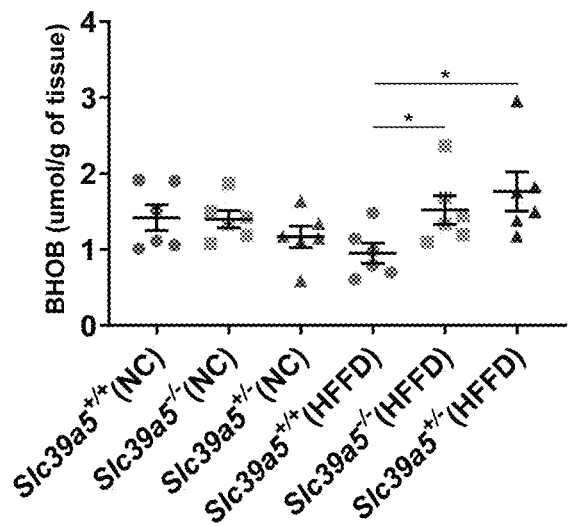
Figure 26B:
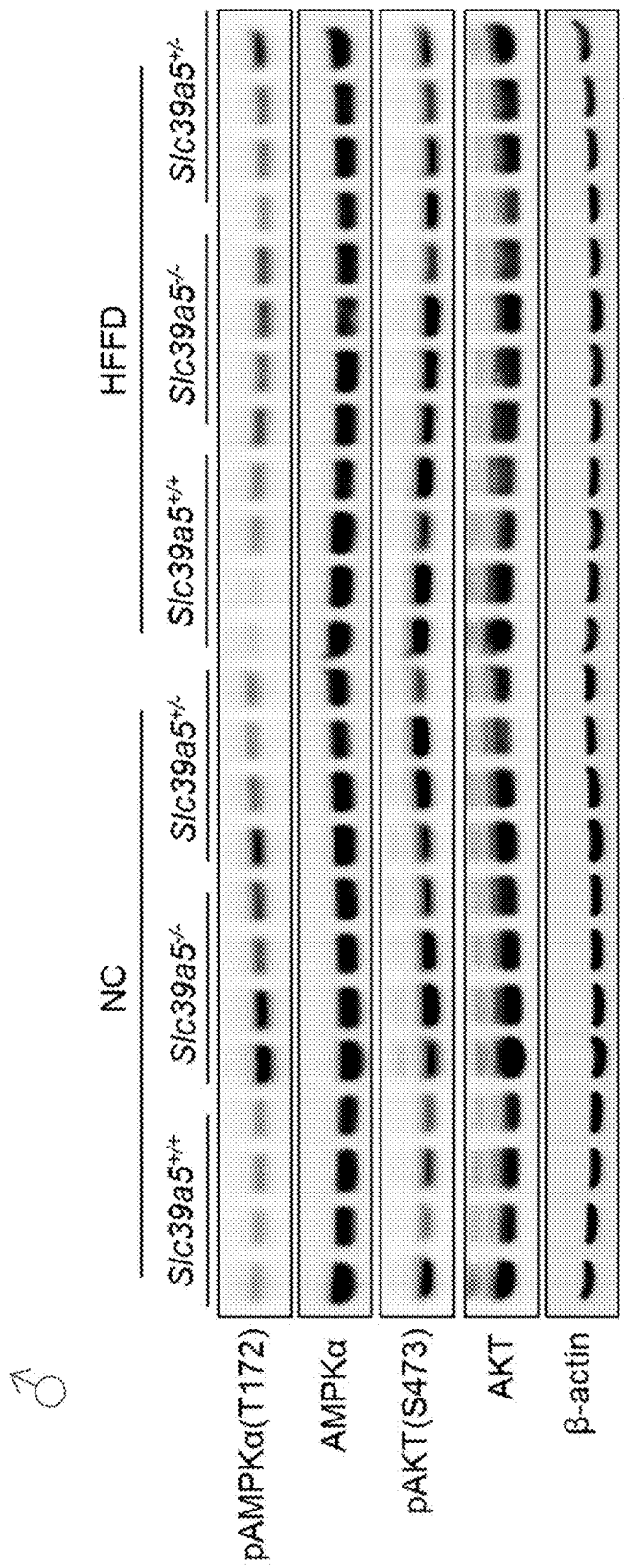
Figure 26B:
Figure 26B:
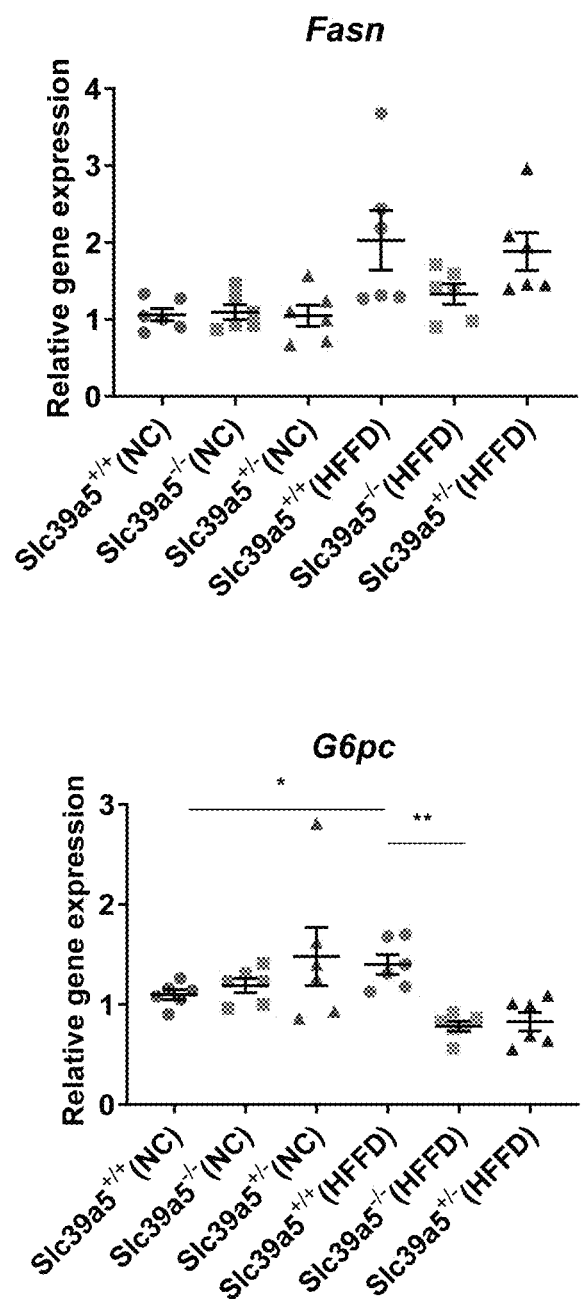
Figure 27:
FIG. 27 shows loss of function of Slc39a5 improves liver function and fasting blood glucose in leptin-receptor deficient mice. Congenital leptin-receptor deficiency results in significant increase in body weight in Lepr$^{-/-}$ and Slc39a5$^{-/-}$; Lepr$^{-/-}$ mice in both sexes. Loss of function of Slc39a5 improves liver function in leptin-receptor deficient mice (both sexes) as assessed by serum ALT and AST at 22 weeks. Loss of function of Slc39a5 significantly improves hyperglycemia in leptin-receptor deficient mice (both sexes) demonstrated by reduced fasting blood glucose levels at 34 weeks.
Figure 27:
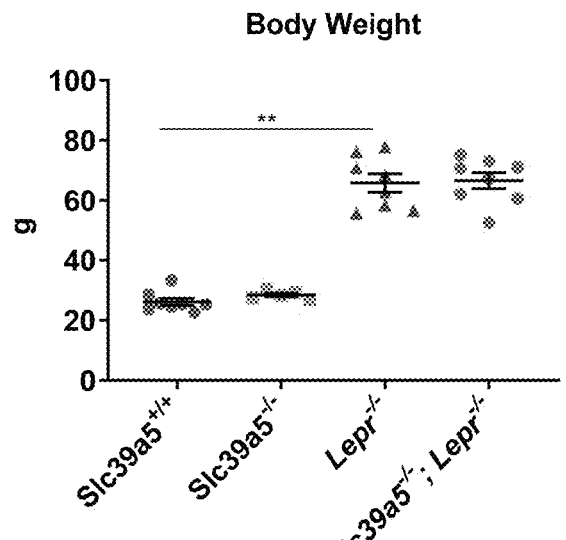
Figure 27:
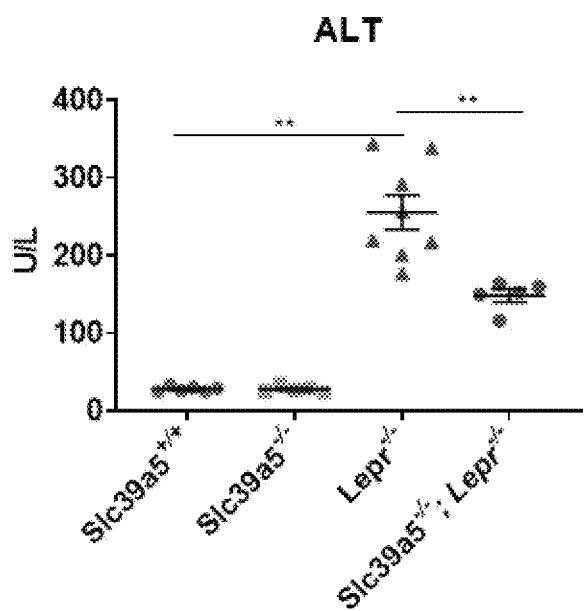
Figure 27:
Figure 27:
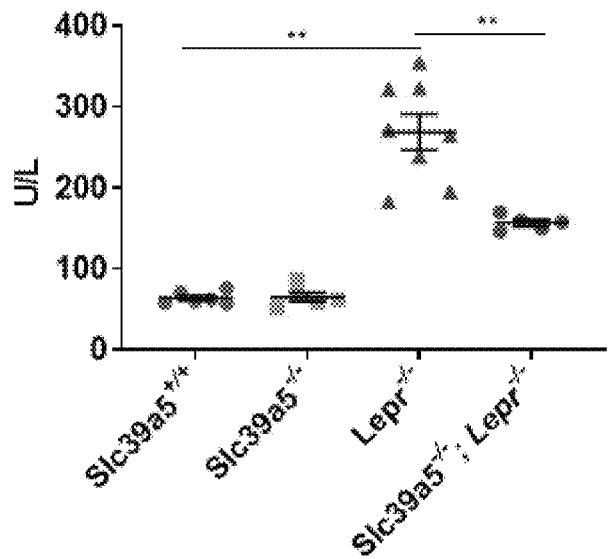
Figure 27:
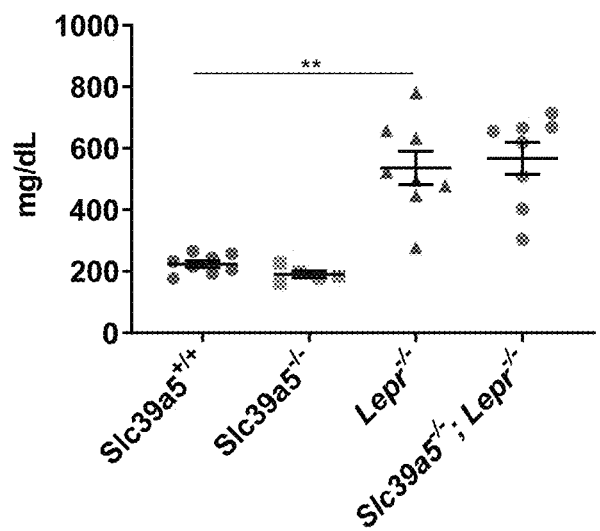
Figure 27:
Figure 27:
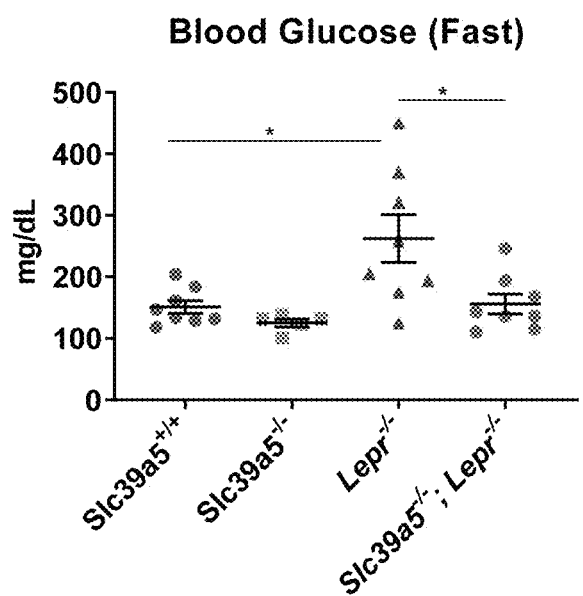
Figure 27:
Figure 27:
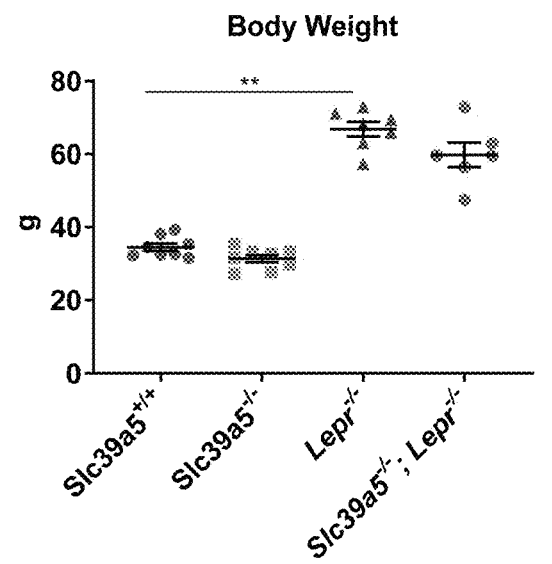
Figure 27:
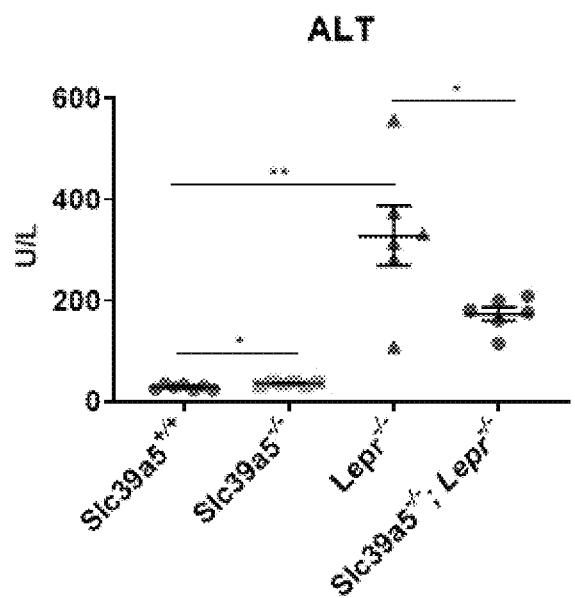
Figure 27:
Figure 27:
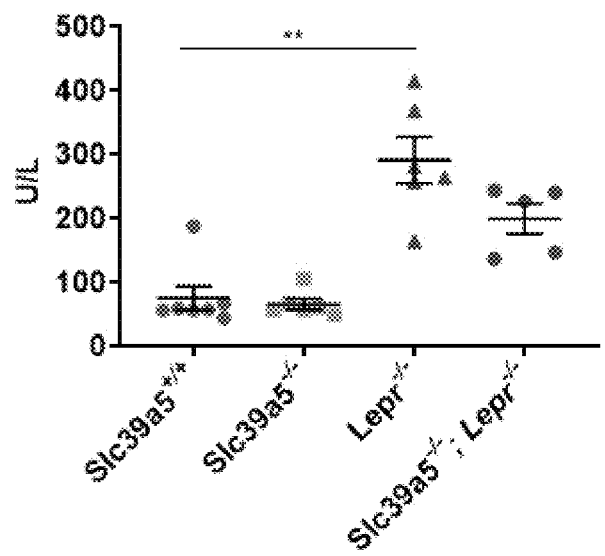
Figure 27:
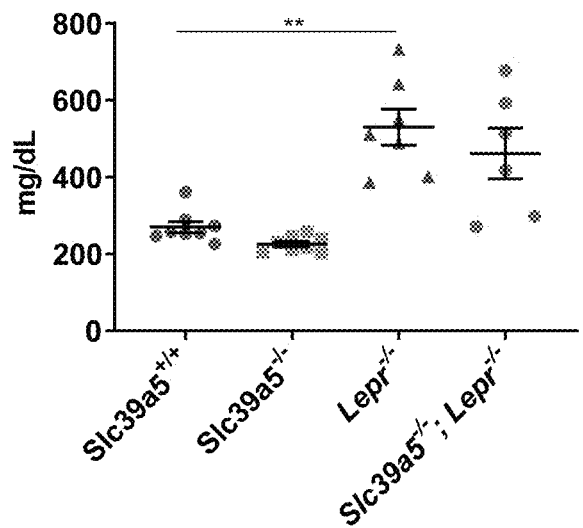
Figure 27:
Figure 27:
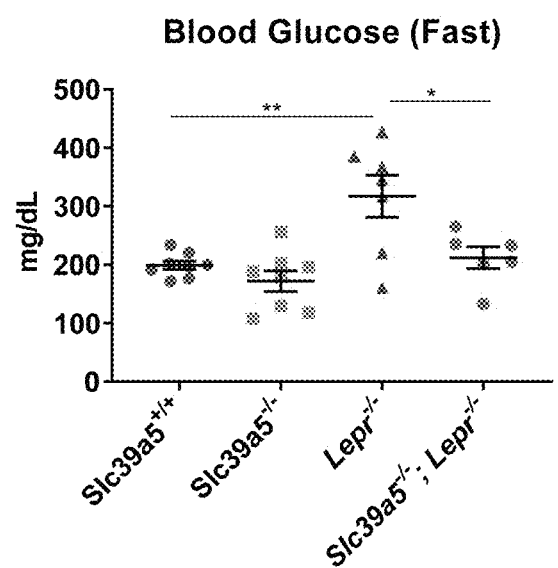
Figure 28:
FIG. 28 shows loss of function of Slc39a5 in leptin-receptor deficient mice (both sexes) results in improved insulin sensitivity as compared to leptin-receptor deficient (Lepr$^{-/-}$) counterparts assessed by oral GTT.
Figure 28:
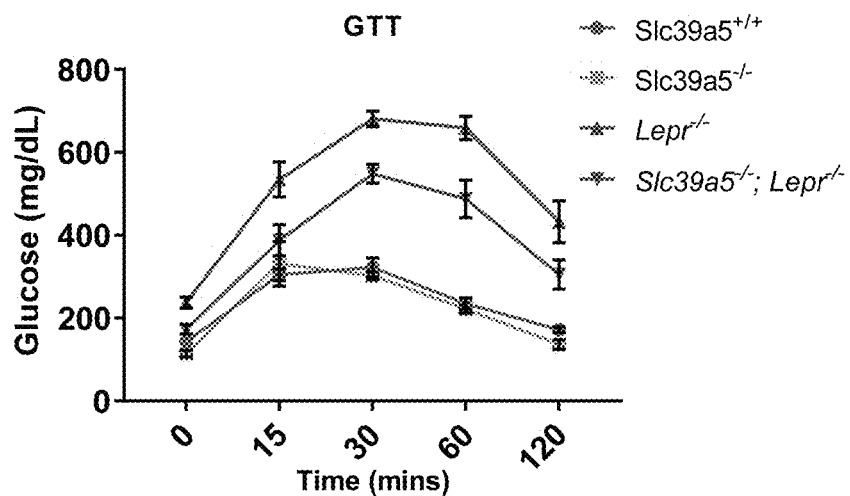
Figure 28:
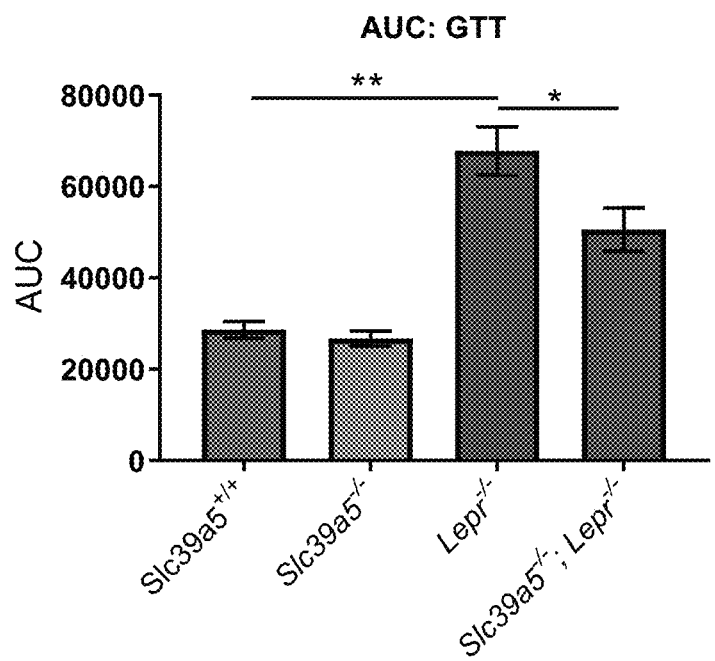
Figure 28:
Figure 28:
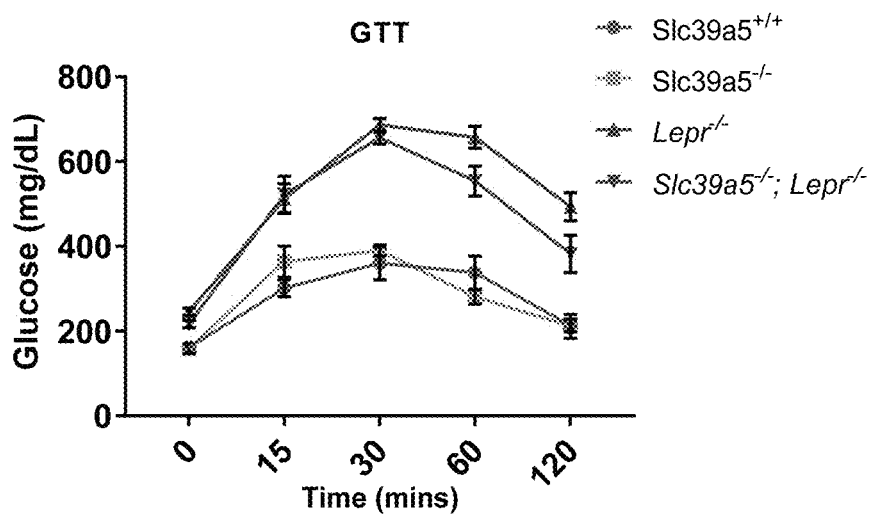
Figure 28:
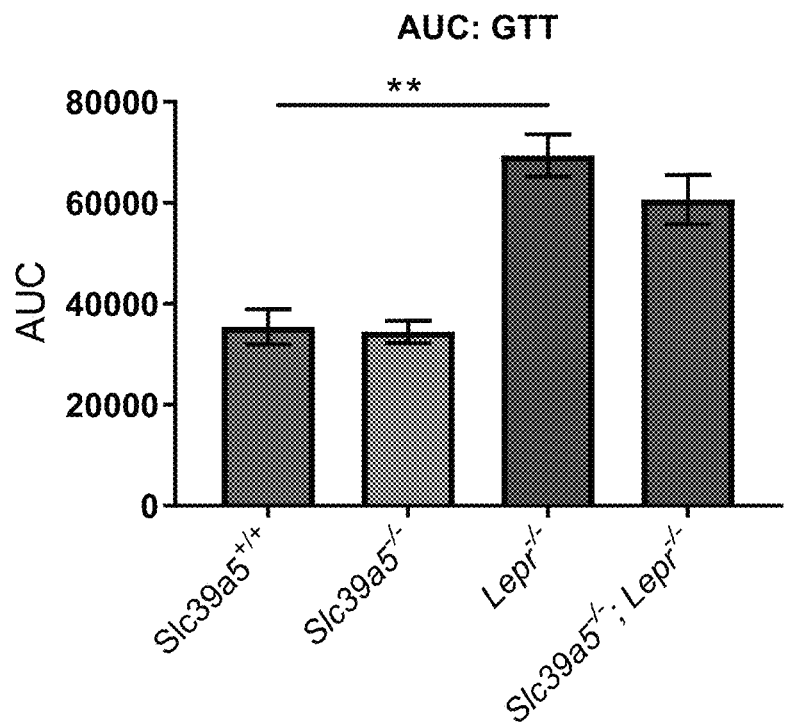
Figure 29:
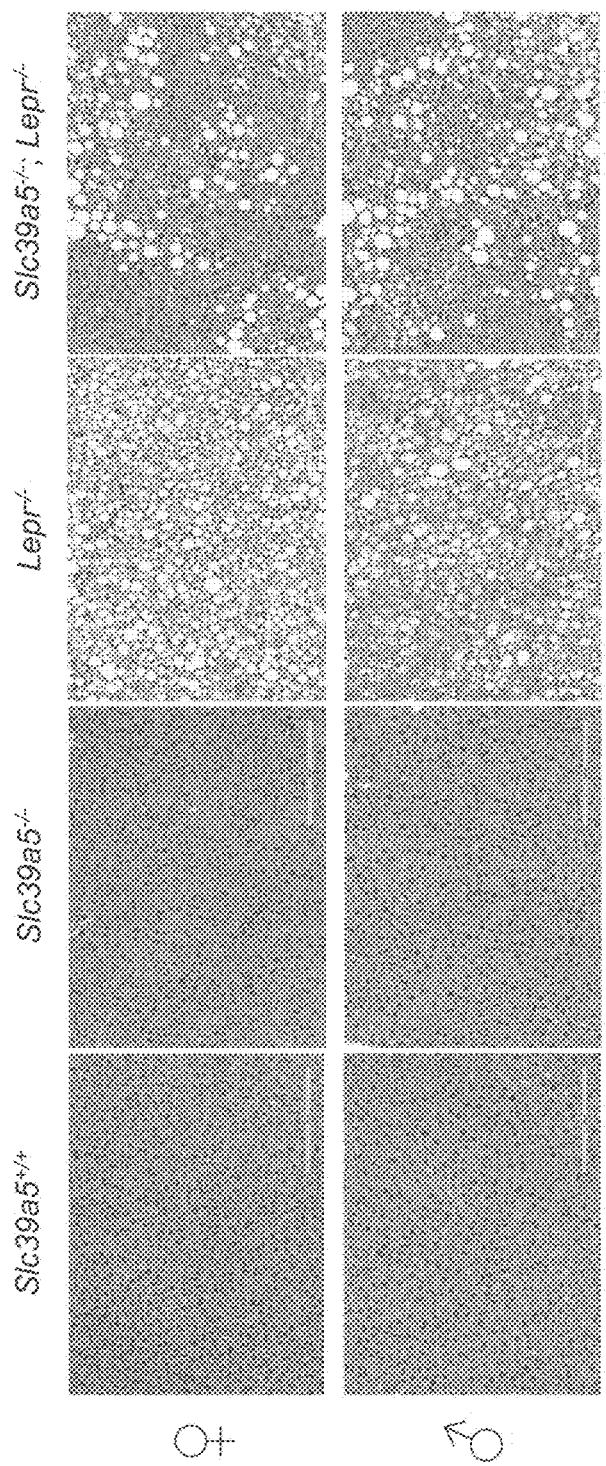
FIG. 29 shows loss of function of Slc39a5 improves hepatic steatosis in leptin-receptor deficient mice (both sexes).
Figure 30:
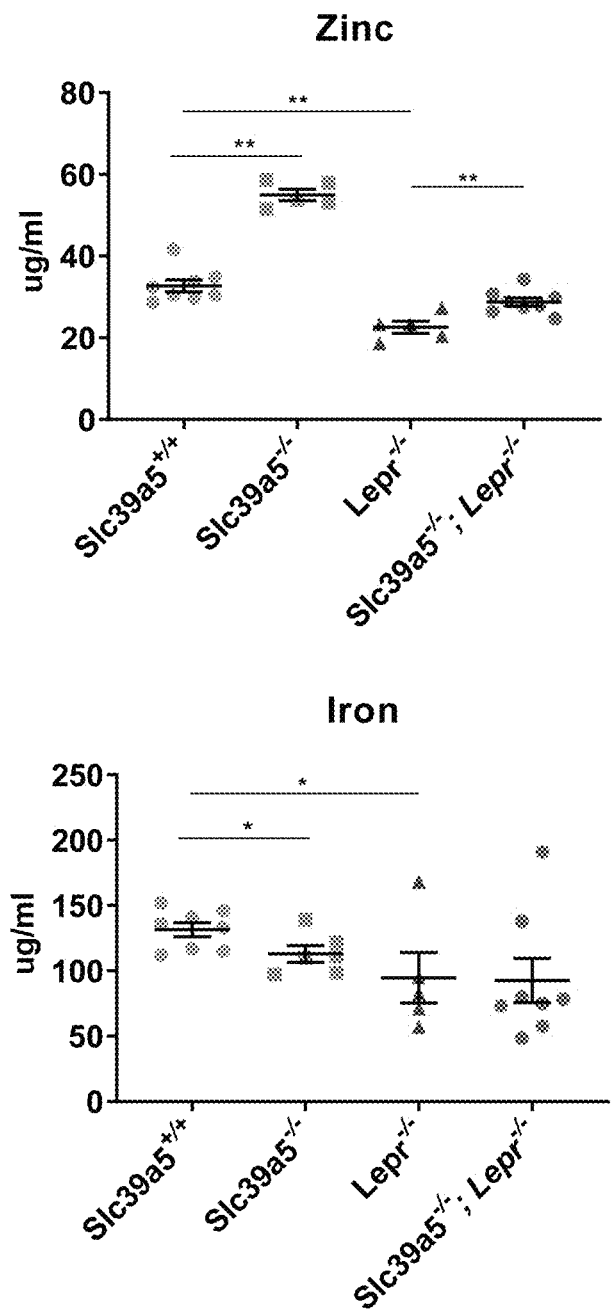
FIG. 30 shows loss of function of Slc39a5 results in increased hepatic zinc levels and a consequent elevation in hepatic metallothionein ("Mt1" and "Mt2") expression in leptin-receptor deficient mice (both sexes). Furthermore, loss function of Slc39a5 does not significantly influence hepatic iron levels in these mice.
Figure 30:
Figure 30:
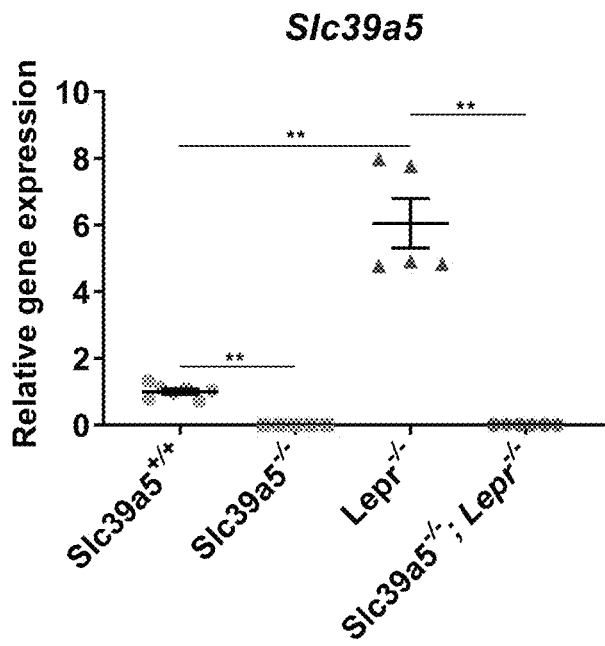
Figure 30:
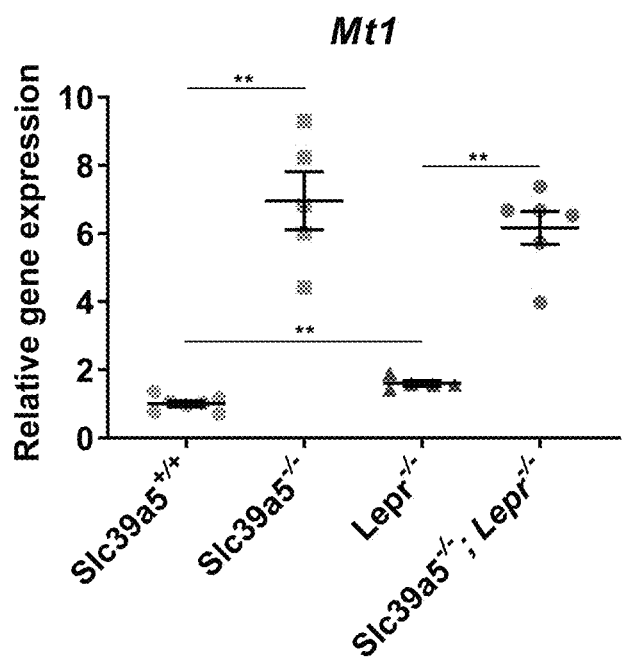
Figure 30:
Figure 30:
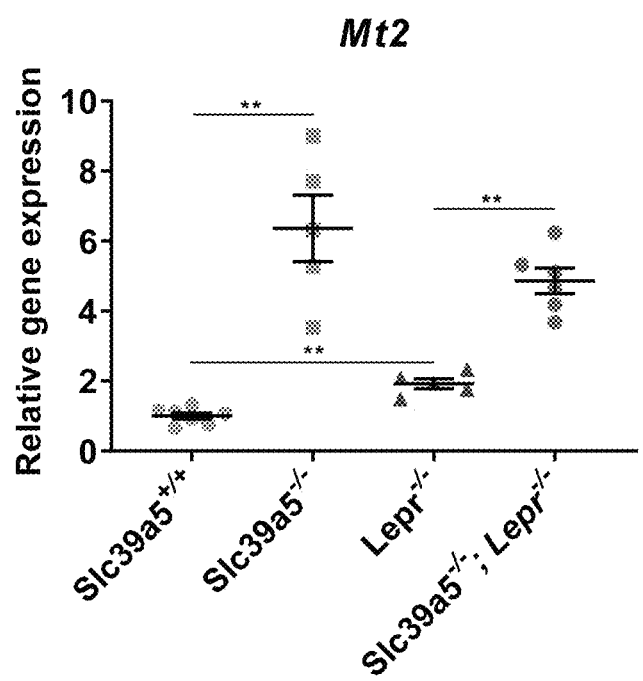
Figure 30:
Figure 30:
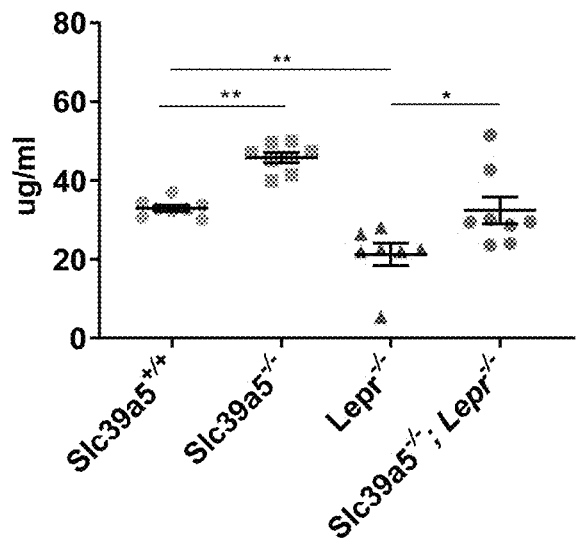
Figure 30:
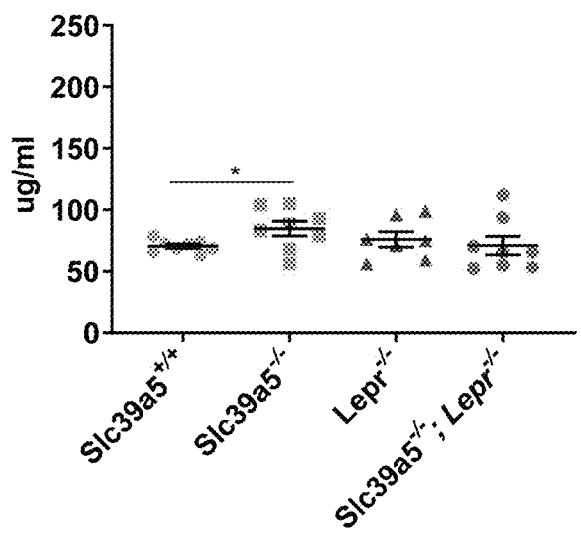
Figure 30:
Figure 30:
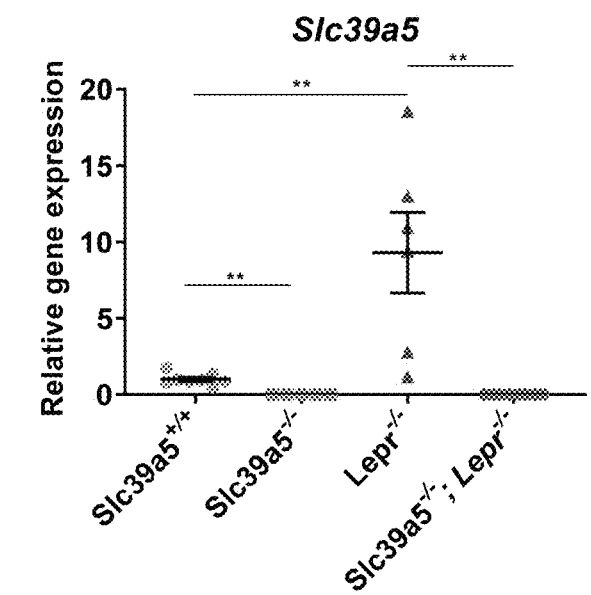
Figure 30:
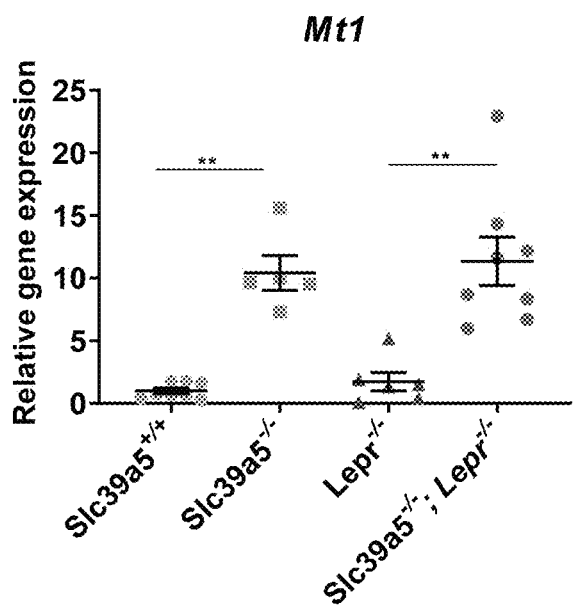
Figure 30:
Figure 30:
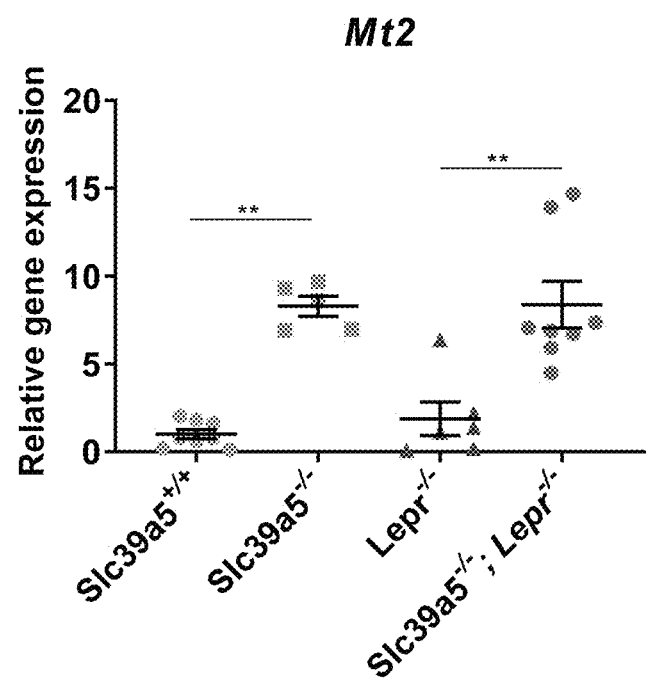
Figure 31A:
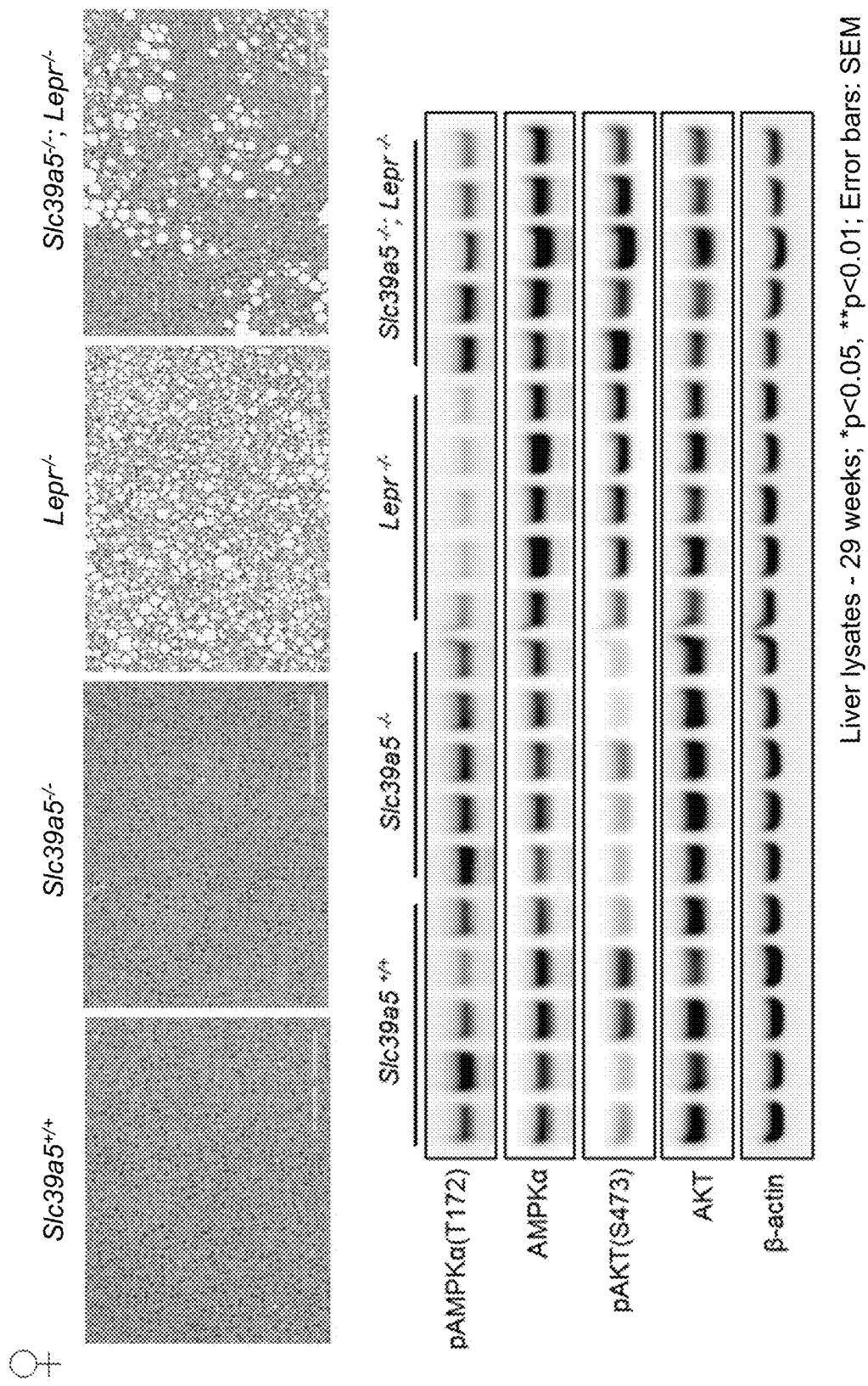
FIGS. 31A and 31B show loss of function of Slc39a5 improves hepatic steatosis in leptin receptor deficient mice in both sexes (FIG. 31A, female.
Figure 31A:
Figure 31A:
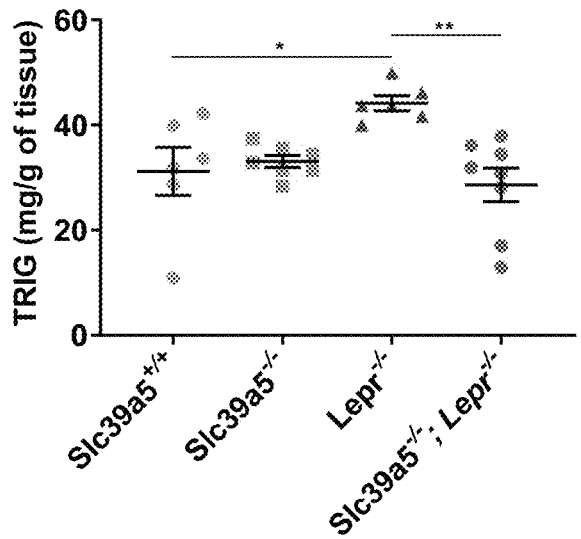
Figure 31A:
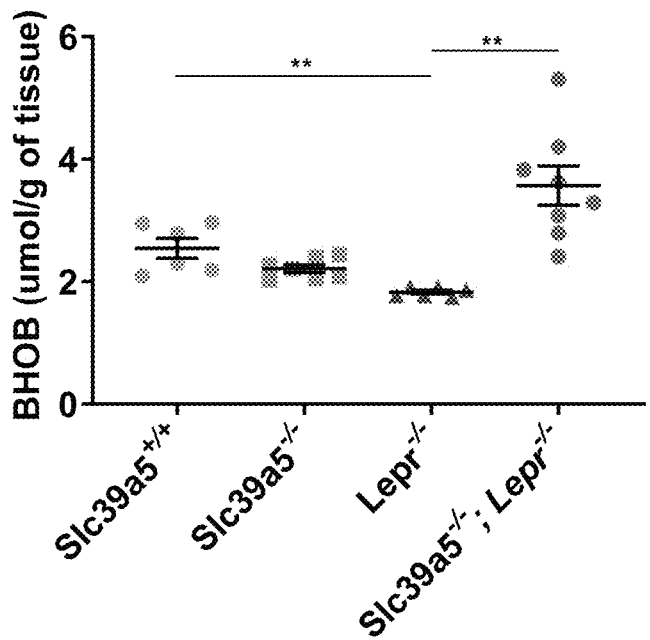
Figure 31A:
Figure 31A:
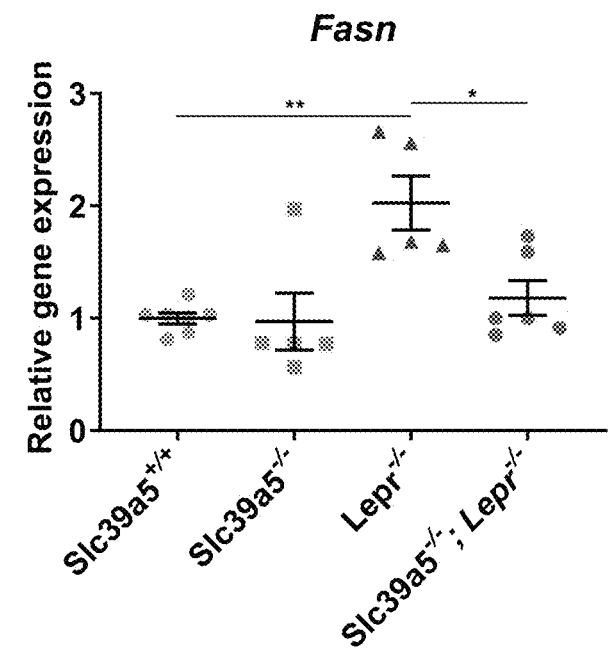
Figure 31A:
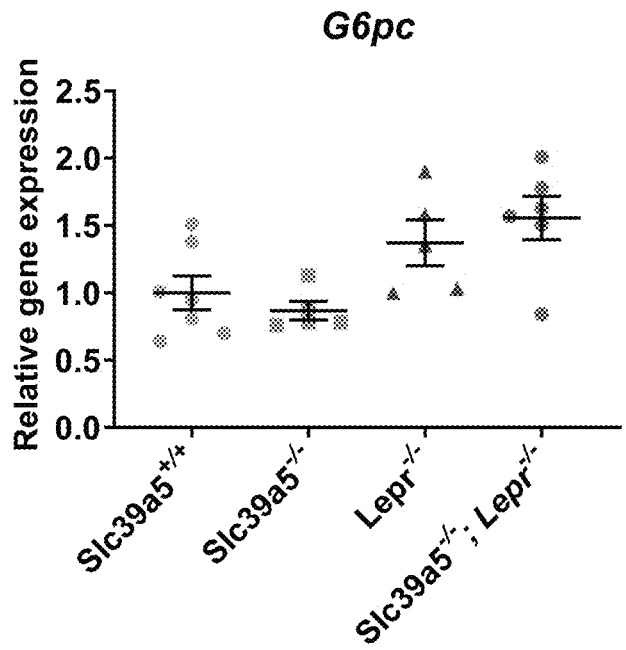
Figure 31B:
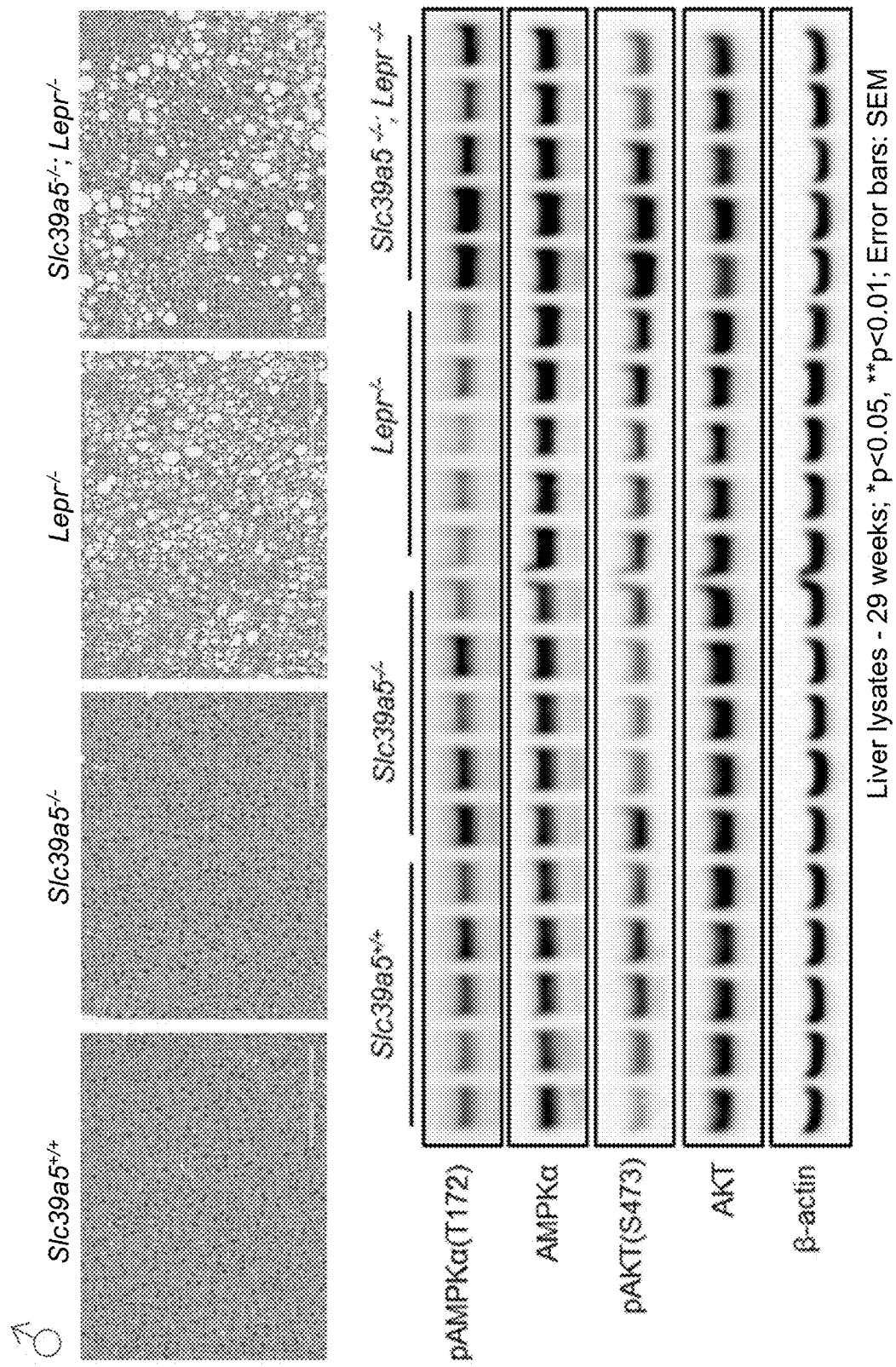
Figure 31B:
Figure 31B:
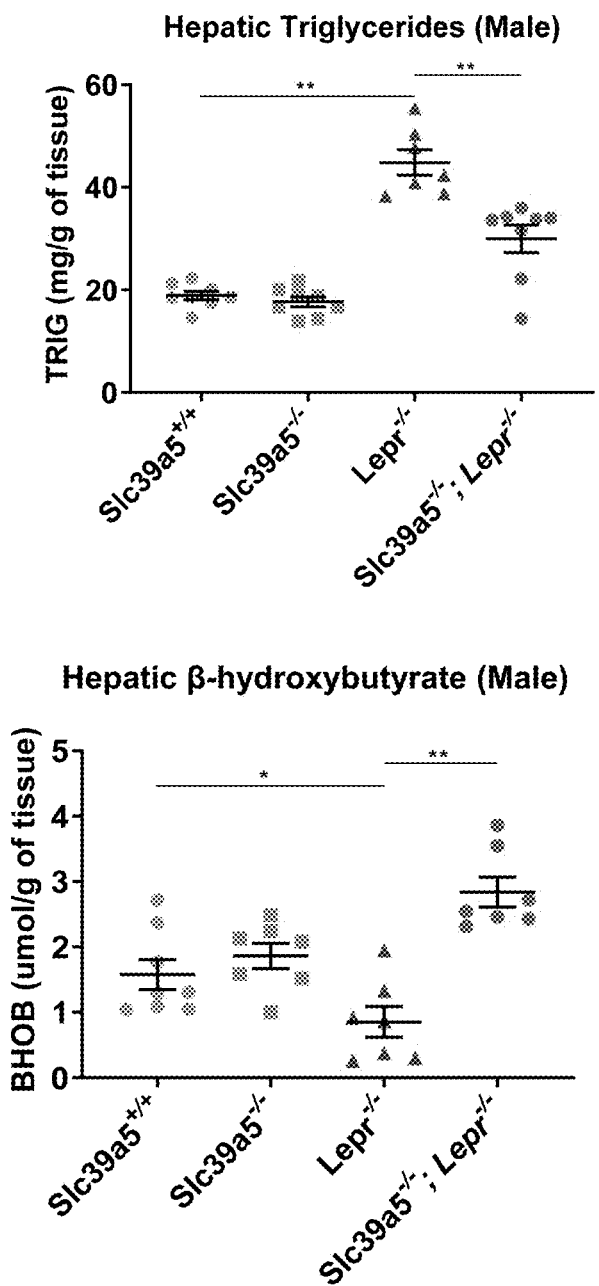
Figure 31B:
Figure 31B:
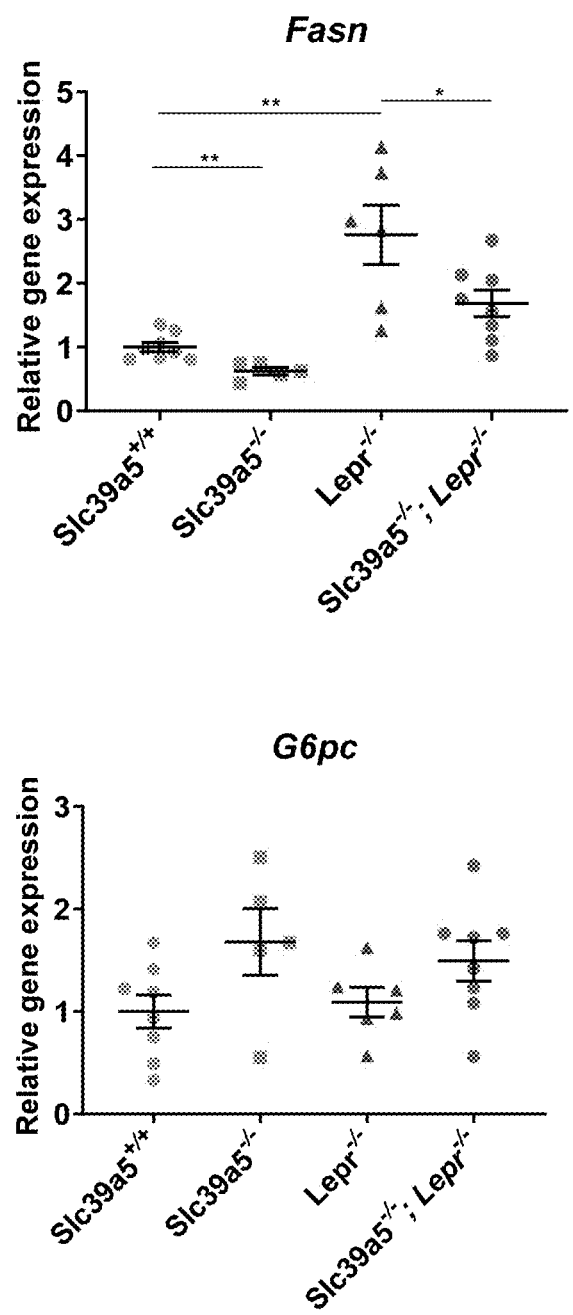

The immunogenic peptide fragment of SLC39A5 for mouse inoculation (SEQ ID NO:67) was selected based on the hydrophilicity of the amino acid sequence (see, FIG. 18). A mouse was inoculated with the immunogenic SLC39A5 fragment. The mouse was sacrificed, and the splenocytes of the mouse were isolated. The splenocytes were fused with hybridoma partner cells. The successfully fused cells were diluted and aliquots of the dilution placed in wells of a microtiter plate where growth of the culture was continued. Antibody-producing clones were identified by assaying the reactivity of antibody in the supernatant fluid of the wells with HEK cells overexpressing mouse SLC39A5 (see, FIG. 19) and HEK cells overexpressing human SLC39A5 (see, FIG. 20). Three positive clones that were reactive against both human and mouse SLC39A5 (see, 10D1, 10D4, and 11C1) were expanded and their monoclonal antibody product was selected.

Example 14: Metabolic Phenotyping of Slc39a5 Loss of Function Mice

Metabolic Phenotyping:

Mice homozygous or heterozygous for Slc39a5 loss of function and wild-type littermates were co-housed in a controlled environment (12 hour light/dark cycle, 22±1° C., 60-70% humidity) and fed ad-libitum with a high fat high fructose diet (Test Diet, Catalog #5WK9) or a control diet (Test Diet, Catalog #58Y2) containing 35 ppm zinc starting at 10 weeks of age. Both male and female mice were used in this study. Longitudinal assessment of serum zinc, fasting blood glucose along with alanine aminotransferase (ALT) and aspartate aminotransferase (AST) (biomarkers of liver injury) were assessed upon an overnight fast (lasting 16 hours). Fed blood glucose was measured prior to the initiation of the fast. Serum and hepatic zinc (at endpoint) analyses were conducted using flame atomic absorption spectroscopy as discussed below.

Mice homozygous for Slc39a5 and Lepr loss of function (Slc39a5$^{-/-}$; Lepr$^{-/-}$) and littermate controls (wildtype, Slc39a5$^{-/-}$, Lepr$^{-/-}$) were co-housed in a controlled environment (12 hour light/dark cycle, 22±1° C., 60-70% humidity) and fed ad-libitum with normal chow (PicoLab Rodent Diet 20, Catalog #5053) containing 87 ppm zinc. Mice were monitored for health and growth kinetics periodically. Upon an overnight fast (lasting 16 hours), serum ALT and AST (biomarkers of liver injury) along with DLDL and fasting blood glucose were measured when the mice were 22 weeks of age. Blood glucose was evaluated using AlphaTrak blood glucose monitoring system (Zoetis United States, Parsippany NJ) by sampling blood from the lateral tail vein. Liver and lipid traits were measured using a Siemens ADVIA Chemistry XPT as described below.

Oral Glucose Tolerance Test:

An oral glucose tolerance test was administered upon an overnight fast (lasting 16 hours) at 20 weeks of age by administering 2 g/kg of body weight of Dextrose (Hospira Inc, NDC 0409-4902-34) by oral gavage. Blood glucose was evaluated at defined time points (0, 15, 30, 60 and 120 minutes) using AlphaTrak blood glucose monitoring system (Zoetis United States, Parsippany NJ) by sampling blood from the lateral tail vein.

Liver and Lipid Traits:

All liver and lipid traits were measured using ADVIA Chemistry XPT System (Siemens Healthineers), an FDA approved clinical analyzer which we maintain and operate according to Siemens' guidelines. The liver and lipid profile contains the following reagents: Alanine Aminotransferase (ALT, Siemens REF 03036926), Aspartate Aminotransferase (AST, Siemens REF 07499718), Cholesterol (CHOL, Siemens REF 10376501), Direct HDL Cholesterol (DHDL, Siemens REF 07511947), LDL Cholesterol Direct (DLDL, Siemens REF 09793248), Non-Esterified Fatty Acids (NEFA, Wako 999-34691, 995-34791, 991-34891, 993-35191), Triglycerides (TRIG, Siemens REF 10335892). These reagents when mixed with sample underwent redox reactions specific to the analyte of interest that bring about a color change proportional to the concentration of the analyte (colorimetric assay). Absorbance of light, in wavelength specific to the analyte, (from a Halogen light source) was measured and concentration determined. Each set of reagents was calibrated as recommended by manufacture and samples with known values (Multilevel Quality Controls) were measured daily. Parameters were never allowed to deviate from known means by more than one standard deviation. Samples were usually assayed undiluted, though they can be diluted up to 1.5x without affecting results. Samples were loaded into the analyzer in 0.6 ml microcentrifuge tubes and all reagent mixing, assay timing, absorbance and concentration calculation was performed by the analyzer.

Metal Ion Quantification:

All ion measurements were performed using an Agilent Technologies 240 FS Atomic Absorption Spectrometer, in flame mode. Serum samples were quantitatively diluted in deionized water and subsequently analyzed. For the serum samples a Seronorm Trace Elements Serum (L-2) was used as reference. Tissue, bone and other material were first digested in nitric acid. The samples were weighed and incubated overnight at 85° C. in nitric. The following day, the samples were cooled down to room temperature and quantitatively transferred to polystyrene tubes with deionized water. Subsequently they were analyzed. For all tissue samples, a bovine liver standard reference material (SRM 1577c) from the National Institute of Standards and Technology was used as reference.

Liver Histology and Immunoblotting:

Explanted liver samples were fixed in 10% phosphate buffered formalin acetate at 4° C. overnight, thoroughly rinsed in phosphate-buffered saline and embedded in paraffin wax. For hematoxylin and eosin staining, unstained 5 μm thick paraffin sections were deparaffinized in xylene then hydrated through graded alcohols up to water. Sections were stained with Carazzi's hematoxylin, washed in tap water, and then put in 95% ethanol. From there, they were put in eosin-phloxine solution then ran through graded alcohols to xylene. After xylene, the stained slides were cover-slipped and imaged stained and imaged using a 20× or 40× objective using the Aperio AT2 slide scanner (Leica Biosystems Inc.).

Liver protein was extracted using RIPA buffer (Cell signaling technology, Cat #9806) with Halt Protease & Phosphatase Inhibitor Cocktail (ThermoFisher Scientific, Cat #78440). Five microgram protein of each sample were separated in NuPAGE 4-12% Bis-Tris protein gel (Invitrogen, Cat #WG1403BOX), and transferred to nitrocellulose membrane using Trans-Blot® Turbo™ Transfer System (BioRad). Blotting was performed using the following Cell Signaling Technology antibodies: Phospho-AMPKα (Thr172) (Cell signaling technology, Cat #2535), AMPKα (Cell signaling technology, Cat #5831), β-Actin (Sigma, Cat #5441), Phospho-AKT (Ser473) (Cell signaling technology, Cat #4060), AKT (Cell signaling technology, Cat #9272), Phospho-LKB1 (Ser428) (Cell signaling technology, Cat #3482), LKB1 (Cell signaling technology, Cat #3050), rabbit IgG conjugated to horseradish peroxidase (HRP) (Cell signaling technology, Cat #7074) and mouse IgG conjugated to HRP (Cell signaling technology, Cat #7076). Blots were developed using SuperSignal West Femto Substrate (ThermoFisher Scientific, Cat #34095). Signals were captured using ImageQuant LAS4000 (GE Healthcare).

The results are shown in FIGS. 21, 22, 23, 24A, 24B, 25A, 25B, 26A, 26B, 27, 28, 29, 30, 31A, and 31B.

Figure 32:
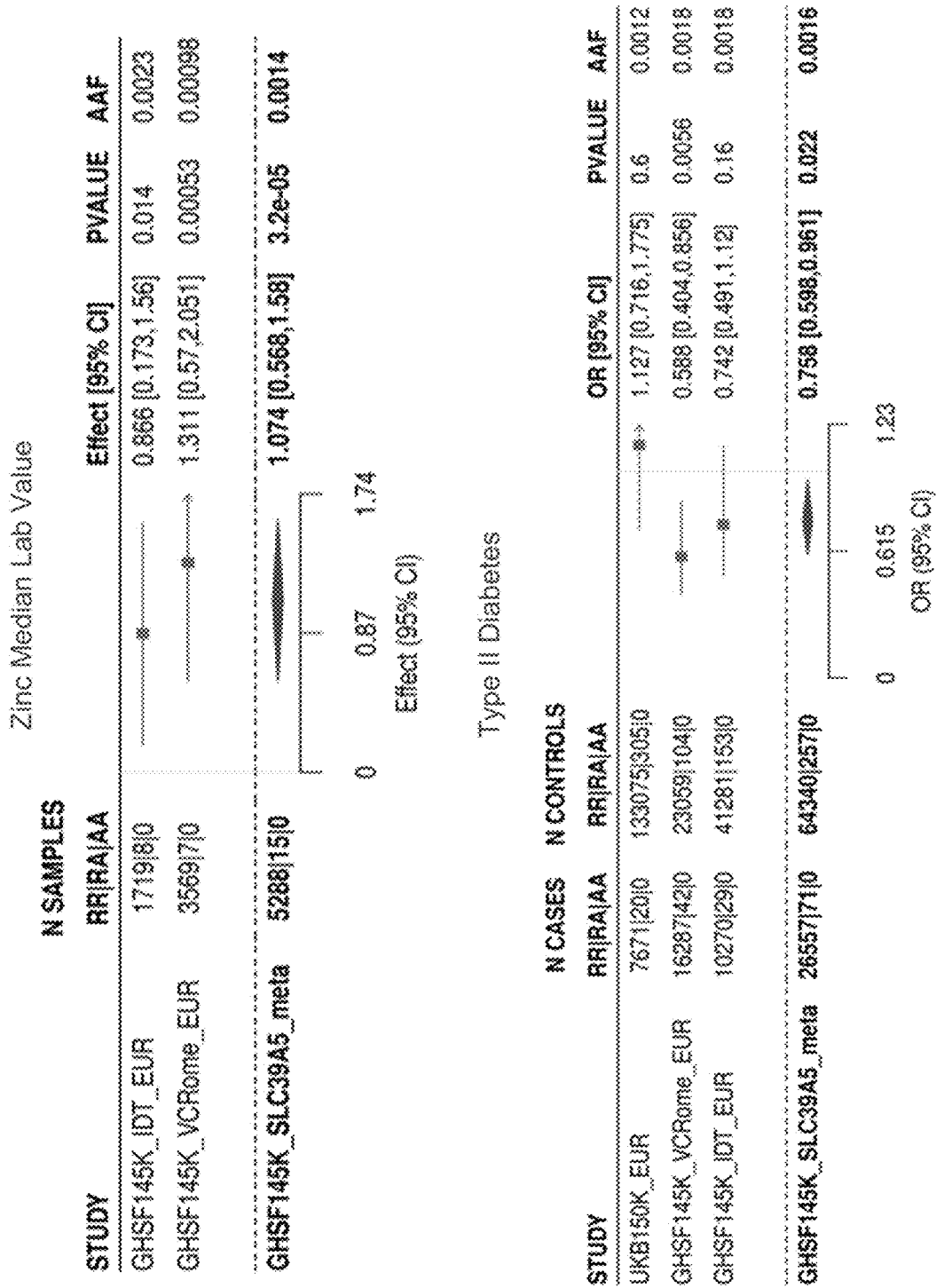
FIG. 32 shows association of loss of function mutations in SLC39A5 with increasing circulating zinc levels and decreased T2D risk (RR: homozygote for reference allele; RA: heterozygote; AA: homozygote for alternative allele; Cases: T2D and HbA1c≥6.5%; Control: neither T1D nor T2D and no HbA1c≥6.5%; M1.1: p.LoF variants only (AAF≤1%).

Example 15: Loss of Function Mutations in SLC39A5 Associate with Increasing Circulating Zinc Levels and Decreased T2D Risk A genome wide association study examining the relationship between SLC39A5 LoF mutations and circulating zinc levels was carried out in a GHSF145K IDT Biobank European cohort and in a GHSF145K VCRome European cohort. Both studies, as well as meta-analysis of the two studies, showed significant association (see, FIG. 32, upper table).

A genome wide association study examining the relationship between SLC39A5 LoF mutations and Type II Diabetes (T2D) was carried out in a GHSF145K IDT Biobank European cohort, in a GHSF145K VCRome European cohort, and in a UK biobank 150K cohort. The meta-analysis of the three studies, showed significant association (see, FIG. 32, lower table).

Example 16: Loss of SLC39A5 Results in Suppression of Phosphatase Activity

Figure 33A:
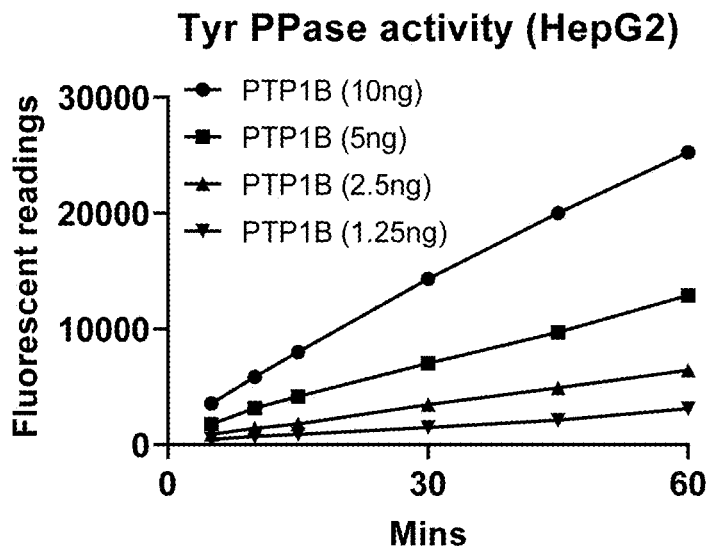
FIG. 33A shows the dependence of tyrosine phosphatase activity on zinc (red line) and magnesium (blue line) concentration.
Figure 33A:
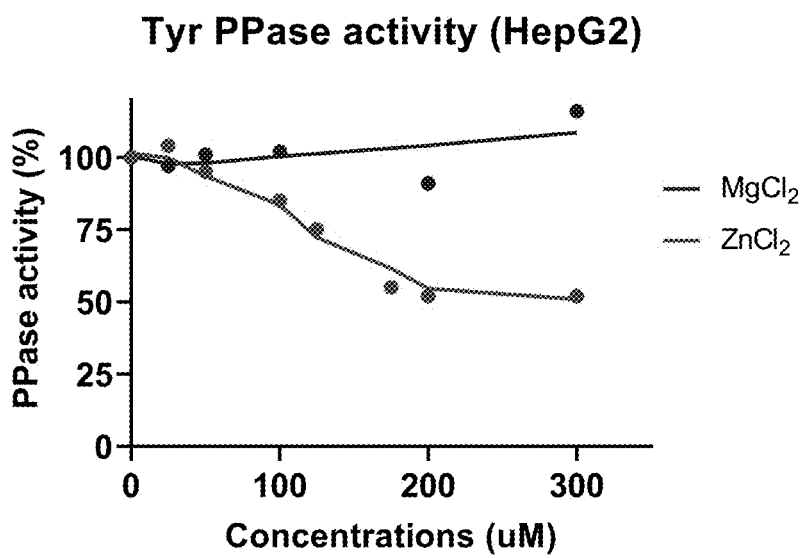
Figure 33B:
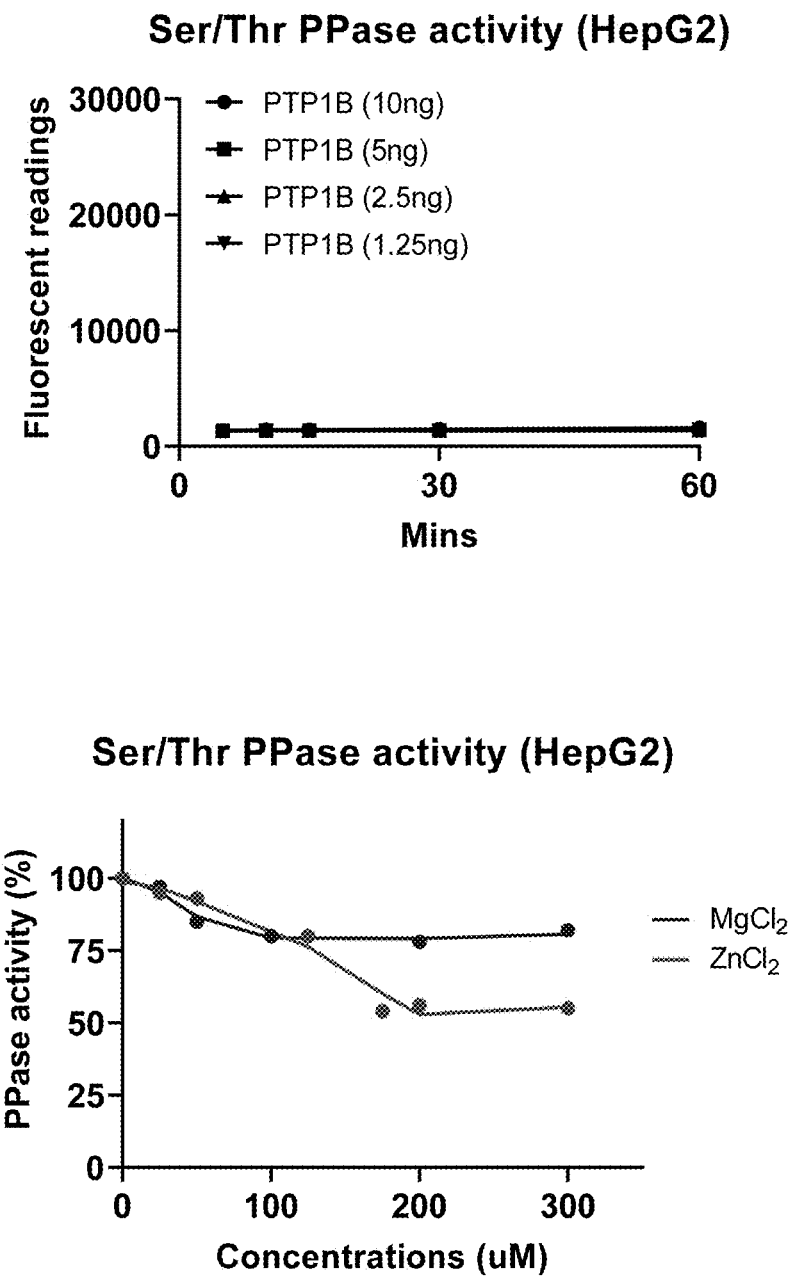
FIG. 33B shows the dependence of serine/threonine phosphatase activity on zinc (red line) and magnesium (blue line) concentration.
Figure 34A:
FIG. 34A shows that loss of SLC39A5 results in zinc-mediated suppression of tyrosine phosphatase activity in female mice fed with either NC diet (right) or HFFD diet (left).
Figure 34A:
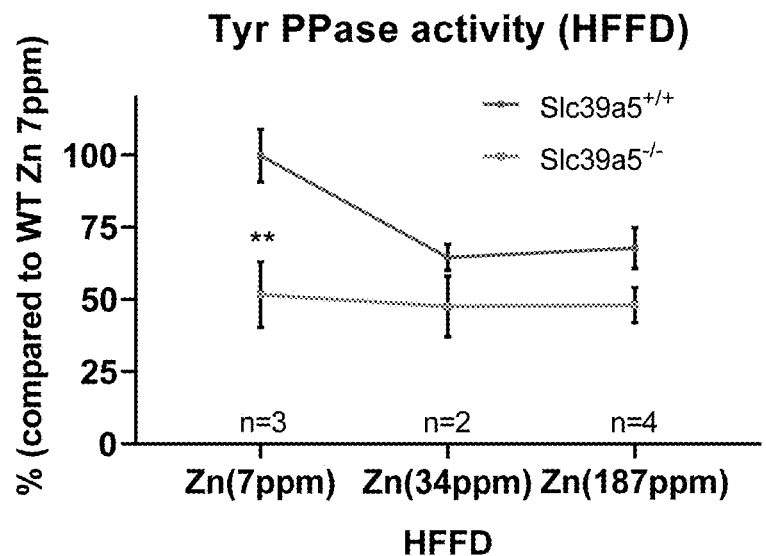
Figure 34A:
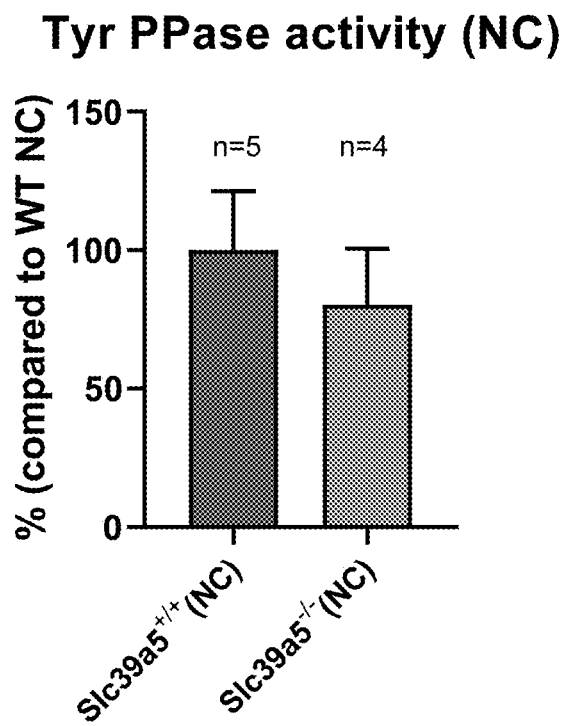
Figure 34B:
FIG. 34B shows that loss of SLC39A5 results in zinc-mediated suppression of serine/threonine phosphatase activity in female mice fed with either NC diet (right) or HFFD diet (left).
Figure 34B:
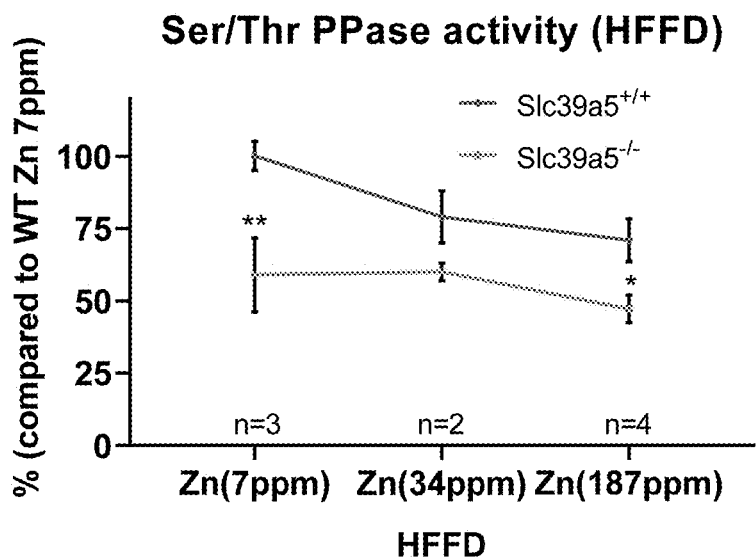
Figure 34B:
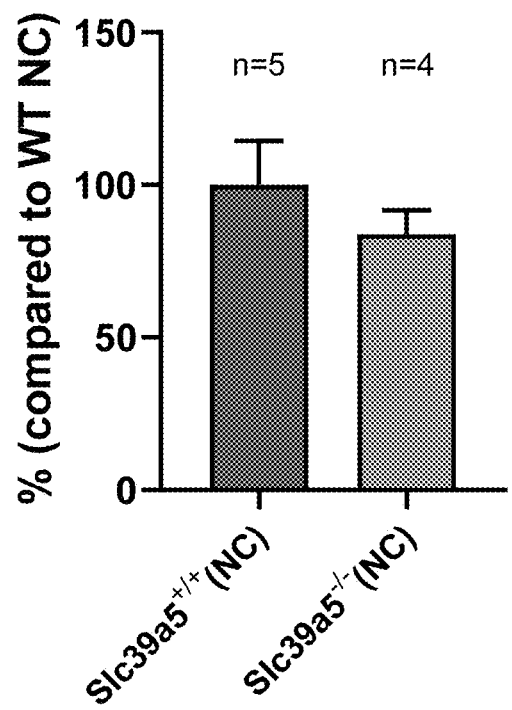
Figure 34C:
FIG. 34C shows that loss of SLC39A5 results in zinc-mediated suppression of tyrosine phosphatase activity in male mice fed with either NC diet (right) or HFFD diet (left).
Figure 34C:
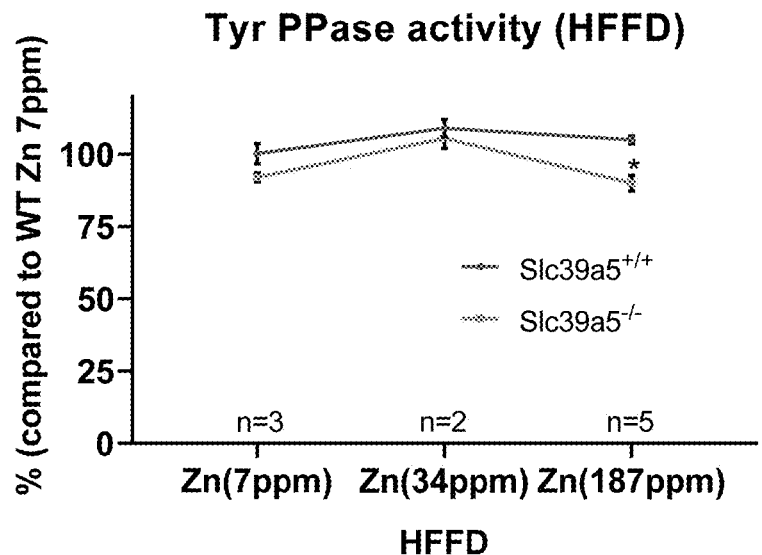
Figure 34C:
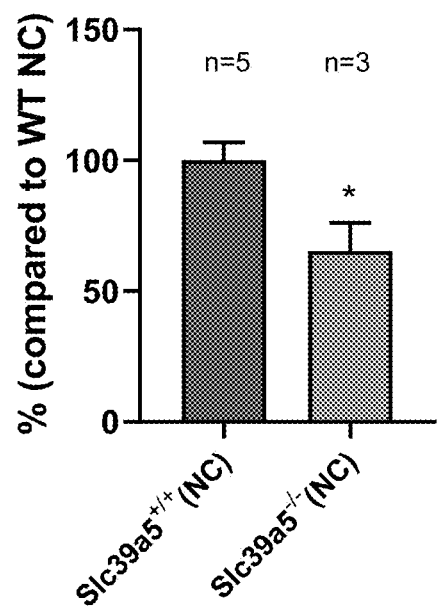
Figure 34D:
FIG. 34D shows that loss of SLC39A5 results in zinc-mediated suppression of serine/threonine phosphatase activity in male mice fed with either NC diet (right) or HFFD diet (left).
Figure 34D:
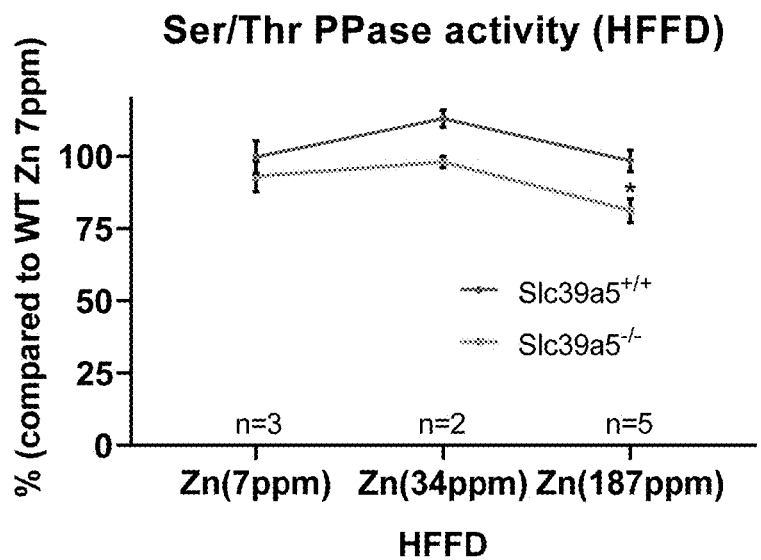
Figure 34D:
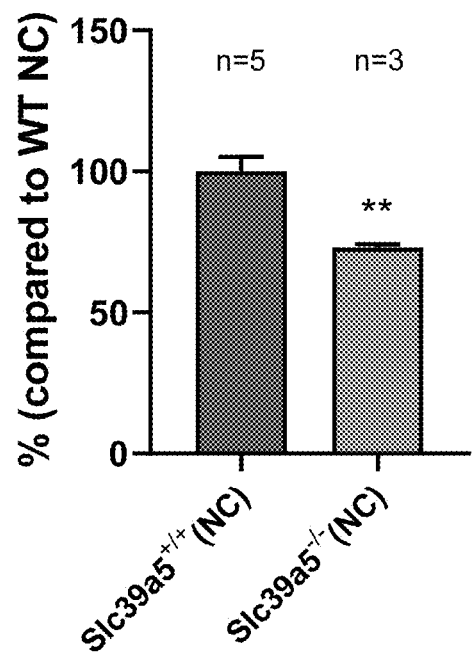

Increased concentrations of zinc suppressed the activity of both tyrosine phosphatase (see, FIG. 33A) and of serine/threonine phosphatase (see, FIG. 33B). Whether loss of SLC39A5 resulted in suppression of phosphatase activity due to increase in zinc concentration was tested in an ex vivo assay. Loss of SLC39A5 resulted in suppression of both tyrosine phosphatase and serine/threonine phosphatase in female (see, FIGS. 34A and 34B) and male (see, FIGS. 34C and 34D) mice. The inhibition did not depend on the diet, and supplementing high fat diets with different zinc concentrations did not rescue the inhibition.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

What is claimed is:

1. A method of treating a female human subject having an increased serum glucose level and/or hyperglycemia, wherein the subject is Solute Carrier Family 39 Member 5 (SLC39A5) reference or heterozygous for an SLC39A5 predicted loss-of-function variant, the method comprising administering an SLC39A5 inhibitor and a therapeutic agent that treats or inhibits increased serum glucose level and/or hyperglycemia to the subject;
   wherein the SLC39A5 inhibitor comprises an antisense nucleic acid molecule, a small interfering RNA (siRNA), or a short hairpin RNA (shRNA) that hybridizes to an SLC39A5 mRNA; and
   wherein the therapeutic agent comprises an estrogen, insulin, a sulfonylurea-based agent, a biguanide, or a GLP-1 agonist.

2. The method according to claim 1, wherein the subject is further administered zinc.

3. The method according to claim 1, wherein the therapeutic agent comprises insulin.

4. The method according to claim 1, wherein the biguanide comprises metformin, phenformin, and/or buformin.

5. The method according to claim 1, wherein the GLP-1 agonist comprises liraglutide, exenatide, lixisenatide, albiglutide, dulaglutide, and/or semaglutide.

6. The method according to claim 1, further comprising detecting the presence or absence of an SLC39A5 predicted loss-of-function variant nucleic acid molecule encoding a human SLC39A5 polypeptide in a biological sample from the subject.

7. The method according to claim 6, wherein the SLC39A5 predicted loss-of-function variant nucleic acid molecule is a nucleic acid molecule encoding SLC39A5 M304T, SLC39A5 G413A, SLC39A5 Y47Stop, SLC39A5 R322Stop, or R311Stop.

8. A method of treating a female human subject with a therapeutic agent that treats or inhibits increased serum glucose level and/or hyperglycemia, wherein the subject is suffering from increased serum glucose level and/or hyperglycemia, the method comprising the steps of:
   determining whether the subject has a Solute Carrier Family 39 Member 5 (SLC39A5) predicted loss-of-function variant nucleic acid molecule encoding a human SLC39A5 polypeptide by:
      obtaining or having obtained a biological sample from the subject; and
      performing or having performed a genotyping assay on the biological sample to determine if the subject has a genotype comprising the SLC39A5 predicted loss-of-function variant nucleic acid molecule; and
   administering or continuing to administer to the subject the therapeutic agent that treats or inhibits increased serum glucose level and/or hyperglycemia and an SLC39A5 inhibitor,
   wherein the presence of a genotype having the SLC39A5 predicted loss-of-function variant nucleic acid molecule encoding the human SLC39A5 polypeptide indicates the subject has a reduced risk of developing increased serum glucose level and/or hyperglycemia;
   wherein the SLC39A5 inhibitor comprises an antisense nucleic acid molecule, a small interfering RNA (siRNA), or a short hairpin RNA (shRNA) that hybridizes to an SLC39A5 mRNA; and
   wherein the therapeutic agent comprises an estrogen, insulin, a sulfonylurea-based agent, a biguanide, or a GLP-1 agonist.

9. The method according to claim 8, wherein the SLC39A5 predicted loss-of-function variant nucleic acid molecule is a nucleic acid molecule encoding SLC39A5 M304T, SLC39A5 G413A, SLC39A5 Y47Stop, SLC39A5 R322Stop, or SLC39A5 R311Stop.

10. The method according to claim 8, wherein the therapeutic agent comprises insulin.

11. The method according to claim 8, wherein the biguanide comprises metformin, phenformin, and/or buformin.

12. The method according to claim 8, wherein the GLP-1 agonist comprises liraglutide, exenatide, lixisenatide, albiglutide, dulaglutide, and/or semaglutide.

* * * * *

SEQUENCE LISTING

```
<160> NUMBER OF SEQ ID NOS: 67

<210> SEQ ID NO 1
<211> LENGTH: 7784
<212> TYPE: DNA
<213> ORGANISM: homo sapien

<400> SEQUENCE: 1
agctggaacc aagaaggttg tgtcccctt cctctgggtg tccttgtctc ctgctatcag      60
gtaatgccaa cctcaacccc ctggaccagt cacccgatc agactttgct tgcctgattt     120
taggccaggt cagacatcag aggagagccc agatccttgt ttcctctccc ccgcagggc     180 ttcccctttc ttggtcatcg atccctagag ctctggctct ttctcttctt ggggtgagaa    240
actgctaaga acagtttatt tcccatgcat gcatctgggc ttgccactga tctgccttt     300 cccccctcct ccccaggtta gggacacctg ggtccaacct tcccaaggaa tatggggatg    360
ggggttggag atgaagttta gtgctagact gtaaggtagg tggggtggaa gtacatgagg    420
gaaagggcta aaatggtact aatggtgtta aggataggt gaattattta agaggaaaaa     480
gactaggccc aggttctcct tagccatgtg gctttcccag ggcagagggt ggccctccc     540 tacccagggg cccagcagag actgactttt gatccctacc ccagagacca gtgaaccatt    600
aactcctctc ttatgtgagc cttcacacac tggcccacc cctgaccccg ccccaaggca    660
```

```
ggtgggctag gagggggtgc atgtccatct cagccttcta tgtgacgtgg cctccgatcc    720
acctggacac ctggaggcta agcctggatt ccccctttccc tgactcagga actgcttaac   780
gtctacagca aggcctaata ggggacctga ggtgacagct cttatgttgc cagtaggggt    840
gaggccctgg ggattgaggg gggataaaga ggtggggcaa agttgagggg tggggtttag    900
gggacaagga atggacggtc agctctggat gaagtatgag gagagctctg actcagggag    960
gtgctccagg aaccagcaaa caagaggctg ctcccgcagg aggcagtgtg aagggagaaa   1020
gaaggctgca gtagggctg ctgctggact cggtggggag caggtgcaag gagctctggc    1080
tcccccatgg acctgagctg gagagcagag cgcagctcca gcccattcct cattcttcca   1140
gggcacagtc ctcaggatgt ttcggggaga ataggagcca gaacctgagc ccctaagcta   1200
ttcccctcac caatgatggg gtccccagtg agtcatctgc tggccggctt ctgtgtgtgg   1260
gtcgtcttgg gctgggtagg gggctcagtc cccaacctgg gccctgctga gcaggagcag   1320
aaccattacc tggcccagct gtttggcctg tacggcgaga atgggacgct gactgcaggg   1380
ggcttggcgc ggcttctcca cagcctgggg ctaggccgag ttcagggggct tcgcctggga   1440
cagcatgggc ctctgactgg acgggctgca tccccagctg cagacaattc cacacacagg   1500
tactgacccc ttcctccact ccacagggcc acatctccca ggtcctctca gtgcttgccc   1560
ccagttgcct cgttctggct tcctcacgag atccctggag ttacaaattc ttcagaaccg   1620
agctccttgg tatctcttca aaacctctca tgcttctatt gccttctctc tcttttcttg   1680
agactggggg tctcgctttg tcacccaggc taaagtgcag tgacacattc acggctcact   1740
gcaacctctg cttcccaggc tgaagccatc ctcccacctc agcctcctga gcagctggga   1800
ccataggcac acaccaccac agccggctaa ttttaaaaat ttttttacaga gacaagggtt   1860
tcgctgtgtt gcccaggctg gtctcaaact cctgggctca gctcagcgat ctgcctgcct   1920
cagcttccca aagtgctggg actacagatg tgaactacca ccctagccct ccgttgcctt   1980
ctaattctct cctcctccaa atctctaagc ccttaaattt cttgctctta gtatcactgt   2040
tcagtgtctc tgggctgatt tggctccaaa ttcgtagact tctttttttct tttcttttct   2100
ttttttttt tttttttttt tgagacagag tctcgctctg tcgcccaggc tggagtgcag   2160
tggtgtgatc ttggctcact gtaacctctg cctccccggt tcaagcgatt ctcctgcctc   2220
ggcctcctga gtagctggga ttacaggcac acaccaccac gccgggctaa ttttttgcaat   2280
tttagtagag acggggtttc accattttgg tcaggctggt ctcgaacttc caacctcagg   2340
tgatccaccc acctcagcct cccaaagtgc tgggattaca ggcgtgagcc accgtgccca   2400
gccattcgta gccttttggg ttgtcgtcct ttttttttctg tccccccag tggcagaaaa   2460
tggacaactc acagatcttc ctaagaatga cattccatgg tttctgggtc ccaggatctc   2520
cagtcagtgg ctagtccccc cattccccct aaaatccctg ggagcctctc aaagcgggtt   2580
gatagagaac acaagggagg ctgacttgct gtctcatcca ttccaggcca cagaaccctg   2640
agctgagtgt ggatgtctgg gcagggatgc ctctgggtcc ctcagggtgg ggtgacctgg   2700
aagagtcaaa ggcccctcac ctaccccgtg ggccagcccc ctcgggcctg gacctccttc   2760
acaggcttct gttgctggac cactcattgg ctgaccacct gaatgaggat gtgagtctga   2820
cggtctctag aggggaagga gccatgggat tagatggcct gaaatgtta aataatcagt   2880
agttttttgt tttgttttgt ttttaaatcc caacgtggac caagcgtggt ggctcacgcc   2940
tgtaatccca cactttggg aggccgaggt gggtggatca cctgaggtca ggagttcgag   3000
```

```
accagcctgg ccaacatggt gaaacccat  ctctactaaa aaatacaaaa attagccggg    3060
tgtggtaaca ggtgtgtgta atcctagcta ctcaggaggc tgaggtgaga aaattgcttg    3120
aacttgggag gcagaggttg cagtgagcca agatggcacc atttgcactc cagcctgggc    3180
aacaagaggg agactctgtc tcaaaaaaaa aaaaaaaaaa aaaaaaaaaa aaaaaaaaat    3240
agctgggcgt ggtggcacat gcctataatc ccagttactc ggaaggctga ggcaggaaaa    3300
tcacttgaac ccaggaggcg gagattgcag tcagccgaga ttgcaccact gcactccagc    3360
ctgggtaaca cagcgagact ctgtctcaaa aatgaaaata aaaaaaataa aaaaataaaa    3420
aaaaaatatc tcactgtggt cttaggggat gttatttcaa tagtgaacta tgttccctct    3480
gggatcagag caggtgagcc catatccaga gctccaagac tcagtttagg ggaatagatg    3540
gcaaagcaga gaatctagag aagcagccca gggtaggatc tggatggtca cctgagagg     3600 agacctgcag ggaatggatg gctgtcttca tccagaaaga cagagaatat attccactta    3660
caccagaggg cagacaaagc tgcctaaccc tgatggaggt ccagtgagtg cccattgcag    3720
gaagcattca agctgaggct ggatgaacat cgacagggct gttgagaggg agattagatg    3780
gcatttcagg gtcttttccc ttttaagatt ctggcatgga gagctctagt tttccaacca    3840
gcttcattta tcaaatcaac aaaatgattg aaatgatcag agtttgcagg gaagatgatg    3900
acaatgctca ctagcaccca gtttgcatca aattgaatac ctgcattgga ctgaatattc    3960
actaataata cacattgatt ataagtaccc ttggccctag tccccaaggt acctgccagt    4020
aggagcaaag gggaccctgg gagagaccca ggagtctatg caatggaagg acaggtgtta    4080
aatatatata tatatatttt tttgaggtag agtctgactc tgtcacccag gctggagtgc    4140
aatggcgtga tcttggctca ctgcaacctc cacctcctgg gttaaagcaa ttctcctgcc    4200
tcagcctccc gagtagctgg gattataggt gttcactact atccccagct aattttttt     4260 ttttttttt  gagatggagt ctcactctgt cgcccaggct ggagtgcact ggtgcaatct    4320
cggctcactg caacctctgc ctcctgggtt caagcgattc tcctgtctca gcctcctgag    4380
tagctgggat acaggtgca  cgccaccatg cccagctaat ttttttgtatt ttagtagaga   4440 cagggttca  ccatgttgcc caggctggtc tcgaactcct gagctcaggc aatctaccca    4500
cctcagcctc ccaaagtgct gggattacag gcgtgagcca ccgcacccgg ctcatcccca    4560
gctaattttt gtattttag  tagagacagg gtttcactat gttggccagg ttggtctcaa    4620
actcctgacc tcagatgata cacccgcctg ggcctctcaa gggctgggat tataggtgtg    4680
agccactaca cctggccagg tgttaaagat ctgagtcata gttcctggtg attctccaat    4740
gtatgaccct caattctcca gtgtctgaac ggctcccagc tgctggtcaa ttttggcttg    4800
agccccgctg ctcctctgac ccctcgtcag tttgctctgc tgtgcccagc cctgctttat    4860
cagatcgaca gccgcgtctg catcggcgct ccggcccctg caccccagg  ggatctacta    4920 tctggtcagc aagtaggagt gggtggggga caccctgaat cctggaagtg gggcccatgc    4980
caaaaaggag gctcactggg gtcctgcctc tccttgtagt gttctctctg ctccacctta    5040
cgtgtgggac cctcctcttg ccctgaccta acttcagccc ctgattctcc ccagccctgc    5100
ttcagagtgc cctggcagtc ctgttgctca gcctcccttc tccccctatcc ctgctgctgc   5160 tgcggctcct gggacctcgt ctactacggc ccttgctggg cttcctgggg gccctggcgg    5220
tgggcactct ttgtggggat gcactgctac atctgctacc gcatgtatgt gaagcccctt    5280
ccttgtaccc ctggcctcca tggatctaag gtgtccccag ccataggaca tcccctccgc    5340 cttttccatca gctcccatat cctactccca gatcctggct tcagcccaca gctgccttct    5400
```

```
agtagagcat atgagcgaag gcttgccaca atccatgcaa ggggatgttg ttgggtatag   5460
gggcttccag agtctgccct gaccttctct ctgtcaggca caagaagggc ggcacgcagg   5520
acctggcgga ctaccagaga aggacctggg cccggggctg tcagtgctcg gaggcctctt   5580
cctgctcttt gtgctggaga acatgctggg cttttgcgg caccgagggc tcaggccagt   5640
gagtgatacc cttttctcct ccttctgctg agaccagagt cccagtcaag aactgggcca   5700
ggccgggcgc ggtggctcac gcctgtaatc ccagcacttt gggagcccaa ggcgggcaga   5760
tcacaaggtt aggagttcga gtccagcctg accaacatgg tgaaaccctg tctctactaa   5820
aaatacaaaa attagctggg cgtggtggtg cgtgtctgta atcccagcta ctcaggaggc   5880
tgaggcagga gaatcgcttg acttgggagg tggaggttgc agcgagctaa gatggcacca   5940
ctgcactcca gcccaggtga cagagcgaga ctccatctca aaaacaacaa caacaacaac   6000
aaaactgggc caaaagcca agagatgagg agcagtgtgt gctcctggat ctctgacatt   6060
tgcctggtgt gcaggaccta tcggctaaca gggagtgggg aggggctcct taagcacaga   6120
cccaggactt ctggccaaat ggcatcctat tctgagctca agtcaacaag aaacagaggg   6180
gaggtgccaa cttgggaaga aggtagaggc caaagaacat cccaggtgcc agaggtggaa   6240
ccaggtgttc atcttcccag cttgtggcct ggcttcccct tagtccctgg ctctgctgcc   6300
tcctccacca ggagggatgc cctcctattt cagagatgct gcaggcgaaa acgaaggaat   6360
ctcgaaacac gcaacttgga tccggagaat ggcagtggga tggcccttca gcccctacag   6420
gcagctccag gtgactagag gagaaaattt gaagagtagg ttccaagctc acagtcctta   6480
cttgcagcca ccaacactgt cctgtgcttc ttcccgcaga gccaggggct cagggccaga   6540
gggagaagaa cagccagcac ccaccagctc tggcccctcc tgggcaccaa ggccacagtc   6600
atgggcacca gggtggcact gatatcacgt ggatggtcct cctgggagat ggtctacaca   6660
acctcactga tgggctggcc ataggtgtga ggggtgggaa cggagggaag caggtccgag   6720
gggaggccag ggctcctagt tatcagctgg ggctaggaga gggccgtcag gaagatgggg   6780
agaggacggg aggaccacgg aacacaggaa cctgcttctg aggagacttt tcttctggac   6840
tgacaacttc cgaccctgct ggccccaggt gctgccttct ctgatggctt ctccagcggc   6900
ctcagtacca ccttagcggt cttctgccat gagctgcccc acgaactggg taggaatggc   6960
aggagcaggg tggggtggac tccagaaagg agatagctcc aaggggtaga gcttggaggc   7020
tggtgggtgg catggatgag gggcacccca gcttactccc tcccatcctg tcctctgtct   7080
ccaataggtg actttgccat gctgctccag tcagggctgt cctttcggcg gctgctgctg   7140
ctgagcctcg tgtctggagc cctgggattg ggggtgcag tcctgggggt ggggctcagc   7200
ctgggccctg tcccctcac tccctgggtg tttggggtca ctgctgggt cttcctctat   7260
gtggcccttg tggacatggt gagagatgtc gggtagagca gagaaatcaa gggcagtggg   7320
gaggcgggag tggagaggga ggtagcagtc cctccgcctc taccattagc tcctggaagg   7380
gcgtcagacc ataggcccgc aaaagtctga gaaacaaggg actaaggtgt ttgggtgggg   7440
gctgctgatg ctttctgaca ccattcctct ggagttgaga ggtcagggc aaggccagaa   7500
tcctgacatc ctctttttct ttcagctacc agccctgctt cgtcctccgg agccctgcc   7560
tacgcccat gtgctcctgc aggggctggg gctgctgctg ggggcggcc tcatgcttgc   7620
cataaccctg ctgaggagc ggctactgcc cgtgaccact gagggctgat ggggccagtg   7680
gaaaggggtc gggttgccct tccttccccc caaccacagg aatggaggcg ggacacaggg   7740
```

```
ccagtaggag caataggatt ttaataaaca gaacccatcc caaa            7784
```

<210> SEQ ID NO 2
<211> LENGTH: 7784
<212> TYPE: DNA
<213> ORGANISM: homo sapien

<400> SEQUENCE: 2

```
agctggaacc aagaaggttg tgtccccctt cctctgggtg tccttgtctc ctgctatcag      60
gtaatgccaa cctcaacccc ctggaccagt caccccgatc agactttgct tgcctgattt     120
taggccaggt cagacatcag aggagagccc agatccttgt ttcctctccc ccgcagggc      180
ttccccttc ttggtcatcg atccctagag ctctggctct ttctcttctt ggggtgagaa      240
actgctaaga acagtttatt tcccatgcat gcatctgggc ttgccactga tctgcctttt     300
cccccctcct ccccaggtta gggacacctg ggtccaacct tccaaggaa tatggggatg      360
ggggttggag atgaagttta gtgctagact gtaaggtagg tggggtggaa gtacatgagg     420
gaaagggcta aaatggtact aatggtgtta aggataggt gaattattta agaggaaaaa      480
gactaggccc aggttctcct tagccatgtg gctttcccag ggcagagggt ggcccctccc     540
tacccagggg cccagcagag actgactttt gatccctacc ccagagacca gtgaaccatt    600
aactcctctc ttatgtgagc cttcacacac tggccccacc cctgaccccg ccccaaggca    660
ggtgggctag gaggggggtgc atgtccatct cagccttcta tgtgacgtgg cctccgatcc    720
acctggacac ctggaggcta agcctggatt ccccttccc tgactcagga actgcttaac     780
gtctacagca aggcctaata ggggacctga ggtgacagct cttatgttgc cagtaggggt    840
gaggccctgg ggattagggg gggataaaga ggtggggcaa agttgagggg tggggtttag    900
gggacaagga atggacggtc agctctggat gaagtatgag gagagctctg actcaggag     960
gtgctccagg aaccagcaaa caagaggctg ctcccgcagg aggcagtgtg aagggagaaa    1020
gaaggctgca gtaggggctg ctgctggact cggtggggag caggtgcaag gagctctggc    1080
tccccccatgg acctgagctg gagagcagag cgcagctcca gcccattcct cattcttcca   1140
gggcacagtc ctcaggatgt ttcggggaga ataggagcca gaacctgagc ccctaagcta    1200
ttccctcac caatgatggg gtccccagtg agtcatctgc tggccggctt ctgtgtgtgg     1260
gtcgtcttgg gctgggtagg gggctcagtc cccaacctgg gccctgctga gcaggagcag   1320
aaccattacc tggcccagct gtttggcctg taaggcgaga atgggacgct gactgcaggg    1380
ggcttggcgc ggcttctcca cagcctgggg ctaggccgag ttcagggct tcgcctggga    1440
cagcatgggc ctctgactgg acgggctgca tccccagctg cagacaattc cacacacagg   1500
tactgacccc ttcctccact ccacagggcc acatctccca ggtcctctca gtgcttgccc   1560
ccagttgcct cgttctggct tcctcacgag atccctggag ttacaaattc ttcagaaccg    1620
agctccttgg tatctcttca aaacctctca tgcttctatt gccttctctc tcttttcttg    1680
agactggggg tctcgctttg tcaccaggc taaagtgcag tgacacattc acggctcact    1740
gcaacctctg cttcccaggc tgaagccatc ctcccacctc agcctcctga gcagctggga   1800
ccataggcac acaccaccac agccggctaa ttttaaaaat tttttacaga gacaagggtt   1860
tcgctgtgtt gcccaggctg gtctcaaact cctgggctca gctcagcgat ctgcctgcct    1920
cagcttccca aagtgctggg actacagatg tgaactacca ccctagccct ccgttgcctt   1980
ctaattctct cctcctccaa atctctaagc ccttaaattt cttgctctta gtatcactgt   2040
tcagtgtctc tgggctgatt tggctccaaa ttcgtagact tctttttct tttctttct    2100
```

```
tttttttttt tttttttttt tgagacagag tctcgctctg tcgcccaggc tggagtgcag    2160
tggtgtgatc ttggctcact gtaacctctg cctccccggt tcaagcgatt ctcctgcctc    2220
ggcctcctga gtagctggga ttacaggcac acaccaccac gccgggctaa ttttttgcaat   2280 tttagtagag acggggtttc accattttgg tcaggctggt ctcgaacttc aacctcagg    2340 tgatccaccc acctcagcct cccaaagtgc tgggattaca ggcgtgagcc accgtgccca    2400
gccattcgta gccttttggg ttgtcgtcct ttttttctg tccccccag tggcagaaaa      2460 tggacaactc acagatcttc ctaagaatga cattccatgg tttctgggtc ccaggatctc    2520
cagtcagtgg ctagtccccc cattcccccct aaaatccctg ggagcctctc aaagcgggtt   2580
gatagagaac acaagggagg ctgacttgct gtctcatcca ttccaggcca cagaaccctg    2640
agctgagtgt ggatgtctgg gcagggatgc ctctgggtcc ctcagggtgg ggtgacctgg    2700
aagagtcaaa ggcccctcac ctaccccgtg ggccagcccc ctcgggcctg gacctccttc    2760
acaggcttct gttgctggac cactcattgg ctgaccacct gaatgaggat gtgagtctga    2820
cggtctctag aggggaagga gccatgggat tagatggcct gaaatgttta aataatcagt    2880
agttttttgt tttgttttgt ttttaaatcc caacgtggac caagcgtggt ggctcacgcc    2940
tgtaatccca cactttggga aggccgaggt gggtggatca cctgaggtca ggagttcgag    3000
accagcctgg ccaacatggt gaaaccccat ctctactaaa aaatacaaaa attagccggg   3060
tgtggtaaca ggtgtgtgta atcctagcta ctcaggaggc tgaggtgaga aaattgcttg    3120
aacttgggag gcagaggttg cagtgagcca agatggcacc atttgcactc cagcctgggc    3180
aacaagaggg agactctgtc tcaaaaaaaa aaaaaaaaa aaaaaaaaa aaaaaaaat      3240 agctgggcgt ggtggcacat gcctataatc ccagttactc ggaaggctga ggcaggaaaa    3300
tcacttgaac ccaggaggcg gagattgcag tcagccgaga ttgcaccact gcactccagc    3360
ctgggtaaca cagcgagact ctgtctcaaa aatgaaaata aaaaaaataa aaaaataaaa   3420
aaaaaatatc tcactgtggt cttaggggat gttatttcaa tagtgaacta tgttccctct    3480
gggatcagag caggtgagcc catatccaga gctccaagac tcagtttagg ggaatagatg    3540
gcaaagcaga gaatctagag aagcagccca gggtaggatc tggatggtca cctggagagg    3600
agacctgcag ggaatggatg gctgtcttca tccagaaaga cagagaatat attccactta    3660
caccagaggg cagacaaagc tgcctaaccc tgatggaggt ccagtgagtg cccattgcag    3720
gaagcattca agctgaggct ggatgaacat cgacagggct gttgagaggg agattagatg    3780
gcatttcagg gtcttttccc ttttaagatt ctggcatgga gagctctagt tttccaacca    3840
gcttcattta tcaaatcaac aaaatgattg aaatgatcag agtttgcagg gaagatgatg    3900
acaatgctca ctagcaccca gtttgcatca aattgaatac ctgcattgga ctgaatattc    3960
actaataata cacattgatt ataagtaccc ttggccctag tccccaaggt acctgccagt    4020
aggagcaaag gggaccctgg gagagaccca ggagtctatg caatggaagg acaggtgtta    4080
aatatatata tatatatttt tttgaggtag agtctgactc tgtcacccag gctggagtgc    4140
aatggcgtga tcttggctca ctgcaacctc cacctcctgg gttaaagcaa ttctcctgcc    4200
tcagcctccc gagtagctgg gattataggt gttcactact atcccagct aattttttttt    4260 tttttttttt gagatggagt ctcactctgt cgcccaggct ggagtgcact ggtgcaatct    4320
cggctcactg caacctctgc ctcctgggtt caagcgattc tcctgtctca gcctcctgag    4380
tagctgggat cacaggtgca cgccaccatg cccagctaat ttttttgtatt ttagtagaga   4440
```

```
cagggtttca ccatgttgcc caggctggtc tcgaactcct gagctcaggc aatctaccca   4500
cctcagcctc ccaaagtgct gggattacag gcgtgagcca ccgcacccgg ctcatcccca   4560 gctaatttt gtatttttag tagagacagg gtttcactat gttggccagg ttggtctcaa    4620
actcctgacc tcagatgata cacccgcctg ggcctctcaa gggctgggat tataggtgtg   4680
agccactaca cctggccagg tgttaaagat ctgagtcata gttcctggtg attctccaat   4740
gtatgaccct caattctcca gtgtctgaac ggctcccagc tgctggtcaa ttttggcttg   4800
agccccgctg ctcctctgac ccctcgtcag tttgctctgc tgtgcccagc cctgctttat   4860
cagatcgaca gccgcgtctg catcggcgct ccggcccctg caccccagg ggatctacta    4920 tctggtcagc aagtaggagt gggtggggga caccctgaat cctggaagtg gggcccatgc   4980
caaaaaggag gctcactggg gtcctgcctc tccttgtagt gttctctctg ctccacctta   5040
cgtgtgggac cctcctcttg ccctgaccta acttcagccc ctgattctcc ccagccctgc   5100
ttcagagtgc cctggcagtc ctgttgctca gcctcccttc tccctatccc tgctgctgc    5160 tgcggctcct gggacctcgt ctactacggc ccttgctggg cttcctgggg ccctggcgg    5220 tgggcactct ttgtggggat gcactgctac atctgctacc gcatgtatgt gaagccccctt  5280 ccttgtaccc ctggcctcca tggatctaag gtgtccccag ccataggaca tcccctccgc   5340
ctttccatca gctcccatat cctactccca gatcctggct tcagcccaca gctgccttct   5400
agtagagcat atgagcgaag gcttgccaca atccatgcaa gggatgttg ttgggtatag    5460 gggcttccag agtctgccct gaccttctct ctgtcaggca caagaagggc ggcacgcagg   5520
acctggcgga ctaccagaga aggacctggg cccggggctg tcagtgctcg gaggcctctt   5580
cctgctcttt gtgctggaga acatgctggg gcttttgcgg caccgagggc tcaggccagt   5640
gagtgatacc cttttctcct ccttctgctg agaccagagt cccagtcaag aactgggcca   5700
ggccgggcgc ggtggctcac gcctgtaatc ccagcacttt gggagcccaa gcgggcaga    5760 tcacaaggtt aggagttcga gtccagcctg accaacatgg tgaaaccctg tctctactaa   5820
aaatacaaaa attagctggg cgtggtggtg cgtgtctgta atcccagcta ctcaggaggc   5880
tgaggcagga gaatcgcttg acttgggagg tggaggttgc agcgagctaa gatggcacca   5940
ctgcactcca gcccaggtga cagagcgaga ctccatctca aaaacaacaa caacaacaac   6000
aaaactgggc caaaaagcca agagatgagg agcagtgtgt gctcctggat ctctgacatt   6060
tgcctggtgt gcaggaccta tcggctaaca gggagtgggt aggggctcct taagcacaga   6120
cccaggactt ctggccaaat ggcatcctat tctgagctca agtcaacaag aaacagaggg   6180
gaggtgccaa cttgggaaga aggtagaggc caaagaacat cccaggtgcc agaggtggaa   6240
ccaggtgttc atcttcccag cttgtggcct ggcttcccct tagtccctgg ctctgctgcc   6300
tcctccacca ggagggatgc cctcctatt cagagatgct gcaggcgaaa acgaaggaat    6360
ctcgaaacac gcaacttgga tccggagaat ggcagtggga tggcccttca gcccctacag   6420
gcagctccag gtgactagag gagaaaattt gaagagtagg ttccaagctc acagtcctta   6480
cttgcagcca ccaacactgt cctgtgcttc ttcccgcaga gccaggggct cagggccaga   6540
gggagaagaa cagccagcac ccaccagctc tggcccctcc tggcaccaa ggccacagtc    6600 atgggcacca gggtggcact gatatcacgt ggatggtcct cctgggagat ggtctacaca   6660
acctcactga tgggctggcc ataggtgtga gggtgggaa cggagggaag caggtccgag    6720
gggaggccag ggctcctagt tatcagctgg ggctaggaga gggccgtcag gaagatgggg   6780
agaggacggg aggaccacgg aacacaggaa cctgcttctg aggagacttt tcttctggac   6840
```

```
tgacaacttc cgaccctgct ggccccaggt gctgccttct ctgatggctt ctccagcggc   6900
ctcagtacca ccttagcggt cttctgccat gagctgcccc acgaactggg taggaatggc   6960
aggagcaggg tggggtggac tccagaaagg agatagctcc aaggggtaga gcttggaggc   7020
tggtgggtgg catggatgag gggcacccca gcttactccc tcccatcctg tcctctgtct   7080
ccaataggtg actttgccat gctgctccag tcagggctgt cctttcggcg gctgctgctg   7140
ctgagcctcg tgtctggagc cctgggattg ggggtgcag tcctggggt ggggctcagc   7200 ctgggccctg tccccctcac tccctgggtg tttggggtca ctgctgggt cttcctctat   7260 gtggcccttg tggacatggt gagagatgtc gggtagagca gagaaatcaa gggcagtggg   7320
gaggcgggag tggagaggga ggtagcagtc cctccgcctc taccattagc tcctggaagg   7380
gcgtcagacc ataggcccgc aaaagtctga gaaacaaggg actaaggtgt ttgggtgggg   7440
gctgctgatg ctttctgaca ccattcctct ggagttgaga ggtcaggggc aaggccagaa   7500
tcctgacatc ctctttttct ttcagctacc agccctgctt cgtcctccgg agcccctgcc   7560
tacgccccat gtgctcctgc aggggctggg gctgctgctg ggggcggcc tcatgcttgc   7620 cataaccctg ctggaggagc ggctactgcc cgtgaccact gagggctgat ggggccagtg   7680
gaaaggggtc gggttgccct tccttccccc caaccacagg aatggaggcg ggacacaggg   7740
ccagtaggag caataggatt ttaataaaca gaacccatcc caaa          7784
```

<210> SEQ ID NO 3
<211> LENGTH: 7784
<212> TYPE: DNA
<213> ORGANISM: homo sapien

<400> SEQUENCE: 3

```
agctggaacc aagaaggttg tgtccccctt cctctgggtg tccttgtctc ctgctatcag     60
gtaatgccaa cctcaacccc ctggaccagt cacccgatc agactttgct tgcctgattt    120
taggccaggt cagacatcag aggagagccc agatccttgt ttcctctccc cccgcagggc    180
ttcccctttc ttggtcatcg atccctagag ctctggctct ttctcttctt ggggtgagaa    240
actgctaaga acagtttatt tcccatgcat gcatctgggc ttgccactga tctgccttt     300 ccccctcct ccccaggtta gggacacctg ggtccaacct tcccaaggaa tatggggatg     360
ggggttggag atgaagttta gtgctagact gtaaggtagg tggggtggaa gtacatgagg    420
gaaagggcta aaatggtact aatggtgtta aggataggt gaattattta agaggaaaaa     480
gactaggccc aggttctcct tagccatgtg gctttcccag gcagagggt ggcccctccc     540 tacccagggg cccagcagag actgactttt gatccctacc ccagagacca gtgaaccatt    600
aactcctctc ttatgtgagc cttcacacac tggcccacc cctgacccg ccccaaggca     660 ggtgggctag gaggggtgc atgtccatct cagccttcta tgtgacgtgg cctccgatcc    720
acctggacac ctgaggcta agcctggatt ccccctcc tgactcagga actgcttaac      780
gtctacagca aggcctaata ggggacctga ggtgacagct cttatgttgc cagtagggt     840 gaggccctgg ggattgaggg gggataaaga ggtggggcaa agttgagggg tggggtttag    900
gggacaagga atgacggtc agctctggat gaagtatgag gagagctctg actcaggag     960 gtgctccagg aaccagcaaa caagaggctg ctcccgcagg aggcagtgtg aagggagaaa   1020
gaaggctgca gtaggggctg ctgctggact cggtggggag caggtgcaag gagctctggc   1080
tcccccatgg acctgagctg gagagcagag cgcagctcca gcccattcct cattcttcca   1140
```

-continued

```
gggcacagtc ctcaggatgt ttcggggaga ataggagcca gaacctgagc ccctaagcta    1200
ttcccctcac caatgatggg gtccccagtg agtcatctgc tggccggctt ctgtgtgtgg    1260
gtcgtcttgg gctgggtagg gggctcagtc cccaacctgg gccctgctga gcaggagcag    1320
aaccattacc tggcccagct gtttggcctg tagggcgaga atgggacgct gactgcaggg    1380
ggcttggcgc ggcttctcca cagcctgggg ctaggccgag ttcagggggct tcgcctggga    1440 cagcatgggc ctctgactgg acgggctgca tccccagctg cagacaattc cacacacagg    1500
tactgacccc ttcctccact ccacagggcc acatctccca ggtcctctca gtgcttgccc    1560
ccagttgcct cgttctggct tcctcacgag atccctggag ttacaaattc ttcagaaccg    1620
agctccttgg tatctcttca aaacctctca tgcttctatt gccttctctc tcttttcttg    1680 agactgggggg tctcgctttg tcacccaggc taaagtgcag tgacacattc acggctcact    1740
gcaacctctg cttcccaggc tgaagccatc ctcccacctc agcctcctga gcagctggga    1800
ccataggcac acaccaccac agccggctaa ttttaaaaat tttttacaga dacaagggtt    1860
tcgctgtgtt gcccaggctg gtctcaaact cctgggctca gctcagcgat ctgcctgcct    1920
cagcttccca aagtgctggg actacagatg tgaactacca ccctagccct ccgttgcctt    1980
ctaattctct cctcctccaa atctctaagc ccttaaattt cttgctctta gtatcactgt    2040
tcagtgtctc tgggctgatt tggctccaaa ttcgtagact tctttttct tttcttttct    2100 tttttttttt tttttttttt tgagacagag tctcgctctg tcgcccaggc tggagtgcag    2160
tggtgtgatc ttggctcact gtaacctctg cctccccggt tcaagcgatt ctcctgcctc    2220
ggcctcctga gtagctggga ttacaggcac acaccaccac gccgggctaa tttttgcaat    2280
tttagtagag acggggtttc accattttgg tcaggctggt ctcgaacttc caacctcagg    2340
tgatccaccc acctcagcct cccaaagtgc tgggattaca ggcgtgagcc accgtgccca    2400
gccattcgta gcccttttgg ttgtcgtcct tttttttctg tccccccag tggcagaaaa    2460 tggacaactc acagatcttc ctaagaatga cattccatgg tttctgggtc ccaggatctc    2520
cagtcagtgg ctagtccccc cattcccccct aaaatccctg ggagcctctc aaagcgggtt    2580
gatagagaac acaagggagg ctgacttgct gtctcatcca ttccaggcca cagaaccctg    2640
agctgagtgt ggatgtctgg gcagggatgc ctctgggtcc ctcagggtgg ggtgacctgg    2700
aagagtcaaa ggcccctcac ctaccccgtg ggccagcccc ctcgggcctg gacctccttc    2760
acaggcttct gttgctggac cactcattgg ctgaccacct gaatgaggat gtgagtctga    2820
cggtctctag aggggaagga gccatgggat tagatggcct gaaatgttta aataatcagt    2880 agtttttttgt tttgttttgt tttttaaatcc caacgtggac caagcgtggt ggctcacgcc    2940
tgtaatccca cactttgggg aggccgaggt gggtggatca cctgaggtca ggagttcgag    3000
accagcctgg ccaacatggt gaaaccccat ctctactaaa aatacaaaa attagccggg    3060 tgtggtaaca ggtgtgtgta atcctagcta ctcaggaggc tgaggtgaga aaattgcttg    3120
aacttgggag gcagaggttg cagtgagcca agatggcacc atttgcactc cagcctgggc    3180
aacaagaggg agactctgtc tcaaaaaaaa aaaaaaaaaa aaaaaaaaa aaaaaaaat    3240 agctgggcgt ggtggcacat gcctataatc ccagttactc ggaaggctga ggcaggaaaa    3300
tcacttgaac ccaggaggcg gagattgcag tcagccgaga ttgcaccact gcactccagc    3360
ctgggtaaca cagcgagact ctgtctcaaa aatgaaaata aaaaaaataa aaaaataaaa    3420
aaaaaatatc tcactgtggt cttaggggat gttatttcaa tagtgaacta tgttccctct    3480
gggatcagag caggtgagcc catatccaga gctccaagac tcagtttagg ggaatagatg    3540
```

```
gcaaagcaga gaatctagag aagcagccca gggtaggatc tggatggtca cctggagagg   3600
agacctgcag ggaatggatg gctgtcttca tccagaaaga cagagaatat attccactta   3660
caccagaggg cagacaaagc tgcctaaccc tgatggaggt ccagtgagtg cccattgcag   3720
gaagcattca agctgaggct ggatgaacat cgacagggct gttgagaggg agattagatg   3780
gcatttcagg gtcttttccc ttttaagatt ctggcatgga gagctctagt tttccaacca   3840
gcttcattta tcaaatcaac aaaatgattg aaatgatcag agtttgcagg gaagatgatg   3900
acaatgctca ctagcaccca gtttgcatca aattgaatac ctgcattgga ctgaatattc   3960
actaataata cacattgatt ataagtaccc ttggccctag tccccaaggt acctgccagt   4020
aggagcaaag gggaccctgg gagagaccca ggagtctatg caatggaagg acaggtgtta   4080
aatatatata tatatatttt tttgaggtag agtctgactc tgtcacccag gctggagtgc   4140
aatggcgtga tcttggctca ctgcaacctc cacctcctgg gttaaagcaa ttctcctgcc   4200
tcagcctccc gagtagctgg gattataggt gttcactact atccccagct aattttttt   4260 tttttttttt gagatggagt ctcactctgt cgcccaggct ggagtgcact ggtgcaatct   4320
cggctcactg caacctctgc ctcctgggtt caagcgattc tcctgtctca gcctcctgag   4380
tagctgggat acaggtgca cgccaccatg cccagctaat ttttttgtatt ttagtagaga   4440 cagggtttca ccatgttgcc caggctggtc tcgaactcct gagctcaggc aatctaccca   4500
cctcagcctc ccaaagtgct gggattacag gcgtgagcca ccgcacccgg ctcatcccca   4560
gctaattttt gtattttag tagagacagg gtttcactat gttggccagg ttggtctcaa   4620
actcctgacc tcagatgata cacccgcctg gcctctcaa gggctgggat tataggtgtg   4680
agccactaca cctggccagg tgttaaagat ctgagtcata gttcctggtg attctccaat   4740
gtatgaccct caattctcca gtgtctgaac ggctcccagc tgctggtcaa ttttggcttg   4800
agccccgctg ctcctctgac ccctcgtcag tttgctctgc tgtgcccagc cctgctttat   4860
cagatcgaca gccgcgtctg catcggcgct ccggcccctg cacccccagg ggatctacta   4920
tctggtcagc aagtaggagt gggtggggga caccctgaat cctggaagtg gggcccatgc   4980 caaaaggag gctcactggg gtcctgcctc tccttgtagt gttctctctg ctccaccttta   5040 cgtgtgggac cctcctcttg ccctgaccta acttcagccc ctgattctcc ccagccctgc   5100
ttcagagtgc cctggcagtc ctgttgctca gcctcccttc tccccatcc ctgctgctgc   5160 tgcggctcct gggacctcgt ctactacggc ccttgctggg cttcctgggg ccctggcgg   5220 tgggcactct ttgtggggat gcactgctac atctgctacc gcatgtatgt gaagcccctt   5280
ccttgtaccc ctggcctcca tggatctaag gtgtccccag ccataggaca tccccctccgc   5340 ctttccatca gctcccatat cctactccca gatcctggct tcagcccaca gctgccttct   5400
agtagagcat atgagcgaag gcttgccaca atccatgcaa ggggatgttg ttgggtatag   5460
gggcttccag agtctgccct gaccttctct ctgtcaggca caagaagggc ggcacgcagg   5520
acctggcgga ctaccagaga aggacctggg cccggggctg tcagtgctcg gaggcctctt   5580
cctgctcttt gtgctggaga acatgctggg gcttttgcgg caccgagggc tcaggccagt   5640
gagtgatacc cttttctcct ccttctgctg agaccagagt cccagtcaag aactgggcca   5700
ggccgggcgc ggtggctcac gcctgtaatc ccagcacttt gggagcccaa ggcgggcaga   5760
tcacaaggtt aggagttcga gtccagcctg accaacatgg tgaaaccctg tctctactaa   5820
aaatacaaaa attagctggg cgtggtggtg cgtgtctgta atcccagcta ctcaggaggc   5880
```

```
tgaggcagga gaatcgcttg acttgggagg tggaggttgc agcgagctaa gatggcacca    5940
ctgcactcca gcccaggtga cagagcgaga ctccatctca aaaacaacaa caacaacaac    6000
aaaactgggc caaaaagcca agagatgagg agcagtgtgt gctcctggat ctctgacatt    6060
tgcctggtgt gcaggaccta tcggctaaca gggagtgggg aggggctcct taagcacaga    6120
cccaggactt ctggccaaat ggcatcctat tctgagctca agtcaacaag aaacagaggg    6180
gaggtgccaa cttgggaaga aggtagaggc caaagaacat cccaggtgcc agaggtggaa    6240
ccaggtgttc atcttcccag cttgtggcct ggcttcccct tagtccctgg ctctgctgcc    6300
tcctccacca ggagggatgc cctcctattt cagagatgct gcaggcgaaa acgaaggaat    6360
ctcgaaacac gcaacttgga tccggagaat ggcagtggga tggcccttca gcccctacag    6420
gcagctccag gtgactagag gagaaaattt gaagagtagg ttccaagctc acagtcctta    6480
cttgcagcca ccaacactgt cctgtgcttc ttcccgcaga gccaggggct cagggccaga    6540
gggagaagaa cagccagcac ccaccagctc tggcccctcc tggcaccaa ggccacagtc     6600 atgggcacca gggtggcact gatatcacgt ggatggtcct cctgggagat ggtctacaca    6660
acctcactga tgggctggcc ataggtgtga ggggtgggaa cggagggaag caggtccgag    6720
gggaggccag ggctcctagt tatcagctgg ggctaggaga gggccgtcag gaagatgggg    6780
agaggacggg aggaccacgg aacacaggaa cctgcttctg aggagacttt tcttctggac    6840
tgacaacttc cgaccctgct ggccccaggt gctgccttct ctgatggctt ctccagcggc    6900
ctcagtacca ccttagcggt cttctgccat gagctgcccc acgaactggg taggaatggc    6960
aggagcaggg tggggtggac tccagaaagg agatagctcc aaggggtaga gcttggaggc    7020
tggtgggtgg catggatgag gggcacccca gcttactccc tcccatcctg tcctctgtct    7080
ccaataggtg actttgccat gctgctccag tcagggctgt cctttcggcg gctgctgctg    7140
ctgagcctcg tgtctggagc cctgggattg ggggtgcag tcctgggggt ggggctcagc     7200
ctgggccctg tcccctcac tccctgggtg tttggggtca ctgctgggt cttcctctat      7260 gtggcccttg tggacatggt gagagatgtc gggtagagca gagaaatcaa gggcagtggg    7320
gaggcgggag tggagaggga ggtagcagtc cctccgcctc taccattagc tcctggaagg    7380
gcgtcagacc ataggcccgc aaaagtctga gaaacaaggg actaaggtgt ttgggtgggg    7440
gctgctgatg ctttctgaca ccattcctct ggagttgaga ggtcagggc aaggccagaa     7500 tcctgacatc ctcttttct tcagctacc agccctgctt cgtcctccgg agcccctgcc      7560
tacgccccat gtgctcctgc aggggctggg gctgctgctg gggggcggcc tcatgcttgc    7620
cataaccctg ctggaggagc ggctactgcc cgtgaccact gagggctgat ggggccagtg    7680
gaaaggggtc gggttgccct tccttccccc caaccacagg aatggaggcg ggacacaggg    7740
ccagtaggag caataggatt ttaataaaca gaacccatcc caaa                     7784

<210> SEQ ID NO 4
<211> LENGTH: 7784
<212> TYPE: DNA
<213> ORGANISM: homo sapien

<400> SEQUENCE: 4
agctggaacc aagaaggttg tgtccccctt cctctgggtg tccttgtctc ctgctatcag      60
gtaatgccaa cctcaacccc ctggaccagt caccccgatc agactttgct tgcctgattt     120
taggccaggt cagacatcag aggagagccc agatccttgt ttcctctccc ccgcagggc      180 ttccccttt cttggtcatcg atccctagag ctctggctct ttctcttctt ggggtgagaa     240
```

```
actgctaaga acagtttatt tcccatgcat gcatctgggc ttgccactga tctgccttt      300
cccccctcct ccccaggtta gggacacctg ggtccaacct tcccaaggaa tatggggatg     360
ggggttggag atgaagttta gtgctagact gtaaggtagg tggggtggaa gtacatgagg     420
gaaagggcta aatggtact aatggtgtta aggatagggt gaattattta agaggaaaaa     480
gactaggccc aggttctcct tagccatgtg gctttcccag ggcagagggt ggcccctccc     540
tacccagggg cccagcagag actgactttt gatccctacc ccagagacca gtgaaccatt     600
aactcctctc ttatgtgagc cttcacacac tggccccacc cctgaccccg ccccaaggca     660
ggtgggctag gaggggggtgc atgtccatct cagccttcta tgtgacgtgg cctccgatcc    720
acctggacac ctggaggcta agcctggatt ccccCttccc tgactcagga actgcttaac    780
gtctacagca aggcctaata ggggacctga ggtgacagct cttatgttgc cagtaggggt    840
gaggccctgg ggattgaggg gggataaaga ggtggggcaa agttgagggg tggggtttag    900
gggacaagga atggacggtc agctctggat gaagtatgag gagagctctg actcaggag     960
gtgctccagg aaccagcaaa caagaggctg ctcccgcagg aggcagtgtg aagggagaaa   1020
gaaggctgca gtaggggctg ctgctggact cggtggggag caggtgcaag gagctctggc   1080
tcccccatgg acctgagctg gagagcagag cgcagctcca gcccattcct cattcttcca   1140
gggcacagtc ctcaggatgt ttcggggaga ataggagcca gaacctgagc ccctaagcta   1200
ttcccctcac caatgatggg gtcccagtg agtcatctgc tggccggctt ctgtgtgtgg    1260
gtcgtcttgg gctgggtagg gggctcagtc cccaacctgg gccctgctga gcaggagcag   1320
aaccattacc tggcccagct gtttggcctg tacggcgaga tgggacgct gactgcaggg    1380
ggcttggcgc ggcttctcca cagcctgggg ctaggccgag ttcaggggct tcgcctggga   1440
cagcatgggc ctctgactgg acgggctgca tccccagctg cagacaattc cacacacagg   1500
tactgacccc ttcctccact ccacagggcc acatctccca ggtcctctca gtgcttgccc   1560
ccagttgcct cgttctggct tcctcacgag atccctggag ttacaaattc ttcagaaccg   1620
agctccttgg tatctcttca aaacctctca tgcttctatt gccttctctc tcttttcttg   1680
agactggggg tctcgctttg tcacccaggc taaagtgcag tgacacattc acggctcact   1740
gcaacctctg cttcccaggc tgaagccatc ctcccacctc agcctcctga gcagctggga   1800
ccataggcac acaccaccac agccggctaa ttttaaaaat ttttacaga gacaaggggtt    1860
tcgctgtgtt gcccaggctg gtctcaaact cctgggctca gctcagcgat ctgcctgcct   1920
cagcttccca aagtgctggg actacagatg tgaactacca ccctagccct ccgttgcctt   1980
ctaattctct cctcctccaa atctctaagc ccttaaattt cttgctctta gtatcactgt   2040
tcagtgtctc tgggctgatt tggctccaaa ttcgtagact tcttttttct tttcttttct   2100
tttttttttt tttttttttt tgagacagag tctcgctctg tcgcccaggc tggagtgcag   2160
tggtgtgatc ttggctcact gtaacctctg cctcccggt tcaagcgatt ctcctgcctc    2220
ggcctcctga gtagctggga ttacaggcac acaccaccac gccgggctaa ttttgcaat    2280
tttagtagag acggggtttc accattttgg tcaggctggt ctcgaacttc caacctcagg   2340
tgatccaccc acctcagcct cccaaagtgc tgggattaca ggcgtgagcc accgtgccca   2400
gccattcgta gccttttggg ttgtcgtcct ttttttttctg tcccccccag tggcagaaaa   2460
tggacaactc acagatcttc ctaagaatga cattccatgg tttctgggtc ccaggatctc   2520
cagtcagtgg ctagtccccc cattcccccct aaaatccctg ggagcctctc aaagcgggtt   2580
```

```
gatagagaac acaagggagg ctgacttgct gtctcatcca ttccaggcca cagaaccctg    2640
agctgagtgt ggatgtctgg gcagggatgc ctctgggtcc ctcagggtgg ggtgacctgg    2700
aagagtcaaa ggcccctcac ctaccccgtg ggccagcccc ctcgggcctg gacctccttc    2760
acaggcttct gttgctggac cactcattgg ctgaccacct gaatgaggat gtgagtctga    2820
cggtctctag aggggaagga gccatgggat tagatggcct gaaatgttta aataatcagt    2880
agttttttgt tttgttttgt ttttaaatcc caacgtggac caagcgtggt ggctcacgcc    2940
tgtaatccca cactttggg aggccgaggt gggtggatca cctgaggtca ggagttcgag    3000
accagcctgg ccaacatggt gaaaccccat ctctactaaa aaatacaaaa attagccggg    3060
tgtggtaaca ggtgtgtgta atcctagcta ctcaggaggc tgaggtgaga aaattgcttg    3120
aacttgggag gcagaggttg cagtgagcca agatggcacc atttgcactc cagcctgggc    3180
aacaagaggg agactctgtc tcaaaaaaaa aaaaaaaaa aaaaaaaaaa aaaaaaaat     3240 agctgggcgt ggtggcacat gcctataatc ccagttactc ggaaggctga ggcaggaaaa    3300
tcacttgaac ccaggaggcg gagattgcag tcagccgaga ttgcaccact gcactccagc    3360
ctgggtaaca cagcgagact ctgtctcaaa aatgaaaata aaaaaaataa aaaaataaaa    3420
aaaaaatatc tcactgtggt cttagggat gttatttcaa tagtgaacta tgttccctct    3480
gggatcagag caggtgagcc catatccaga gctccaagac tcagtttagg gaatagatg    3540 gcaaagcaga gaatctagag aagcagccca gggtaggatc tggatggtca cctggagagg    3600
agacctgcag ggaatggatg gctgtcttca tccagaaaga cagagaatat attccactta    3660
caccagaggg cagacaaagc tgcctaaccc tgatggaggt ccagtgagtg cccattgcag    3720
gaagcattca agctgaggct ggatgaacat cgacagggct gttgagaggg agattagatg    3780
gcatttcagg gtcttttccc ttttaagatt ctggcatgga gagctctagt tttccaacca    3840
gcttcattta tcaaatcaac aaaatgattg aaatgatcag agtttgcagg gaagatgatg    3900
acaatgctca ctagcaccca gtttgcatca aattgaatac ctgcattgga ctgaatattc    3960
actaataata cacattgatt ataagtaccc ttggccctag tccccaaggt acctgccagt    4020
aggagcaaag gggaccctgg gagagaccca ggagtctatg caatggaagg acaggtgtta    4080
aatatatata tatatatttt tttgaggtag agtctgactc tgtcacccag gctggagtgc    4140 aatgcgtga tcttggctca ctgcaaccctc cacctcctgg gttaaagcaa ttctcctgcc    4200
tcagcctccc gagtagctgg gattataggt gttcactact atccccagct aattttttttt    4260 tttttttttt gagatggagt ctcactctgt cgcccaggct ggagtgcact ggtgcaatct    4320
cggctcactg caacctctgc ctcctgggtt caagcgattc tcctgtctca gcctcctgag    4380
tagctgggat cacaggtgca cgccaccatg cccagctaat ttttttgtatt ttagtagaga    4440 cagggtttca ccatgttgcc caggctggtc tcgaactcct gagctcaggc aatctaccca    4500
cctcagcctc ccaaagtgct gggattacag gcgtgagcca ccgcaccggg ctcatcccca    4560
gctaattttt gtattttag tagagacagg gtttcactat gttggccagg ttggtctcaa    4620
actcctgacc tcagatgata cacccgcctg ggcctctcaa gggctgggat tataggtgtg    4680
agccactaca cctggccagg tgttaaagat ctgagtcata gttcctggtg attctccaat    4740
gtatgaccct caattctcca gtgtctgaac ggctcccagc tgctggtcaa ttttggcttg    4800
agccccgctg ctcctctgac ccctcgtcag tttgctctgc tgtgcccagc cctgctttat    4860
cagatcgaca gccgcgtctg catcggcgct ccggcccctg cacccccagg ggatctacta    4920
tctggtcagc aagtaggagt gggtggggga caccctgaat cctggaagtg gggcccatgc    4980
```

```
caaaaaggag gctcactggg gtcctgcctc tccttgtagt gttctctctg ctccacctta    5040
cgtgtgggac cctcctcttg ccctgaccta acttcagccc ctgattctcc ccagccctgc    5100
ttcagagtgc cctggcagtc ctgttgctca gcctcccttc tccctatcc ctgctgctgc    5160
tgcggctcct gggacctcgt ctactacggc ccttgctggg cttcctgggg ccctggcgg    5220
tgggcactct ttgtggggat gcactgctac atctgctacc gcatgtatgt gaagcccctt    5280
ccttgtaccc ctggcctcca tgatctaag gtgtccccag ccataggaca tcccctccgc     5340
cttcccatca gctcccatat cctactccca gatcctggct tcagcccaca gctgccttct    5400
agtagagcat atgagcgaag gcttgccaca atccatgcaa gggatgttg ttgggtatag     5460
gggcttccag agtctgccct gaccttctct ctgtcaggca caagaagggc ggcacgcagg    5520
acctggcgga ctaccagaga aggacctggg cccggggctg tcagtgctcg gaggcctctt    5580
cctgctcttt gtgctggaga acacgctggg gcttttgcgg caccgagggc tcaggccagt    5640
gagtgatacc ctttctcct ccttctgctg agaccagagt cccagtcaag aactgggcca     5700
ggccgggcgc ggtggctcac gcctgtaatc ccagcacttt gggagcccaa ggcgggcaga    5760
tcacaaggtt aggagttcga gtccagcctg accaacatgg tgaaaccctg tctctactaa    5820
aaatacaaaa attagctggg cgtggtggtg cgtgtctgta atcccagcta ctcaggaggc    5880
tgaggcagga aatcgcttg acttgggagg tggaggttgc agcgagctaa gatggcacca    5940
ctgcactcca gcccaggtga cagagcgaga ctccatctca aaaacaacaa caacaacaac    6000
aaaactgggc caaaaagcca agagatgagg agcagtgtgt gctcctggat ctctgacatt    6060
tgcctggtgt gcaggaccta tcggctaaca gggagtgggt aggggctcct taagcacaga    6120
cccaggactt ctggccaaat ggcatcctat tctgagctca agtcaacaag aaacagaggg    6180
gaggtgccaa cttgggaaga aggtagaggc caaagaacat cccaggtgcc agaggtggaa    6240
ccaggtgttc atcttcccag cttgtggcct ggcttcccct tagtccctgg ctctgctgcc    6300
tcctccacca ggagggatgc cctcctattt cagagatgct gcaggcgaaa acgaaggaat    6360
ctcgaaacac gcaacttgga tccggagaat ggcagtggga tggcccttca gcccctacag    6420
gcagctccag gtgactagag gagaaaattt gaagagtagg ttccaagctc acagtcctta    6480
cttgcagcca ccaacactgt cctgtgcttc ttcccgcaga gccaggggct cagggccaga    6540
gggagaagaa cagccagcac ccaccagctc tggcccctcc tgggcaccaa ggccacagtc    6600
atgggcacca gggtggcact gatatcacgt ggatggtcct cctgggagat ggtctacaca    6660
acctcactga tgggctggcc ataggtgtga ggggtgggaa cggagggaag caggtccgag    6720
ggaggccag ggctcctagt tatcagctgg ggctaggaga gggccgtcag gaagatgggg     6780
agaggacggg aggaccacgg aacacaggaa cctgcttctg aggagacttt tcttctggac    6840
tgacaacttc cgaccctgct ggccccaggt gctgccttct ctgatggctt ctccagcggc    6900
ctcagtacca ccttagcggt cttctgccat gagctgcccc acgaactggg taggaatggc    6960
aggagcaggg tggggtggac tccagaaagg agatagctcc aaggggtaga gcttggaggc    7020
tggtgggtgg catggatgag gggcacccca gcttactccc tcccatcctg tcctctgtct    7080
ccaataggtg actttgccat gctgctccag tcagggctgt cctttcggcg gctgctgctg    7140
ctgagcctcg tgtctggagc cctgggattg gggggtgcag tcctgggggt ggggctcagc    7200
ctgggccctg tccccctcac tccctgggtg tttggggtca ctgctggggt cttcctctat    7260
gtggcccttg tggacatggt gagagatgtc gggtagagca gagaaatcaa gggcagtggg    7320
```

| | |
|---|---:|
| gaggcgggag tggagaggga ggtagcagtc cctccgcctc taccattagc tcctggaagg | 7380 |
| gcgtcagacc ataggcccgc aaaagtctga gaaacaaggg actaaggtgt ttgggtgggg | 7440 |
| gctgctgatg ctttctgaca ccattcctct ggagttgaga ggtcagggc aaggccagaa | 7500 |
| tcctgacatc ctcttttct ttcagctacc agccctgctt cgtcctccgg agccctgcc | 7560 |
| tacgccccat gtgctcctgc aggggctggg gctgctgctg gggggcggcc tcatgcttgc | 7620 |
| cataaccctg ctggaggagc ggctactgcc cgtgaccact gagggctgat ggggccagtg | 7680 |
| gaaaggggtc gggttgccct tccttccccc caaccacagg aatggaggcg ggacacaggg | 7740 |
| ccagtaggag caataggatt ttaataaaca gaacccatcc caaa | 7784 |

<210> SEQ ID NO 5
<211> LENGTH: 7784
<212> TYPE: DNA
<213> ORGANISM: homo sapien

<400> SEQUENCE: 5

| | |
|---|---:|
| agctggaacc aagaaggttg tgtccccctt cctctgggtg tccttgtctc ctgctatcag | 60 |
| gtaatgccaa cctcaacccc ctggaccagt caccccgatc agactttgct tgcctgattt | 120 |
| taggccaggt cagacatcag aggagagccc agatccttgt ttcctctccc ccgcagggc | 180 |
| ttccccttc ttggtcatcg atccctagag ctctggctct ttctcttctt ggggtgagaa | 240 |
| actgctaaga acagtttatt tcccatgcat gcatctgggc ttgccactga tctgcctttt | 300 |
| ccccctcct ccccaggtta gggacacctg gtccaacct cccaaggaa tatggggatg | 360 |
| ggggttggag atgaagttta gtgctagact gtaaggtagg tggggtggaa gtacatgagg | 420 |
| gaaagggcta aaatggtact aatggtgtta aggataggt gaattattta agaggaaaaa | 480 |
| gactaggccc aggttctcct tagccatgtg gctttcccag gcagagggt ggcccctccc | 540 |
| tacccagggg cccagcagag actgactttt gatccctacc ccagagacca gtgaaccatt | 600 |
| aactcctctc ttatgtgagc cttcacacac tggcccacc cctgacccg ccccaaggca | 660 |
| ggtgggctag gagggggtgc atgtccatct cagccttcta tgtgacgtgg cctccgatcc | 720 |
| acctggacac ctggaggcta agcctggatt ccccctccc tgactcagga actgcttaac | 780 |
| gtctacagca aggcctaata ggggacctga ggtgacagct cttatgttgc cagtagggt | 840 |
| gaggccctgg ggattgaggg gggataaaga ggtggggcaa agttgagggg tggggtttag | 900 |
| gggacaagga atggacggtc agctctggat gaagtatgag gagagctctg actcagggag | 960 |
| gtgctccagg aaccagcaaa caagaggctg ctcccgcagg aggcagtgtg aagggagaaa | 1020 |
| gaaggctgca gtagggctg ctgctggact cggtggggag caggtgcaag gagctctggc | 1080 |
| tccccccatgg acctgagctg gagagcagag cgcagctcca gcccattcct cattcttcca | 1140 |
| gggcacagtc ctcaggatgt ttcggggaga ataggagcca gaacctgagc ccctaagcta | 1200 |
| ttcccctcac caatgatggg gtccccagtg agtcatctgc tggccggctt ctgtgtgtgg | 1260 |
| gtcgtcttgg gctgggtagg gggctcagtc cccaacctgg gccctgctga gcaggagcag | 1320 |
| aaccattacc tggcccagct gtttggcctg tacggcgaga atgggacgct gactgcaggg | 1380 |
| ggcttggcgc ggcttctcca cagcctgggg ctaggccgag ttcaggggct tcgcctggga | 1440 |
| cagcatgggc ctctgactgg acgggctgca tccccagctg cagacaattc cacacacagg | 1500 |
| tactgacccc ttcctccact ccacagggcc acatctccca ggtcctctca gtgcttgccc | 1560 |
| ccagttgcct cgttctggct tcctcacgag atccctggag ttacaaattc ttcagaaccg | 1620 |
| agctccttgg tatctcttca aaacctctca tgcttctatt gccttctctc tctttttcttg | 1680 |

```
agactgggggg tctcgctttg tcacccaggc taaagtgcag tgacacattc acggctcact   1740
gcaacctctg cttcccaggc tgaagccatc ctcccacctc agcctcctga gcagctggga   1800
ccataggcac acaccaccac agccggctaa ttttaaaaat ttttttacaga gacaagggtt   1860 tcgctgtgtt gcccaggctg gtctcaaact cctgggctca gctcagcgat ctgcctgcct   1920
cagcttccca aagtgctggg actacagatg tgaactacca ccctagccct ccgttgcctt   1980
ctaattctct cctcctccaa atctctaagc ccttaaattt cttgctctta gtatcactgt   2040
tcagtgtctc tgggctgatt tggctccaaa ttcgtagact tcttttttct tttcttttct   2100
tttttttttt tttttttttt tgagacagag tctcgctctg tcgcccaggc tggagtgcag   2160
tggtgtgatc ttggctcact gtaacctctg cctcccggt tcaagcgatt ctcctgcctc   2220
ggcctcctga gtagctggga ttacaggcac acaccaccac gccgggctaa tttttgcaat   2280
tttagtagag acggggtttc accattttgg tcaggctggt ctcgaacttc aacctcagg   2340 tgatccaccc acctcagcct cccaaagtgc tgggattaca ggcgtgagcc accgtgccca   2400
gccattcgta gccctttgg ttgtcgtcct tttttttctg tccccccag tggcagaaaa   2460 tggacaactc acagatcttc ctaagaatga cattccatgg tttctgggtc caggatctc   2520 cagtcagtgg ctagtcccc cattccccct aaaatccctg ggagcctctc aaagcgggtt   2580
gatagagaac acaagggagg ctgacttgct gtctcatcca ttccaggcca cagaaccctg   2640
agctgagtgt ggatgtctgg gcagggatgc ctctgggtcc ctcagggtgg ggtgacctgg   2700
aagagtcaaa ggcccctcac ctaccccgtg ggccagcccc ctcgggcctg gacctccttc   2760
acaggcttct gttgctggac cactcattgg ctgaccacct gaatgaggat gtgagtctga   2820
cggtctctag aggggaagga gccatgggat tagatggcct gaaatgttta aataatcagt   2880
agttttttgt tttgttttgt tttaaatcc caacgtggac caagcgtggt ggctcacgcc   2940
tgtaatccca cactttggg aggccgaggt gggtggatca cctgaggtca ggagttcgag   3000
accagcctgg ccaacatggt gaaaccccat ctctactaaa aaatacaaaa attagccggg   3060
tgtggtaaca ggtgtgtgta atcctagcta ctcaggaggc tgaggtgaga aaattgcttg   3120
aacttgggag gcagaggttg cagtgagcca agatggcacc atttgcactc agcctgggc   3180 aacaagaggg agactctgtc tcaaaaaaaa aaaaaaaaa aaaaaaaaa aaaaaaaat   3240 agctgggcgt ggtggcacat gcctataatc ccagttactc ggaaggctga ggcaggaaaa   3300
tcacttgaac ccaggaggcg gagattgcag tcagccgaga ttgcaccact gcactccagc   3360
ctgggtaaca cagcgagact ctgtctcaaa aatgaaaata aaaaaaataa aaaaataaaa   3420
aaaaaatatc tcactgtggt cttagggat gttatttcaa tagtgaacta tgttccctct   3480
gggatcagag caggtgagcc catatccaga gctccaagac tcagtttagg ggaatagatg   3540
gcaaagcaga gaatctagag aagcagccca gggtaggatc tggatggtca cctggagagg   3600
agacctgcag ggaatggatg gctgtcttca tccagaaaga cagagaatat attccactta   3660
caccagaggg cagacaaagc tgcctaaccc tgatggaggt ccagtgagtg cccattgcag   3720
gaagcattca agctgaggct ggatgaacat cgacagggct gttgagaggg agattagatg   3780
gcatttcagg gtcttttccc ttttaagatt ctggcatgga gagctctagt tttccaacca   3840
gcttcattta tcaaatcaac aaaatgattg aaatgatcag agtttgcagg gaagatgatg   3900
acaatgctca ctagcaccca gtttgcatca aattgaatac ctgcattgga ctgaatattc   3960
actaataata cacattgatt ataagtaccc ttggccctag tccccaaggt acctgccagt   4020
```

```
aggagcaaag gggaccctgg gagagaccca ggagtctatg caatggaagg acaggtgtta    4080
aatatatata tatatatttt tttgaggtag agtctgactc tgtcacccag gctggagtgc    4140
aatggcgtga tcttggctca ctgcaacctc cacctcctgg gttaaagcaa ttctcctgcc    4200
tcagcctccc gagtagctgg gattataggt gttcactact atccccagct aattttttt    4260
ttttttttt gagatggagt ctcactctgt cgcccaggct ggagtgcact ggtgcaatct    4320
cggctcactg caacctctgc ctcctgggtt caagcgattc tcctgtctca gcctcctgag    4380
tagctgggat cacaggtgca cgccaccatg cccagctaat ttttgtatt ttagtagaga    4440
cagggtttca ccatgttgcc caggctggtc tcgaactcct gagctcaggc aatctaccca    4500
cctcagcctc ccaaagtgct gggattacag gcgtgagcca ccgcacccgg ctcatcccca    4560
gctaatttt gtattttag tagagacagg gtttcactat gttggccagg ttggtctcaa    4620
actcctgacc tcagatgata cacccgcctg ggcctctcaa gggctgggat tataggtgtg    4680
agccactaca cctggccagg tgttaaagat ctgagtcata gttcctggtg attctccaat    4740
gtatgaccct caattctcca gtgtctgaac ggctcccagc tgctggtcaa ttttggcttg    4800
agccccgctg ctcctctgac ccctcgtcag tttgctctgc tgtgcccagc cctgctttat    4860
cagatcgaca gccgcgtctg catcggcgct ccggcccctg caccccagg ggatctacta    4920
tctggtcagc aagtaggagt gggtggggga caccctgaat cctggaagtg gggcccatgc    4980
caaaaggag gctcactggg gtcctgcctc tccttgtagt gttctctctg ctccaccta    5040
cgtgtgggac cctcctcttg ccctgaccta acttcagccc ctgattctcc ccagccctgc    5100
ttcagagtgc cctggcagtc ctgttgctca gcctcccttc tccctatcc ctgctgctgc    5160
tgcggctcct gggacctcgt ctactacggc ccttgctggg cttcctgggg gccctggcgg    5220
tgggcactct ttgtggggat gcactgctac atctgctacc gcatgtatgt gaagccccttt    5280
ccttgtaccc ctggcctcca tggatctaag gtgtccccag ccataggaca tccctccgc    5340
ctttccatca gctcccatat cctactccca gatcctggct tcagcccaca gctgccttct    5400
agtagagcat atgagcgaag gcttgccaca atccatgcaa ggggatgttg ttgggtatag    5460
gggcttccag agtctgccct gaccttctct ctgtcaggca caagaagggc ggcacgcagg    5520
acctggcgga ctaccagaga aggacctggg cccggggctg tcagtgctcg gaggcctctt    5580
cctgctcttt gtgctggaga acatgctggg cttttgcgg caccgagggc tcaggccagt    5640
gagtgatacc cttttctcct ccttctgctg agaccagagt cccagtcaag aactgggcca    5700
ggccgggcgc ggtggctcac gcctgtaatc ccagcacttt gggagcccaa ggcgggcaga    5760
tcacaaggtt aggagttcga gtccagcctg accaacatgg tgaaaccctg tctctactaa    5820
aaatacaaaa attagctggg cgtggtggtg cgtgtctgta atcccagcta ctcaggaggc    5880
tgaggcagga gaatcgcttg acttgggagg tggaggttgc agcgagctaa gatggcacca    5940
ctgcactcca gcccaggtga cagagcgaga ctccatctca aaacaacaa caacaacaac    6000
aaaactgggc caaaaagcca agagatgagg agcagtgtgt gctcctggat ctctgacatt    6060
tgcctggtgt gcaggaccta tcggctaaca gggagtgggt aggggctcct taagcacaga    6120
cccaggactt ctggccaaat ggcatcctat tctgagctca agtcaacaag aaacagaggg    6180
gaggtgccaa cttgggaaga aggtagaggc caaagaacat cccaggtgcc agaggtggaa    6240
ccaggtgttc atcttcccag cttgtggcct ggcttcccct tagtccctgg ctctgctgcc    6300
tcctccacca ggagggatgc cctcctattt cagagatgct gcaggcgaaa atgaaggaat    6360
ctcgaaacac gcaacttgga tccggagaat ggcagtggga tggcccttca gcccctacag    6420
```

-continued

```
gcagctccag gtgactagag gagaaaattt gaagagtagg ttccaagctc acagtcctta    6480
cttgcagcca ccaacactgt cctgtgcttc ttcccgcaga gccaggggct cagggccaga    6540
gggagaagaa cagccagcac ccaccagctc tggcccctcc tgggcaccaa ggccacagtc    6600
atgggcacca gggtggcact gatatcacgt ggatggtcct cctgggagat ggtctacaca    6660
acctcactga tgggctggcc ataggtgtga ggggtgggaa cggagggaag caggtccgag    6720
gggaggccag ggctcctagt tatcagctgg ggctaggaga gggccgtcag gaagatgggg    6780
agaggacggg aggaccacgg aacacaggaa cctgcttctg aggagacttt tcttctggac    6840
tgacaacttc cgaccctgct ggccccaggt gctgccttct ctgatggctt ctccagcggc    6900
ctcagtacca ccttagcggt cttctgccat gagctgcccc acgaactggg taggaatggc    6960
aggagcaggg tggggtggac tccagaaagg agatagctcc aagggtaga gcttggaggc    7020 tggtgggtgg catggatgag gggcacccca gcttactccc tcccatcctg tcctctgtct    7080
ccaataggtg actttgccat gctgctccag tcagggctgt cctttcggcg gctgctgctg    7140
ctgagcctcg tgtctggagc cctgggattg ggggtgcag tcctgggggt ggggctcagc    7200
ctgggccctg tcccctcac tccctgggtg tttggggtca ctgctggggt cttcctctat    7260
gtggcccttg tggacatggt gagagatgtc gggtagagca gagaaatcaa gggcagtggg    7320
gaggcgggag tggagaggga ggtagcagtc cctccgcctc taccattagc tcctggaagg    7380
gcgtcagacc ataggcccgc aaaagtctga gaaacaaggg actaaggtgt ttgggtgggg    7440
gctgctgatg ctttctgaca ccattcctct ggagttgaga ggtcagggc aaggccagaa    7500 tcctgacatc ctcttttct ttcagctacc agccctgctt cgtcctccgg agccctgcc    7560 tacgccccat gtgctcctgc aggggctggg gctgctgctg ggggcgcc tcatgcttgc    7620 cataaccctg ctggaggagc ggctactgcc cgtgaccact gagggctgat ggggccagtg    7680
gaaaggggtc gggttgccct tccttccccc caaccacagg aatggaggcg gacacaggg    7740 ccagtaggag caataggatt ttaataaaca gaacccatcc caaa                      7784
```

<210> SEQ ID NO 6
<211> LENGTH: 7784
<212> TYPE: DNA
<213> ORGANISM: homo sapien

<400> SEQUENCE: 6

```
agctggaacc aagaaggttg tgtcccctt cctctgggtg tccttgtctc ctgctatcag     60
gtaatgccaa cctcaacccc ctggaccagt caccccgatc agactttgct tgcctgattt    120
taggccaggt cagacatcag aggagagccc agatccttgt ttcctctccc cccgcagggc    180 ttccccttc ttggtcatcg atccctagag ctctggctct ttctcttctt ggggtgagaa    240
actgctaaga acagtttatt tcccatgcat gcatctgggc ttgccactga tctgccttt    300 ccccctcct ccccaggtta gggacacctg gtccaacct tccaaggaa tatgggatg      360 ggggttggag atgaagttta gtgctagact gtaaggtagg tggggtggaa gtacatgagg    420
gaaagggcta aaatggtact aatggtgtta aggataggt gaattattta agaggaaaaa     480
gactaggccc aggttctcct tagccatgtg gctttcccag gcagagggt gcccctccc      540 tacccagggg cccagcagag actgactttt gatccctacc ccagagacca gtgaaccatt    600
aactcctctc ttatgtgagc cttcacacac tggcccacc cctgacccg ccccaaggca    660 ggtgggctag gaggggtgc atgtccatct cagccttcta tgtgacgtgg cctccgatcc    720
```

| | |
|---|---|
| acctggacac ctggaggcta agcctggatt cccccttccc tgactcagga actgcttaac | 780 |
| gtctacagca aggcctaata ggggacctga ggtgacagct cttatgttgc cagtaggggt | 840 |
| gaggccctgg ggattgaggg gggataaaga ggtggggcaa agttgagggg tggggtttag | 900 |
| gggacaagga atggacggtc agctctggat gaagtatgag gagagctctg actcagggag | 960 |
| gtgctccagg aaccagcaaa caagaggctg ctcccgcagg aggcagtgtg aagggagaaa | 1020 |
| gaaggctgca gtaggggctg ctgctggact cggtggggag caggtgcaag gagctctggc | 1080 |
| tcccccatgg acctgagctg gagagcagag cgcagctcca gcccattcct cattcttcca | 1140 |
| gggcacagtc ctcaggatgt ttcggggaga ataggagcca gaacctgagc ccctaagcta | 1200 |
| ttcccctcac caatgatggg gtccccagtg agtcatctgc tggccggctt ctgtgtgtgg | 1260 |
| gtcgtcttgg gctgggtagg gggctcagtc cccaacctgg gccctgctga gcaggagcag | 1320 |
| aaccattacc tggcccagct gtttggcctg tacggcgaga atgggacgct gactgcaggg | 1380 |
| ggcttggcgc ggcttctcca cagcctgggg ctaggccgag ttcaggggct tcgcctggga | 1440 |
| cagcatgggc ctctgactgg acgggctgca tccccagctg cagacaattc cacacacagg | 1500 |
| tactgacccc ttcctccact ccacagggcc acatctccca ggtcctctca gtgcttgccc | 1560 |
| ccagttgcct cgttctggct tcctcacgag atccctggag ttacaaattc ttcagaaccg | 1620 |
| agctccttgg tatctcttca aaacctctca tgcttctatt gccttctctc tcttttcttg | 1680 |
| agactggggg tctcgctttg tcacccaggc taaagtgcag tgacacattc acggctcact | 1740 |
| gcaacctctg cttcccaggc tgaagccatc ctcccacctc agcctcctga gcagctggga | 1800 |
| ccataggcac acaccaccac agccggctaa ttttaaaaat ttttacaga gacaagggtt | 1860 |
| tcgctgtgtt gcccaggctg gtctcaaact cctgggctca gctcagcgat ctgcctgcct | 1920 |
| cagcttccca aagtgctggg actacagatg tgaactacca ccctagccct ccgttgcctt | 1980 |
| ctaattctct cctcctccaa atctctaagc ccttaaattt cttgctctta gtatcactgt | 2040 |
| tcagtgtctc tgggctgatt tggctccaaa ttcgtagact tcttttttct tttcttttct | 2100 |
| tttttttttt ttttttttt tgagacagag tctcgctctg tcgcccaggc tggagtgcag | 2160 |
| tggtgtgatc ttggctcact gtaacctctg cctcccggt tcaagcgatt ctcctgcctc | 2220 |
| ggcctcctga gtagctggga ttacaggcac acaccaccac gccgggctaa tttttgcaat | 2280 |
| tttagtagag acgggttttc accatttggg tcaggctggt ctcgaacttc caacctcagg | 2340 |
| tgatccaccc acctcagcct cccaaagtgc tgggattaca ggcgtgagcc accgtgccca | 2400 |
| gccattcgta gcccttttgg ttgtcgtcct tttttttctg tcccccccag tggcagaaaa | 2460 |
| tggacaactc acagatcttc ctaagaatga cattccatgg tttctgggtc ccaggatctc | 2520 |
| cagtcagtgg ctagtccccc cattcccct aaaatccctg ggagcctctc aaagcgggtt | 2580 |
| gatagagaac acaagggagg ctgacttgct gtctcatcca ttccaggcca cagaaccctg | 2640 |
| agctgagtgt ggatgtctgg gcagggatgc ctctgggtcc ctcagggtgg ggtgacctgg | 2700 |
| aagagtcaaa ggcccctcac ctaccccgtg ggccagcccc ctcgggcctg gacctccttc | 2760 |
| acaggcttct gttgctggac cactcattgg ctgaccacct gaatgaggat gtgagtctga | 2820 |
| cggtctctag agggaagga gccatgggat tagatggcct gaaatgttta aataatcagt | 2880 |
| agttttttgt tttgttttgt tttaaatcc caacgtggac caagcgtggt ggctcacgcc | 2940 |
| tgtaatccca cactttggg aggccgaggt gggtggatca cctgaggtca ggagttcgag | 3000 |
| accagcctgg ccaacatggt gaaacccat ctctactaaa aaatacaaaa attagccggg | 3060 |
| tgtggtaaca ggtgtgtgta atcctagcta ctcaggaggc tgaggtgaga aaattgcttg | 3120 |

```
aacttgggag gcagaggttg cagtgagcca agatggcacc atttgcactc cagcctgggc    3180
aacaagaggg agactctgtc tcaaaaaaaa aaaaaaaaa aaaaaaaaaa aaaaaaaaat    3240
agctgggcgt ggtggcacat gcctataatc ccagttactc ggaaggctga ggcaggaaaa    3300
tcacttgaac ccaggaggcg gagattgcag tcagccgaga ttgcaccact gcactccagc    3360
ctgggtaaca cagcgagact ctgtctcaaa aatgaaaata aaaaaataa aaaaataaaa    3420 aaaaaatatc tcactgtggt cttaggggat gttatttcaa tagtgaacta tgttccctct    3480
gggatcagag caggtgagcc catatccaga gctccaagac tcagtttagg ggaatagatg    3540
gcaaagcaga gaatctagag aagcagccca gggtaggatc tggatggtca cctggagagg    3600
agacctgcag ggaatggatg gctgtcttca tccagaaaga cagagaatat attccactta    3660
caccagaggg cagacaaagc tgcctaaccc tgatggaggt ccagtgagtg cccattgcag    3720
gaagcattca agctgaggct ggatgaacat cgacagggct gttgagaggg agattagatg    3780
gcatttcagg gtcttttccc ttttaagatt ctggcatgga gagctctagt tttccaacca    3840
gcttcattta tcaaatcaac aaaatgattg aaatgatcag agtttgcagg gaagatgatg    3900
acaatgctca ctagcaccca gtttgcatca aattgaatac ctgcattgga ctgaatattc    3960
actaataata cacattgatt ataagtaccc ttggccctag tccccaaggt acctgccagt    4020
aggagcaaag gggaccctgg gagagaccca ggagtctatg caatgggaagg acaggtgtta    4080 aatatatata tatatatttt tttgaggtag agtctgactc tgtcacccag gctggagtgc    4140
aatggcgtga tcttggctca ctgcaacctc cacctcctgg gttaaagcaa ttctcctgcc    4200
tcagcctccc gagtagctgg gattataggt gttcactact atccccagct aattttttt    4260 tttttttttt gagatggagt ctcactctgt cgcccaggct ggagtgcact ggtgcaatct    4320
cggctcactg caacctctgc ctcctgggtt caagcgattc tcctgtctca gcctcctgag    4380
tagctgggat tacaggtgca cgccaccatg cccagctaat ttttttgtatt ttagtagaga    4440 cagggtttca ccatgttgcc caggctggtc tcgaactcct gagctcaggc aatctaccca    4500
cctcagcctc ccaaagtgct gggattacag gcgtgagcca ccgcacccgg ctcatcccca    4560
gctaattttt gtatttttag tagagacagg gtttcactat gttggccagg ttggtctcaa    4620
actcctgacc tcagatgata cacccgcctg ggcctctcaa gggctgggat tataggtgtg    4680
agccactaca cctggccagg tgttaaagat ctgagtcata gttcctggtg attctccaat    4740
gtatgaccct caattctcca gtgtctgaac ggctcccagc tgctggtcaa ttttggcttg    4800
agccccgctg ctcctctgac ccctcgtcag tttgctctgc tgtgcccagc cctgctttat    4860
cagatcgaca gccgcgtctg catcggcgct ccggcccctg cacccccagg ggatctacta    4920
tctggtcagc aagtaggagt gggtggggga caccctgaat cctggaagtg gggcccatgc    4980 caaaaggag gctcactggg gtcctgcctc tccttgtagt gttctctctg ctccaccta    5040 cgtgtgggac cctcctcttg ccctgaccta acttcagccc ctgattctcc ccagccctgc    5100
ttcagagtgc cctggcagtc ctgttgctca gcctcccttc tcccctatcc ctgctgctgc    5160
tgcggctcct gggacctcgt ctactacggc ccttgctggg cttcctgggg gcctggcgg    5220 tgggcactct ttgtggggat gcactgctac atctgctacc gcatgtatgt gaagcccctt    5280
ccttgtaccc ctggcctcca tggatctaag gtgtccccag ccataggaca tcccctccgc    5340
ctttccatca gctcccatat cctactccca gatcctggct tcagcccaca gctgccttct    5400
agtagagcat atgagcgaag gcttgccaca atccatgcaa ggggatgttg ttgggtatag    5460
```

```
gggcttccag agtctgccct gaccttctct ctgtcaggca caagaagggc ggcacgcagg    5520
acctggcgga ctaccagaga aggacctggg cccggggctg tcagtgctcg gaggcctctt    5580
cctgctcttt gtgctggaga acatgctggg gcttttgcgg caccgagggc tcaggccagt    5640
gagtgatacc cttttctcct ccttctgctg agaccagagt cccagtcaag aactgggcca    5700
ggccgggcgc ggtggctcac gcctgtaatc ccagcacttt gggagcccaa ggcgggcaga    5760
tcacaaggtt aggagttcga gtccagcctg accaacatgg tgaaaccctg tctctactaa    5820
aaatacaaaa attagctggg cgtggtggtg cgtgtctgta atcccagcta ctcaggaggc    5880
tgaggcagga gaatcgcttg acttgggagg tggaggttgc agcgagctaa gatggcacca    5940
ctgcactcca gcccaggtga cagagcgaga ctccatctca aaacaacaa caacaacaac    6000
aaaactgggc caaaaagcca agagatgagg agcagtgtgt gctcctggat ctctgacatt    6060
tgcctggtgt gcaggaccta tcggctaaca gggagtgggt aggggctcct taagcacaga    6120
cccaggactt ctggccaaat ggcatcctat tctgagctca agtcaacaag aaacagaggg    6180
gaggtgccaa cttgggaaga aggtagaggc caaagaacat cccaggtgcc agaggtggaa    6240
ccaggtgttc atcttcccag cttgtggcct ggcttcccct tagtccctgg ctctgctgcc    6300
tcctccacca ggagggatgc cctcctattt cagagatgct gcaggcgaaa acgaaggaat    6360
ctcgaaacac gcaacttgga tccggagaat ggcagtggga tggcccttca gcccctacag    6420
gcagctccag gtgactagag gagaaaattt gaagagtagg ttccaagctc acagtcctta    6480
cttgcagcca ccaacactgt cctgtgcttc ttcccgcaga gccaggggct cagggccaga    6540
gggagaagaa cagccagcac ccaccagctc tggcccctcc tgggcaccaa ggccacagtc    6600
atgggcacca gggtggcact gatatcacgt ggatggtcct cctgggagat ggtctacaca    6660
acctcactga tgggctggcc ataggtgtga ggggtgggaa cggagggaag caggtccgag    6720
gggaggccag ggctcctagt tatcagctgg ggctaggaga gggccgtcag gaagatgggg    6780
agaggacggg aggaccacgg aacacaggaa cctgcttctg aggagacttt tcttctggac    6840
tgacaacttc cgaccctgct ggccccaggt gctgccttct ctgatggctt ctccagcgcc    6900
ctcagtacca ccttagcggt cttctgccat gagctgcccc acgaactggg taggaatggc    6960
aggagcaggg tggggtggac tccagaaagg agatagctcc aaggggtaga gcttggaggc    7020
tggtgggtgg catggatgag gggcacccca gcttactccc tcccatcctg tcctctgtct    7080
ccaataggtg actttgccat gctgctccag tcagggctgt cctttcggcg gctgctgctg    7140
ctgagcctcg tgtctggagc cctgggattg ggggtgcag tcctgggggt ggggctcagc    7200
ctgggccctg tcccctcac tccctgggtg tttggggtca ctgctggggt cttcctctat    7260
gtggcccttg tggacatggt gagagatgtc gggtagagca gagaaatcaa ggcagtgggg    7320
gaggcgggag tggagaggga ggtagcagtc cctccgcctc taccattagc tcctggaagg    7380
gcgtcagacc ataggcccgc aaaagtctga gaaacaaggg actaaggtgt ttgggtgggg    7440
gctgctgatg ctttctgaca ccattcctct ggagttgaga ggtcaggggc aaggccagaa    7500
tcctgacatc ctcttttttct ttcagctacc agccctgctt cgtcctccgg agcccctgcc    7560
tacgccccat gtgctcctgc aggggctggg gctgctgctg ggggcggcc tcatgcttgc    7620
cataaccctg ctggaggagc ggctactgcc cgtgaccact gagggctgat ggggccagtg    7680
gaaaggggtc gggttgccct tccttccccc caaccacagg aatggaggcg gacacaggg    7740
ccagtaggag caataggatt ttaataaaca gaacccatcc caaa                    7784
```

```
<210> SEQ ID NO 7
<211> LENGTH: 7784
<212> TYPE: DNA
<213> ORGANISM: homo sapien

<400> SEQUENCE: 7
agctggaacc aagaaggttg tgtccccctt cctctgggtg tccttgtctc ctgctatcag      60
gtaatgccaa cctcaacccc ctggaccagt caccccgatc agactttgct tgcctgattt     120
taggccaggt cagacatcag aggagagccc agatccttgt ttcctctccc cccgcagggc     180 ttccccttc ttggtcatcg atccctagag ctctggctct ttctcttctt ggggtgagaa      240
actgctaaga acagtttatt tcccatgcat gcatctgggc ttgccactga tctgccttt      300 ccccctcct ccccaggtta gggacacctg gtccaacct tcccaaggaa tatggggatg       360 gggttggag atgaagttta gtgctagact gtaaggtagg tggggtggaa gtacatgagg      420
gaaagggcta aaatggtact aatggtgtta aggatagggt gaattattta agaggaaaaa     480
gactaggccc aggttctcct tagccatgtg gctttcccag ggcagagggt ggccctccc     540 tacccagggg cccagcagag actgactttt gatccctacc ccagagacca gtgaaccatt    600
aactcctctc ttatgtgagc cttcacacac tggccccacc cctgacccg ccccaaggca     660 ggtgggctag gaggggtgc atgtccatct cagccttcta tgtgacgtgg cctccgatcc     720
acctggacac ctggaggcta agcctggatt cccccttccc tgactcagga actgcttaac    780
gtctacagca aggcctaata ggggacctga ggtgacagct cttatgttgc cagtaggggt    840
gaggccctgg ggattgaggg gggataaaga ggtggggcaa agttgagggg tggggtttag    900
gggacaagga atggacggtc agctctggat gaagtatgag gagagctctg actcagggag    960
gtgctccagg aaccagcaaa caagaggctg ctcccgcagg aggcagtgtg aagggagaaa   1020
gaaggctgca gtagggctg ctgctggact cggtggggag caggtgcaag gagctctggc    1080
tcccccatgg acctgagctg gagagcagag cgcagctcca gcccattcct cattcttcca    1140
gggcacagtc ctcaggatgt ttcggggaga ataggagcca gaacctgagc ccctaagcta   1200
ttcccctcac caatgatggg gtccccagtg agtcatctgc tggccggctt ctgtgtgtgg    1260
gtcgtcttgg gctgggtagg gggctcagtc cccaacctgg gccctgctga gcaggagcag   1320
aaccattacc tggcccagct gttggcctg tacggcgaga atgggacgct gactgcaggg    1380
ggcttggcgc ggcttctcca cagcctgggg ctaggccgag ttcaggggct cgcctggga    1440 cagcatgggc ctctgactgg acgggctgca tccccagctg cagacaattc cacacacagg   1500
tactgacccc ttcctccact ccacagggcc acatctccca ggtcctctca gtgcttgccc   1560
ccagttgcct cgttctggct tcctcacgag atccctggag ttacaaattc ttcagaaccg   1620
agctccttgg tatctcttca aaacctctca tgcttctatt gccttctctc tcttttcttg   1680
agactggggg tctcgctttg tcacccaggc taaagtgcag tgacacattc acggctcact   1740
gcaacctctg cttcccaggc tgaagccatc ctcccacctc agcctcctga gcagctggga   1800
ccataggcac acaccaccac agccggctaa ttttaaaaat tttttacaga gacaagggtt   1860
tcgctgtgtt gcccaggctg gtctcaaact cctgggctca gctcagcgat ctgcctgcct   1920
cagcttccca aagtgctggg actacagatg tgaactacca ccctagccct ccgttgcctt   1980
ctaattctct cctcctccaa atctctaagc ccttaaattt cttgctctta gtatcactgt   2040
tcagtgtctc tgggctgatt tggctccaaa ttcgtagact tctttttct tttcttttct    2100 tttttttttt tttttttttt tgagacagag tctcgctctg tcgcccaggc tggagtgcag   2160
```

```
tggtgtgatc ttggctcact gtaacctctg cctccccggt tcaagcgatt ctcctgcctc    2220
ggcctcctga gtagctggga ttacaggcac acaccaccac gccgggctaa tttttgcaat    2280
tttagtagag acggggtttc accattttgg tcaggctggt ctcgaacttc aacctcagg    2340 tgatccaccc acctcagcct cccaaagtgc tgggattaca ggcgtgagcc accgtgccca    2400
gccattcgta gcccttttgg ttgtcgtcct ttttttttctg tcccccccag tggcagaaaa    2460
tggacaactc acagatcttc ctaagaatga cattccatgg tttctgggtc caggatctc    2520 cagtcagtgg ctagtccccc cattcccccct aaaatccctg ggagcctctc aaagcgggtt    2580
gatagagaac acaagggagg ctgacttgct gtctcatcca ttccaggcca cagaaccctg    2640
agctgagtgt ggatgtctgg gcagggatgc ctctgggtcc ctcagggtgg ggtgacctgg    2700
aagagtcaaa ggcccctcac ctaccccgtg ggccagcccc ctcgggcctg gacctccttc    2760
acaggcttct gttgctggac cactcattgg ctgaccacct gaatgaggat gtgagtctga    2820
cggtctctag aggggaagga gccatgggat tagatggcct gaaatgttta ataatcagt    2880 agttttttgt tttgttttgt ttttaaatcc caacgtggac caagcgtggt ggctcacgcc    2940
tgtaatccca cactttggg aggccgaggt gggtggatca cctgaggtca ggagttcgag    3000
accagcctgg ccaacatggt gaaacccat ctctactaaa aaatacaaaa attagccggg    3060
tgtggtaaca ggtgtgtgta atcctagcta ctcaggaggc tgaggtgaga aaattgcttg    3120
aacttgggag gcagaggttg cagtgagcca agatggcacc atttgcactc cagcctgggc    3180
aacaagaggg agactctgtc tcaaaaaaaa aaaaaaaaa aaaaaaaaa aaaaaaaat    3240 agctgggcgt ggtggcacat gcctataatc ccagttactc ggaaggctga ggcaggaaaa    3300
tcacttgaac ccaggaggcg gagattgcag tcagccgaga ttgcaccact gcactccagc    3360
ctgggtaaca cagcgagact ctgtctcaaa aatgaaaata aaaaaaataa aaaaataaaa    3420
aaaaaatatc tcactgtggt cttaggggat gttatttcaa tagtgaacta tgttccctct    3480
gggatcagag caggtgagcc catatccaga gctccaagac tcagtttagg gaatagatg    3540 gcaaagcaga gaatctagag aagcagccca gggtaggatc tggatggtca cctggagagg    3600
agacctgcag ggaatggatg gctgtcttca tccagaaaga cagagaatat attccactta    3660
caccagaggg cagacaaagc tgcctaaccc tgatggaggt ccagtgagtg cccattgcag    3720
gaagcattca gctgaggct ggatgaacat cgacagggct gttgagaggg agattagatg    3780
gcatttcagg gtcttttccc ttttaagatt ctggcatgga gagctctagt tttccaacca    3840
gcttcattta tcaaatcaac aaaatgattg aaatgatcag agtttgcagg gaagatgatg    3900
acaatgctca ctagcaccca gtttgcatca aattgaatac ctgcattgga ctgaatattc    3960
actaataata cacattgatt ataagtaccc ttggccctag tccccaaggt acctgccagt    4020
aggagcaaag gggaccctgg gagagaccca ggagtctatg caatggaagg acaggtgtta    4080
aatatatata tatatatttt tttgaggtag agtctgactc tgtcacccag gctggagtgc    4140
aatggcgtga tcttggctca ctgcaacctc cacctcctgg gttaaagcaa ttctcctgcc    4200
tcagcctccc gagtagctgg gattataggt gttcactact atccccagct aattttttt    4260 tttttttttt gagatggagt ctcactctgt cgcccaggct ggagtgcact ggtgcaatct    4320
cggctcactg caacctctgc ctcctgggtt caagcgattc tcctgtctca gcctcctgag    4380
tagctgggat cacaggtgca cgccaccatg cccagctaat ttttttgtatt ttagtagaga    4440 cagggtttca ccatgttgcc caggctggtc tcgaactcct gagctcaggc aatctaccca    4500
cctcagcctc ccaaagtgct gggattacag gcgtgagcca ccgcacccgg ctcatcccca    4560
```

```
gctaatttttt gtattttttag tagagacagg gtttcactat gttggccagg ttggtctcaa    4620
actcctgacc tcagatgata cacccgcctg ggcctctcaa gggctgggat tataggtgtg    4680
agccactaca cctggccagg tgttaaagat ctgagtcata gttcctggtg attctccaat    4740
gtatgaccct caattctcca gtgtctgaac ggctcccagc tgctggtcaa ttttggcttg    4800
agccccgctg ctcctctgac ccctcgtcag tttgctctgc tgtgcccagc cctgctttat    4860
cagatcgaca gccgcgtctg catcggcgct ccggcccctg cacccccagg ggatctacta    4920
tctggtcagc aagtaggagt gggtggggga caccctgaat cctggaagtg gggcccatgc    4980
caaaaaggag gctcactggg gtcctgcctc tccttgtagt gttctctctg ctccacctta    5040
cgtgtgggac cctcctcttg ccctgaccta acttcagccc ctgattctcc ccagccctgc    5100
ttcagagtgc cctggcagtc ctgttgctca gcctcccttc tccctatcc ctgctgctgc    5160 tgcggctcct gggacctcgt ctactacggc ccttgctggg cttcctgggg gccctggcgg    5220
tgggcactct ttgtggggat gcactgctac atctgctacc gcatgtatgt gaagcccctt    5280
ccttgtaccc ctggcctcca tggatctaag gtgtccccag ccataggaca tcccctccgc    5340
ctttccatca gctcccatat cctactccca gatcctggct tcagcccaca gctgccttct    5400
agtagagcat atgagcgaag gcttgccaca atccatgcaa ggggatgttg ttgggtatag    5460
gggcttccag agtctgccct gaccttctct ctgtcaggca caagaagggc ggcacgcagg    5520
acctggcgga ctaccagaga aggacctggg cccggggctg tcagtgctcg gaggcctctt    5580
cctgctcttt gtgctggaga acatgctggg gcttttgcgg cactgagggc tcaggccagt    5640
gagtgatacc ctttttctcct ccttctgctg agaccagagt cccagtcaag aactgggcca    5700
ggccgggcgc ggtggctcac gcctgtaatc ccagcacttt gggagcccaa ggcgggcaga    5760
tcacaaggtt aggagttcga gtccagcctg accaacatgg tgaaaccctg tctctactaa    5820
aaatacaaaa attagctggg cgtggtggtg cgtgtctgta atcccagcta ctcaggaggc    5880
tgaggcagga gaatcgcttg acttgggagg tggaggttgc agcgagctaa gatggcacca    5940
ctgcactcca gcccaggtga cagagcgaga ctccatctca aaaacaacaa caacaacaac    6000
aaaactgggc caaaaagcca agagatgagg agcagtgtgt gctcctggat ctctgacatt    6060
tgcctggtgt gcaggaccta tcggctaaca gggagtgggt aggggctcct taagcacaga    6120
cccaggactt ctggccaaat ggcatcctat tctgagctca agtcaacaag aaacagaggg    6180
gaggtgccaa cttgggaaga aggtagaggc caaagaacat cccaggtgcc agaggtggaa    6240
ccaggtgttc atcttcccag cttgtggcct ggcttcccct tagtccctgg ctctgctgcc    6300
tcctccacca ggagggatgc cctcctattt cagagatgct gcaggcgaaa acgaaggaat    6360
ctcgaaacac gcaacttgga tccggagaat ggcagtggga tggcccttca gcccctacag    6420
gcagctccag gtgactagag gagaaaattt gaagagtagg ttccaagctc acagtcctta    6480
cttgcagcca ccaacactgt cctgtgcttc ttcccgcaga gccaggggct cagggccaga    6540
gggagaagaa cagccagcac ccaccagctc tggcccctcc tgggcaccaa ggccacagtc    6600
atgggcacca gggtggcact gatatcacgt ggatggtcct cctgggagat ggtctacaca    6660
acctcactga tgggctggcc ataggtgtga ggggtgggaa cggagggaag caggtccgag    6720
gggaggccag ggctcctagt tatcagctgg ggctaggaga gggccgtcag gaagatgggg    6780
agaggacggg aggaccacgg aacacaggaa cctgcttctg aggagacttt tcttctggac    6840
tgacaacttc cgaccctgct ggccccaggt gctgccttct ctgatggctt ctccagcggc    6900
```

| | |
|---|---|
| ctcagtacca ccttagcggt cttctgccat gagctgcccc acgaactggg taggaatggc | 6960 |
| aggagcaggg tggggtggac tccagaaagg agatagctcc aagggtaga gcttggaggc | 7020 |
| tggtgggtgg catggatgag gggcacccca gcttactccc tcccatcctg tcctctgtct | 7080 |
| ccaataggtg actttgccat gctgctccag tcagggctgt cctttcggcg gctgctgctg | 7140 |
| ctgagcctcg tgtctggagc cctgggattg gggggtgcag tcctgggggt ggggctcagc | 7200 |
| ctgggccctg tcccctcac tccctgggtg tttggggtca ctgctgggt cttcctctat | 7260 |
| gtggcccttg tggacatggt gagagatgtc gggtagagca gagaaatcaa gggcagtggg | 7320 |
| gaggcgggag tggagaggga ggtagcagtc cctccgcctc taccattagc tcctggaagg | 7380 |
| gcgtcagacc ataggcccgc aaaagtctga gaaacaaggg actaaggtgt tgggtgggg | 7440 |
| gctgctgatg ctttctgaca ccattcctct ggagttgaga ggtcagggc aaggccagaa | 7500 |
| tcctgacatc ctcttttct ttcagctacc agccctgctt cgtcctccgg agccctgcc | 7560 |
| tacgccccat gtgctcctgc aggggctggg gctgctgctg ggggcggcc tcatgcttgc | 7620 |
| cataaccctg ctggaggagc ggctactgcc cgtgaccact gagggctgat ggggccagtg | 7680 |
| gaaaggggtc gggttgccct tccttcccc caaccacagg aatggaggcg ggacacaggg | 7740 |
| ccagtaggag caataggatt ttaataaaca gaacccatcc caaa | 7784 |

<210> SEQ ID NO 8
<211> LENGTH: 1968
<212> TYPE: DNA
<213> ORGANISM: homo sapien

<400> SEQUENCE: 8

| | |
|---|---|
| agcuggaacc aagaagguug ugcccccuu ccucuggug uccuugucuc cugcuaucag | 60 |
| ggcuucccu ucuuggguca ucgaucccua gagcucuggc ucuuucucuu cuuggggaac | 120 |
| ugcuuaacgu cuacagcaag gccuaauagg ggaccugagg gcacaguccu caggauguuu | 180 |
| cggggagaau aggagccaga accugagccc cuaagcuauu ccccucacca augauggggu | 240 |
| ccccagugag ucaucugcug gccggcuucu gugugugggu cgucuugggc ugggauggg | 300 |
| gcucaguccc caaccugggc ccugcugagc aggagcagaa ccauuaccug gcccagcugu | 360 |
| uuggccugua cggcgagaau gggacgcuga cugcaggggg cuuggcgcgg cuucuccaca | 420 |
| gccuggggcu aggccgaguu caggggcuuc gccuggaca gcaugggccu cugacuggac | 480 |
| gggcugcauc cccagcugca gacaauucca cacacaggcc acagaacccu gagcugagug | 540 |
| uggaugucug ggcagggaug ccucugggcc ccucagggug gggugaccug gaagagucaa | 600 |
| aggccccuca ccuaccccgu gggccagccc ccucgggccu ggaccuccuu cacaggcuuc | 660 |
| uguugcugga ccacucauug gcugaccacc ugaaugagga uugucugaac ggcucccagc | 720 |
| ugcuggucaa uuuggcuug agccccgcug cuccucugac cccucgucag uuugcucugc | 780 |
| ugugcccagc ccugcuuuau cagaucgaca gccgcgucug caucgcgcu ccggcccccug | 840 |
| cacccccagg ggaucuacua ucugcccgc uucagaguac ccuggcaguc cuguugcuca | 900 |
| gccucccuuc uccccuaucc cugcugcugc ugcggcuccu gggaccucgu cuacuacggc | 960 |
| ccuugcugcc cuccggggg gccuggcgg ugggcacucu uuguggggau gcacugcuac | 1020 |
| aucugcuacc gcaugcacaa gaaggcggc acgcaggacc uggcggacua ccagagaagg | 1080 |
| accugggccc ggggcuguca gugcucggag gccucuuccu gcucuuugug cuggagaaca | 1140 |
| ugcuggggcu uuugcggcac cgagggcuca ggccaagaug cugcaggcga aaacgaagga | 1200 |
| aucucgaaac acgcaacuug gauccggaga auggcagugg gauggcccuu cagccccuac | 1260 |

| aggcagcucc agagccaggg gcucagggcc agagggagaa gaacagccag cacccaccag | 1320 |
| cucuggcccc uccugggcac caaggccaca gucaugggca ccaggguggc acugauauca | 1380 |
| cguggauggu ccuccuggga gauggucuac acaaccucac ugaugggcug gccauaggug | 1440 |
| cugccuucuc ugauggcuuc uccagcggcc ucaguaccac cuuagcgguc uucugccaug | 1500 |
| agcugcccca cgaacugggu gacuuugcca ugcugcucca gucagggcug uccuuucggc | 1560 |
| ggcugcugcu gcugagccuc ugucuggag cccugggauu gggggugca guccugggg | 1620 |
| uggggcucag ccugggcccu guccccuca cucccugggu guuggggguc acugcugggg | 1680 |
| ucuuccucua uguggcccuu guggacaugc uaccagcccu gcuucguccu ccggagcccc | 1740 |
| ugccuacgcc ccaugugcuc cugcaggggc uggggcugcu gcuggggggc ggccucaugc | 1800 |
| uugccauaac ccugcuggag gagcggcuac ugcccgugac cacugagggc ugaugggcc | 1860 |
| aguggaaagg ggucgggguug cccuuccuuc ccccccaacca caggaaugga ggcgggacac | 1920 |
| agggccagua ggagcaauag gauuuuaaua aacagaaccc aucccaaa | 1968 |

<210> SEQ ID NO 9
<211> LENGTH: 1968
<212> TYPE: DNA
<213> ORGANISM: homo sapien

<400> SEQUENCE: 9

| agcuggaacc aagaagguug uguccccuu ccucuggguug uccuugcuc cugcuaucag | 60 |
| ggcuuccccu uucuuggguca ucgaucccua gagcucuggc ucuuucucuu cuuggggaac | 120 |
| ugcuuaacgu cuacagcaag gccuaauagg ggaccugagg gcacaguccu caggaauguuu | 180 |
| cggggagaau aggagccaga accugagccc cuaagcuauu ccccucacca augauggggu | 240 |
| ccccagugag ucaucugcug gccggcuucu gugugugggu cgucuuggc ugguaggg | 300 |
| gcucagucccc caaccugggc ccugcugagc aggagcagaa ccauuaccug gcccagcugu | 360 |
| uuggccugua aggcgagaau gggacgcuga cugcagggg cuuggcgcgg cuucuccaca | 420 |
| gccugggggcu aggccgaguu caggggcuuc gccuggggaca gcaugggccu cugacuggac | 480 |
| gggcugcauc cccagcugca gacaauucca cacacaggcc acagaacccu gagcugagug | 540 |
| uggaugucug ggcagggaug ccucuggguuc ccuccagggug gggugaccug gaagagucaa | 600 |
| aggccccuca ccuaccccgu gggccagccc ccugggccu ggaccuccuu cacaggcuuc | 660 |
| uguugcugga ccacucauug gcugaccacc ugaaugagga uugcugaac ggcucccagc | 720 |
| ugcugguca uuuggcuug agccccgcgu cuccucgac cccugucag uuugcucugc | 780 |
| ugugcccagc ccugcuuuau cagaucgaca gccgcgucug caucggcgcu ccggccccug | 840 |
| cacccccagg ggaucuacua ucugcccgc uucagagugc ccuggcaguc cuguugcuca | 900 |
| gccucccuuc uccccuaucc cugcugcugc ugcggcuccu gggaccucgu cuacuacggc | 960 |
| ccuugcuggg cuuccugggg gcccuggcgg ugggcacucu uugugggau gcacugcuac | 1020 |
| aucugcuacc gcaugcacaa gaagggcggc acgcaggacc uggcggacua ccagagaagg | 1080 |
| accugggccc gggggcuguca gugcucggag gccucuuccu gcucuuugug cuggagaaca | 1140 |
| ugcuggggcu uuucgggcac cgagggcuca ggccaagaug cugcaggcga aaacgaagga | 1200 |
| aucucgaaac acgcaacuug gauccggaga auggcagugg gauggcccuu cagcccuac | 1260 |
| aggcagcucc agagccaggg gcucagggcc agagggagaa gaacagccag cacccaccag | 1320 |
| cucuggcccc uccugggcac caaggccaca gucaugggca ccaggguggc acugauauca | 1380 |

| | |
|---|---:|
| cguggauggu ccuccuggga gauggucuac acaaccucac ugaugggcug gccauaggug | 1440 |
| cugccuucuc ugauggcuuc uccagcggcc ucaguaccac cuuagcgguc uucugccaug | 1500 |
| agcugcccca cgaacugggu gacuuugcca ugcugcucca gucagggcug uccuuucggc | 1560 |
| ggcugcugcu gcugagccuc ugucuggag cccugggauu ggggggugca guccugggg | 1620 |
| uggggcucag ccugggcccu guccccucca cucccugggu guuggggguc acugcugggg | 1680 |
| ucuuccucua uguggcccuu guggacaugc uaccagcccu gcuucguccu ccggagcccc | 1740 |
| ugccuacgcc ccaugugcuc cugcagggc uggggcugcu gcuggggggc ggccucaugc | 1800 |
| uugccauaac ccugcuggag gagcggcuac ugcccgugac cacugagggc ugaugggggcc | 1860 |
| aguggaaagg ggucggguug cccuuccuuc cccccaacca caggaaugga ggcgggacac | 1920 |
| agggccagua ggagcaauag gauuuuaaua aacagaaccc aucccaaa | 1968 |

<210> SEQ ID NO 10
<211> LENGTH: 1968
<212> TYPE: DNA
<213> ORGANISM: homo sapien

<400> SEQUENCE: 10

| | |
|---|---:|
| agcuggaacc aagaagguug uguccccccuu ccucugggug uccuugcucuc cugcuaucag | 60 |
| ggcuuccccu uucuuggguca ucgaucccua gagcucuggc ucuuucucuu cuuggggaac | 120 |
| ugcuuaacgu cuacagcaag gccuaauagg ggaccgagg gcacaguccu caggauguuu | 180 |
| cggggagaau aggagccaga accugagccc cuaagcuauu ccccucacca augauggggu | 240 |
| ccccagugag ucaucugcug gccggcuucu gugugugggu cgucuggggc ugggguaggg | 300 |
| gcucagucc caaccugggc ccugcugagc aggagcagaa ccauuaccug gcccagcugu | 360 |
| uuggccugua gggcgagaau gggacgcuga cugcaggggg cuuggcgcgg cuucuccaca | 420 |
| gccuggggcu aggccgaguu caggggcuuc gccugggaca gcaugggccu cugacuggac | 480 |
| gggcugcauc cccagcugca gacaauucca cacacaggcc acagaacccu gagcugagug | 540 |
| uggaugucug ggcagggaug ccucuggguc ccucagggug gggugaccug gaagagucaa | 600 |
| aggccccuca ccuaccccgu gggccagccc ccugggccu ggaccuccuu cacaggcuuc | 660 |
| uguugcugga ccacucauug gcugaccacc ugaaugagga uugucgaac ggcucccagc | 720 |
| ugcuggucaa uuuggcuug agcccgcug cuccucugac cccucgucag uuugcucugc | 780 |
| ugugcccagc ccugcuuuau cagaucgaca gccgcgucug caucggcgcu ccggccccug | 840 |
| cacccccagg ggaucuacua ucugcccugc uucagagugc ccggcaguc cuguugcuca | 900 |
| gccucccuuc uccccuaucc cugcugcugc ugcggcuccu gggaccucgu cuacuacggc | 960 |
| ccuugcuggg cuuccggggg gcccuggcgg ugggcacucu uugugggggau gcacugcuac | 1020 |
| aucugcuacc gcaugcacaa gaagggcggc acgcaggacc uggcggacua ccagagaagg | 1080 |
| accugggccc ggggcuguca gugcucggag gccucuccu gcucuuugug cuggagaaca | 1140 |
| ugcuggggcu uuugcggcac cgagggcuca ggccaagaug cugcaggcga aaacgaagga | 1200 |
| aucucgaaac acgcaacuug gauccggaga auggcagugg gauggcccuu cagccccuac | 1260 |
| aggcagcucc agagccaggg gcucaggcc agagggagaa gaacagccag caccaccag | 1320 |
| cucuggcccc uccugggcac caaggccaca gucaugggca ccaggguggc acugauauca | 1380 |
| cguggauggu ccuccuggga gauggucuac acaaccucac ugaugggcug gccauagggug | 1440 |
| cugccuucuc ugauggcuuc uccagcggcc ucaguaccac cuuagcgguc uucugccaug | 1500 |
| agcugcccca cgaacugggu gacuuugcca ugcugcucca gucagggcug uccuuucggc | 1560 |

```
ggcugcugcu gcugagccuc gugucuggag cccugggauu gggggugca guccuggggg    1620 ugggcucag ccugggcccu gucccccuca cucccugggu guuuggguc acugcugggg     1680 ucuuccucua guggcccuu guggacaugc uaccagcccu gcuucguccu ccggagcccc    1740
ugccuacgcc ccaugugcuc cugcagggc uggcugcu gcggggggc ggccucaugc       1800 uugccauaac ccugcuggag gagcggcuac ugcccgugac cacugagggc ugauggggcc   1860 agugaaagg ggucgggguug cccuuccuuc ccccaacca caggaaugga ggcgggacac    1920
agggccagua ggagcaauag gauuuuaaua aacagaaccc aucccaaa                1968
```

<210> SEQ ID NO 11
<211> LENGTH: 1968
<212> TYPE: DNA
<213> ORGANISM: homo sapien

<400> SEQUENCE: 11

```
agcuggaacc aagaagguug ugccccccuu ccucuggug uccuugucuc cugcuaucag     60
ggcuuccccu uucuuggucaa ucgaucccua gagcucuggc ucuuucucuu cuuggggaac    120
ugcuuaacgu cuacagcaag gccuaauagg ggaccgagg gcacaguccu caggauguuu      180
cggggagaau aggagccaga accugagccc cuaagcuauu ccccucacca augaugggu      240 ccccagugag ucaucugcug gccggcuucu gugugugggu cgucuuggc ugggguaggg      300 gcucaguccc caaccugggc ccugcugagc aggagcagaa ccauuaccug gcccagcugu     360
uuggccugua cggcgagaau gggacgcuga cugcagggg cuggcgcggg cuucuccaca     420
gccuggggcu aggccgaguu cagggggcuuc gccugggaca gcaugggccu cugacuggac    480
gggcugcauc cccagcugca gacaauucca cacacaggcc acagaacccu gagcugagug     540
uggaugucug ggcagggaug ccucugggguc ccucaggguc gggugaccug gaagagucaa    600
aggcccucag ccuaccccguc gggccagccc ccucgggccu ggaccuccuu cacaggcuuc    660 guugcugga ccaucauug gcugaccacc ugaaugagga uugucugaac ggcucccagc       720
ugcuggucaa uuuuggcuug agccccgcug cuccucugac cccucgcag uuugcucugc     780 ugugcccagc ccugcuuuau cagaucgaca gccgcgucug caucggcgcu ccggcccug     840 cacccccagg ggaucuacua ucugcccugc uucagagugc ccuggcaguc cuguugcuca    900 gccuccccuuc uccccuaucc cugcugcugc ugcggcuccu gggaccucgu cuacuacggc   960
ccuugcuggg cuuccugggg gcccuggcgg ugggcacucu uguggggau gcacugcuac     1020 aucugcuacc gcaugcacaa gaaggggcggc acgcaggacc uggcggacua ccagagaagg   1080 accuggggccc ggggcuguca gugcucggag gccucuuccu gcucuuugug cuggagaaca    1140 cgcugggcu uuugcggcac cgagggcuca ggccaagaug cugcaggcga aacgaagga     1200 aucucgaaac acgcaacuug gauccggaga augcagugg gauggcccuu cagccccuac     1260
aggcagcucc agagccaggg gcucagggcc agagggagaa gaacagccag cacccaccag    1320
cucuggcccc uccugggcac caaggccaca gucaugggca ccaggguggc acugauauca    1380
cguggauggu ccuccuggga gauggucuac acaaccucac ugaugggcug gccauaggug    1440
cugccuucuc ugauggcuuc uccagcggcc ucaguaccac cuuagcgguc uucugccaug    1500
agcugcccca cgaacugggu gacuuugcca ugcugcucca gucagggcug uccuuucggc    1560
ggcugcugcu gcugagccuc gugucuggag cccugggauu gggggguca guccuggggg    1620 ugggcucag ccugggcccu gucccccuca cucccugggu guuggguc acugcugggg       1680
```

| | |
|---|---|
| ucuuccucua uguggcccuu guggacaugc uaccagcccu gcuucguccu ccggagcccc | 1740 |
| ugccuacgcc ccaugugcuc cugcaggggc uggggcugcu gcgggggggc ggccucaugc | 1800 |
| uugccauaac ccugcuggag gagcggcuac ugcccgugac cacugagggc ugauggggcc | 1860 |
| aguggaaagg ggucggguug cccuuccuuc cccccaacca caggaaugga ggcgggacac | 1920 |
| agggccaguag ggagcaauag gauuuuaaua aacagaaccc aucccaaa | 1968 |

```
<210> SEQ ID NO 12
<211> LENGTH: 1968
<212> TYPE: DNA
<213> ORGANISM: homo sapien

<400> SEQUENCE: 12
```

| | |
|---|---|
| agcuggaacc aagaagguug uguccccuu ccucugggug uccuugucuc cugcuaucag | 60 |
| ggcuuccccu ucuuggguca ucgaucccua gagcucuggc ucuuucucuu cuuggggaac | 120 |
| ugcuuaacgu cuacagcaag gccuaauagg ggaccugagg gcacaguccu caggauguuu | 180 |
| cggggagaau aggagccaga accugagccc cuaagcuauu ccccucacca augauggggu | 240 |
| ccccagugag ucaucugcug gccggcuucu gugugugggu cgucuugggc ugggauggg | 300 |
| gcucagucccc caaccugggc ccugcugagc aggagcagaa ccauuaccug gcccagcugu | 360 |
| uuggccugua cggcgagaau gggacgcuga cugcaggggg cuuggcgcgg cuucuccaca | 420 |
| gccuggggcu aggccgaguu cagggggcuuc gccugggaca gcaugggccu cugacuggac | 480 |
| gggcugcauc cccagcugca gacaauucca cacacaggcc acagaacccu gagcugagug | 540 |
| uggaugucug ggcagggaug ccucugggguc ccucagggug gggugaccug gaagagucaa | 600 |
| aggcccccuca ccuaccccgu gggccagccc ccucgggccu ggaccuccuu cacaggcuuc | 660 |
| uguugcugga ccacucauug gcugaccacc ugaaugagga uugucugaac ggcuccagc | 720 |
| ugcuggucaa uuuuggcuug agcccgcug cuccucugac cccucgucag uuugcucugc | 780 |
| ugugcccagc ccugcuuuau cagaucgaca gccgcgucug caucggcgcu ccggcccug | 840 |
| caccccccagg ggaucuacua ucugcccugc uucagagugc ccuggcaguc cuguugcuca | 900 |
| gccucccuuc uccccuaucc cugcugcugc ugcggcuccu gggaccucgu cuacuacggc | 960 |
| ccuugcuggg cuuccugggg gccuggcgg ugggcacucu uguggggau gcacugcuac | 1020 |
| aucugcuacc gcaugcacaa gaagggcggc acgcaggacc uggcggacua ccagagaagg | 1080 |
| accugggccc ggggcugucca gugcucggag gccucuuccu gcucuuugug cuggagaaca | 1140 |
| ugcuggggcu uuucgggcac cgaggggcuca ggccaagaug cugcaggcga aaaugaagga | 1200 |
| aucucgaaac acgcaacuug gauccggaga auggcagugg gauggcccuu cagcccuac | 1260 |
| aggcagcucc agagccaggg gcucagggcc agagggagaa gaacagccag cacccaccag | 1320 |
| cucuggcccc uccugggcac caaggccaca gucauggcca caggguggc acugauauca | 1380 |
| cguggaugu cuccugggga gauggucuac acaaccucac ugaugggcug gccauaggug | 1440 |
| cugccuucuc ugauggcuuc uccagcggcc ucaguaccac cuuagcgguc uucugccaug | 1500 |
| agcugcccca cgaacugggu gacuuugcca ugcugcucca gucagggcug uccuucggc | 1560 |
| ggcugcugcu gcuagccuc gugucuggag cccuggauu gggggugca guccggggg | 1620 |
| uggggcucag ccugggcccu gucccccuca cucccugggu guuggggguc acugcugggg | 1680 |
| ucuuccucua guggcccuu guggacaugc uaccagcccu gcuucguccu ccggagcccc | 1740 |
| ugccuacgcc ccaugugcuc cugcaggggc uggggcugcu gcgggggggc ggccucaugc | 1800 |
| uugccauaac ccugcuggag gagcggcuac ugcccgugac cacugagggc ugauggggcc | 1860 |

| | |
|---|---|
| aguggaaagg ggucggguug cccuuccuuc cccccaacca caggaaugga ggcgggacac | 1920 |
| agggccagua ggagcaauag gauuuuaaua aacagaaccc aucccaaa | 1968 |

<210> SEQ ID NO 13
<211> LENGTH: 1968
<212> TYPE: DNA
<213> ORGANISM: homo sapien

<400> SEQUENCE: 13

| | |
|---|---|
| agcuggaacc aagaagguug uguccccuu ccucuggug uccuugcuc cugcuaucag | 60 |
| ggcuucccu ucuuggguca ucgaucccua gagcucuggc ucuuucucuu cuuggggaac | 120 |
| ugcuuaacgu cuacagcaag gccuaauagg ggaccugagg gcacaguccu caggauguuu | 180 |
| cggggagaau aggagccaga accugagccc cuaagcuauu ccccucacca augaugggu | 240 |
| ccccagugag ucaucugcug gccggcuucu gugugugggu cgucuggggc uggguagggg | 300 |
| gcucaguccc caaccuggc ccugcugagc aggagcagaa ccauuaccug cccagcugu | 360 |
| uuggccugua cggcgagaau gggacgcuga cugcagggg cuuggcgcgg cuucuccaca | 420 |
| gccuggggcu aggccgaguu caggggcuuc gccuggaca gcaugggccu cugacuggac | 480 |
| gggcugcauc cccagcugca gacaauucca cacacaggcc acagaacccu gagcugagug | 540 |
| uggaugucug gcagggaug ccucggggc ccucagggug gggugaccug gaagagucaa | 600 |
| aggcccucca ccuaccccgu gggccagccc ccucgggccu ggaccuccuu cacaggcuuc | 660 |
| uguugcugga ccacucauug gcugaccacc ugaaugagga uugucugaac ggcucccagc | 720 |
| ugcuggucaa uuuuggcuug agcccgcugc cuccucugac cccucgucag uuugcucugc | 780 |
| ugugcccagc ccugcuuuau cagaucgaca gccgcgucug caucggcgcu ccggcccug | 840 |
| cacccccagg ggaucuacua ucugcccugc uucagagugc ccuggcaguc cuguugcuca | 900 |
| gccucccuuc uccccuaucc cugcugcugc ucggguccu ggaccucgu cuacuacggc | 960 |
| ccuugcuggg cuuccugggg gccugggcgg uggcacucu uuguggggau gcacugcuac | 1020 |
| aucugcuacc gcaugcacaa gaagggcggc acgcaggacc uggcggacua ccagagaagg | 1080 |
| accuggggccc gggggcuguca gugccgggag ccucuuccu gcucuuugug cuggagaaca | 1140 |
| ugcuggggcu uuugcggcac cgaggggcuca ggccaagaug cugcaggcga aaacgaagga | 1200 |
| aucucgaaac acgcaacuug gauccggaga auggcagugg gaugggccuu cagcccuac | 1260 |
| aggcagcucc agagccaggg gcucagggcc agaggagaa gaacagccag caccaccag | 1320 |
| cucuggcccc uccuggcac caaggccaca gucaugggcc cagggguggc acugauauca | 1380 |
| cguggauggu ccuccuggga gauggucuac acaaccucac ugaugggcug gccauaggug | 1440 |
| cugccuucuc ugauggcuuc uccagcgccc ucaguaccac cuuagcgguc uucugccaug | 1500 |
| agcugcccca cgaacugggu gacuuugcca ugcugcucca gucagggcug uccuuucggc | 1560 |
| ggcugcugcu gcugagccuc gugucuggag cccuggauu gggggugca guccuggggg | 1620 |
| ugggggcucag ccuggggccu gucccccuca cucccugggu guugggguc acugcugggg | 1680 |
| ucuuccucua gugggcccuu guggacaugc uaccagcccu gcuucguccu ccggagcccc | 1740 |
| ugccuacgcc ccaugugcuc cugcaggggc uggggcugcu gcgggggc ggccucaugc | 1800 |
| uugccauaac ccugcuggag gagcggcuac ugcccgugac cacugagggc ugauggggcc | 1860 |
| aguggaaagg ggucggguug cccuuccuuc cccccaacca caggaaugga ggcgggacac | 1920 |
| agggccagua ggagcaauag gauuuuaaua aacagaaccc aucccaaa | 1968 |

<210> SEQ ID NO 14
<211> LENGTH: 1968
<212> TYPE: DNA
<213> ORGANISM: homo sapien

<400> SEQUENCE: 14

| | | | | | |
|---|---|---|---|---|---|
| agcuggaacc | aagaagguug | ugucccccuu | ccucugggug | uccuugcucu | cugcuaucag | 60 |
| ggcuuccccu | uucuugguca | ucgaucccua | gagcucuggc | ucuuucucuu | cuugggaac | 120 |
| ugcuuaacgu | cuacagcaag | gccuaauagg | ggaccugagg | gcacaguccu | caggauguuu | 180 |
| cggggagaau | aggagccaga | accugagccc | cuaagcuauu | ccccucacca | augauggggu | 240 |
| ccccagugag | ucaucugcug | gccggcuucu | guguguggu | cgucuugggc | uggguagggg | 300 |
| gcucaguccc | caaccugggc | ccugcugagc | aggagcagaa | ccauuaccug | gcccagcugu | 360 |
| uuggccugua | cggcgagaau | gggacgcuga | cugcagggg | cuuggcgcgg | cuucuccaca | 420 |
| gccuggggcu | aggccgaguu | cagggggcuuc | gccuggaca | gcaugggccu | cugacuggac | 480 |
| gggcugcauc | cccagcugca | gacaauucca | cacacaggcc | acagaacccu | gagcugagug | 540 |
| uggaugucug | gcagggaug | ccucuggguc | ccucaggug | gggugaccug | gaagagucaa | 600 |
| aggcccccuca | ccuaccccgu | gggccagccc | ccucgggccu | ggaccuccuu | cacaggcuuc | 660 |
| uguugcugga | ccacucauug | gcugaccacc | ugaaugagga | ugucugaac | ggcucccagc | 720 |
| ugcugguca | uuuggcuug | agccccgcug | cuccucugac | cccucgucag | uuugcucugc | 780 |
| ugugcccagc | ccugcuuuau | cagaucgaca | gccgcgucug | caucggcgcu | ccggccccug | 840 |
| cacccccagg | ggaucuacua | ucugcccgc | uucagagugc | ccuggcaguc | cuguugcuca | 900 |
| gccucccuuc | uccccuaucc | cugcugcugc | ugcggcuccu | gggaccucgu | cuacuacggc | 960 |
| ccuugcuggg | cuuccgggg | gcccuggcgg | ugggcacucu | uuguggggau | gcacugcuac | 1020 |
| aucugcuacc | gcaugcacaa | gaagggcggc | acgcaggacc | uggcggacua | ccagagaagg | 1080 |
| accugggccc | ggggcuguca | gugcucggag | gccucuuccu | gcucuuugu | cuggagaaca | 1140 |
| ugcuggggcu | uuugcggcac | ugagggcuca | ggccaagaug | cugcaggcga | aaacgaagga | 1200 |
| aucucgaaac | acgcaacuug | gauccggaga | auggcagugg | gauggcccuu | cagcccuac | 1260 |
| aggcagcucc | agagccaggg | gcucagggcc | agagggagaa | gaacagccag | cacccaccag | 1320 |
| cucuggcccc | uccugggcac | caaggccaca | gucauggca | ccaggguggc | acugauauca | 1380 |
| cguggauggu | ccuccuggga | gauggucuac | acaaccucac | ugaugggcug | gccauaggug | 1440 |
| cugccuucuc | ugauggcuuc | uccagcggcc | ucaguaccac | cuuagcgguc | uucugccaug | 1500 |
| agcugcccca | cgaacugggu | gacuuugcca | ugcugcucca | gucagggcug | uccuucggc | 1560 |
| ggcugcugcu | gcuagccuc | gugucuggag | cccugggauu | ggggggugca | guccuggggg | 1620 |
| uggggcucag | ccugggcccu | guccccuca | cucccugggu | guuggggguc | acugcugggg | 1680 |
| ucuuccucua | ugugcccuu | guggacaugc | uaccagcccu | gcuucguccu | ccggagcccc | 1740 |
| ugccuacgcc | ccaugugcuc | cugcaggggc | uggggcugcu | gcuggggggc | ggccucaugc | 1800 |
| uugccauaac | ccugcuggag | gagcggcuac | ugcccgugac | cacugagggc | ugauggggcc | 1860 |
| agugaaagg | ggucggguug | cccuuccuuc | ccccuaacca | caggaaugga | ggcgggacac | 1920 |
| agggccagua | ggagcaauag | gauuuuaaua | aacagaaccc | auccccaaa | | 1968 |

<210> SEQ ID NO 15
<211> LENGTH: 1968
<212> TYPE: DNA
<213> ORGANISM: homo sapien

<400> SEQUENCE: 15

```
agctggaacc aagaaggttg tgtccccctt cctctgggtg tccttgtctc ctgctatcag      60
ggcttcccct ttcttggtca tcgatcccta gagctctggc tctttctctt cttggggaac     120
tgcttaacgt ctacagcaag gcctaatagg ggacctgagg gcacagtcct caggatgttt     180
cggggagaat aggagccaga acctgagccc ctaagctatt cccctcacca atgatggggt     240
ccccagtgag tcatctgctg gccggcttct gtgtgtgggt cgtcttgggc tgggtagggg     300
gctcagtccc caacctgggc cctgctgagc aggagcagaa ccattacctg gcccagctgt     360
ttggcctgta cggcgagaat gggacgctga ctgcagggggcttggcgcgg cttctccaca     420
gcctggggct aggccgagtt caggggcttc gcctgggaca gcatgggcct ctgactggac     480
gggctgcatc cccagctgca gacaattcca cacacaggcc acagaaccct gagctgagtg     540
tggatgtctg ggcagggatg cctctgggtc cctcagggtg gggtgacctg aagagtcaa      600
aggcccctca cctaccccgt gggccagccc cctcgggcct ggacctcctt cacaggcttc     660
tgttgctgga ccactcattg gctgaccacc tgaatgagga ttgtctgaac ggctcccagc     720
tgctggtcaa ttttggcttg agccccgctg ctcctctgac ccctcgtcag tttgctctgc     780
tgtgcccagc cctgctttat cagatcgaca gccgcgtctg catcggcgct ccggcccctg     840
cacccccagg ggatctacta tctgccctgc ttcagagtgc cctggcagtc ctgttgctca     900
gcctcccttc tcccctatcc ctgctgctgc tgcggctcct gggacctcgt ctactacggc     960
ccttgctggg cttcctgggg gcctggcgg tgggcactct ttgtggggat gcactgctac    1020
atctgctacc gcatgcacaa gaagggcggc acgcaggacc tggcggacta ccagagaagg    1080
acctgggccc ggggctgtca gtgctcggag gcctcttcct gctctttgtg ctggagaaca    1140
tgctggggct tttgcggcac cgagggctca ggccaagatg ctgcaggcga aaacgaagga    1200
atctcgaaac acgcaacttg gatccggaga atggcagtgg gatggccctt cagcccctac    1260
aggcagctcc agagccaggg gctcagggcc agagggagaa gaacagccag cacccaccag    1320
ctctggcccc tcctgggcac caaggccaca gtcatgggca ccagggtggc actgatatca    1380
cgtggatggt cctcctggga gatggtctac acaacctcac tgatgggctg gccataggtg    1440
ctgccttctc tgatggcttc tccagcggcc tcagtaccac cttagcggtc ttctgccatg    1500
agctgcccca cgaactgggt gactttgcca tgctgctcca gtcagggctg tccttcggc     1560
ggctgctgct gctgagcctc gtgtctggag ccctgggatt gggggtgca gtcctggggg    1620
tggggctcag cctgggccct gtcccccctca ctccctgggt gtttgggtc actgctgggg    1680
tcttcctcta tgtggccctt gtggacatgc taccagccct gcttcgtcct ccggagcccc    1740
tgcctacgcc ccatgtgctc ctgcagggggc tgggctgct gctgggggc ggcctcatgc    1800
ttgccataac cctgctggag gagcggctac tgcccgtgac cactgagggc tgatggggcc    1860
agtggaaagg ggtcggggttg ccctccttc ccccaacca caggaatgga ggcgggacac    1920
agggccagta ggagcaatag gattttaata aacagaaccc atcccaaa               1968
```

<210> SEQ ID NO 16
<211> LENGTH: 1968
<212> TYPE: DNA
<213> ORGANISM: homo sapien

<400> SEQUENCE: 16

```
agctggaacc aagaaggttg tgtccccctt cctctgggtg tccttgtctc ctgctatcag      60
```

```
ggcttcccct ttcttggtca tcgatccta gagctctggc tctttctctt cttggggaac    120
tgcttaacgt ctacagcaag gcctaatagg ggacctgagg gcacagtcct caggatgttt    180
cggggagaat aggagccaga acctgagccc ctaagctatt ccctcacca atgatggggt     240
ccccagtgag tcatctgctg gccggcttct gtgtgtgggt cgtcttgggc tgggtagggg    300
gctcagtccc caacctgggc cctgctgagc aggagcagaa ccattacctg gcccagctgt    360
ttggcctgta aggcgagaat gggacgctga ctgcaggggg cttggcgcgg cttctccaca    420
gcctggggct aggccgagtt caggggcttc gcctgggaca gcatgggcct ctgactggac    480
gggctgcatc cccagctgca gacaattcca cacacaggcc acagaaccct gagctgagtg    540
tggatgtctg gcagggatg cctctgggtc cctcagggtg gggtgacctg aagagtcaa     600
aggcccctca cctaccccgt gggccagccc cctcgggcct ggacctcctt cacaggcttc    660
tgttgctgga ccactcattg gctgaccacc tgaatgagga ttgtctgaac ggctcccagc    720
tgctggtcaa ttttggcttg agccccgctg ctccctctgac ccctcgtcag tttgctctgc   780
tgtgcccagc cctgctttat cagatcgaca gccgcgtctg catcggcgct ccggcccctg   840
caccccaggg ggatctacta tctgccctgc ttcagagtgc cctggcagtc ctgttgctca   900
gcctcccttc tccctatcc ctgctgctgc tgcggctcct gggacctcgt ctactacggc    960
ccttgctggg cttcctgggg gccctggcgg tgggcactct tgtgggggat gcactgctac    1020
atctgctacc gcatgcacaa gaagggcggc acgcaggacc tggcggacta ccagagaagg    1080
acctgggccc ggggctgtca gtgctcggag gcctcttcct gctctttgtg ctggagaaca    1140
tgctggggct tttgcggcac cgagggctca ggccaagatg ctgcaggcga aaacgaagga   1200
atctcgaaac acgcaacttg gatccggaga atggcagtgg gatggcccctt cagcccctac  1260
aggcagctcc agagccaggg gctcaggggcc agagggagaa gaacagccag cacccaccag   1320
ctctggcccc tcctgggcac caaggccaca gtcatgggca ccagggtggc actgatatca   1380
cgtggatggt cctcctggga gatggtctac acaacctcac tgatgggctg ccataggtg    1440
ctgccttctc tgatggcttc tccagcggcc tcagtaccac cttagcggtc ttctgccatg    1500
agctgcccca cgaactgggt gacttttgcca tgctgctcca gtcagggctg tccttcgc    1560
ggctgctgct gctgagcctc gtgtctggag ccctgggatt gggggggtgca gtcctggggg   1620
tggggctcag cctgggccct gtcccctca ctccctgggt gtttgggggtc actgctgggg   1680
tcttcctcta tgtggccctt gtggacatgc taccagccct gcttcgtcct ccggagcccc    1740
tgcctacgcc ccatgtgctc ctgcaggggc tgggctgct gctgggggc ggcctcatgc     1800
ttgccataac cctgctggag gagcggctac tgcccgtgac cactgagggc tgatggggcc    1860
agtggaaagg ggtcgggttg ccttccttc ccccaaccaa caggaatgga ggcgggacac    1920
agggccagta ggagcaatag gattttaata aacagaaccc atcccaaa                 1968
```

<210> SEQ ID NO 17
<211> LENGTH: 1968
<212> TYPE: DNA
<213> ORGANISM: homo sapien

<400> SEQUENCE: 17

```
agctggaacc aagaaggttg tgtcccctt cctctgggtg tccttgtctc ctgctatcag      60
ggcttcccct ttcttggtca tcgatccta gagctctggc tctttctctt cttggggaac    120
tgcttaacgt ctacagcaag gcctaatagg ggacctgagg gcacagtcct caggatgttt   180
cggggagaat aggagccaga acctgagccc ctaagctatt ccctcacca atgatggggt    240
```

```
cccagtgag tcatctgctg gccggcttct gtgtgtgggt cgtcttgggc tgggtagggg      300
gctcagtccc caacctgggc cctgctgagc aggagcagaa ccattacctg cccagctgt      360 ttggcctgta gggcgagaat gggacgctga ctgcagggg cttggcgcgg cttctccaca      420
gcctggggct aggccgagtt caggggcttc gcctgggaca gcatgggcct ctgactggac      480
gggctgcatc cccagctgca gacaattcca cacacaggcc acagaaccct gagctgagtg      540
tggatgtctg gcagggatg cctctgggtc cctcagggtg gggtgacctg gaagagtcaa      600
aggcccctca cctaccccgt gggccagccc cctcgggcct ggacctcctt cacaggcttc      660
tgttgctgga ccactcattg gctgaccacc tgaatgagga ttgtctgaac ggctcccagc      720
tgctggtcaa ttttggcttg agcccgctg ctcctctgac ccctcgtcag tttgctctgc      780
tgtgcccagc cctgctttat cagatcgaca gccgcgtctg catcggcgct ccggcccctg      840 caccccagg ggatctacta tctgccctgc ttcagagtgc cctggcagtc ctgttgctca      900
gcctcccttc tcccctatcc ctgctgctgc tgcggctcct gggacctcgt ctactacggc      960
ccttgctggg cttcctgggg gccctggcgg tgggcactct ttgtggggat gcactgctac     1020
atctgctacc gcatgcacaa gaagggcggc acgcaggacc tggcggacta ccagagaagg     1080
acctgggccc ggggctgtca gtgctcggag gcctcttcct gctcttttgtg ctggagaaca     1140 tgctggggct tttgcggcac cgagggctca ggccaagatg ctgcaggcga aaacgaagga     1200
atctcgaaac acgcaacttg gatccggaga atggcagtgg gatggcccctt cagcccctac     1260 aggcagctcc agagccaggg gctcaggcc agagggagaa aacagccag cacccaccag     1320 ctctggcccc tcctgggcac caaggccaca gtcatgggca ccagggtggc actgatatca     1380
cgtggatggt cctcctggga gatggtctac acaacctcac tgatgggctg ccataggtg     1440 ctgccttctc tgatggcttc tccagcggcc tcagtaccac cttagcggtc ttctgccatg     1500
agctgcccca cgaactgggt gactttgcca tgctgctcca gtcagggctg tccttttcggc     1560 ggctgctgct gctgagcctc gtgtctggag ccctgggatt gggggggtgca gtcctggggg     1620 tggggctcag cctgggccct gtcccccctca ctccctgggt gtttgggggtc actgctgggg     1680 tcttcctcta tgtggcccctt gtggacatgc taccagcccc gcttcgtcct ccggagcccc     1740
tgcctacgcc ccatgtgctc ctgcagggc tggggctgct gctgggggggc ggcctcatgc     1800 ttgccataac cctgctggag gagcggctac tgcccgtgac cactgagggc tgatggggcc     1860
agtggaaagg ggtcgggttg cccttccttc cccccaacca caggaatgga ggcgggacac     1920
agggccagta ggagcaatag gattttaata aacagaaccc atcccaaa                  1968
```

<210> SEQ ID NO 18
<211> LENGTH: 1968
<212> TYPE: DNA
<213> ORGANISM: homo sapien

<400> SEQUENCE: 18

```
agctggaacc aagaaggttg tgtcccccctt cctctgggtg tccttgtctc ctgctatcag       60
ggcttcccct ttcttggtca tcgatcccta gagctctggc tctttctctt cttggggaac      120
tgcttaacgt ctacagcaag gcctaatagg ggacctgagg gcacagtcct caggatgttt      180
cggggagaat aggagccaga acctgagccc ctaagctatt cccctcacca atgatggggt      240
ccccagtgag tcatctgctg gccggcttct gtgtgtgggt cgtcttgggc tgggtagggg      300
gctcagtccc caacctgggc cctgctgagc aggagcagaa ccattacctg cccagctgt      360
```

| | |
|---|---|
| ttggcctgta cggcgagaat gggacgctga ctgcaggggg cttggcgcgg cttctccaca | 420 |
| gcctggggct aggccgagtt caggggcttc gcctgggaca gcatgggcct ctgactggac | 480 |
| gggctgcatc cccagctgca gacaattcca cacacaggcc acagaaccct gagctgagtg | 540 |
| tggatgtctg gcagggatg cctctgggtc cctcagggtg gggtgacctg gaagagtcaa | 600 |
| aggcccctca cctaccccgt gggccagccc cctcgggcct ggacctcctt cacaggcttc | 660 |
| tgttgctgga ccactcattg gctgaccacc tgaatgagga ttgtctgaac ggctcccagc | 720 |
| tgctggtcaa ttttggcttg agccccgctg ctcctctgac ccctcgtcag tttgctctgc | 780 |
| tgtgcccagc cctgctttat cagatcgaca gccgcgtctg catcggcgct ccggcccctg | 840 |
| caccccagg ggatctacta tctgccctgc ttcagagtgc cctggcagtc ctgttgctca | 900 |
| gcctcccttc tccctatcc ctgctgctgc tgcggctcct gggacctcgt ctactacggc | 960 |
| ccttgctggg cttcctgggg gccctggcgg tgggcactct tgtggggat gcactgctac | 1020 |
| atctgctacc gcatgcacaa gaagggcggc acgcaggacc tggcggacta ccagagaagg | 1080 |
| acctgggccc ggggctgtca gtgctcggag gcctcttcct gctctttgtg ctggagaaca | 1140 |
| cgctggggct tttgcggcac cgagggctca ggccaagatg ctgcaggcga aaacgaagga | 1200 |
| atctcgaaac acgcaacttg gatccggaga atggcagtgg gatggccctt cagcccctac | 1260 |
| aggcagctcc agagccaggg gctcagggcc agagggagaa gaacagccag cacccaccag | 1320 |
| ctctggcccc tcctgggcac caaggccaca gtcatgggca ccaggtggc actgatatca | 1380 |
| cgtggatggt cctcctggga gatggtctac acaacctcac tgatgggctg gccataggtg | 1440 |
| ctgccttctc tgatggcttc tccagcggcc tcagtaccac cttagcggtc ttctgccatg | 1500 |
| agctgcccca cgaactgggt gactttgcca tgctgctcca gtcagggctg tcctttcggc | 1560 |
| ggctgctgct gctgagcctc gtgtctggag ccctgggatt ggggggtgca gtcctggggg | 1620 |
| tggggctcag cctgggccct gtcccctca ctccctgggt gtttgggtc actgctgggg | 1680 |
| tcttcctcta tgtggccctt gtggacatgc taccagccct gcttcgtcct ccggagcccc | 1740 |
| tgcctacgcc ccatgtgctc ctgcaggggc tggggctgct gctgggggc ggcctcatgc | 1800 |
| ttgccataac cctgctggag gagcggctac tgcccgtgac cactgagggc tgatggggcc | 1860 |
| agtggaaagg ggtcgggttg cccttccttc ccccaacca caggaatgga ggcgggacac | 1920 |
| agggccagta ggagcaatag gattttaata aacagaaccc atcccaaa | 1968 |

<210> SEQ ID NO 19
<211> LENGTH: 1968
<212> TYPE: DNA
<213> ORGANISM: homo sapien

<400> SEQUENCE: 19

| | |
|---|---|
| agctggaacc aagaaggttg tgtccccctt cctctgggtg tccttgtctc ctgctatcag | 60 |
| ggcttcccct ttcttggtca tcgatcccta gagctctggc tctttctctt cttggggaac | 120 |
| tgcttaacgt ctacagcaag gcctaatagg ggacctgagg gcacagtcct caggatgttt | 180 |
| cggggagaat aggagccaga acctgagccc ctaagctatt cccctcacca atgatggggt | 240 |
| ccccagtgag tcatctgctg gccggcttct gtgtgtgggt cgtcttgggc tgggtagggg | 300 |
| gctcagtccc caacctgggc cctgctgagc aggagcagaa ccattacctg gcccagctgt | 360 |
| ttggcctgta cggcgagaat gggacgctga ctgcaggggg cttggcgcgg cttctccaca | 420 |
| gcctggggct aggccgagtt caggggcttc gcctgggaca gcatgggcct ctgactggac | 480 |
| gggctgcatc cccagctgca gacaattcca cacacaggcc acagaaccct gagctgagtg | 540 |

```
tggatgtctg ggcagggatg cctctgggtc cctcagggtg gggtgacctg gaagagtcaa      600
aggcccctca cctaccccgt gggccagccc cctcgggcct ggacctcctt cacaggcttc      660
tgttgctgga ccactcattg gctgaccacc tgaatgagga ttgtctgaac ggctcccagc      720
tgctggtcaa ttttggcttg agcccgctg ctcctctgac ccctcgtcag tttgctctgc       780
tgtgcccagc cctgctttat cagatcgaca gccgcgtctg catcggcgct ccggcccctg      840
cacccccagg ggatctacta tctgcccctgc ttcagagtgc cctggcagtc ctgttgctca     900
gcctcccttc tccctatcc ctgctgctgc tgcggctcct gggacctcgt ctactacggc       960
ccttgctggg cttcctgggg gccctggcgg tgggcactct ttgtggggat gcactgctac     1020
atctgctacc gcatgcacaa gaagggcggc acgcaggacc tggcggacta ccagagaagg     1080
acctgggccc ggggctgtca gtgctcggag gcctcttcct gctctttgtg ctggagaaca     1140
tgctggggct tttgcggcac cgagggctca ggccaagatg ctgcaggcga aaatgaagga     1200
atctcgaaac acgcaacttg gatccggaga atggcagtgg gatggccctt cagcccctac     1260
aggcagctcc agagccaggg gctcagggcc agagggagaa gaacagccag cacccaccag     1320
ctctggcccc tcctgggcac caaggccaca gtcatgggca ccagggtggc actgatatca     1380
cgtggatggt cctcctggga gatggtctac acaacctcac tgatgggctg ccataggtg     1440 ctgccttctc tgatggcttc tccagcggcc tcagtaccac cttagcggtc ttctgccatg     1500
agctgcccca cgaactgggt gactttgcca tgctgctcca gtcagggctg tcctttcggc     1560
ggctgctgct gctgagcctc gtgtctggag ccctgggatt gggggggtgca gtcctggggg     1620 tggggctcag cctgggccct gtcccctca ctccctgggt gtttgggtc actgctgggg      1680 tcttcctcta tgtggccctt gtggacatgc taccagccct gcttcgtcct ccggagcccc     1740
tgcctacgcc ccatgtgctc ctgcaggggc tggggctgct gctgggggc ggcctcatgc      1800 ttgccataac cctgctggag gagcggctac tgcccgtgac cactgagggc tgatggggcc     1860
agtggaaagg ggtcgggttg cccttccttc cccccaacca caggaatgga ggcgggacac     1920
agggccagta ggagcaatag gattttaata aacagaaccc atcccaaa                 1968
```

<210> SEQ ID NO 20  
<211> LENGTH: 1968  
<212> TYPE: DNA  
<213> ORGANISM: homo sapien

<400> SEQUENCE: 20

```
agctggaacc aagaaggttg tgtccccctt cctctgggtg tccttgtctc ctgctatcag       60
ggcttcccct ttcttggtca tcgatcccta gagctctggc tctttctctt cttggggaac      120
tgcttaacgt ctacagcaag gcctaatagg ggacctgagg gcacagtcct caggatgttt      180
cggggagaat aggagccaga acctgagccc ctaagctatt cccctcacca atgatggggt      240
ccccagtgag tcatctgctg gccggcttct gtgtgtgggt cgtcttgggc tgggtagggg      300
gctcagtccc caacctgggc cctgctgagc aggagcagaa ccattacctg cccagctgt      360 ttggcctgta cggcgagaat gggacgctga ctgcagggggg cttggcgcgg cttctccaca     420
gcctggggct aggccgagtt caggggcttc gcctgggaca gcatgggcct ctgactggac     480
gggctgcatc cccagctgca gacaattcca cacacaggcc acagaaccct gagctgagtg      540
tggatgtctg ggcagggatg cctctgggtc cctcagggtg gggtgacctg gaagagtcaa     600
aggcccctca cctaccccgt gggccagccc cctcgggcct ggacctcctt cacaggcttc     660
```

| | |
|---|---|
| tgttgctgga ccactcattg gctgaccacc tgaatgagga ttgtctgaac ggctcccagc | 720 |
| tgctggtcaa ttttggcttg agccccgctg ctcctctgac ccctcgtcag tttgctctgc | 780 |
| tgtgcccagc cctgctttat cagatcgaca gccgcgtctg catcggcgct ccggcccctg | 840 |
| caccccagg ggatctacta tctgccctgc ttcagagtgc cctggcagtc ctgttgctca | 900 |
| gcctcccttc tccoctatcc ctgctgctgc tgcggctcct gggacctcgt ctactacggc | 960 |
| ccttgctggg cttcctgggg gccctggcgg tgggcactct ttgtggggat gcactgctac | 1020 |
| atctgctacc gcatgcacaa aagggcggc acgcaggacc tggcggacta ccagagaagg | 1080 |
| acctgggccc ggggctgtca gtgctcgag gcctcttcct gctctttgtg ctggagaaca | 1140 |
| tgctggggct tttgcggcac cgagggctca ggccaagatg ctgcaggcga aaacgaagga | 1200 |
| atctcgaaac acgcaacttg gatccggaga atggcagtgg gatggccctt cagcccctac | 1260 |
| aggcagctcc agagccaggg gctcagggcc agagggagaa gaacagccag cacccaccag | 1320 |
| ctctggcccc tcctgggcac caaggccaca gtcatgggca ccagggtggc actgatatca | 1380 |
| cgtggatggt cctcctggga gatggtctac acaacctcac tgatgggctg ccataggtg | 1440 |
| ctgccttctc tgatggcttc tccagcgccc tcagtaccac cttagcggtc ttctgccatg | 1500 |
| agctgcccca cgaactgggt gactttgcca tgctgctcca gtcagggctg tccttcggc | 1560 |
| ggctgctgct gctgagcctc gtgtctggag ccctgggatt gggggggtgca gtcctggggg | 1620 |
| tggggctcag cctgggccct gtccccctca ctccctgggt gtttgggtc actgctgggg | 1680 |
| tcttcctcta tgtggccctt gtggacatgc taccagccct gcttcgtcct ccggagcccc | 1740 |
| tgcctacgcc ccatgtgctc ctgcagggc tgggctgct gctgggggc ggcctcatgc | 1800 |
| ttgccataac cctgctggag gagcggctac tgcccgtgac cactgagggc tgatgggggcc | 1860 |
| agtggaaagg ggtcgggttg cccttccttc ccccaacca caggaatgga ggcgggacac | 1920 |
| agggccagta ggagcaatag gatttaata aacagaaccc atcccaaa | 1968 |

<210> SEQ ID NO 21
<211> LENGTH: 1968
<212> TYPE: DNA
<213> ORGANISM: homo sapien

<400> SEQUENCE: 21

| | |
|---|---|
| agctggaacc aagaaggttg tgtcccccctt cctctgggtg tccttgtctc ctgctatcag | 60 |
| ggcttcccct ttcttggtca tcgatcccta gagctctggc tctttctctt cttggggaac | 120 |
| tgcttaacgt ctacagcaag gcctaatagg ggacctgagg gcacagtcct caggatgttt | 180 |
| cggggagaat aggagccaga acctgagccc ctaagctatt cccctcacca atgatggggt | 240 |
| ccccagtgag tcatctgctg gccggcttct gtgtgtgggt cgtcttggc tgggtagggg | 300 |
| gctcagtccc caacctgggc cctgctgagc aggagcagaa ccattacctg cccagctgt | 360 |
| ttggcctgta cggcgagaat gggacgctga ctgcagggg cttggcgcgg cttctccaca | 420 |
| gcctggggct aggccgagtt cagggcttc gcctgggaca gcatgggcct ctgactggac | 480 |
| gggctgcatc cccagctgca gacaattcca cacacaggcc acagaaccct gagctgagtg | 540 |
| tggatgtctg gcagggatg cctctgggtc cctcagggtg gggtgacctg gaagagtcaa | 600 |
| aggcccctca cctaccccgt gggccagccc cctcgggcct ggacctcctt cacaggcttc | 660 |
| tgttgctgga ccactcattg gctgaccacc tgaatgagga ttgtctgaac ggctcccagc | 720 |
| tgctggtcaa ttttggcttg agccccgctg ctcctctgac ccctcgtcag tttgctctgc | 780 |
| tgtgcccagc cctgctttat cagatcgaca gccgcgtctg catcggcgct ccggcccctg | 840 |

-continued

```
cacccccagg ggatctacta tctgccctgc ttcagagtgc cctggcagtc ctgttgctca      900
gcctcccttc tcccctatcc ctgctgctgc tgcggctcct gggacctcgt ctactacggc      960
ccttgctggg cttcctgggg gccctggcgg tgggcactct tgtggggat gcactgctac      1020 atctgctacc gcatgcacaa gaagggcggc acgcaggacc tggcggacta ccagagaagg      1080
acctgggccc ggggctgtca gtgctcggag gcctcttcct gctctttgtg ctggagaaca      1140
tgctggggct tttgcggcac tgagggctca ggccaagatg ctgcaggcga aaacgaagga      1200
atctcgaaac acgcaacttg gatccggaga atggcagtgg gatggcccctt cagcccctac      1260 aggcagctcc agagccaggg gctcagggcc agagggagaa gaacagccag cacccaccag      1320
ctctggcccc tcctgggcac caaggccaca gtcatgggca ccagggtggc actgatatca      1380
cgtggatggt cctcctggga gatggtctac acaacctcac tgatgggctg ccataggtg       1440 ctgccttctc tgatggcttc tccagcggcc tcagtaccac cttagcggtc ttctgccatg      1500
agctgcccca cgaactgggt gactttgcca tgctgctcca gtcagggctg tcctttcggc      1560
ggctgctgct gctgagcctc gtgtctggag ccctgggatt ggggggtgca gtcctggggg      1620
tggggctcag cctgggccct gtccccctca ctccctgggt gtttgggtgtc actgctgggg     1680 tcttcctcta tgtggccctt gtggacatgc taccagccct gcttcgtcct ccggagcccc      1740
tgcctacgcc ccatgtgctc ctgcagggc tggggctgct gctgggggc ggcctcatgc       1800 ttgccataac cctgctggag gagcggctac tgcccgtgac cactgagggc tgatggggcc      1860
agtggaaagg ggtcgggttg cccttccttc cccccaacca caggaatgga ggcgggacac      1920
agggccagta ggagcaatag gattttaata aacagaaccc atcccaaa                   1968
```

<210> SEQ ID NO 22
<211> LENGTH: 540
<212> TYPE: PRT
<213> ORGANISM: homo sapien

<400> SEQUENCE: 22

```
Met Met Gly Ser Pro Val Ser His Leu Leu Ala Gly Phe Cys Val Trp
1               5                   10                  15

Val Val Leu Gly Trp Val Gly Gly Ser Val Pro Asn Leu Gly Pro Ala
            20                  25                  30

Glu Gln Glu Gln Asn His Tyr Leu Ala Gln Leu Phe Gly Leu Tyr Gly
        35                  40                  45

Glu Asn Gly Thr Leu Thr Ala Gly Leu Ala Arg Leu Leu His Ser
    50                  55                  60

Leu Gly Leu Gly Arg Val Gln Gly Leu Arg Leu Gly Gln His Gly Pro
65                  70                  75                  80

Leu Thr Gly Arg Ala Ala Ser Pro Ala Ala Asp Asn Ser Thr His Arg
                85                  90                  95

Pro Gln Asn Pro Glu Leu Ser Val Asp Val Trp Ala Gly Met Pro Leu
            100                 105                 110

Gly Pro Ser Gly Trp Gly Asp Leu Glu Glu Ser Lys Ala Pro His Leu
        115                 120                 125

Pro Arg Gly Pro Ala Pro Ser Gly Leu Asp Leu His Arg Leu Leu
    130                 135                 140

Leu Leu Asp His Ser Leu Ala Asp His Leu Asn Glu Asp Cys Leu Asn
145                 150                 155                 160

Gly Ser Gln Leu Leu Val Asn Phe Gly Leu Ser Pro Ala Ala Pro Leu
                165                 170                 175
```

Thr Pro Arg Gln Phe Ala Leu Leu Cys Pro Ala Leu Leu Tyr Gln Ile
            180                 185                 190

Asp Ser Arg Val Cys Ile Gly Ala Pro Ala Pro Pro Gly Asp
        195                 200             205

Leu Leu Ser Ala Leu Leu Gln Ser Ala Leu Ala Val Leu Leu Leu Ser
    210                 215                 220

Leu Pro Ser Pro Leu Ser Leu Leu Leu Arg Leu Leu Gly Pro Arg
225                 230                 235                 240

Leu Leu Arg Pro Leu Leu Gly Phe Leu Gly Ala Leu Ala Val Gly Thr
                245                 250                 255

Leu Cys Gly Asp Ala Leu Leu His Leu Leu Pro His Ala Gln Glu Gly
            260                 265                 270

Arg His Ala Gly Pro Gly Gly Leu Pro Glu Lys Asp Leu Gly Pro Gly
        275                 280                 285

Leu Ser Val Leu Gly Gly Leu Phe Leu Leu Phe Val Leu Glu Asn Met
    290                 295                 300

Leu Gly Leu Leu Arg His Arg Gly Leu Arg Pro Arg Cys Cys Arg Arg
305                 310                 315                 320

Lys Arg Arg Asn Leu Glu Thr Arg Asn Leu Asp Pro Glu Asn Gly Ser
                325                 330                 335

Gly Met Ala Leu Gln Pro Leu Gln Ala Ala Pro Glu Pro Gly Ala Gln
            340                 345                 350

Gly Gln Arg Glu Lys Asn Ser Gln His Pro Pro Ala Leu Ala Pro Pro
        355                 360                 365

Gly His Gln Gly His Ser His Gly His Gln Gly Gly Thr Asp Ile Thr
    370                 375                 380

Trp Met Val Leu Leu Gly Asp Gly Leu His Asn Leu Thr Asp Gly Leu
385                 390                 395                 400

Ala Ile Gly Ala Ala Phe Ser Asp Gly Phe Ser Ser Gly Leu Ser Thr
                405                 410                 415

Thr Leu Ala Val Phe Cys His Glu Leu Pro His Glu Leu Gly Asp Phe
            420                 425                 430

Ala Met Leu Leu Gln Ser Gly Leu Ser Phe Arg Arg Leu Leu Leu Leu
        435                 440                 445

Ser Leu Val Ser Gly Ala Leu Gly Leu Gly Gly Ala Val Leu Gly Val
    450                 455                 460

Gly Leu Ser Leu Gly Pro Val Pro Leu Thr Pro Trp Val Phe Gly Val
465                 470                 475                 480

Thr Ala Gly Val Phe Leu Tyr Val Ala Leu Val Asp Met Leu Pro Ala
                485                 490                 495

Leu Leu Arg Pro Pro Glu Pro Leu Pro Thr Pro His Val Leu Leu Gln
            500                 505                 510

Gly Leu Gly Leu Leu Leu Gly Gly Leu Met Leu Ala Ile Thr Leu
        515                 520                 525

Leu Glu Glu Arg Leu Leu Pro Val Thr Thr Glu Gly
    530                 535                 540

<210> SEQ ID NO 23
<211> LENGTH: 46
<212> TYPE: PRT
<213> ORGANISM: homo sapien

<400> SEQUENCE: 23

Met Met Gly Ser Pro Val Ser His Leu Leu Ala Gly Phe Cys Val Trp

-continued

```
                1               5                      10                      15

Val Val Leu Gly Trp Val Gly Gly Ser Val Pro Asn Leu Gly Pro Ala
                            20                      25                      30
            Glu Gln Glu Gln Asn His Tyr Leu Ala Gln Leu Phe Gly Leu
                            35                      40                      45
```

<210> SEQ ID NO 24
<211> LENGTH: 540
<212> TYPE: PRT
<213> ORGANISM: homo sapien

<400> SEQUENCE: 24

```
Met Met Gly Ser Pro Val Ser His Leu Leu Ala Gly Phe Cys Val Trp
  1               5                  10                  15

Val Val Leu Gly Trp Val Gly Gly Ser Val Pro Asn Leu Gly Pro Ala
             20                  25                  30

Glu Gln Glu Gln Asn His Tyr Leu Ala Gln Leu Phe Gly Leu Tyr Gly
         35                  40                  45

Glu Asn Gly Thr Leu Thr Ala Gly Gly Leu Ala Arg Leu Leu His Ser
     50                  55                  60

Leu Gly Leu Gly Arg Val Gln Gly Leu Arg Leu Gly Gln His Gly Pro
 65                  70                  75                  80

Leu Thr Gly Arg Ala Ala Ser Pro Ala Ala Asp Asn Ser Thr His Arg
                 85                  90                  95

Pro Gln Asn Pro Glu Leu Ser Val Asp Val Trp Ala Gly Met Pro Leu
            100                 105                 110

Gly Pro Ser Gly Trp Gly Asp Leu Glu Glu Ser Lys Ala Pro His Leu
        115                 120                 125

Pro Arg Gly Pro Ala Pro Ser Gly Leu Asp Leu Leu His Arg Leu Leu
    130                 135                 140

Leu Leu Asp His Ser Leu Ala Asp His Leu Asn Glu Asp Cys Leu Asn
145                 150                 155                 160

Gly Ser Gln Leu Leu Val Asn Phe Gly Leu Ser Pro Ala Ala Pro Leu
                165                 170                 175

Thr Pro Arg Gln Phe Ala Leu Leu Cys Pro Ala Leu Leu Tyr Gln Ile
            180                 185                 190

Asp Ser Arg Val Cys Ile Gly Ala Pro Ala Pro Ala Pro Pro Gly Asp
        195                 200                 205

Leu Leu Ser Ala Leu Leu Gln Ser Ala Leu Ala Val Leu Leu Leu Ser
    210                 215                 220

Leu Pro Ser Pro Leu Ser Leu Leu Leu Arg Leu Leu Gly Pro Arg
225                 230                 235                 240

Leu Leu Arg Pro Leu Gly Phe Leu Gly Ala Leu Ala Val Gly Thr
                245                 250                 255

Leu Cys Gly Asp Ala Leu Leu His Leu Pro His Ala Gln Glu Gly
            260                 265                 270

Arg His Ala Gly Pro Gly Leu Pro Glu Lys Asp Leu Gly Pro Gly
        275                 280                 285

Leu Ser Val Leu Gly Gly Leu Phe Leu Leu Phe Val Leu Glu Asn Thr
    290                 295                 300

Leu Gly Leu Leu Arg His Arg Gly Leu Arg Pro Arg Cys Cys Arg Arg
305                 310                 315                 320

Lys Arg Arg Asn Leu Glu Thr Arg Asn Leu Asp Pro Glu Asn Gly Ser
                325                 330                 335
```

```
Gly Met Ala Leu Gln Pro Leu Gln Ala Ala Pro Glu Pro Gly Ala Gln
            340                 345                 350

Gly Gln Arg Glu Lys Asn Ser Gln His Pro Pro Ala Leu Ala Pro Pro
            355                 360                 365

Gly His Gln Gly His Ser His Gly His Gln Gly Gly Thr Asp Ile Thr
            370                 375                 380

Trp Met Val Leu Leu Gly Asp Gly Leu His Asn Leu Thr Asp Gly Leu
385                 390                 395                 400

Ala Ile Gly Ala Ala Phe Ser Asp Gly Phe Ser Ser Gly Leu Ser Thr
                405                 410                 415

Thr Leu Ala Val Phe Cys His Glu Leu Pro His Glu Leu Gly Asp Phe
            420                 425                 430

Ala Met Leu Leu Gln Ser Gly Leu Ser Phe Arg Arg Leu Leu Leu Leu
            435                 440                 445

Ser Leu Val Ser Gly Ala Leu Gly Leu Gly Gly Ala Val Leu Gly Val
            450                 455                 460

Gly Leu Ser Leu Gly Pro Val Pro Leu Thr Pro Trp Val Phe Gly Val
465                 470                 475                 480

Thr Ala Gly Val Phe Leu Tyr Val Ala Leu Val Asp Met Leu Pro Ala
                485                 490                 495

Leu Leu Arg Pro Pro Glu Pro Leu Pro Thr Pro His Val Leu Leu Gln
            500                 505                 510

Gly Leu Gly Leu Leu Leu Gly Gly Leu Met Leu Ala Ile Thr Leu
            515                 520                 525

Leu Glu Glu Arg Leu Leu Pro Val Thr Thr Glu Gly
530                 535                 540

<210> SEQ ID NO 25
<211> LENGTH: 321
<212> TYPE: PRT
<213> ORGANISM: homo sapien

<400> SEQUENCE: 25

Met Met Gly Ser Pro Val Ser His Leu Leu Ala Gly Phe Cys Val Trp
1               5                   10                  15

Val Val Leu Gly Trp Val Gly Gly Ser Val Pro Asn Leu Gly Pro Ala
            20                  25                  30

Glu Gln Glu Gln Asn His Tyr Leu Ala Gln Leu Phe Gly Leu Tyr Gly
            35                  40                  45

Glu Asn Gly Thr Leu Thr Ala Gly Gly Leu Ala Arg Leu Leu His Ser
        50                  55                  60

Leu Gly Leu Gly Arg Val Gln Gly Leu Arg Leu Gly Gln His Gly Pro
65              70                  75                  80

Leu Thr Gly Arg Ala Ala Ser Pro Ala Ala Asp Asn Ser Thr His Arg
                85                  90                  95

Pro Gln Asn Pro Glu Leu Ser Val Asp Val Trp Ala Gly Met Pro Leu
            100                 105                 110

Gly Pro Ser Gly Trp Gly Asp Leu Glu Glu Ser Lys Ala Pro His Leu
            115                 120                 125

Pro Arg Gly Pro Ala Pro Ser Gly Leu Asp Leu His Arg Leu Leu
            130                 135                 140

Leu Leu Asp His Ser Leu Ala Asp His Leu Asn Glu Asp Cys Leu Asn
145                 150                 155                 160

Gly Ser Gln Leu Leu Val Asn Phe Gly Leu Ser Pro Ala Ala Pro Leu
                165                 170                 175
```

```
Thr Pro Arg Gln Phe Ala Leu Leu Cys Pro Ala Leu Leu Tyr Gln Ile
            180                 185                 190

Asp Ser Arg Val Cys Ile Gly Ala Pro Ala Pro Pro Gly Asp
        195                 200                 205

Leu Leu Ser Ala Leu Leu Gln Ser Ala Leu Ala Val Leu Leu Leu Ser
    210                 215                 220

Leu Pro Ser Pro Leu Ser Leu Leu Leu Arg Leu Leu Gly Pro Arg
225                 230                 235                 240

Leu Leu Arg Pro Leu Leu Gly Phe Leu Gly Ala Leu Ala Val Gly Thr
                245                 250                 255

Leu Cys Gly Asp Ala Leu Leu His Leu Leu Pro His Ala Gln Glu Gly
                260                 265                 270

Arg His Ala Gly Pro Gly Gly Leu Pro Glu Lys Asp Leu Gly Pro Gly
            275                 280                 285

Leu Ser Val Leu Gly Gly Leu Phe Leu Leu Phe Val Leu Glu Asn Met
            290                 295                 300

Leu Gly Leu Leu Arg His Arg Gly Leu Arg Pro Arg Cys Cys Arg Arg
305                 310                 315                 320

Lys

<210> SEQ ID NO 26
<211> LENGTH: 540
<212> TYPE: PRT
<213> ORGANISM: homo sapien

<400> SEQUENCE: 26

Met Met Gly Ser Pro Val Ser His Leu Leu Ala Gly Phe Cys Val Trp
1               5                   10                  15

Val Val Leu Gly Trp Val Gly Gly Ser Val Pro Asn Leu Gly Pro Ala
                20                  25                  30

Glu Gln Glu Gln Asn His Tyr Leu Ala Gln Leu Phe Gly Leu Tyr Gly
            35                  40                  45

Glu Asn Gly Thr Leu Thr Ala Gly Gly Leu Ala Arg Leu Leu His Ser
50                  55                  60

Leu Gly Leu Gly Arg Val Gln Gly Leu Arg Leu Gly Gln His Gly Pro
65                  70                  75                  80

Leu Thr Gly Arg Ala Ala Ser Pro Ala Ala Asp Asn Ser Thr His Arg
                85                  90                  95

Pro Gln Asn Pro Glu Leu Ser Val Asp Val Trp Ala Gly Met Pro Leu
            100                 105                 110

Gly Pro Ser Gly Trp Gly Asp Leu Glu Glu Ser Lys Ala Pro His Leu
        115                 120                 125

Pro Arg Gly Pro Ala Pro Ser Gly Leu Asp Leu His Arg Leu Leu
    130                 135                 140

Leu Leu Asp His Ser Leu Ala Asp His Leu Asn Glu Asp Cys Leu Asn
145                 150                 155                 160

Gly Ser Gln Leu Leu Val Asn Phe Gly Leu Ser Pro Ala Ala Pro Leu
                165                 170                 175

Thr Pro Arg Gln Phe Ala Leu Leu Cys Pro Ala Leu Leu Tyr Gln Ile
            180                 185                 190

Asp Ser Arg Val Cys Ile Gly Ala Pro Ala Pro Pro Gly Asp
        195                 200                 205

Leu Leu Ser Ala Leu Leu Gln Ser Ala Leu Ala Val Leu Leu Leu Ser
    210                 215                 220
```

```
Leu Pro Ser Pro Leu Ser Leu Leu Leu Arg Leu Leu Gly Pro Arg
225                 230                 235                 240

Leu Leu Arg Pro Leu Leu Gly Phe Leu Gly Ala Leu Ala Val Gly Thr
            245                 250                 255

Leu Cys Gly Asp Ala Leu Leu His Leu Leu Pro His Ala Gln Glu Gly
        260                 265                 270

Arg His Ala Gly Pro Gly Gly Leu Pro Glu Lys Asp Leu Gly Pro Gly
    275                 280                 285

Leu Ser Val Leu Gly Gly Leu Phe Leu Leu Phe Val Leu Glu Asn Met
290                 295                 300

Leu Gly Leu Leu Arg His Arg Gly Leu Arg Pro Arg Cys Cys Arg Arg
305                 310                 315                 320

Lys Arg Arg Asn Leu Glu Thr Arg Asn Leu Asp Pro Glu Asn Gly Ser
                325                 330                 335

Gly Met Ala Leu Gln Pro Leu Gln Ala Ala Pro Glu Pro Gly Ala Gln
            340                 345                 350

Gly Gln Arg Glu Lys Asn Ser Gln His Pro Pro Ala Leu Ala Pro Pro
        355                 360                 365

Gly His Gln Gly His Ser His Gly His Gln Gly Gly Thr Asp Ile Thr
    370                 375                 380

Trp Met Val Leu Leu Gly Asp Gly Leu His Asn Leu Thr Asp Gly Leu
385                 390                 395                 400

Ala Ile Gly Ala Ala Phe Ser Asp Gly Phe Ser Ser Ala Leu Ser Thr
                405                 410                 415

Thr Leu Ala Val Phe Cys His Glu Leu Pro His Glu Leu Gly Asp Phe
            420                 425                 430

Ala Met Leu Leu Gln Ser Gly Leu Ser Phe Arg Arg Leu Leu Leu Leu
        435                 440                 445

Ser Leu Val Ser Gly Ala Leu Gly Leu Gly Gly Ala Val Leu Gly Val
    450                 455                 460

Gly Leu Ser Leu Gly Pro Val Pro Leu Thr Pro Trp Val Phe Gly Val
465                 470                 475                 480

Thr Ala Gly Val Phe Leu Tyr Val Ala Leu Val Asp Met Leu Pro Ala
                485                 490                 495

Leu Leu Arg Pro Pro Glu Pro Leu Pro Thr Pro His Val Leu Leu Gln
            500                 505                 510

Gly Leu Gly Leu Leu Leu Gly Gly Gly Leu Met Leu Ala Ile Thr Leu
        515                 520                 525

Leu Glu Glu Arg Leu Leu Pro Val Thr Thr Glu Gly
    530                 535                 540

<210> SEQ ID NO 27
<211> LENGTH: 310
<212> TYPE: PRT
<213> ORGANISM: homo sapien

<400> SEQUENCE: 27

Met Met Gly Ser Pro Val Ser His Leu Leu Ala Gly Phe Cys Val Trp
1               5                   10                  15

Val Val Leu Gly Trp Val Gly Ser Val Pro Asn Leu Gly Pro Ala
            20                  25                  30

Glu Gln Glu Gln Asn His Tyr Leu Ala Gln Leu Phe Gly Leu Tyr Gly
        35                  40                  45

Glu Asn Gly Thr Leu Thr Ala Gly Gly Leu Ala Arg Leu Leu His Ser
```

```
            50                   55                  60
Leu Gly Leu Gly Arg Val Gln Gly Leu Arg Leu Gly Gln His Gly Pro
 65                  70                  75                  80

Leu Thr Gly Arg Ala Ala Ser Pro Ala Ala Asp Asn Ser Thr His Arg
                 85                  90                  95

Pro Gln Asn Pro Glu Leu Ser Val Asp Val Trp Ala Gly Met Pro Leu
            100                 105                 110

Gly Pro Ser Gly Trp Gly Asp Leu Glu Glu Ser Lys Ala Pro His Leu
        115                 120                 125

Pro Arg Gly Pro Ala Pro Ser Gly Leu Asp Leu Leu His Arg Leu Leu
    130                 135                 140

Leu Leu Asp His Ser Leu Ala Asp His Leu Asn Glu Asp Cys Leu Asn
145                 150                 155                 160

Gly Ser Gln Leu Leu Val Asn Phe Gly Leu Ser Pro Ala Ala Pro Leu
                165                 170                 175

Thr Pro Arg Gln Phe Ala Leu Leu Cys Pro Ala Leu Leu Tyr Gln Ile
            180                 185                 190

Asp Ser Arg Val Cys Ile Gly Ala Pro Ala Pro Ala Pro Pro Gly Asp
        195                 200                 205

Leu Leu Ser Ala Leu Leu Gln Ser Ala Leu Ala Val Leu Leu Leu Ser
    210                 215                 220

Leu Pro Ser Pro Leu Ser Leu Leu Leu Arg Leu Leu Gly Pro Arg
225                 230                 235                 240

Leu Leu Arg Pro Leu Leu Gly Phe Leu Gly Ala Leu Ala Val Gly Thr
                245                 250                 255

Leu Cys Gly Asp Ala Leu Leu His Leu Leu Pro His Ala Gln Glu Gly
            260                 265                 270

Arg His Ala Gly Pro Gly Gly Leu Pro Glu Lys Asp Leu Gly Pro Gly
        275                 280                 285

Leu Ser Val Leu Gly Gly Leu Phe Leu Leu Phe Val Leu Glu Asn Met
    290                 295                 300

Leu Gly Leu Leu Arg His
305                 310

<210> SEQ ID NO 28
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 28
cgcaacttgg atccggagaa tgg                                            23

<210> SEQ ID NO 29
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 29
gaatctcgaa acacgcaact tgg                                            23

<210> SEQ ID NO 30
<211> LENGTH: 23
<212> TYPE: DNA
<213> ORGANISM: artificial sequence
```

```
<220> FEATURE:
<223> OTHER INFORMATION: Guide RNA Recognition Sequence

<400> SEQUENCE: 30
cgaaacacgc aacttggatc cgg                                              23

<210> SEQ ID NO 31
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 31
tggatccgga gaatggcagt ggg                                              23

<210> SEQ ID NO 32
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 32
aggcagctcc aggtgactag agg                                              23

<210> SEQ ID NO 33
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 33
gatggccctt cagcccctac agg                                              23

<210> SEQ ID NO 34
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 34
aaataggagg gcatccctcc tgg                                              23

<210> SEQ ID NO 35
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 35
ttggatccgg agaatggcag tgg                                              23

<210> SEQ ID NO 36
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 36
gtcacctgga gctgcctgta ggg                                              23
```

```
<210> SEQ ID NO 37
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 37
aattttctcc tctagtcacc tgg                                              23

<210> SEQ ID NO 38
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 38
tcacctggag ctgcctgtag ggg                                              23

<210> SEQ ID NO 39
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 39
tcctatttca gagatgctgc agg                                              23

<210> SEQ ID NO 40
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 40
tgcagcatct ctgaaatagg agg                                              23

<210> SEQ ID NO 41
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 41
gtgttcatct tcccagcttg tgg                                              23

<210> SEQ ID NO 42
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 42
tgaacacctg gttccacctc tgg                                              23

<210> SEQ ID NO 43
<211> LENGTH: 23
<212> TYPE: DNA
<213> ORGANISM: artificial sequence
<220> FEATURE:
<223> OTHER INFORMATION: Guide RNA Recognition Sequence
```

```
<400> SEQUENCE: 43
catcttccca gcttgtggcc tgg                                               23

<210> SEQ ID NO 44
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 44
taggagggca tccctcctgg tgg                                               23

<210> SEQ ID NO 45
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 45
gatgctgcag gcgaaaatga agg                                               23

<210> SEQ ID NO 46
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 46
aagctgggaa gatgaacacc tgg                                               23

<210> SEQ ID NO 47
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 47
gcagcatctc tgaaatagga ggg                                               23

<210> SEQ ID NO 48
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 48
cagcagagcc agggactaag ggg                                               23

<210> SEQ ID NO 49
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 49
gcctgcagca tctctgaaat agg                                               23

<210> SEQ ID NO 50
```

```
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 50
gccatcccac tgccattctc cgg                                              23

<210> SEQ ID NO 51
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 51
gggaagccag gccacaagct ggg                                              23

<210> SEQ ID NO 52
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 52
agctgcctgt aggggctgaa ggg                                              23

<210> SEQ ID NO 53
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 53
ggggaagcca ggccacaagc tgg                                              23

<210> SEQ ID NO 54
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 54
agtcacctgg agctgcctgt agg                                              23

<210> SEQ ID NO 55
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 55
gcagcagagc cagggactaa ggg                                              23

<210> SEQ ID NO 56
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 56
```

```
cctggcttcc ccttagtccc tgg                                          23
```

<210> SEQ ID NO 57
<211> LENGTH: 351
<212> TYPE: DNA
<213> ORGANISM: Mus musculus

<400> SEQUENCE: 57

```
caggtgcagc tgaaggagtc aggacctggc ctggtggcgc cctcacagag cctgtccatc   60
acatgcaccg tctcagggtt ctcattaacc ggctatgctg taaactgggt tcgccagcct  120
ccaggacagg gctggagtg gctgggagtg atttggggtg atggaagaac agactataat   180
tcagttctca aatccagact gagcatcaac aaggacaact ccaagagcca agttttctta  240
aaaatgaaca gtctgcaaac tgatgacaca gccaggtact actgtgccag atttggtaac  300
tcctatgctc tggactactg gggtcaagga acctcagtca ccgtctcctc a           351
```

<210> SEQ ID NO 58
<211> LENGTH: 117
<212> TYPE: PRT
<213> ORGANISM: Mus musculus

<400> SEQUENCE: 58

```
Gln Val Gln Leu Lys Glu Ser Gly Pro Gly Leu Val Ala Pro Ser Gln
1               5                   10                  15
Ser Leu Ser Ile Thr Cys Thr Val Ser Gly Phe Ser Leu Thr Gly Tyr
            20                  25                  30
Ala Val Asn Trp Val Arg Gln Pro Pro Gly Gln Gly Leu Glu Trp Leu
        35                  40                  45
Gly Val Ile Trp Gly Asp Gly Arg Thr Asp Tyr Asn Ser Val Leu Lys
    50                  55                  60
Ser Arg Leu Ser Ile Asn Lys Asp Asn Ser Lys Ser Gln Val Phe Leu
65                  70                  75                  80
Lys Met Asn Ser Leu Gln Thr Asp Asp Thr Ala Arg Tyr Tyr Cys Ala
                85                  90                  95
Arg Phe Gly Asn Ser Tyr Ala Leu Asp Tyr Trp Gly Gln Gly Thr Ser
            100                 105                 110
Val Thr Val Ser Ser
        115
```

<210> SEQ ID NO 59
<211> LENGTH: 336
<212> TYPE: DNA
<213> ORGANISM: Mus musculus

<400> SEQUENCE: 59

```
gacattgtga tgtcacagtc tccatcctcc ctggctgtgt cagcaggaga gaaggtcact   60
atgagctgca atccagtca gagtctgctc aacagtagaa cccgaaagaa ctacttggct  120
tggtaccagc agaaaccagg gcagtctcct aaactgctga tctactgggc atccactagg  180
gaatctgggg tccctgatcg cttcacaggc agtggatctg ggacagattt cactctcacc  240
atcagcagtg tgcaggctga agacctggca gtttattact gcaagcaatc ttataatctt  300
cacacgttcg gagggggac caagctggaa ataaaa                             336
```

<210> SEQ ID NO 60
<211> LENGTH: 112
<212> TYPE: PRT

<213> ORGANISM: Mus musculus

<400> SEQUENCE: 60

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu His Thr Phe Gly Gly Gly Thr Lys Leu Glu Ile Lys
            100                 105                 110

<210> SEQ ID NO 61
<211> LENGTH: 9
<212> TYPE: PRT
<213> ORGANISM: mus musculus

<400> SEQUENCE: 61

Phe Ser Leu Thr Gly Tyr Ala Val Asn
1               5

<210> SEQ ID NO 62
<211> LENGTH: 13
<212> TYPE: PRT
<213> ORGANISM: mus musculus

<400> SEQUENCE: 62

Trp Leu Gly Val Ile Trp Gly Asp Gly Arg Thr Asp Tyr
1               5                   10

<210> SEQ ID NO 63
<211> LENGTH: 11
<212> TYPE: PRT
<213> ORGANISM: mus musculus

<400> SEQUENCE: 63

Ala Arg Phe Gly Asn Ser Tyr Ala Leu Asp Tyr
1               5                   10

<210> SEQ ID NO 64
<211> LENGTH: 14
<212> TYPE: PRT
<213> ORGANISM: mus musculus

<400> SEQUENCE: 64

Gln Ser Leu Leu Asn Ser Arg Thr Arg Lys Asn Tyr Leu Ala
1               5                   10

<210> SEQ ID NO 65
<211> LENGTH: 11
<212> TYPE: PRT
<213> ORGANISM: mus musculus

<400> SEQUENCE: 65

Leu Leu Ile Tyr Trp Ala Ser Thr Arg Glu Ser
1               5                   10

```
<210> SEQ ID NO 66
<211> LENGTH: 7
<212> TYPE: PRT
<213> ORGANISM: mus musculus

<400> SEQUENCE: 66

Lys Gln Ser Tyr Asn Leu His
1               5

<210> SEQ ID NO 67
<211> LENGTH: 18
<212> TYPE: PRT
<213> ORGANISM: mus musculus

<400> SEQUENCE: 67

Gly Pro Ser Gly Trp Gly Asp Gln Glu Glu Ser Lys Ala Pro Asp Leu
1               5                   10                  15

His Gly
```